US009493754B2

(12) United States Patent
Teller et al.

(10) Patent No.: US 9,493,754 B2
(45) Date of Patent: Nov. 15, 2016

(54) ***ASPERGILLUS* CONTAINING BETA-GLUCOSIDASE, BETA-GLUCOSIDASES AND NUCLEIC ACIDS ENCODING THE SAME**

(71) Applicant: CLEAN-VANTAGE LLC, Richland, WA (US)

(72) Inventors: Philip Teller, Hellerup (DK); Peter Lubeck, Kgs. Lyngby (DK); Annette Sorensen, Koge (DK); Birgitte K Ahring, Richland, WA (US)

(73) Assignee: CLEAN-VANTAGE LLC, Richland, WA (US)

( * ) Notice: Subject to any disclaimer, the term of this patent is extended or adjusted under 35 U.S.C. 154(b) by 0 days.

(21) Appl. No.: 14/519,084

(22) Filed: Oct. 20, 2014

(65) Prior Publication Data

US 2015/0203833 A1 Jul. 23, 2015

Related U.S. Application Data

(62) Division of application No. 13/813,031, filed as application No. PCT/DK2011/050296 on Aug. 1, 2011, now Pat. No. 8,865,448.

(30) Foreign Application Priority Data

Jul. 30, 2010 (DK) ................................ 2010 70347

(51) Int. Cl.

| | |
|---|---|
| ***C12N 9/00*** | (2006.01) |
| ***C12N 9/42*** | (2006.01) |
| ***C12P 7/10*** | (2006.01) |
| ***C12P 19/02*** | (2006.01) |
| ***C12R 1/66*** | (2006.01) |

(52) U.S. Cl.

CPC ............... *C12N 9/2445* (2013.01); *C12P 7/10* (2013.01); *C12P 19/02* (2013.01); *C12R 1/66* (2013.01); *C12Y 302/01021* (2013.01); *Y02E 50/16* (2013.01); *Y02P 20/52* (2015.11)

(58) Field of Classification Search

USPC ......................... 435/252.3, 15, 183; 530/350

See application file for complete search history.

(56) References Cited

U.S. PATENT DOCUMENTS

| | | | |
|---|---|---|---|
| 8,044,264 | B2 | 10/2011 | Leon et al. |
| 8,323,944 | B2 | 12/2012 | Harris et al. |
| 2009/0019608 | A1 | 1/2009 | Leon et al. |

FOREIGN PATENT DOCUMENTS

| | | | |
|---|---|---|---|
| WO | 2004031378 | A2 | 4/2004 |
| WO | 2005074647 | A2 | 8/2005 |
| WO | 2005074656 | A2 | 8/2005 |
| WO | 2008148131 | A1 | 12/2008 |

OTHER PUBLICATIONS

Decker Claudia H et al: "beta-glucosidases from five black *Aspergillus* species: Study of their physico-chemical and biocatalytic properties", Journal of Agricultural and Food Chemistry, American Chemical Society, US, vo 1 • 48. No. 10. Oct. 1, 2000, pp. 4929-4936, XP008145015, ISSN: 0021-8561, DOI: 10.1021/JF000434D.

Himmel Michael E et al: "Isolation and characterization of two forms of beta-D-glucosidase from Aspergillus niger", Applied Biochemistry and Biotechnology, The Humana Press, Inc, US, vol. 39-40, No. 1, Sep. 1, 1993, pp. 213-225, XP008144996, ISSN: 0273-2289, DOI: 10.1007/BF02918991.

International Search Report and Written Opinion of the International Searching Authority, issued Aug. 3, 2012 in International Application No. PCT/DK2011/050296.

International Search Report for PCT/US2008/065393 Dated May 8, 2008.

J ager Szilvia et al: "Production and characterization of beta-glucosidases from different Aspergillus strains", World Journal of Microbiology and Biotechnology, vol. 17, No. 5, Jul. 2001, pp. 455-461, XP002663174, ISSN: 0959-3993.

Sorensen Annette et al: "Onsite Enzyme Production During Bioethanol Production from Biomass: Screening for Suitable Fungal Strains", Applied Biochemistry and Biotechnology, vol. 164, No. 7, Aug. 2011, pp. 1058-1070. XP002663173.

*Primary Examiner* — Maryam Monshipouri

(74) *Attorney, Agent, or Firm* — Jeffrey Parry Intellectual Property Law Group PLLC; Jeffrey C. Parry

(57) ABSTRACT

A novel microorganism is provided named *Aspergillus saccharolyticus*. Further, beta-glucosidase enzymes encoded by said microorganism are provided, and the use thereof in the degradation of lignocellulosic material. Also, host organisms comprising the polypeptides of the invention and/or polynucleotides encoding these are provided. In addition, methods, compositions, and kit-of-parts are provided which comprise any component of the invention, and optionally any additional components.

13 Claims, 45 Drawing Sheets

- FIGURE 1 –
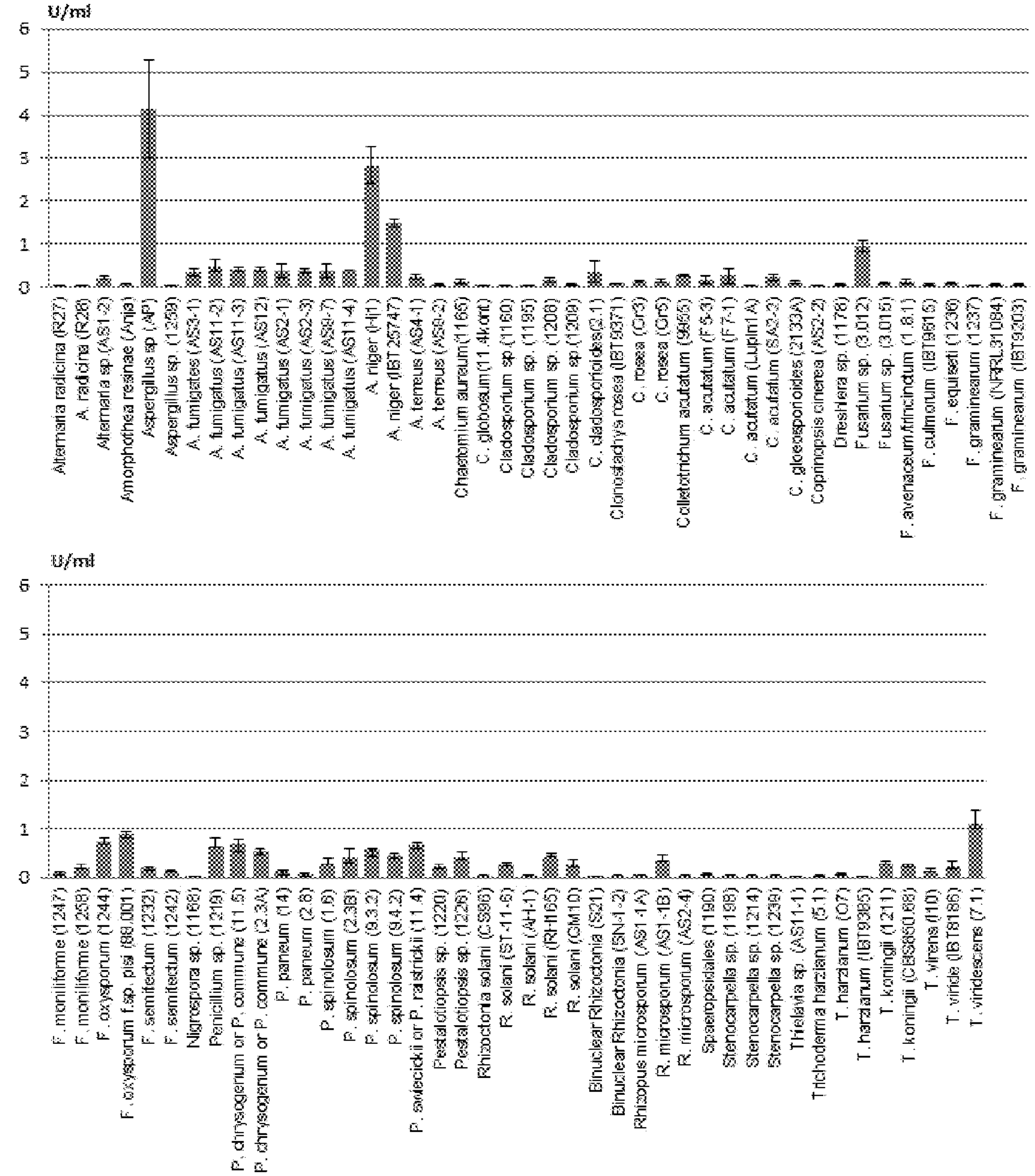

- FIGURE 2 -
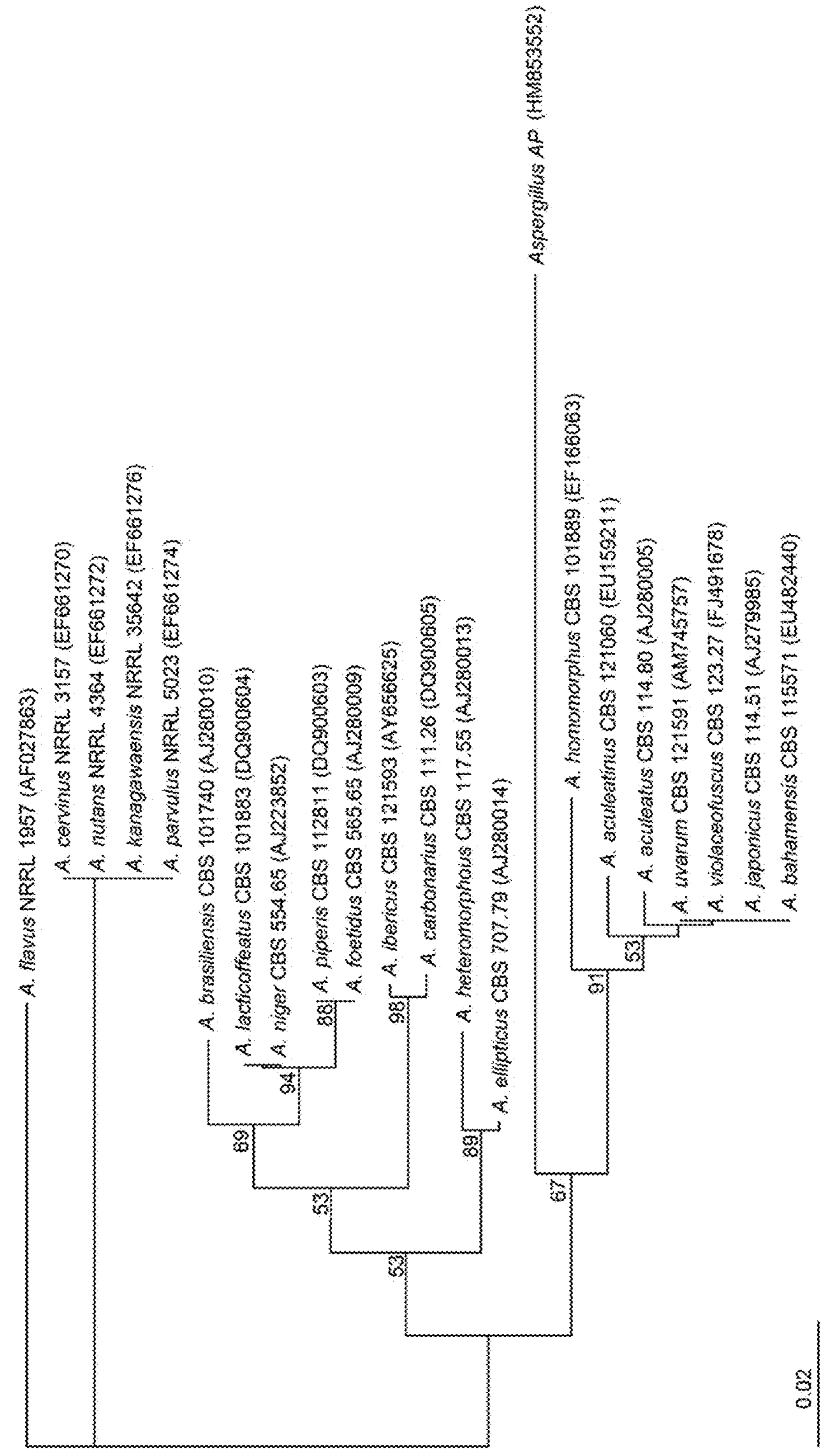

- FIGURE 3 –
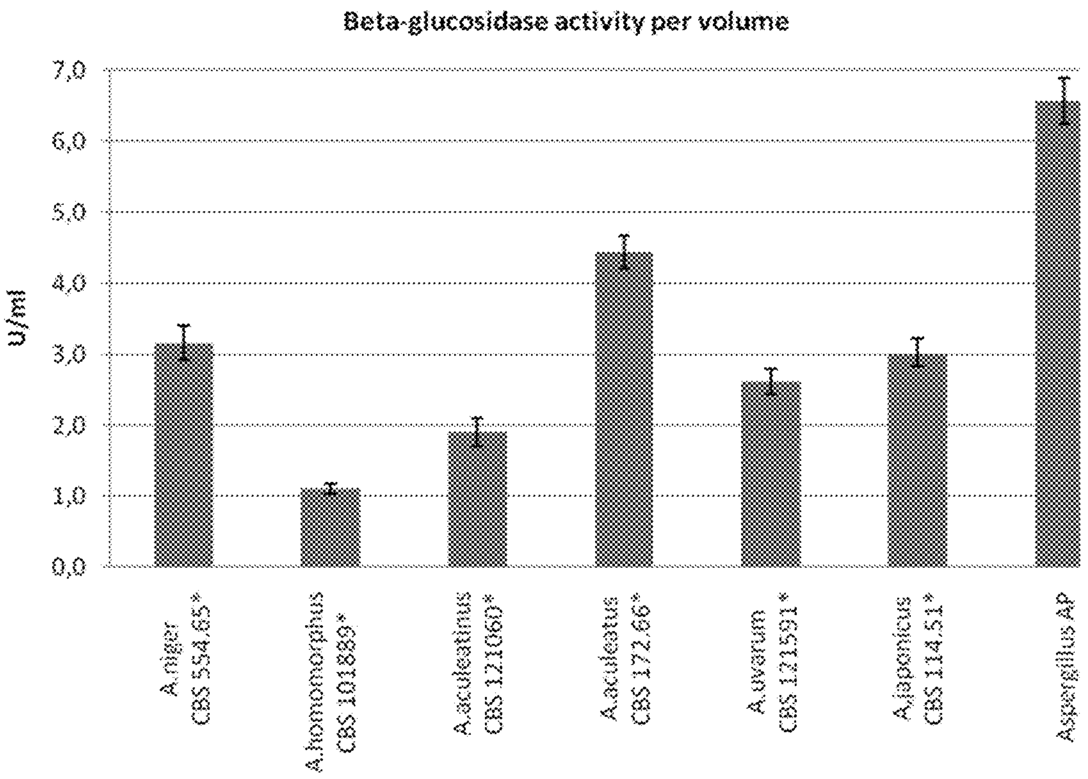

- FIGURE 4 –
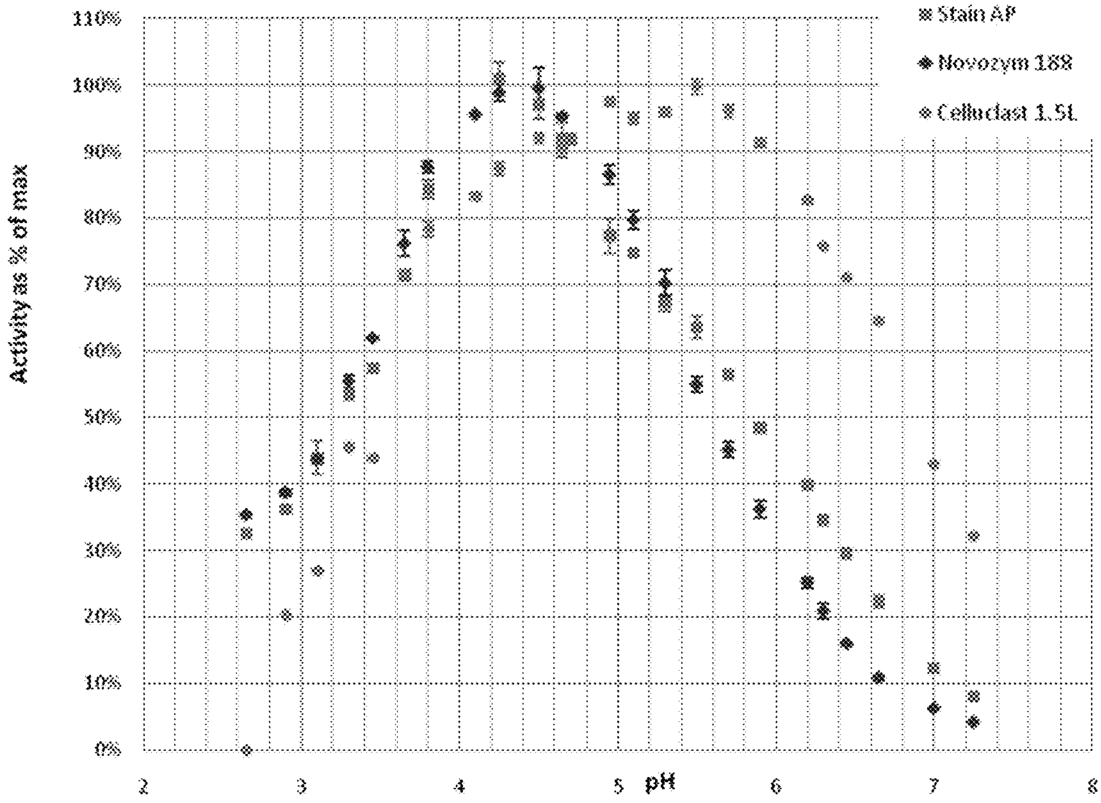

- FIGURE 5 –
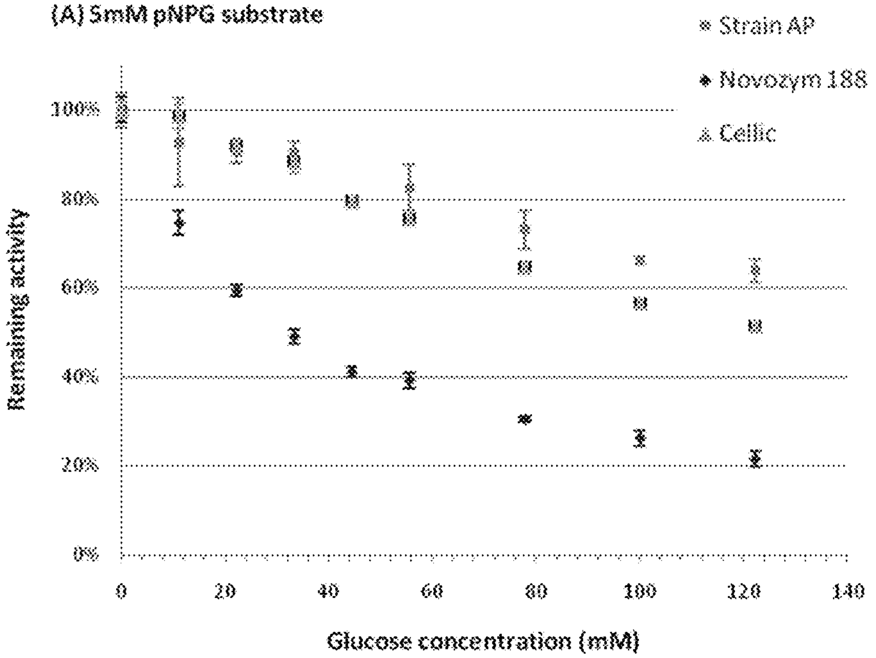
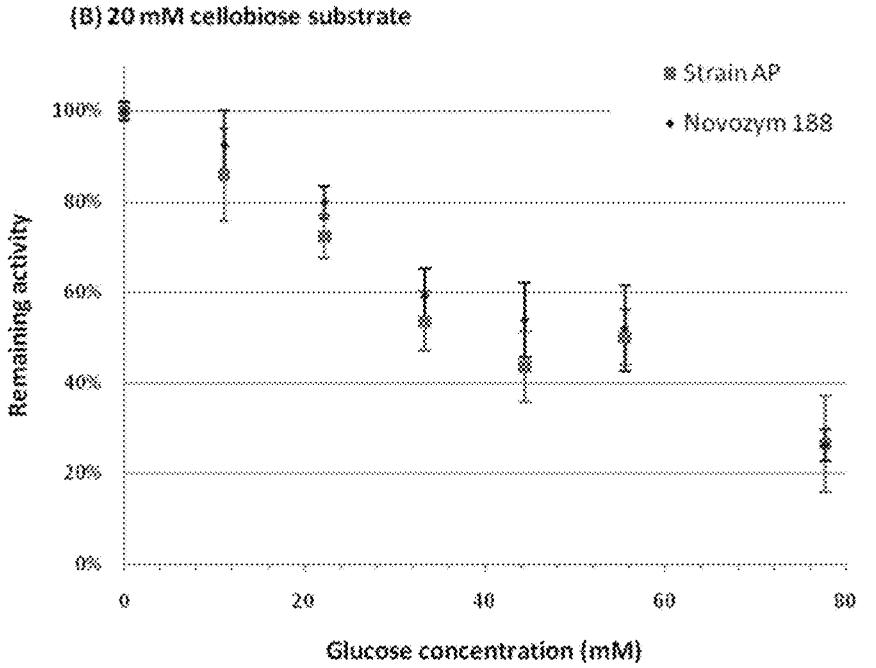

- FIGURE 6 –
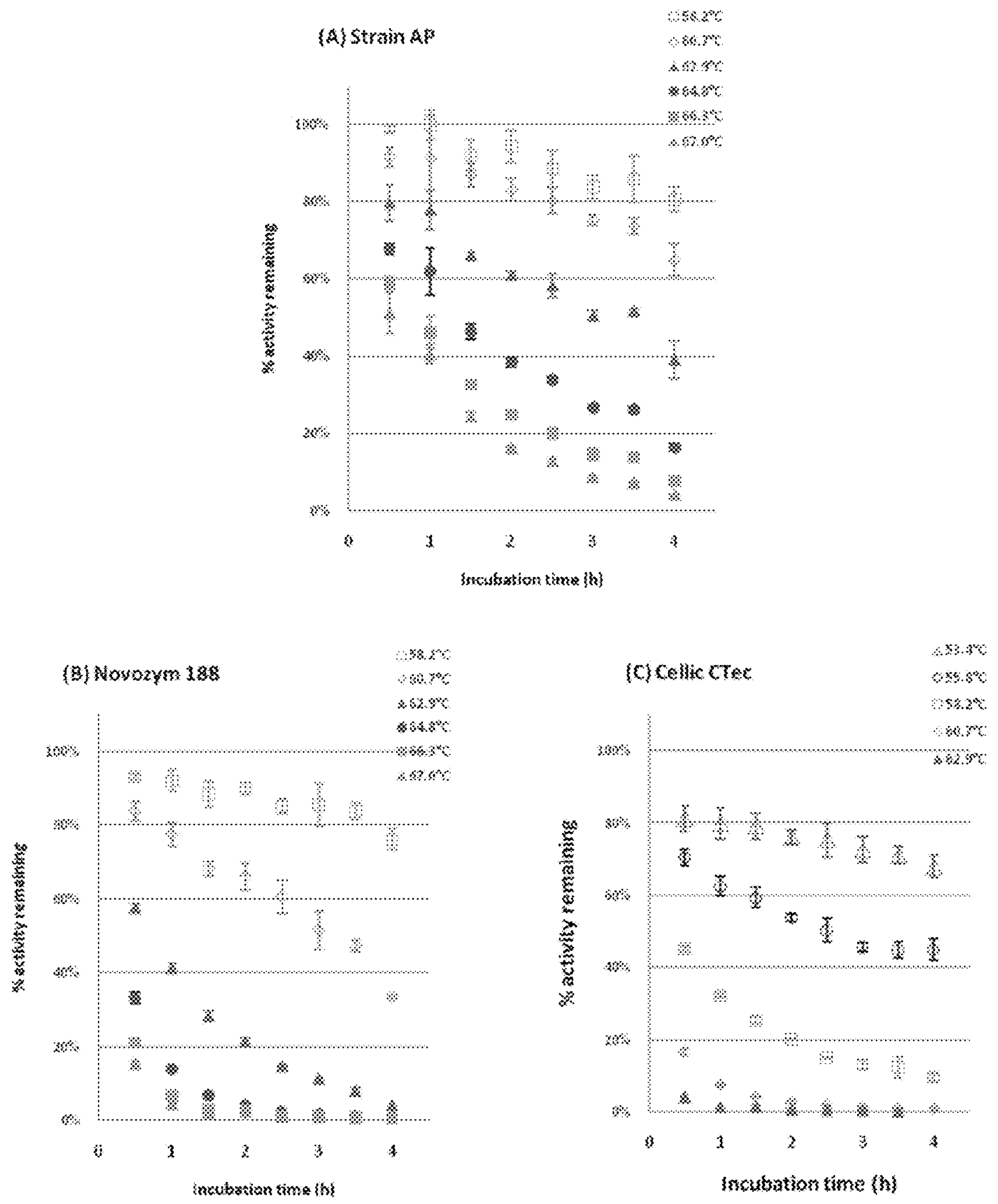

- FIGURE 7 –
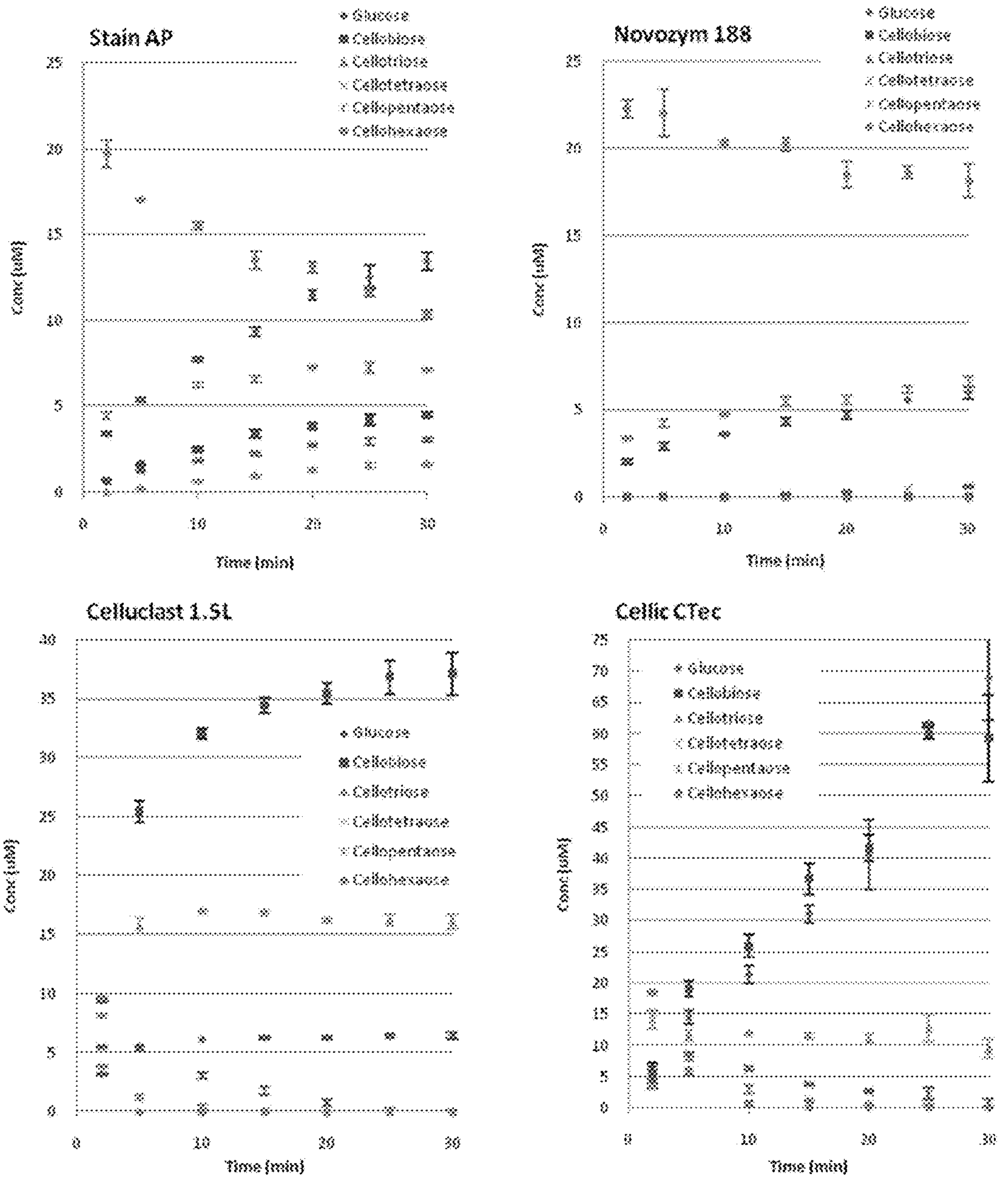

- FIGURE 8 –
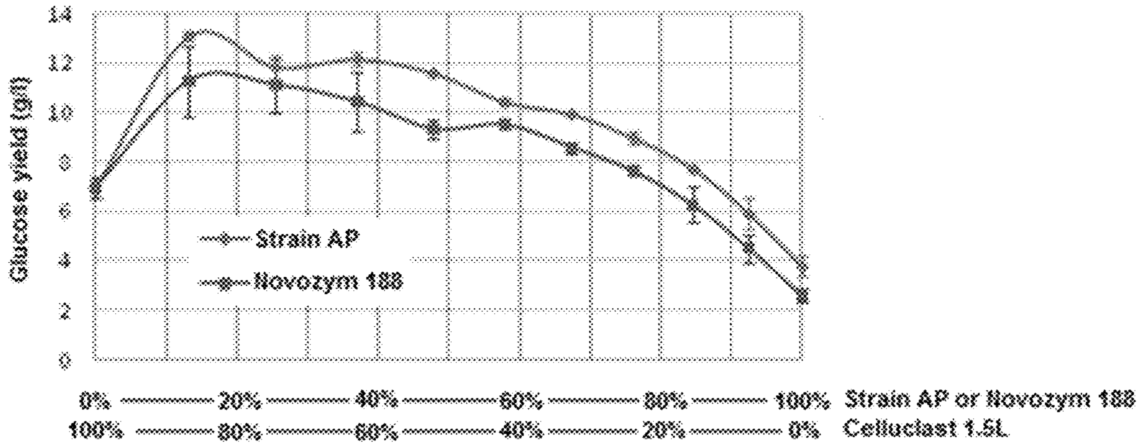

- FIGURE 9 –
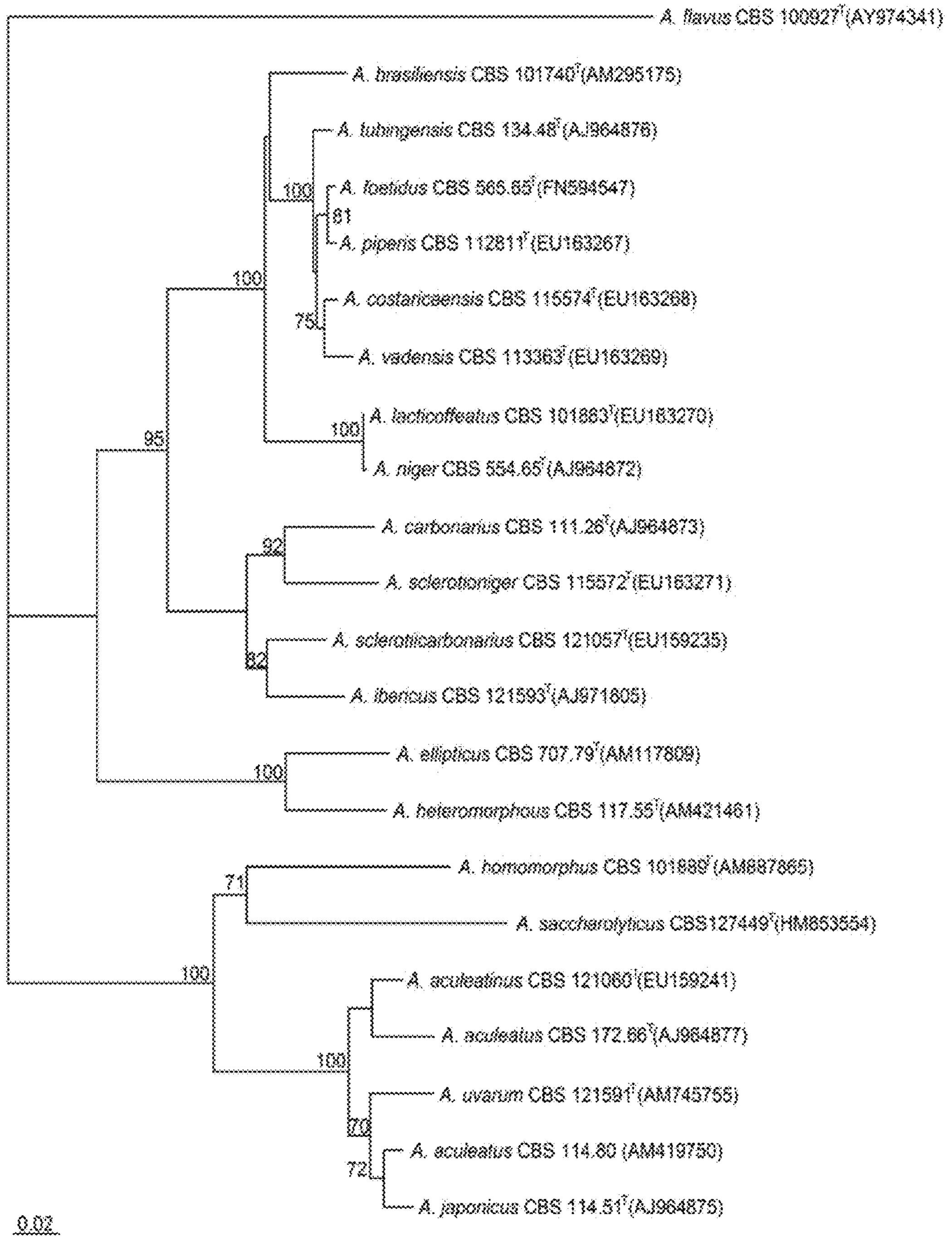

- FIGURE 10 –
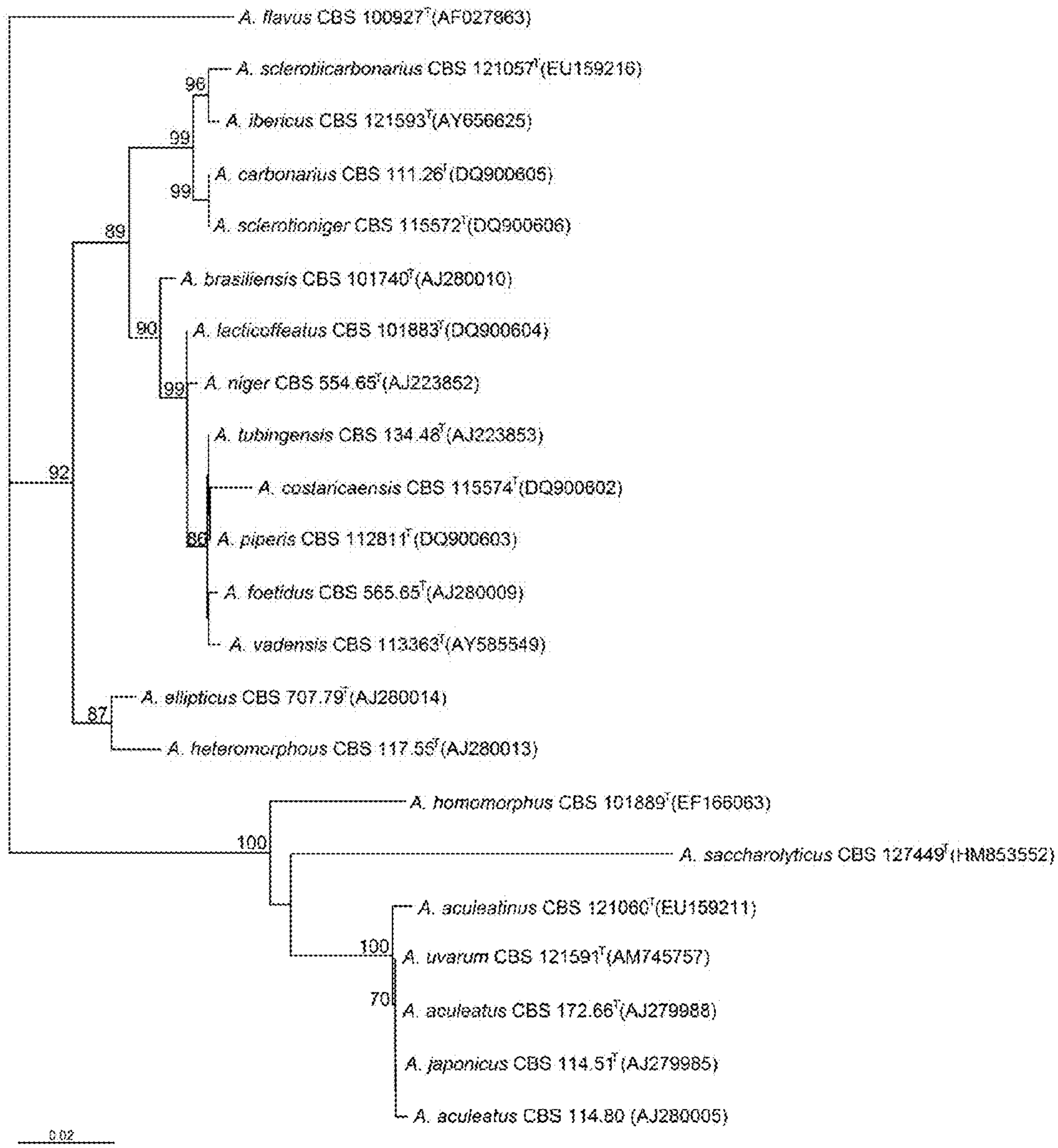

- FIGURE 11 -
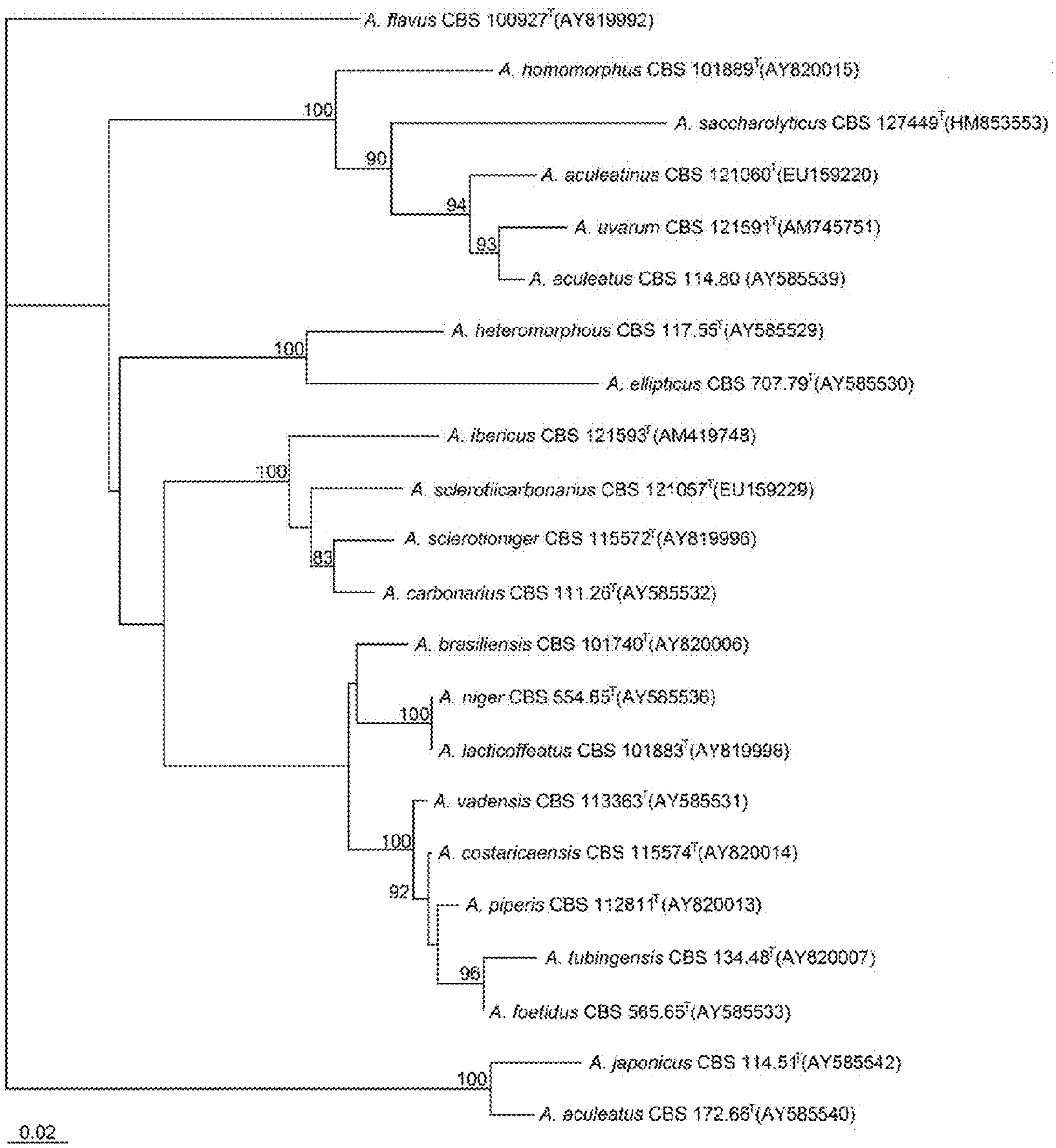

- FIGURE 12 –
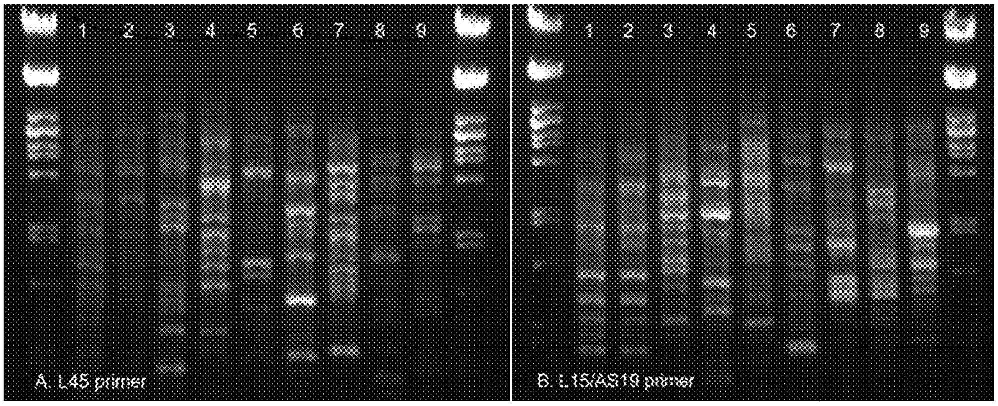

- FIGURE 13 -
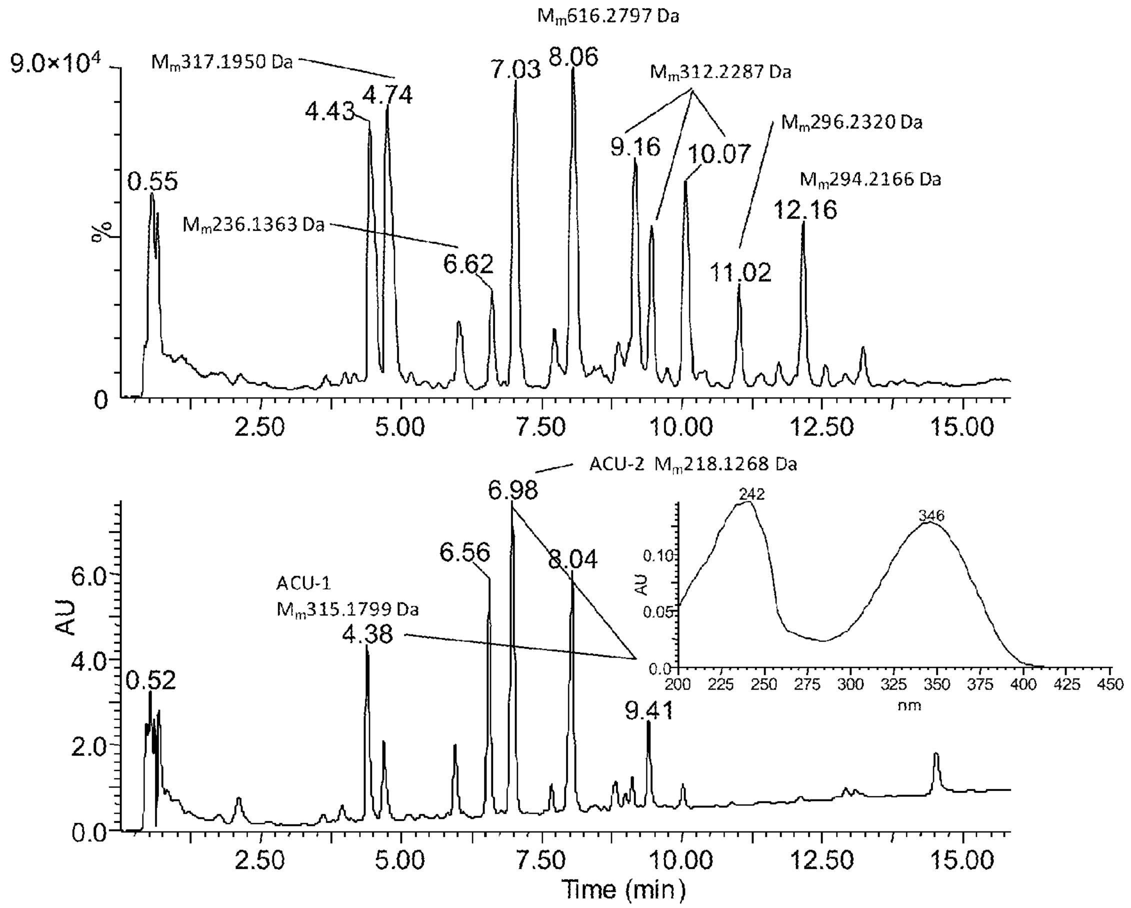

- FIGURE 14 –
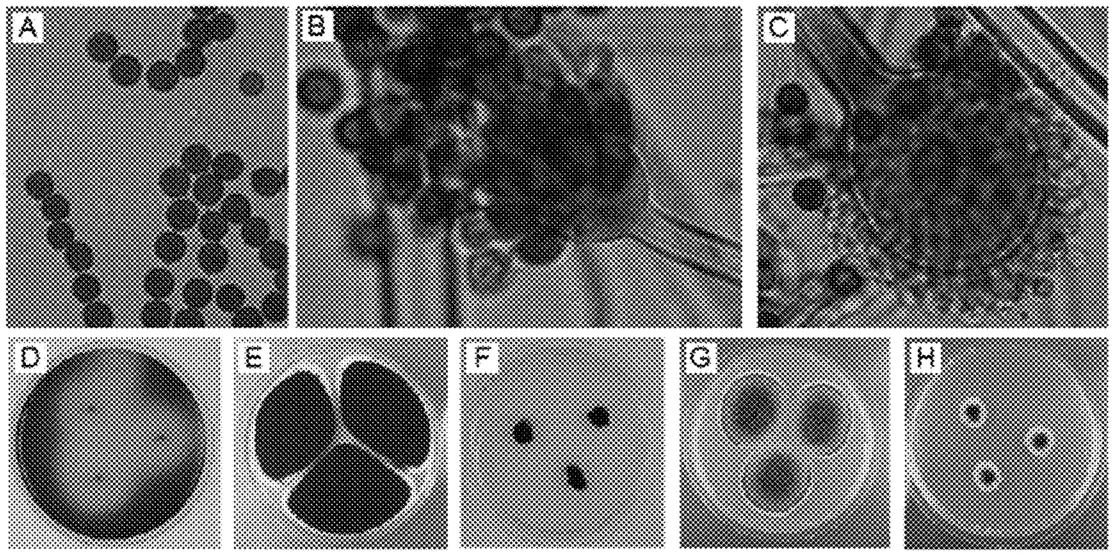

- FIGURE 15 –
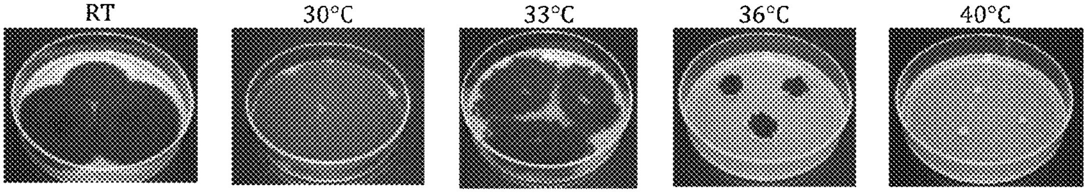

- FIGURE 16 –
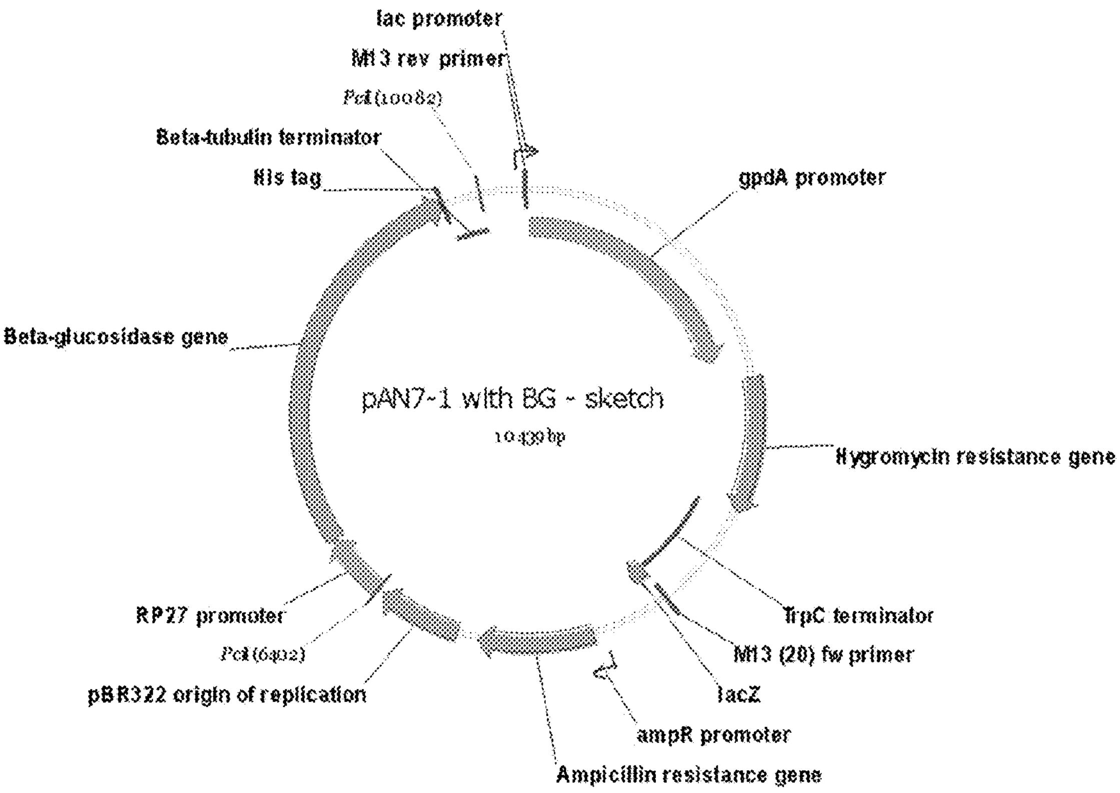

- FIGURE 17 -
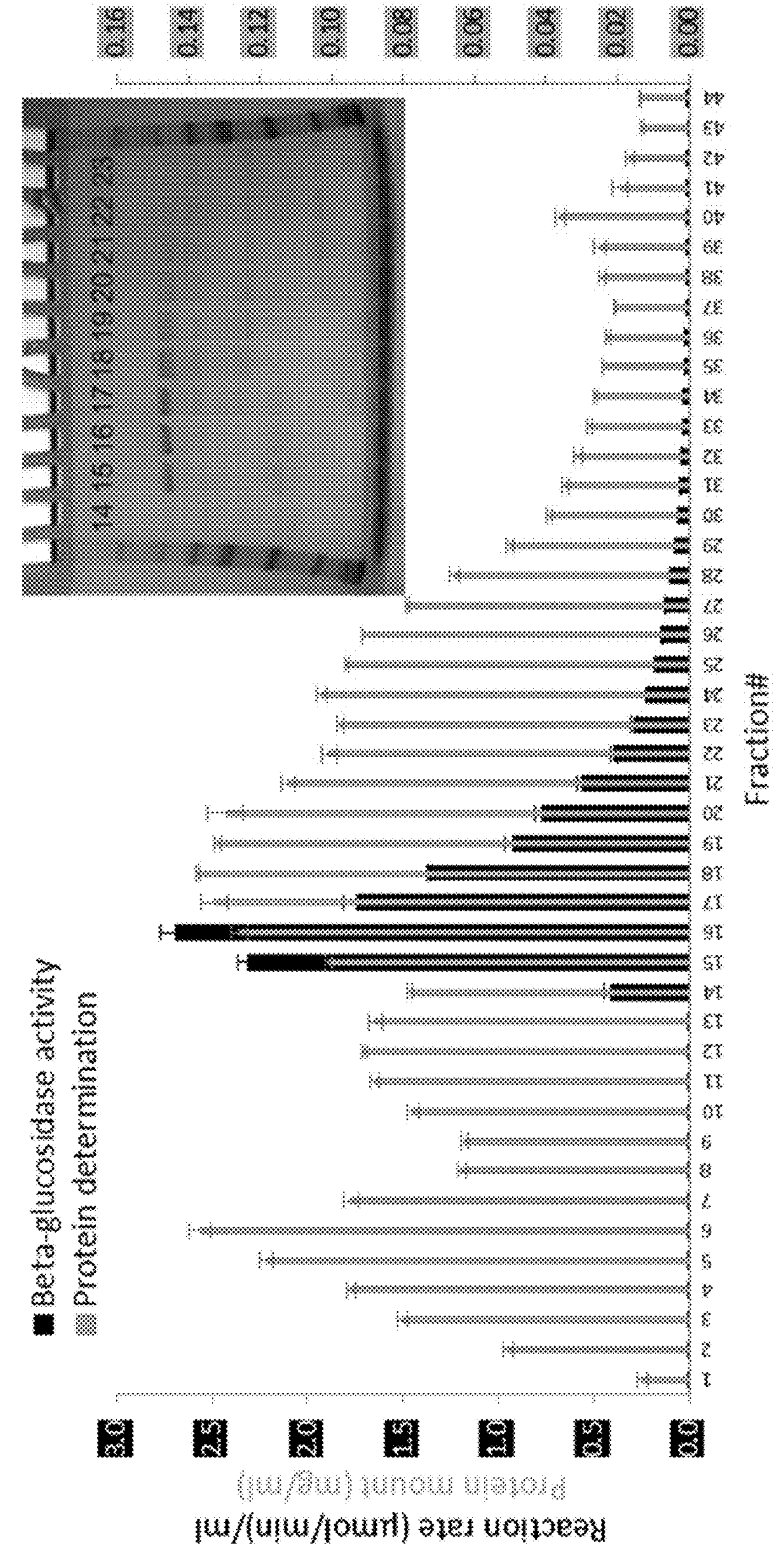

- FIGURE 18 –
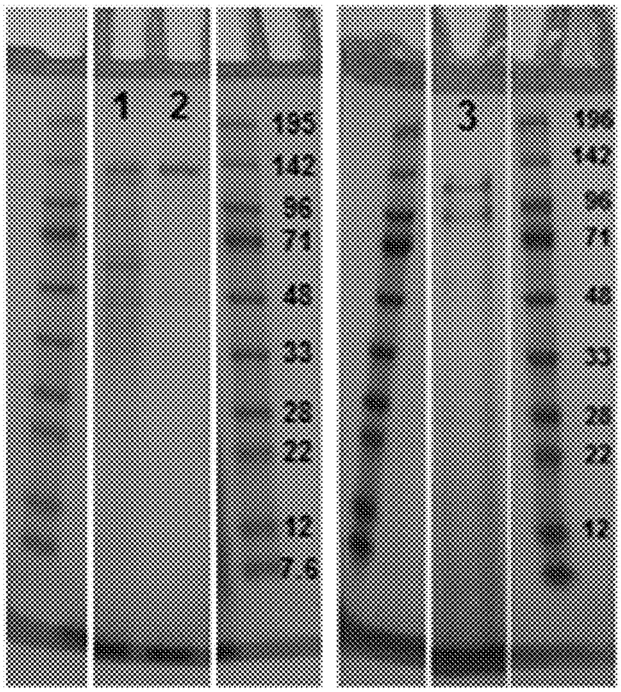

- FIGURE 19 –

| | | |
|---|---|---|
| A. saccharolyticus (HM853555) | (241) | SYTLNK LLKSELGFQGFVMSDWGA HHSGVG |
| A. aculeatus (BAA10968) | (241) | SYTLNK LLKAELGFQGFVMSDWGA HHSGVG |
| A. niger (CAK48740) | (241) | SYTLNK LLKAELGFQGFVMSDWAA HHAGVS |
| A. avenaceus (AAX39011) | (242) | SLTLNK LLKAELGFQGFVMSDWSA HHSGVG |
| A. kawachii (BAA19913) | (241) | SYTLNK LLKAELGFQGFVMSDWAA HHAGVS |
| A. terreus (ACY03273) | (242) | SLTLNK LLKAELGFQGFVMSDWSA HHSGVG |
| A. oryzae (BAE54829) | (242) | SETLNK LLKAELGFQGFVMSDWTA HHSGVG |
| A. fumigatus (EAL88289) | (252) | SQTLNK LLKAELGFQGFVMSDWSA HHSGVG |

- FIGURE 20 –
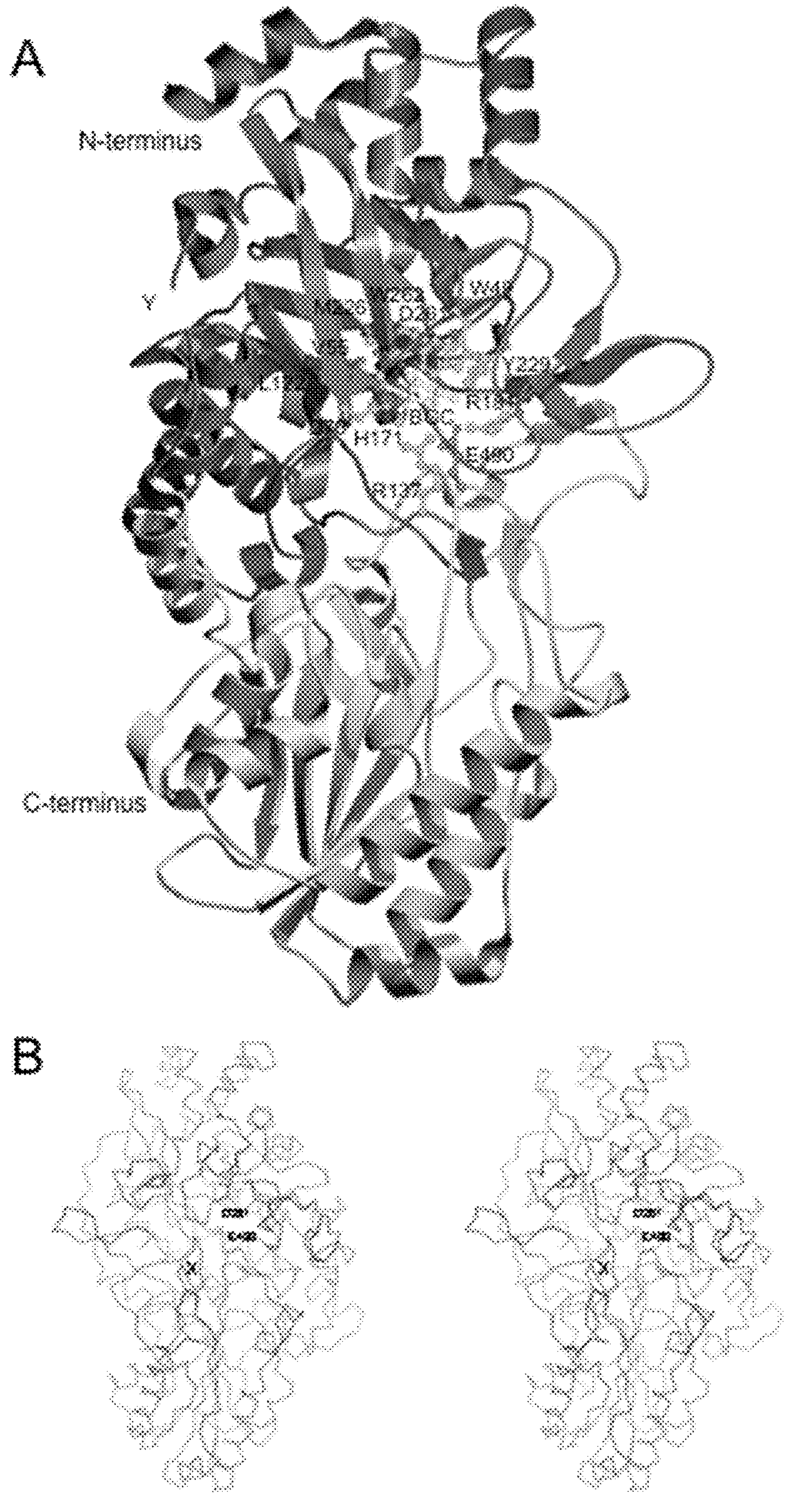

- FIGURE 21 –
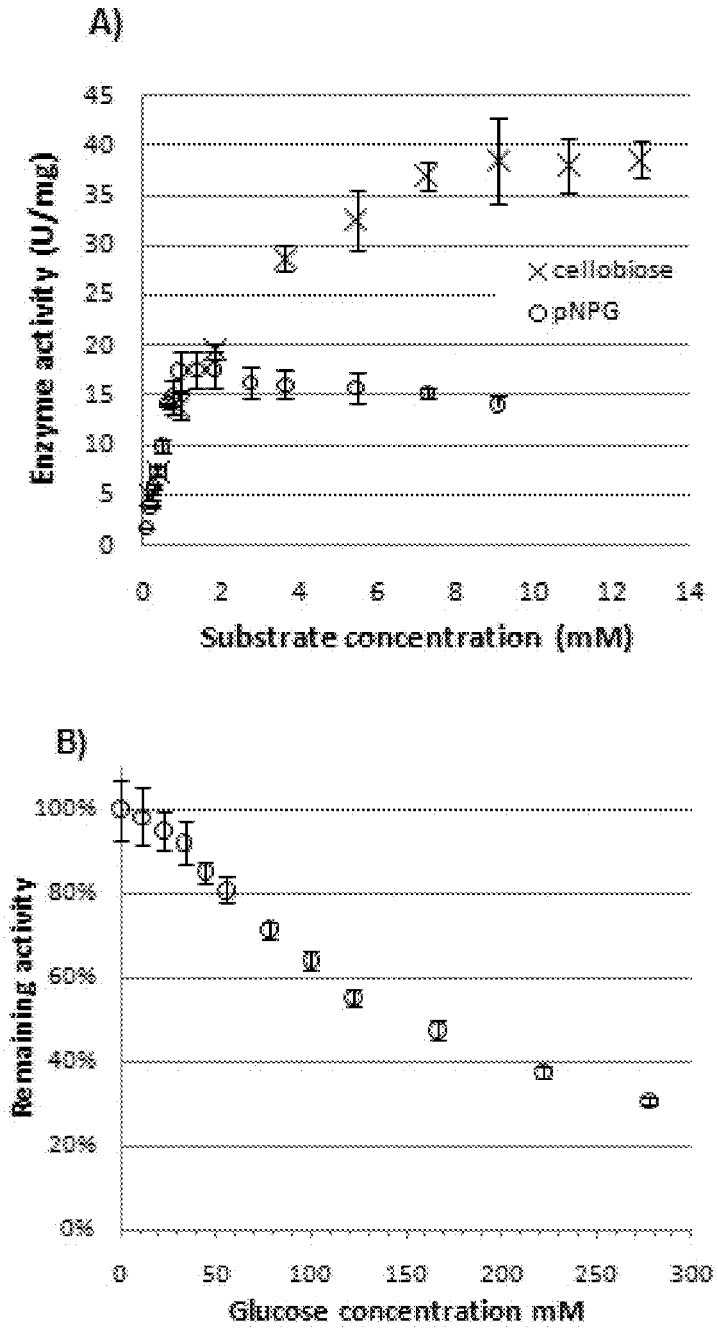

- FIGURE 22 –
A)
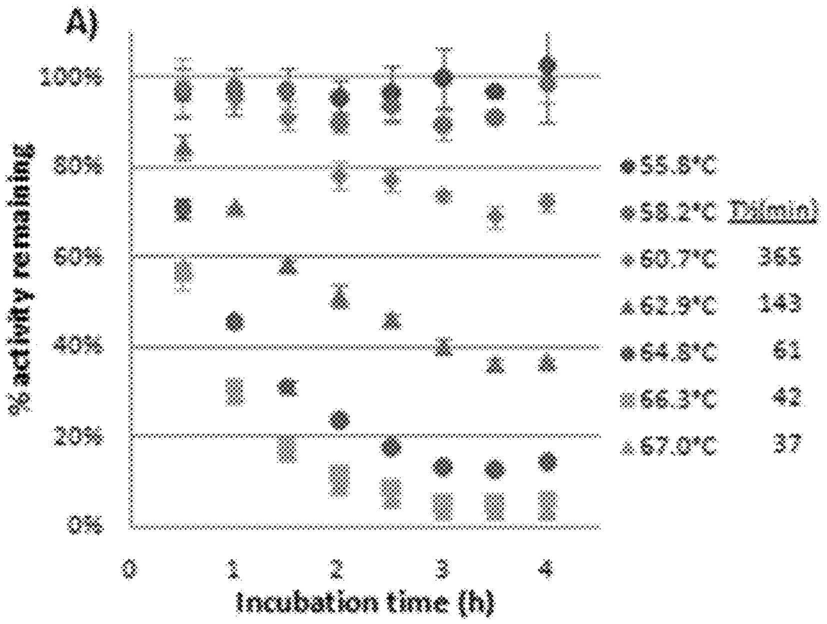
B)
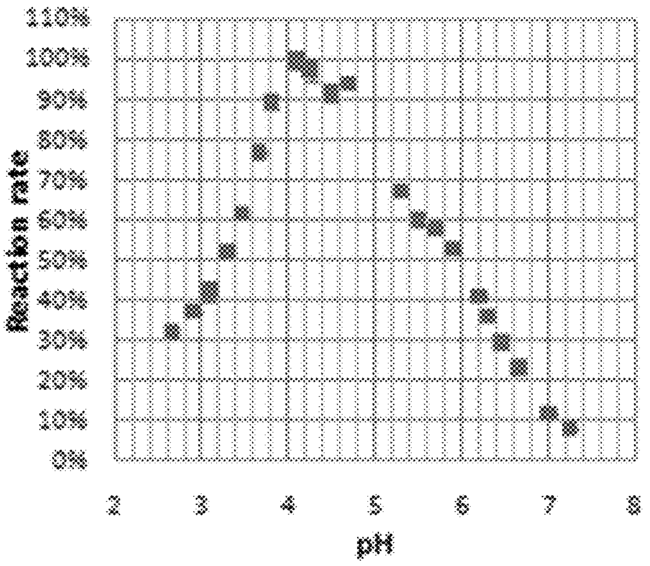

- FIGURE 23 –
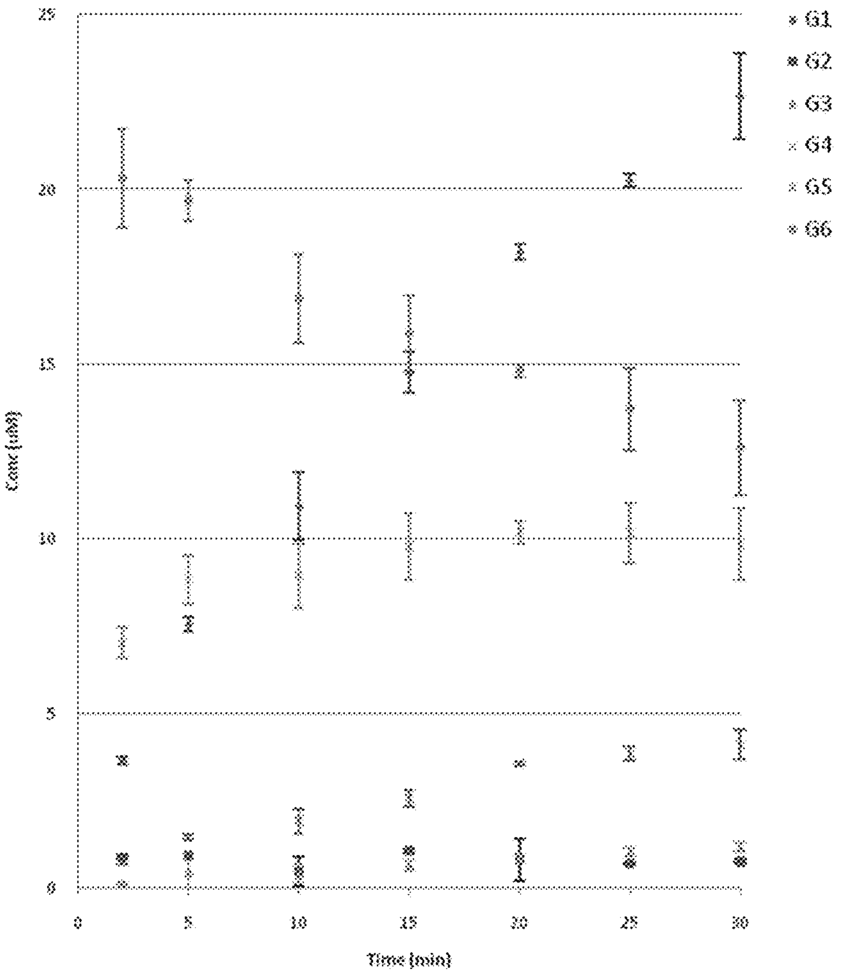

- FIGURE 24 –

NCBI Blastn of BGL1 gDNA:

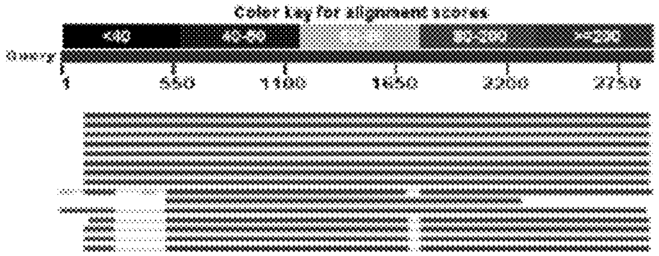

Sequences producing significant alignments:

| Accession | Description | Max score | Total score | Query coverage | E value | Max ident |
|---|---|---|---|---|---|---|
| AJ132386.1 | Aspergillus niger bgl1 gene, exons 1-7 | 1710 | 1710 | 95% | 0.0 | 74% |
| AB003470.1 | Aspergillus kawachii DNA for beta-D-glucosidase, complete cds | 1692 | 1692 | 95% | 0.0 | 73% |
| DQ832261.1 | Aspergillus niger beta-glucosidase precursor (bglA) gene, complete cds | 1687 | 1687 | 95% | 0.0 | 73% |
| GQ471883.1 | Aspergillus niger strain BCRC 31494 beta-glucosidase II gene, complete cds | 1620 | 1620 | 95% | 0.0 | 73% |
| DQ220804.1 | Aspergillus niger strain As3.350 beta-glucosidase (bgl1) gene, complete cds | 1615 | 1615 | 95% | 0.0 | 73% |
| AM270402.1 | Aspergillus niger contig An18c0100, genomic contig | 1613 | 1613 | 95% | 0.0 | 73% |
| EF809417.1 | Aspergillus niger strain NIBGE 06 beta-glucosidase gene, complete cds | 1584 | 1584 | 95% | 0.0 | 73% |
| FJ794717.1 | Aspergillus niger strain NIBGE beta-glucosidase precursor, gene, complete cds | 1572 | 1572 | 95% | 0.0 | 72% |
| D64088.1 | Aspergillus aculeatus mRNA for beta-glucosidase, complete cds | 1364 | 2760 | 89% | 0.0 | 80% |
| AF121777.1 | Aspergillus niger similar to beta-glucosidase gene sequence | 1104 | 1104 | 59% | 0.0 | 74% |
| BN001302.1 | TPA: TPA_reasm: Aspergillus nidulans FGSC A4 chromosome II | 1025 | 1159 | 90% | 0.0 | 72% |
| FJ431207.1 | Aspergillus niger strain FTA008 beta-glucosidase mRNA, partial cds | 901 | 1655 | 83% | 0.0 | 81% |
| FN430671.1 | Aspergillus niger mRNA for beta-glucosidase (bgl gene), strain NRRL 3135 | 882 | 1668 | 84% | 0.0 | 78% |
| DQ655704.1 | Aspergillus niger strain As3.350 beta-glucosidase (bgl1) mRNA, complete cds | 880 | 1653 | 84% | 0.0 | 78% |
| XM_001398779.2 | Aspergillus niger CBS 513.88 beta-glucosidase A, mRNA | 877 | 1648 | 84% | 0.0 | 78% |
| EU262991.1 | Aspergillus niger strain zju-2 beta-glucosidase mRNA, complete cds | 877 | 1639 | 84% | 0.0 | 78% |
| EU233788.1 | Aspergillus niger beta-glucosidase (bgl) mRNA, complete cds | 877 | 1648 | 84% | 0.0 | 78% |
| AP007150.1 | Aspergillus oryzae RIB40 DNA, SC009 | 785 | 1433 | 90% | 0.0 | 72% |
| XM_001269581.1 | Aspergillus clavatus NRRL 1 beta-glucosidase, putative (ACLA_028810), partial mRNA | 771 | 1298 | 80% | 0.0 | 75% |
| XM_001212225.1 | Aspergillus terreus NIH2624 beta-glucosidase 1 precursor (ATEG_03047) partial mRNA | 766 | 1341 | 81% | 0.0 | 76% |
| GU979571.1 | Aspergillus terreus strain SUK-1 beta-glucosidase mRNA, complete cds | 753 | 1352 | 80% | 0.0 | 75% |
| AY943971.1 | Aspergillus avenaceus extracellular beta-glucosidase (bgl1) mRNA, complete cds | 746 | 1291 | 81% | 0.0 | 76% |
| XM_002561892.1 | Penicillium chrysogenum Wisconsin 54-1255 hypothetical protein (Pc13g01940) mRNA, complete cds | 734 | 824 | 66% | 0.0 | 70% |

- FIGURE 25 –

NCBI blastn of BGL1 cDNA (without signal seq):

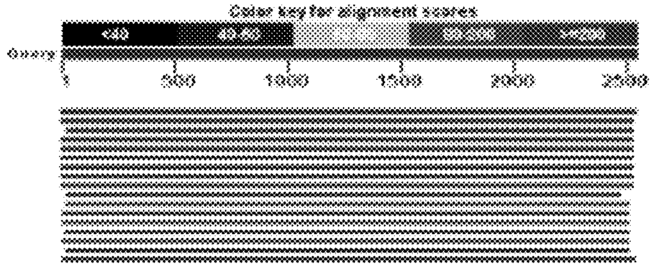

Sequences producing significant alignments:

| Accession | Description | Max score | Total score | Query coverage | E value | Max ident |
|---|---|---|---|---|---|---|
| D64088.1 | Aspergillus aculeatus mRNA for beta-glucosidase, complete cds | 2807 | 2807 | 100% | 0.0 | 84% |
| FN430671.1 | Aspergillus niger mRNA for beta-glucosidase (bgl gene), strain NRRL 3135 | 1784 | 1784 | 99% | 0.0 | 75% |
| FJ431207.1 | Aspergillus niger strain FTA008 beta-glucosidase mRNA, partial cds | 1772 | 1772 | 98% | 0.0 | 75% |
| DQ655704.1 | Aspergillus niger strain As3.350 beta-glucosidase (bgl1) mRNA, complete cds | 1770 | 1770 | 99% | 0.0 | 75% |
| XM_001398779.2 | Aspergillus niger CBS 513.88 beta-glucosidase A, mRNA | 1766 | 1766 | 99% | 0.0 | 75% |
| EU233788.1 | Aspergillus niger beta-glucosidase (bgl) mRNA, complete cds | 1766 | 1766 | 99% | 0.0 | 75% |
| FJ262301.1 | Aspergillus niger strain zju-2 beta-glucosidase mRNA, complete cds | 1752 | 1752 | 99% | 0.0 | 75% |
| XM_001820779.2 | Aspergillus oryzae RIB40 beta-glucosidase A, mRNA | 1422 | 1422 | 99% | 0.0 | 72% |
| XM_002383199.1 | Aspergillus flavus NRRL3357 beta-glucosidase, putative, mRNA | 1415 | 1415 | 99% | 0.0 | 72% |
| GU078571.1 | Aspergillus terreus strain SUK-1 beta-glucosidase mRNA, complete cds | 1393 | 1393 | 96% | 0.0 | 72% |
| XM_001212225.1 | Aspergillus terreus NIH2624 beta-glucosidase 1 precursor (ATEG_03047) partial mRNA | 1393 | 1393 | 97% | 0.0 | 72% |
| HQ680475.1 | Aspergillus fumigatus strain Z5 extracellular beta-glucosidase/cellulase BGL3 precursor (bgl3) mRNA, complete cds | 1364 | 1364 | 98% | 0.0 | 72% |
| XM_745234.1 | Aspergillus fumigatus Af293 beta-glucosidase (AFUA_1G05770), partial mRNA | 1364 | 1364 | 98% | 0.0 | 72% |
| XM_001269583.1 | Aspergillus clavatus NRRL 1 beta-glucosidase, putative (ACLA_028810), partial mRNA | 1348 | 1348 | 98% | 0.0 | 72% |
| XM_001265080.1 | Neosartorya fischeri NRRL 181 beta-glucosidase, putative (NFIA_018950) partial mRNA | 1346 | 1346 | 98% | 0.0 | 72% |
| AY943971.1 | Aspergillus avenaceus extracellular beta-glucosidase (bgl1) mRNA, complete cds | 1342 | 1342 | 97% | 0.0 | 72% |
| GU320212.1 | Penicillium decumbens strain CICC 40361 beta-glucosidase I (bgl1) mRNA, complete cds | 1148 | 1148 | 99% | 0.0 | 70% |
| AP007150.1 | Aspergillus oryzae RIB40 DNA, SC009 | 1128 | 1437 | 95% | 0.0 | 75% |
| XM_658014.1 | Aspergillus nidulans FGSC A4 hypothetical protein AN4102.2 partial mRNA | 1088 | 1174 | 93% | 0.0 | 76% |
| DQ114397.1 | Thermoascus aurantiacus thermostable beta-glucosidase (bgl1) mRNA, complete cds | 1077 | 1077 | 99% | 0.0 | 69% |

- FIGURE 26 –

NCBI Blastx of BGL1 gDNA:

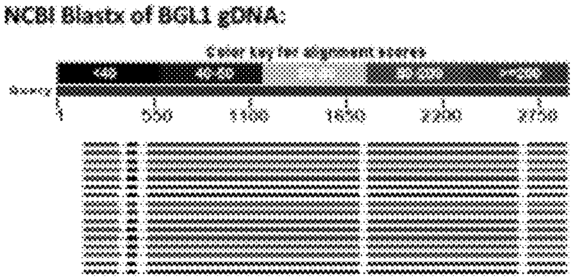

Sequences producing significant alignments:

| Accession | Description | Max score | Total score | Query coverage | E value | Max ident |
|---|---|---|---|---|---|---|
| P48825.1 | RecName: Full=Beta-glucosidase 1; AltName: Full=Beta-D-glucoside glucohydrolase; AltName: Full=Cellobiase; AltName: Full=Gentiobiase; Flags: Precursor >dbj\|BAA10968.1\| BETA-GLUCOSIDASE PRECURSOR [Aspergillus aculeatus] | 783 | 1564 | 87% | 0.0 | 98% |
| CBA02054.1 | beta-glucosidase [Aspergillus niger] | 724 | 1432 | 88% | 0.0 | 65% |
| XP_001398816.1 | beta-glucosidase A [Aspergillus niger CBS 513.88] >sp\|A2RAL4.1\|BGLA_ASPNC RecName: Full=Probable beta-glucosidase A; AltName: Full=Beta-D-glucoside glucohydrolase A; AltName: Full=Cellobiase A; AltName: Full=Gentiobiase A; Flags: Precursor >emb\|CAK48740.1\| beta-glucosidase bgl1-Aspergillus niger | 724 | 1430 | 88% | 0.0 | 65% |
| ACK44497.1 | beta-glucosidase [Aspergillus niger] | 724 | 1425 | 88% | 0.0 | 65% |
| ABN87293.1 | beta-glucosidase [Aspergillus niger] | 723 | 1429 | 88% | 0.0 | 65% |
| ABN73101.1 | beta-glucosidase [Aspergillus niger] | 723 | 1428 | 88% | 0.0 | 65% |
| ABB13285.1 | beta-glucosidase [Aspergillus niger] >gb\|ABG46337.1\| beta-glucosidase [Aspergillus niger] | 722 | 1429 | 87% | 0.0 | 65% |
| AEB98885.1 | beta-glucosidase [synthetic construct] | 721 | 1429 | 87% | 0.0 | 65% |
| ACN87908.1 | beta-glucosidase precursor [Aspergillus niger] | 721 | 1428 | 88% | 0.0 | 65% |
| P87076.1 | RecName: Full=Beta-glucosidase A; AltName: Full=Beta-D-glucoside glucohydrolase A; AltName: Full=Cellobiase A; AltName: Full=Gentiobiase A; Flags: Precursor >dbj\|BAA19913.1\| beta-D-glucosidase [Aspergillus kawachii] | 721 | 1423 | 87% | 0.0 | 65% |
| ACX20083.1 | beta-glucosidase [Aspergillus niger] | 720 | 1420 | 88% | 0.0 | 63% |
| CAB75696.1 | beta-glucosidase [Aspergillus niger] | 720 | 1429 | 87% | 0.0 | 65% |
| ABH01182.1 | beta-glucosidase precursor [Aspergillus niger] | 719 | 1429 | 87% | 0.0 | 65% |
| ACY91071.1 | beta-glucosidase 3 [Aspergillus niger] | 719 | 1427 | 88% | 0.0 | 65% |
| XP_001816832.1 | beta-glucosidase A [Aspergillus oryzae RIB40] >sp\|Q2UUD6.1\|BGLA_ASPOR RecName: Full=Probable beta-glucosidase A; AltName: Full=Beta-D-glucoside glucohydrolase A; AltName: Full=Cellobiase A; AltName: Full=Gentiobiase A; Flags: Precursor >dbj\|BAE54829.1\| unnamed protein product [Aspergillus oryzae RIB40] | 689 | 1360 | 87% | 0.0 | 79% |
| XP_002383240.1 | beta-glucosidase, putative [Aspergillus flavus NRRL3357] >sp\|B8NRX2.1\|BGLA_ASPFN RecName: Full=Probable beta-glucosidase A; AltName: Full=Beta-D-glucoside glucohydrolase A; AltName: Full=Cellobiase A; AltName: Full=Gentiobiase A; Flags: Precursor >gb\|EED47060.1\| beta-glucosidase, putative [Aspergillus flavus NRRL3357] | 688 | 1360 | 87% | 0.0 | 79% |
| XP_001265391.1 | beta-glucosidase, putative [Neosartorya fischeri NRRL 181] >sp\|A1D451.1\|BGLA_NEOFI RecName: Full=Probable beta-glucosidase A; AltName: Full=Beta-D-glucoside glucohydrolase A; AltName: Full=Cellobiase A; AltName: Full=Gentiobiase A; Flags: Precursor >gb\|EAW23194.1\| beta-glucosidase, putative [Neosartorya fischeri NRRL 181] | 671 | 1339 | 89% | 0.0 | 78% |

- FIGURE 27 –

NCBI Blastx of BGL1 cDNA (without signal seq):

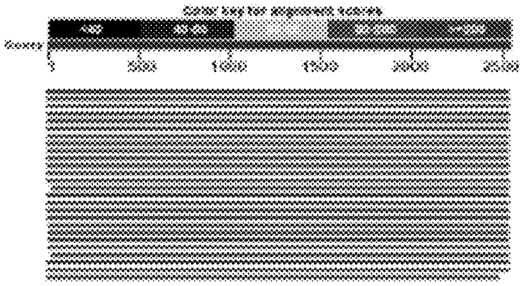

Sequences producing significant alignments:

| Accession | Description | Max score | Total score | Query coverage | E value | Max ident |
|---|---|---|---|---|---|---|
| P48825.1 | RecName: Full=Beta-glucosidase 1; AltName: Full=Beta-D-glucoside glucohydrolase; AltName: Full=Cellobiase; AltName: Full=Gentiobiase; Flags: Precursor >dbj\|BAA10968.1\| BETA-GLUCOSIDASE PRECURSOR [Aspergillus aculeatus] | 1610 | 1610 | 99% | 0.0 | 81% |
| CBA02054.1 | beta-glucosidase [Aspergillus niger] | 1476 | 1476 | 99% | 0.0 | 82% |
| XP_001398816.1 | beta-glucosidase A [Aspergillus niger CBS 513.88] >sp\|A2RAL4.1\|BGLA_ASPNC RecName: Full=Probable beta-glucosidase A; AltName: Full=Beta-D-glucoside glucohydrolase A; AltName: Full=Cellobiase A; AltName: Full=Gentiobiase A; Flags: Precursor >emb\|CAK48740.1\| beta-glucosidase bgl1-Aspergillus niger | 1474 | 1474 | 99% | 0.0 | 82% |
| CAB75696.1 | beta-glucosidase [Aspergillus niger] | 1473 | 1473 | 99% | 0.0 | 82% |
| AEB00985.1 | beta-glucosidase [synthetic construct] | 1472 | 1472 | 99% | 0.0 | 82% |
| ABW87793.1 | beta-glucosidase [Aspergillus niger] | 1472 | 1472 | 99% | 0.0 | 82% |
| ABH01182.1 | beta-glucosidase precursor [Aspergillus niger] | 1472 | 1472 | 99% | 0.0 | 82% |
| ABB23285.1 | beta-glucosidase [Aspergillus niger] >gb\|ABG46337.1\| beta-glucosidase [Aspergillus niger] | 1472 | 1472 | 99% | 0.0 | 82% |
| ABN73103.1 | beta-glucosidase [Aspergillus niger] | 1471 | 1471 | 99% | 0.0 | 82% |
| ACV91073.1 | beta-glucosidase II [Aspergillus niger] | 1470 | 1470 | 99% | 0.0 | 82% |
| ACN67968.1 | beta-glucosidase precursor [Aspergillus niger] | 1469 | 1469 | 99% | 0.0 | 82% |
| P87076.1 | RecName: Full=Beta-glucosidase A; AltName: Full=Beta-D-glucoside glucohydrolase A; AltName: Full=Cellobiase A; AltName: Full=Gentiobiase A; Flags: Precursor >dbj\|BAA19913.1\| beta-D-glucosidase [Aspergillus kawachii] | 1467 | 1467 | 99% | 0.0 | 82% |
| ACB32084.1 | beta-glucosidase [Aspergillus niger] | 1463 | 1463 | 99% | 0.0 | 82% |
| ACB64487.1 | beta-glucosidase [Aspergillus niger] | 1460 | 1460 | 99% | 0.0 | 82% |
| XP_002383240.1 | beta-glucosidase, putative [Aspergillus flavus NRRL3357] >sp\|B8NRX2.1\|BGLA_ASPFN RecName: Full=Probable beta-glucosidase A; AltName: Full=Beta-D-glucoside glucohydrolase A; AltName: Full=Cellobiase A; AltName: Full=Gentiobiase A; Flags: Precursor >gb\|EED47060.1\| beta-glucosidase, putative [Aspergillus flavus NRRL3357] | 1399 | 1399 | 99% | 0.0 | 77% |
| XP_001816831.1 | beta-glucosidase A [Aspergillus oryzae RIB40] >sp\|Q2UUD6.1\|BGLA_ASPOR RecName: Full=Probable beta-glucosidase A; AltName: Full=Beta-D-glucoside glucohydrolase A; AltName: Full=Cellobiase A; AltName: Full=Gentiobiase A; Flags: Precursor >dbj\|BAE54829.1\| unnamed protein product [Aspergillus oryzae RIB40] | 1399 | 1399 | 99% | 0.0 | 77% |
| D0VKF5.1 | RecName: Full=Probable beta-glucosidase A; AltName: Full=Beta-D-glucoside glucohydrolase A; AltName: Full=Cellobiase A; AltName: Full=Gentiobiase A; Flags: Precursor >gb\|ACV83273.1\| beta-glucosidase [Aspergillus terreus] | 1392 | 1392 | 99% | 0.0 | 77% |

- FIGURE 28 –

Blastp of mature BGL1 polypeptide (without signal peptide):

Closest identity = 91% (*Aspergillus aculeatus*)

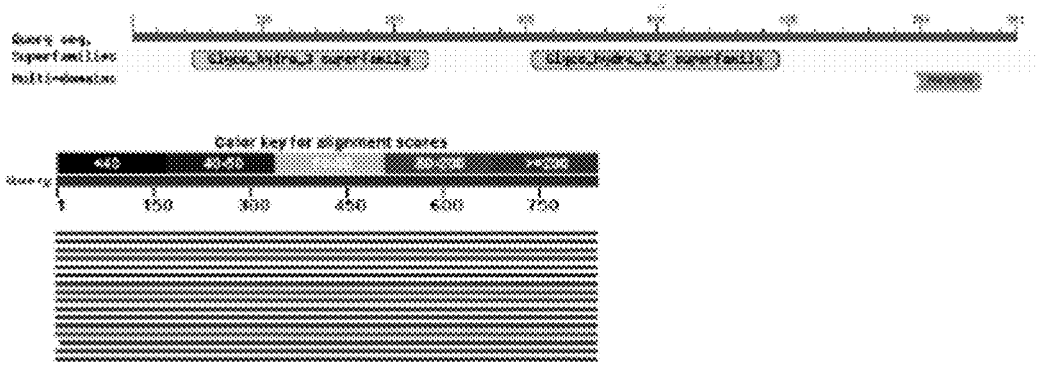

Sequences producing significant alignments:

| Accession | Description | Max score | Total score | Query coverage | E value |
|---|---|---|---|---|---|
| P48825.1 | RecName: Full=Beta-glucosidase 1; AltName: Full=Beta-D-glucoside glucohydrolase; AltName: Full=Cellobiase; AltName: Full=Gentiobiase; Flags: Precursor >dbj\|BAA10968.1\| BETA-GLUCOSIDASE PRECURSOR [Aspergillus aculeatus] | 1613 | 1613 | 100% | 0.0 |
| CAB02054.1 | beta-glucosidase [Aspergillus niger] | 1457 | 1457 | 100% | 0.0 |
| XP_001398816.1 | beta-glucosidase A [Aspergillus niger CBS 513.88] >sp\|A2QAL4.1\|BGLA_ASPNC RecName: Full=Probable beta-glucosidase A; AltName: Full=Beta-D-glucoside glucohydrolase A; AltName: Full=Cellobiase A; AltName: Full=Gentiobiase A; Flags: Precursor >emb\|CAK48740.1\| beta-glucosidase bgl1-Aspergillus niger | 1456 | 1456 | 100% | 0.0 |
| ABW87793.1 | beta-glucosidase [Aspergillus niger] | 1456 | 1456 | 100% | 0.0 |
| ABB29285.1 | beta-glucosidase [Aspergillus niger] >gb\|ABG46337.1\| beta-glucosidase [Aspergillus niger] | 1454 | 1454 | 100% | 0.0 |
| ABN73102.1 | beta-glucosidase [Aspergillus niger] | 1453 | 1453 | 100% | 0.0 |
| ACV91073.1 | beta-glucosidase 8 [Aspergillus niger] | 1453 | 1453 | 100% | 0.0 |
| ACB87998.1 | beta-glucosidase precursor [Aspergillus niger] | 1451 | 1451 | 100% | 0.0 |
| ABH01182.1 | beta-glucosidase precursor [Aspergillus niger] | 1446 | 1446 | 100% | 0.0 |
| CAB75696.1 | beta-glucosidase [Aspergillus niger] | 1446 | 1446 | 100% | 0.0 |
| AEB98385.1 | beta-glucosidase [synthetic construct] | 1446 | 1446 | 100% | 0.0 |
| ACK82084.1 | beta-glucosidase [Aspergillus niger] | 1445 | 1445 | 100% | 0.0 |
| P87076.1 | RecName: Full=Beta-glucosidase A; AltName: Full=Beta-D-glucoside glucohydrolase A; AltName: Full=Cellobiase A; AltName: Full=Gentiobiase A; Flags: Precursor >dbj\|BAA19913.1\| beta-D-glucosidase [Aspergillus kawachii] | 1441 | 1441 | 100% | 0.0 |
| ACK84437.1 | beta-glucosidase [Aspergillus niger] | 1439 | 1439 | 99% | 0.0 |
| XP_002383240.1 | beta-glucosidase, putative [Aspergillus flavus NRRL3357] >sp\|B8NRX2.1\|BGLA_ASPFN RecName: Full=Probable beta-glucosidase A; AltName: Full=Beta-D-glucoside glucohydrolase A; AltName: Full=Cellobiase A; AltName: Full=Gentiobiase A; Flags: Precursor >gb\|EED47060.1\| beta-glucosidase, putative [Aspergillus flavus NRRL3357] | 1395 | 1395 | 100% | 0.0 |
| XP_001818631.1 | beta-glucosidase A [Aspergillus oryzae RIB40] >sp\|Q2UUD6.1\|BGLA_ASPOR RecName: Full=Probable beta-glucosidase A; AltName: Full=Beta-D-glucoside glucohydrolase A; AltName: Full=Cellobiase A; AltName: Full=Gentiobiase A; Flags: Precursor >dbj\|BAE54829.1\| unnamed protein product [Aspergillus oryzae RIB40] | 1395 | 1395 | 100% | 0.0 |

- FIGURE 29 –

NCBI Blastn of BGL2 gDNA:

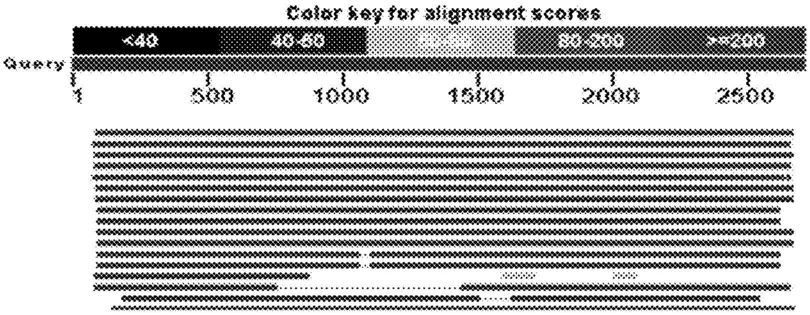

Sequences producing significant alignments:

| Accession | Description | Max score | Total score | Query coverage | E value | Max ident |
|---|---|---|---|---|---|---|
| AP007154.1 | Aspergillus oryzae RIB40 DNA, SC001 | 783 | 853 | 95% | 0.0 | 78% |
| XM_745666.1 | Aspergillus fumigatus Af293 beta glucosidase (AFUA_6G08700), partial mRNA | 767 | 767 | 95% | 0.0 | 66% |
| XM_001215795.1 | Aspergillus terreus NIH2624 hypothetical protein (ATEG_06617) partial mRNA | 726 | 726 | 95% | 0.0 | 66% |
| XM_001257985.1 | Neosartorya fischeri NRRL 181 beta glucosidase, putative (NFIA_054350) partial mRNA | 717 | 717 | 95% | 0.0 | 66% |
| BN001302.1 | TPA: TPA_reasm: Aspergillus nidulans FGSC A4 chromosome II | 681 | 761 | 94% | 0.0 | 76% |
| XM_001819003.1 | Aspergillus oryzae RIB40 beta-glucosidase F, mRNA | 677 | 677 | 95% | 0.0 | 65% |
| XM_002382000.1 | Aspergillus flavus NRRL3357 beta glucosidase, putative, mRNA | 663 | 663 | 95% | 0.0 | 65% |
| DQ011524.1 | Thermoascus aurantiacus beta-glucosidase (bgl2) mRNA, complete cds | 654 | 654 | 93% | 0.0 | 65% |
| EU263993.1 | Thermoascus aurantiacus var. levisporus beta-1,4-glucosidase (bgl2) mRNA, complete cds | 650 | 650 | 93% | 0.0 | 65% |
| AM920427.1 | Penicillium chrysogenum Wisconsin 54-1255 complete genome, contig Pc00c12 | 634 | 634 | 94% | 1e-177 | 66% |
| XM_002557885.1 | Penicillium chrysogenum Wisconsin 54-1255 hypothetical protein (Pc12g11110) mRNA, complete cds | 527 | 527 | 94% | 1e-145 | 64% |
| EU263992.1 | Thermoascus aurantiacus var. levisporus beta-1,4-glucosidase (bgl2) gene, complete cds | 506 | 808 | 91% | 4e-139 | 71% |
| DQ011523.1 | Thermoascus aurantiacus beta-glucosidase (bgl2) gene, complete cds | 506 | 808 | 91% | 4e-139 | 71% |
| AM270241.1 | Aspergillus niger contig An11c0240, genomic contig | 489 | 489 | 29% | 3e-134 | 73% |
| XM_001394555.2 | Aspergillus niger CBS 513.88 beta-glucosidase F partial mRNA | 459 | 809 | 70% | 5e-125 | 75% |
| XM_001268101.1 | Aspergillus clavatus NRRL 1 beta glucosidase, putative (ACLA_083710), partial mRNA | 432 | 644 | 82% | 7e-117 | 66% |
| XM_002145875.1 | Penicillium marneffei ATCC 18224 beta glucosidase, putative, mRNA | 421 | 421 | 93% | 1e-113 | 63% |
| XM_002478144.1 | Talaromyces stipitatus ATCC 10500 beta glucosidase, putative, mRNA | 367 | 367 | 93% | 2e-97 | 63% |
| AM270240.1 | Aspergillus niger contig An11c0230, genomic contig | 345 | 345 | 44% | 9e-91 | 66% |

- FIGURE 30 –

NCBI blastn of BGL2 cDNA (without signal seq):

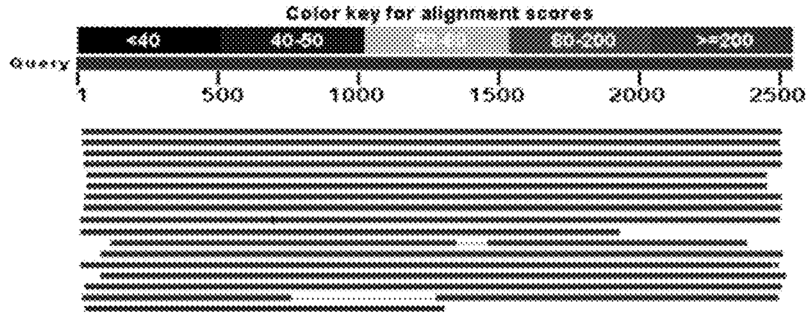

Sequences producing significant alignments:

| Accession | Description | Max score | Total score | Query coverage | E value | Max ident |
|---|---|---|---|---|---|---|
| XM_001215795.1 | Aspergillus terreus NIH2624 hypothetical protein (ATEG_06617) partial mRNA | 897 | 897 | 97% | 0.0 | 68% |
| XM_001257088.1 | Neosartorya fischeri NRRL 181 beta glucosidase, putative (NFIA_054350) partial mRNA | 884 | 884 | 97% | 0.0 | 68% |
| XM_001819003.1 | Aspergillus oryzae RIB40 beta-glucosidase F, mRNA | 850 | 850 | 97% | 0.0 | 68% |
| XM_002382000.1 | Aspergillus flavus NRRL3357 beta glucosidase, putative, mRNA | 834 | 834 | 97% | 0.0 | 67% |
| DQ011524.1 | Thermoascus aurantiacus beta-glucosidase (bgl2) mRNA, complete cds | 830 | 830 | 95% | 0.0 | 68% |
| EU263993.1 | Thermoascus aurantiacus var. levisporus beta-1,4-glucosidase (bgl2) mRNA, complete cds | 827 | 827 | 95% | 0.0 | 68% |
| XM_002557885.1 | Penicillium chrysogenum Wisconsin 54-1255 hypothetical protein (Pc12g11110) mRNA, complete cds | 686 | 686 | 97% | 0.0 | 66% |
| AP007154.1 | Aspergillus oryzae RIB40 DNA, SC001 | 648 | 718 | 97% | 0.0 | 78% |
| XM_745886.1 | Aspergillus fumigatus Af293 beta glucosidase (AFUA_8G08700), partial mRNA | 641 | 893 | 97% | 7e-180 | 68% |
| XM_656416.1 | Aspergillus nidulans FGSC A4 hypothetical protein AN3904.2 partial mRNA | 609 | 909 | 75% | 4e-170 | 67% |
| XM_001268101.1 | Aspergillus clavatus NRRL 1 beta glucosidase, putative (ACLA_083710), partial mRNA | [illegible] | 812 | 84% | 2e-167 | 71% |
| XM_002145875.1 | Penicillium marneffei ATCC 18224 beta glucosidase, putative, mRNA | 594 | 594 | 95% | 9e-166 | 66% |
| BN001303.1 | TPA: TPA_reasm: Aspergillus nidulans FGSC A4 chromosome II | 565 | 862 | 96% | 4e-157 | 68% |
| XM_002478144.1 | Talaromyces stipitatus ATCC 10500 beta glucosidase, putative, mRNA | 535 | 535 | 95% | 8e-148 | 65% |
| AM920427.1 | Penicillium chrysogenum Wisconsin 54-1255 complete genome, contig Pc00c12 | 520 | 520 | 97% | 2e-143 | 64% |
| XM_001394555.2 | Aspergillus niger CBS 513.88 beta-glucosidase F partial mRNA | 515 | 860 | 77% | 7e-142 | 75% |
| XM_003238048.1 | Trichophyton rubrum CBS 118892 beta-1,4-glucosidase (TERG_00088) mRNA, complete cds | 500 | 500 | 50% | 2e-137 | 69% |

- FIGURE 31 –

NCBI Blastx of BGL2 gDNA

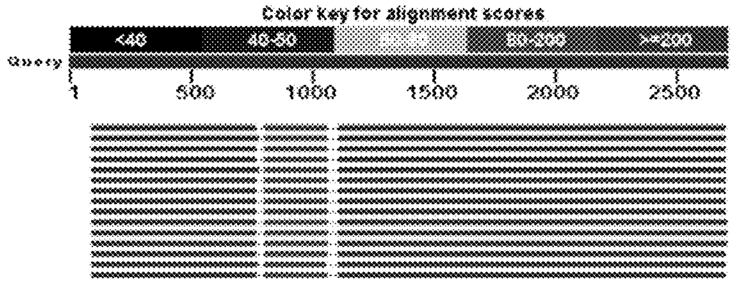

Sequences producing significant alignments:

| Accession | Description | Max score | Total score | Query coverage | E value | Max ident |
|---|---|---|---|---|---|---|
| B0Y7Q8.2 | RecName: Full=Probable beta-glucosidase F; AltName: Full=Beta-D-glucoside glucohydrolase F; AltName: Full=Cellobiase F; AltName: Full=Gentiobiase F; Flags: Precursor | 751 | 1246 | 93% | 0.0 | 84% |
| EDP49439.1 | beta glucosidase, putative [Aspergillus fumigatus A1163] | 751 | 1247 | 93% | 0.0 | 84% |
| Q4WMU3.2 | RecName: Full=Probable beta-glucosidase F; AltName: Full=Beta-D-glucoside glucohydrolase F; AltName: Full=Cellobiase F; AltName: Full=Gentiobiase F; Flags: Precursor | 746 | 1241 | 93% | 0.0 | 84% |
| XP_001257986.1 | beta glucosidase, putative [Neosartorya fischeri NRRL 181] >sp\|A1DMR8.1\|BGLF_NEOFI RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EAW16089.1\| beta glucosidase, putative [Neosartorya fischeri NRRL 183] | 746 | 1246 | 93% | 0.0 | 84% |
| XP_750758.1 | beta glucosidase [Aspergillus fumigatus Af293] >gb\|EAL88721.1\| beta glucosidase, putative [Aspergillus fumigatus Af293] | 746 | 1242 | 93% | 0.0 | 84% |
| XP_002382081.1 | beta glucosidase, putative [Aspergillus flavus NRRL3357] >sp\|B8NPG5.1\|BGLF_ASPFN RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EED48625.1\| beta glucosidase, putative [Aspergillus flavus NRRL3357] | 738 | 1237 | 93% | 0.0 | 81% |
| XP_001819055.1 | beta-glucosidase F [Aspergillus oryzae RIB40] >sp\|Q2UN12.1\|BGLF_ASPOR RecName: Full=Probable beta-glucosidase F; AltName: Full=Beta-D-glucoside glucohydrolase F; AltName: Full=Cellobiase F; AltName: Full=Gentiobiase F; Flags: Precursor >dbj\|BAE57053.1\| unnamed protein product [Aspergillus oryzae RIB40] | 737 | 1236 | 93% | 0.0 | 81% |
| XP_002145911.1 | beta glucosidase, putative [Penicillium marneffei ATCC 18224] >gb\|EEA25364.1\| beta glucosidase, putative [Penicillium marneffei ATCC 18224] | 736 | 1228 | 93% | 0.0 | 81% |
| XP_002478189.1 | beta glucosidase, putative [Talaromyces stipitatus ATCC 10500] >gb\|EED21226.1\| beta glucosidase, putative [Talaromyces stipitatus ATCC 10500] | 728 | 1202 | 93% | 0.0 | 80% |
| AAY33982.1 | beta-glucosidase [Thermoascus aurantiacus] >gb\|AAY33983.1\| beta-glucosidase [Thermoascus aurantiacus] | 725 | 1232 | 93% | 0.0 | 87% |
| ABX56927.1 | beta-1,4-glucosidase [Thermoascus aurantiacus var. levisporus] | 725 | 1230 | 93% | 0.0 | 85% |
| ABX56926.1 | beta-1,4-glucosidase [Thermoascus aurantiacus var. levisporus] | 725 | 1232 | 93% | 0.0 | 87% |
| XP_002557931.1 | Pc12g11110 [Penicillium chrysogenum Wisconsin 54-1255] >emb\|CAP80738.1\| Pc12g11110 [Penicillium chrysogenum Wisconsin 54-1255] | 702 | 1207 | 93% | 0.0 | 81% |
| XP_001215795.1 | hypothetical protein ATEG_06617 [Aspergillus terreus NIH2624] >sp\|Q0CI67.1\|BGLF_ASPTN RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EAU33161.1\| hypothetical protein ATEG_06617 [Aspergillus terreus NIH2624] | 702 | 1197 | 93% | 0.0 | 79% |

- FIGURE 32 -

NCBI Blastx of BGL2 cDNA (without signal seq):

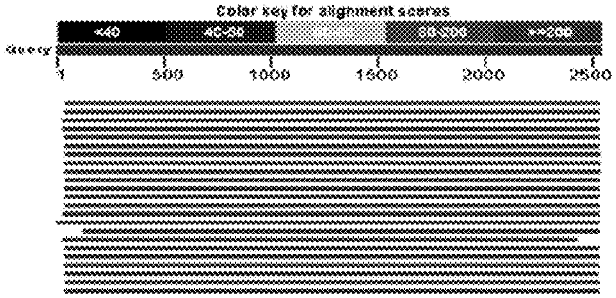

Sequences producing significant alignments:

| Accession | Description | Max score | Total score | Query coverage | E value | Max ident |
|---|---|---|---|---|---|---|
| B0Y7Q8.2 | RecName: Full=Probable beta-glucosidase F; AltName: Full=Beta-D-glucoside glucohydrolase F; AltName: Full=Cellobiase F; AltName: Full=Gentiobiase F; Flags: Precursor | 1231 | 1231 | 98% | 0.0 | 73% |
| XP_001257985.1 | beta glucosidase, putative [Neosartorya fischeri NRRL 181] >sp\|A1DMR8.1\|BGLF_NEOFI RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EAW16089.1\| beta glucosidase, putative [Neosartorya fischeri NRRL 181] | 1230 | 1230 | 98% | 0.0 | 73% |
| XP_002382041.1 | beta glucosidase, putative [Aspergillus flavus NRRL3357] >sp\|B8NP65.1\|BGLF_ASPFN RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EED48625.1\| beta glucosidase, putative [Aspergillus flavus NRRL3357] | 1227 | 1227 | 98% | 0.0 | 72% |
| XP_001818055.1 | beta-glucosidase F [Aspergillus oryzae RIB40] >sp\|Q2UN12.1\|BGLF_ASPOR RecName: Full=Probable beta-glucosidase F; AltName: Full=Beta-D-glucoside glucohydrolase F; AltName: Full=Cellobiase F; AltName: Full=Gentiobiase F; Flags: Precursor >dbj\|BAE57053.1\| unnamed protein product [Aspergillus oryzae RIB40] | 1226 | 1226 | 98% | 0.0 | 72% |
| Q4WMU3.1 | RecName: Full=Probable beta-glucosidase F; AltName: Full=Beta-D-glucoside glucohydrolase F; AltName: Full=Cellobiase F; AltName: Full=Gentiobiase F; Flags: Precursor | 1226 | 1226 | 98% | 0.0 | 73% |
| EDP49439.1 | beta glucosidase, putative [Aspergillus fumigatus A1163] | 1219 | 1219 | 98% | 0.0 | 72% |
| AAY33982.1 | beta-glucosidase [Thermoascus aurantiacus] >gb\|AAY33983.1\| beta-glucosidase [Thermoascus aurantiacus] | 1218 | 1218 | 98% | 0.0 | 72% |
| ABX56926.1 | beta-1,4-glucosidase [Thermoascus aurantiacus var. levisporus] | 1217 | 1217 | 98% | 0.0 | 72% |
| ABX56927.1 | beta-1,4-glucosidase [Thermoascus aurantiacus var. levisporus] | 1216 | 1216 | 98% | 0.0 | 72% |
| XP_750258.1 | beta glucosidase [Aspergillus fumigatus Af293] >gb\|EAL88721.1\| beta glucosidase, putative [Aspergillus fumigatus Af293] | 1213 | 1214 | 98% | 0.0 | 71% |
| XP_002145911.1 | beta glucosidase, putative [Penicillium marneffei ATCC 18224] >gb\|EEA25364.1\| beta glucosidase, putative [Penicillium marneffei ATCC 18224] | 1214 | 1214 | 98% | 0.0 | 72% |
| XP_002557931.1 | Pc12g11110 [Penicillium chrysogenum Wisconsin 54-1255] >emb\|CAP80738.1\| Pc12g11110 [Penicillium chrysogenum Wisconsin 54-1255] | 1192 | 1192 | 98% | 0.0 | 70% |
| XP_002478180.1 | beta glucosidase, putative [Talaromyces stipitatus ATCC 10500] >gb\|EED21226.1\| beta glucosidase, putative [Talaromyces stipitatus ATCC 10500] | 1188 | 1188 | 98% | 0.0 | 70% |
| Q5B6C6.2 | RecName: Full=Probable beta-glucosidase F; AltName: Full=Beta-D-glucoside glucohydrolase F; AltName: Full=Cellobiase F; AltName: Full=Gentiobiase F; Flags: Precursor >tpe\|CBF75129.1\| TPA: beta-1,4-glucosidase (Eurofung) [Aspergillus nidulans FGSC A4] | 1188 | 1188 | 98% | 0.0 | 69% |

- FIGURE 33 -

Blastp of mature BGL2 polypeptide (without signal peptide):

Closest identity = 73% (*Aspergillus fumigatus*)

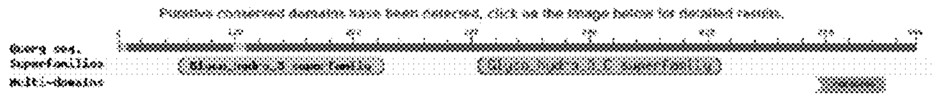

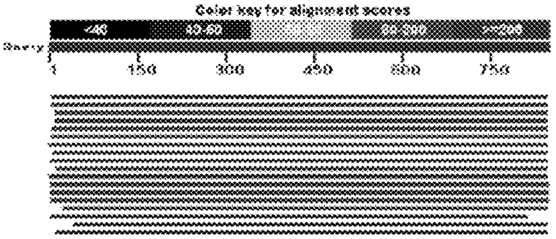

Sequences producing significant alignments:

| Accession | Description | Max score | Total score | Query coverage | E value: |
|---|---|---|---|---|---|
| B0Y7Q8.2 | RecName: Full=Probable beta-glucosidase F; AltName: Full=Beta-D-glucoside glucohydrolase F; AltName: Full=Cellobiase F; AltName: Full=Gentiobiase F; Flags: Precursor | 1266 | 1266 | 99% | 0.0 |
| Q4WMU3.2 | RecName: Full=Probable beta-glucosidase F; AltName: Full=Beta-D-glucoside glucohydrolase F; AltName: Full=Cellobiase F; AltName: Full=Gentiobiase F; Flags: Precursor | 1261 | 1261 | 99% | 0.0 |
| XP_002382041.1 | beta glucosidase, putative [Aspergillus flavus NRRL3357] >sp\|B8NP6S.1\|BGLF_ASPFN RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EED48625.1\| beta glucosidase, putative [Aspergillus flavus NRRL3357] | 1257 | 1257 | 98% | 0.0 |
| XP_001819055.1 | beta-glucosidase F [Aspergillus oryzae RIB40] >sp\|Q2UN12.1\|BGLF_ASPOR RecName: Full=Probable beta-glucosidase F; AltName: Full=Beta-D-glucoside glucohydrolase F; AltName: Full=Cellobiase F; AltName: Full=Gentiobiase F; Flags: Precursor >dbj\|BAE57053.1\| unnamed protein product [Aspergillus oryzae RIB40] | 1256 | 1256 | 98% | 0.0 |
| EDP48429.1 | beta glucosidase, putative [Aspergillus fumigatus A1163] | 1256 | 1256 | 99% | 0.0 |
| XP_750758.1 | beta glucosidase [Aspergillus fumigatus Af293] >gb\|EAL88721.1\| beta glucosidase, putative [Aspergillus fumigatus Af293] | 1250 | 1250 | 99% | 0.0 |
| XP_002145911.1 | beta glucosidase, putative [Penicillium marneffei ATCC 18224] >gb\|EEA25364.1\| beta glucosidase, putative [Penicillium marneffei ATCC 18224] | 1249 | 1249 | 99% | 0.0 |
| XP_001257988.1 | beta glucosidase, putative [Neosartorya fischeri NRRL 181] >sp\|A1DMR5.1\|BGLF_NEOFI RecName: Full=Probable beta-glucosidase F; AltName: Full=Beta-D-glucoside glucohydrolase F; AltName: Full=Cellobiase F; AltName: Full=Gentiobiase F; Flags: Precursor >gb\|EAW16089.1\| beta glucosidase, putative [Neosartorya fischeri NRRL 181] | 1238 | 1238 | 98% | 0.0 |
| Q5B6C6.2 | RecName: Full=Probable beta-glucosidase F; AltName: Full=Beta-D-glucoside glucohydrolase F; AltName: Full=Cellobiase F; AltName: Full=Gentiobiase F; Flags: Precursor >tpe\|CBF75129.1\| TPA: beta-1,4-glucosidase (Eurofung) [Aspergillus nidulans FGSC A4] | 1231 | 1231 | 99% | 0.0 |
| XP_002478169.1 | beta glucosidase, putative [Talaromyces stipitatus ATCC 10500] >gb\|EED21226.1\| beta glucosidase, putative [Talaromyces stipitatus ATCC 10500] | 1224 | 1224 | 98% | 0.0 |

- FIGURE 34 –

NCBI Blastn of BLG3 gDNA:

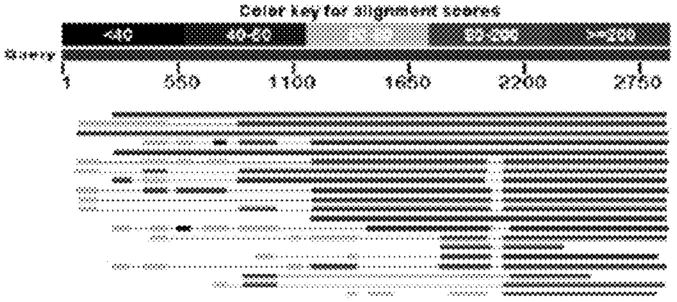

Sequences producing significant alignments:

| Accession | Description | Max score | Total score | Query coverage | E value | Max ident |
|---|---|---|---|---|---|---|
| AM270384.1 | Aspergillus niger contig An17c0020, genomic contig | 1321 | 1321 | 91% | 0.0 | 71% |
| AP007164.1 | Aspergillus oryzae RIB40 DNA, SC111 | 958 | 1032 | 84% | 0.0 | 70% |
| AM920437.1 | Penicillium chrysogenum Wisconsin 54-1255 complete genome, contig Pc00c22 | 789 | 789 | 97% | 0.0 | 66% |
| XM_001274083.1 | Aspergillus clavatus NRRL 1 beta-glucosidase, putative (ACLA_010340), partial mRNA | 784 | 1050 | 73% | 0.0 | 78% |
| BN001307.1 | TPA: TPA_reasm: Aspergillus nidulans FGSC A4 chromosome VII | 711 | 711 | 90% | 0.0 | 68% |
| XM_001259972.1 | Neosartorya fischeri NRRL 181 beta-glucosidase, putative (NFIA_080180) partial mRNA | 565 | 1221 | 69% | 5e-157 | 80% |
| XM_001398222.2 | Aspergillus niger CBS 513.88 beta-glucosidase, mRNA | 547 | 1200 | 75% | 1e-151 | 80% |
| XM_001217335.1 | Aspergillus terreus NIH2624 conserved hypothetical protein (ATEG_09314) partial mRNA | 528 | 1087 | 74% | 7e-149 | 83% |
| XM_748833.1 | Aspergillus fumigatus Af293 beta-glucosidase (AFUA_5G07080), partial mRNA | 524 | 1162 | 72% | 2e-144 | 76% |
| XM_001823087.2 | Aspergillus oryzae RIB40 beta-glucosidase, mRNA | 508 | 894 | 58% | 3e-140 | 75% |
| XM_002378434.1 | Aspergillus flavus NRRL3357 beta-glucosidase, putative, mRNA | 509 | 991 | 65% | 3e-140 | 75% |
| XM_654729.1 | Aspergillus nidulans FGSC A4 hypothetical protein AN2217.2 partial mRNA | 385 | 385 | 58% | 1e-103 | 64% |
| XM_002565346.1 | Penicillium chrysogenum Wisconsin 54-1255 hypothetical protein (Pc22g14710) mRNA, complete cds | 363 | 941 | 64% | 3e-96 | 80% |
| XM_002145427.1 | Penicillium marneffei ATCC 18224 beta-glucosidase, putative, mRNA | 273 | 623 | 46% | 4e-69 | 86% |
| AB223891.1 | Aspergillus oryzae cDNA, contig sequence: AoEST0732 | 273 | 536 | 18% | 4e-69 | 84% |
| XM_003052551.1 | Nectria haematococca mpVI 77-13-4 glycoside hydrolase family 3, mRNA | 268 | 499 | 38% | 5e-68 | 88% |
| XM_002487020.1 | Talaromyces stipitatus ATCC 10500 beta-glucosidase, putative, mRNA | 199 | 626 | 51% | 8e-47 | 85% |
| XM_001936085.1 | Pyrenophora tritici-repentis Pt-1C-BFP periplasmic beta-glucosidase precursor, mRNA | 163 | 344 | 23% | 6e-36 | 73% |
| XM_003300849.1 | Pyrenophora teres f. teres 0-1 hypothetical protein, mRNA | 149 | 303 | 34% | 1e-31 | 76% |
| XM_388785.1 | Gibberella zeae PH-1 hypothetical protein partial mRNA | 136 | 327 | 37% | 8e-28 | 86% |
| AM920431.1 | Penicillium chrysogenum Wisconsin 54-1255 complete genome, contig Pc00c06 | 131 | 211 | 25% | 3e-26 | 70% |

- FIGURE 35 –

NCBI blastn of BGL3 cDNA (without signal seq):

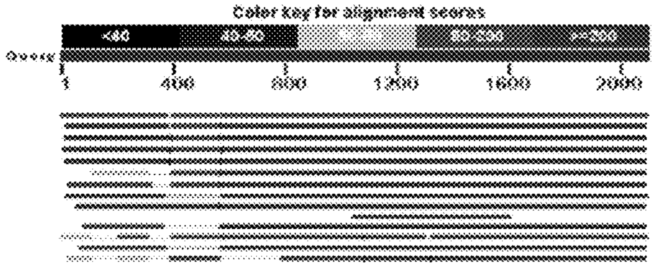

Sequences producing significant alignments:

| Accession | Description | Max score | Total score | Query coverage | E value | Max ident |
|---|---|---|---|---|---|---|
| XM_001398222.2 | Aspergillus niger CBS 513.88 beta-glucosidase, mRNA | 1162 | 1648 | 98% | 0.0 | 80% |
| XM_001259972.1 | Neosartorya fischeri NRRL 181 beta-glucosidase, putative (NFIA_080180) partial mRNA | 1108 | 1486 | 98% | 0.0 | 78% |
| XM_748833.1 | Aspergillus fumigatus Af293 beta-glucosidase (AFUA_5G07080), partial mRNA | 1088 | 1479 | 99% | 0.0 | 76% |
| XM_001217935.1 | Aspergillus terreus NIH2624 conserved hypothetical protein (ATEG_09314) partial mRNA | 1054 | 1414 | 99% | 0.0 | 75% |
| XM_001274033.1 | Aspergillus clavatus NRRL 1 beta-glucosidase, putative (ACLA_010340), partial mRNA | 1045 | 1359 | 99% | 0.0 | 75% |
| XM_002378434.1 | Aspergillus flavus NRRL3357 beta-glucosidase, putative, mRNA | 1020 | 1183 | 90% | 0.0 | 75% |
| XM_001823087.2 | Aspergillus oryzae RIB40 beta-glucosidase, mRNA | 1016 | 1268 | 95% | 0.0 | 75% |
| XM_002565346.1 | Penicillium chrysogenum Wisconsin 54-1255 hypothetical protein (Pc22g14710) mRNA, complete cds | 782 | 1049 | 97% | 0.0 | 72% |
| XM_654723.1 | Aspergillus nidulans FGSC A4 hypothetical protein AN2217.2 partial mRNA | 670 | 877 | 97% | 0.0 | 70% |
| AB223891.1 | Aspergillus oryzae cDNA, contig sequence: AoEST0732 | 580 | 580 | 27% | 2e-161 | 82% |
| XM_002145427.1 | Penicillium marneffei ATCC 18224 beta-glucosidase, putative, mRNA | 578 | 722 | 88% | 6e-161 | 70% |
| AM270384.1 | Aspergillus niger contig An17c0020, genomic contig | 547 | 1430 | 90% | 1e-151 | 81% |
| XM_002487020.1 | Talaromyces stipitatus ATCC 10500 beta-glucosidase, putative, mRNA | 513 | 671 | 87% | 2e-141 | 71% |
| AP007164.1 | Aspergillus oryzae RIB40 DNA, SC111 | 509 | 1154 | 80% | 2e-140 | 84% |
| XM_003052551.1 | Nectria haematococca mpVI 77-13-4 glycoside hydrolase family 3, mRNA | 484 | 538 | 66% | 1e-132 | 73% |
| BN001307.1 | TPA: TPA_reasm: Aspergillus nidulans FGSC A4 chromosome VII | 480 | 667 | 73% | 1e-131 | 81% |
| AM920437.1 | Penicillium chrysogenum Wisconsin 54-1255 complete genome, contig Pc00c22 | 361 | 814 | 74% | 8e-96 | 80% |
| XM_001559150.1 | Botryotinia fuckeliana B05.10 hypothetical protein (BC1G_02364) partial mRNA | 295 | 429 | 82% | 1e-75 | 72% |
| XM_001589594.1 | Sclerotinia sclerotiorum 1980 hypothetical protein (SS1G_09366) partial mRNA | 280 | 434 | 69% | 2e-71 | 73% |
| XM_388795.1 | Gibberella zeae PH-1 hypothetical protein partial mRNA | 277 | 277 | 62% | 3e-70 | 65% |

- FIGURE 36 –

NCBI Blastx of BGL3 gDNA:

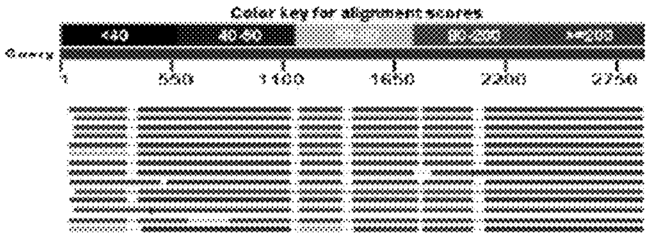

Sequences producing significant alignments:

| Accession | Description | Max score | Total score | Query coverage | E value | Max ident |
|---|---|---|---|---|---|---|
| XP_001398258.1 | beta-glucosidase [Aspergillus niger CBS 513.88] | 378 | 1182 | 89% | 0.0 | 86% |
| XP_001258973.1 | beta-glucosidase, putative [Neosartorya fischeri NRRL 181] >gb\|EAW18076.1\| beta-glucosidase, putative [Neosartorya fischeri NRRL 181] | 362 | 1136 | 89% | 0.0 | 81% |
| EDP51456.1 | beta-glucosidase, putative [Aspergillus fumigatus A1163] | 360 | 1147 | 89% | 0.0 | 80% |
| XP_752826.1 | beta-glucosidase [Aspergillus fumigatus Af293] >gb\|EAL91888.1\| beta-glucosidase, putative [Aspergillus fumigatus Af293] | 360 | 1147 | 89% | 0.0 | 79% |
| XP_001274034.1 | beta-glucosidase, putative [Aspergillus clavatus NRRL 1] >gb\|EAW12608.1\| beta-glucosidase, putative [Aspergillus clavatus NRRL 1] | 342 | 1108 | 89% | 0.0 | 80% |
| XP_001823139.1 | beta-glucosidase [Aspergillus oryzae RIB40] >dbj\|BAE62006.1\| unnamed protein product [Aspergillus oryzae RIB40] | 368 | 1093 | 89% | 0.0 | 86% |
| XP_001217936.1 | conserved hypothetical protein [Aspergillus terreus NIH2624] >gb\|EAU30851.1\| conserved hypothetical protein [Aspergillus terreus NIH2624] | 354 | 1091 | 89% | 0.0 | 85% |
| CAK97390.1 | unnamed protein product [Aspergillus niger] | 377 | 1156 | 89% | 0.0 | 92% |
| XP_002378475.1 | beta-glucosidase, putative [Aspergillus flavus NRRL3357] >gb\|EED51468.1\| beta-glucosidase, putative [Aspergillus flavus NRRL3357] | 368 | 1073 | 90% | 0.0 | 86% |
| XP_002565392.1 | Pc22g14710 [Penicillium chrysogenum Wisconsin 54-1255] >emb\|CAP98759.1\| Pc22g14710 [Penicillium chrysogenum Wisconsin 54-1255] | 347 | 1065 | 88% | 0.0 | 80% |
| XP_002145463.1 | beta-glucosidase, putative [Penicillium marneffei ATCC 18224] >gb\|EEA28948.1\| beta-glucosidase, putative [Penicillium marneffei ATCC 18224] | 337 | 1061 | 89% | 0.0 | 84% |
| XP_002487065.1 | beta-glucosidase, putative [Talaromyces stipitatus ATCC 10500] >gb\|EED12954.1\| beta-glucosidase, putative [Talaromyces stipitatus ATCC 10500] | 339 | 1073 | 91% | 0.0 | 87% |
| XP_659821.1 | hypothetical protein AN2217.2 [Aspergillus nidulans FGSC A4] >gb\|EAA63874.1\| hypothetical protein AN2217.2 [Aspergillus nidulans FGSC A4] >tpe\|CBF86402.1\| TPA: beta-1,4-xylosidase (Eurofung) [Aspergillus nidulans FGSC A4] | 343 | 1083 | 82% | 0.0 | 85% |
| EFQ30231.1 | glycosyl hydrolase family 3 N terminal domain-containing protein [Glomerella graminicola M1.001] | 274 | 836 | 88% | 0.0 | 67% |
| XP_003052397.1 | glycoside hydrolase family 3 [Nectria haematococca mpVI 77-13-4] >gb\|EEU46884.1\| glycoside hydrolase family 3 [Nectria haematococca mpVI 77-13-4] | 276 | 818 | 87% | 0.0 | 67% |
| XP_003001750.1 | periplasmic beta-glucosidase [Verticillium albo-atrum VaMs.102] >gb\|EEY21899.1\| periplasmic beta-glucosidase [Verticillium albo-atrum VaMs.102] | 253 | 809 | 86% | 0.0 | 56% |
| XP_002470406.1 | hypothetical protein POSPLDRAFT_46815 [Postia placenta Mad-698-R] >gb\|EED84431.1\| hypothetical protein POSPLDRAFT_46815 [Postia placenta Mad-698-R] | 212 | 608 | 90% | 7e-139 | 46% |
| XP_363470.2 | hypothetical protein MGG_01396 [Magnaporthe oryzae 70-15] >gb\|EDK04902.1\| hypothetical protein MGG_01396 [Magnaporthe oryzae 70-15] | 253 | 813 | 89% | 9e-134 | 65% |

- FIGURE 37 –

NCBI Blastx of BGL3 cDNA (without signal seq):

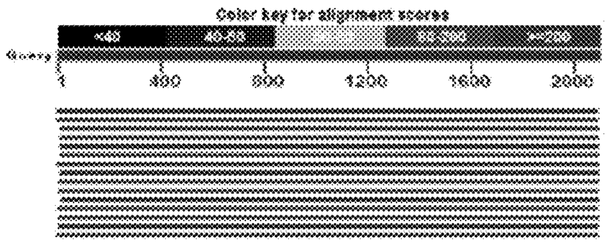

Sequences producing significant alignments:

| Accession | Description | Max score | Total score | Query coverage | E value | Max ident |
|---|---|---|---|---|---|---|
| XP_001398259.2 | beta-glucosidase [Aspergillus niger CBS 513.88] | 1091 | 1091 | 99% | 0.0 | 75% |
| CAK87390.1 | unnamed protein product [Aspergillus niger] | 1051 | 1051 | 99% | 0.0 | 71% |
| XP_001259973.1 | beta-glucosidase, putative [Neosartorya fischeri NRRL 181] >gb\|EAW18076.1\| beta-glucosidase, putative [Neosartorya fischeri NRRL 181] | 1046 | 1046 | 99% | 0.0 | 72% |
| EDP51456.1 | beta-glucosidase, putative [Aspergillus fumigatus A1163] | 1040 | 1040 | 99% | 0.0 | 70% |
| XP_753926.1 | beta-glucosidase [Aspergillus fumigatus Af293] >gb\|EAL91888.1\| beta-glucosidase, putative [Aspergillus fumigatus Af293] | 1040 | 1040 | 99% | 0.0 | 70% |
| XP_001217936.1 | conserved hypothetical protein [Aspergillus terreus NIH2624] >gb\|EAU30451.1\| conserved hypothetical protein [Aspergillus terreus NIH2624] | 1028 | 1028 | 99% | 0.0 | 70% |
| XP_659821.1 | hypothetical protein AN2217.2 [Aspergillus nidulans FGSC A4] >gb\|EAA63874.1\| hypothetical protein AN2217.2 [Aspergillus nidulans FGSC A4] >tpe\|CBF86402.1\| TPA: beta-1,4-xylosidase (Eurofung) [Aspergillus nidulans FGSC A4] | 1024 | 1024 | 100% | 0.0 | 71% |
| XP_001274034.1 | beta-glucosidase, putative [Aspergillus clavatus NRRL 1] >gb\|EAW12808.1\| beta-glucosidase, putative [Aspergillus clavatus NRRL 1] | 1021 | 1021 | 99% | 0.0 | 71% |
| XP_001823139.1 | beta-glucosidase [Aspergillus oryzae RIB40] >dbj\|BAE62006.1\| unnamed protein product [Aspergillus oryzae RIB40] | 1005 | 1005 | 99% | 0.0 | 70% |
| XP_002487065.1 | beta-glucosidase, putative [Talaromyces stipitatus ATCC 10500] >gb\|EED12954.1\| beta-glucosidase, putative [Talaromyces stipitatus ATCC 10500] | 984 | 984 | 99% | 0.0 | 69% |
| XP_002565392.1 | Pc22g14710 [Penicillium chrysogenum Wisconsin 54-1255] >emb\|CAP98758.1\| Pc22g14710 [Penicillium chrysogenum Wisconsin 54-1255] | 974 | 974 | 99% | 0.0 | 69% |
| XP_002145403.1 | beta-glucosidase, putative [Penicillium marneffei ATCC 18224] >gb\|EEA28948.1\| beta-glucosidase, putative [Penicillium marneffei ATCC 18224] | 972 | 972 | 99% | 0.0 | 68% |
| XP_002378475.1 | beta-glucosidase, putative [Aspergillus flavus NRRL3357] >gb\|EED51468.1\| beta-glucosidase, putative [Aspergillus flavus NRRL3357] | 927 | 927 | 99% | 0.0 | 64% |
| XP_001559200.1 | hypothetical protein BC1G_02364 [Botryotinia fuckeliana B05.10] >gb\|EDN31214.1\| hypothetical protein BC1G_02364 [Botryotinia fuckeliana B05.10] | 866 | 866 | 99% | 0.0 | 62% |
| XP_001589544.1 | hypothetical protein SS1G_09366 [Sclerotinia sclerotiorum 1980] >gb\|EDN93499.1\| hypothetical protein SS1G_09366 [Sclerotinia sclerotiorum 1980 UF-70] | 860 | 860 | 99% | 0.0 | 61% |
| CBX93517.1 | hypothetical protein [Leptosphaeria maculans] | 815 | 815 | 98% | 0.0 | 59% |
| XP_001802834.1 | hypothetical protein SNOG_15694 [Phaeosphaeria nodorum SN15] >gb\|EAT77069.2\| hypothetical protein SNOG_15694 [Phaeosphaeria nodorum SN15] | 804 | 804 | 98% | 0.0 | 60% |
| XP_003306697.1 | hypothetical protein PTT_19903 [Pyrenophora teres f. teres 0-1] >gb\|EFQ85196.1\| hypothetical protein PTT_19903 [Pyrenophora teres f. teres 0-1] | 796 | 796 | 98% | 0.0 | 58% |

- FIGURE 38 –

Blastp of mature BGL3 polypeptide (without signal peptide):

Closest identity = 75% (*Aspergillus niger*)

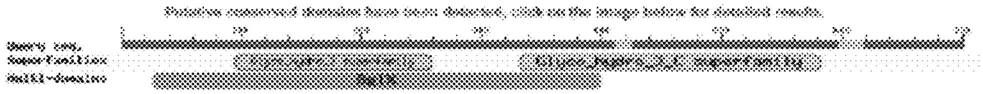

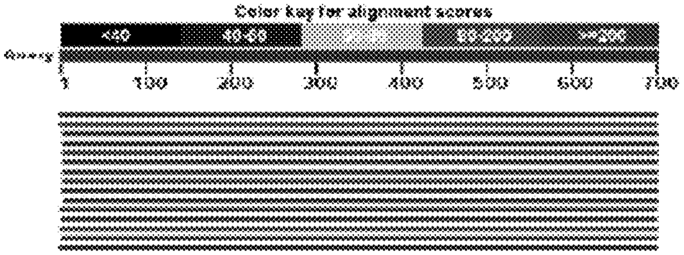

Sequences producing significant alignments:

| Accession | Description | Max score | Total score | Query coverage | E value |
|---|---|---|---|---|---|
| XP_001398259.1 | beta-glucosidase [Aspergillus niger CBS 513.88] | 1179 | 1179 | 99% | 0.0 |
| CAK97390.1 | unnamed protein product [Aspergillus niger] | 1141 | 1141 | 99% | 0.0 |
| XP_001217936.1 | conserved hypothetical protein [Aspergillus terreus NIH2624] >gb\|EAU30451.1\| conserved hypothetical protein [Aspergillus terreus NIH2624] | 1121 | 1121 | 99% | 0.0 |
| XP_001259873.1 | beta-glucosidase, putative [Neosartorya fischeri NRRL 181] >gb\|EAW18076.1\| beta-glucosidase, putative [Neosartorya fischeri NRRL 181] | 1120 | 1120 | 99% | 0.0 |
| EDP51456.1 | beta-glucosidase, putative [Aspergillus fumigatus A1163] | 1113 | 1113 | 99% | 0.0 |
| XP_753816.1 | beta-glucosidase [Aspergillus fumigatus Af293] >gb\|EAL91888.1\| beta-glucosidase, putative [Aspergillus fumigatus Af293] | 1111 | 1111 | 99% | 0.0 |
| XP_659821.1 | hypothetical protein AN2217.2 [Aspergillus nidulans FGSC A4] >gb\|EAA63874.1\| hypothetical protein AN2217.2 [Aspergillus nidulans FGSC A4] >tpe\|CBF86402.1\| TPA: beta-1,4-xylosidase (Eurofung) [Aspergillus nidulans FGSC A4] | 1110 | 1110 | 99% | 0.0 |
| XP_001274034.1 | beta-glucosidase, putative [Aspergillus clavatus NRRL 1] >gb\|EAW12608.1\| beta-glucosidase, putative [Aspergillus clavatus NRRL 1] | 1103 | 1103 | 99% | 0.0 |
| XP_001821139.1 | beta-glucosidase [Aspergillus oryzae RIB40] >dbj\|BAE62006.1\| unnamed protein product [Aspergillus oryzae RIB40] | 1088 | 1088 | 99% | 0.0 |
| XP_002563392.1 | Pc22g14710 [Penicillium chrysogenum Wisconsin 54-1255] >emb\|CAP98759.1\| Pc22g14710 [Penicillium chrysogenum Wisconsin 54-1255] | 1064 | 1064 | 99% | 0.0 |
| XP_002145463.1 | beta-glucosidase, putative [Penicillium marneffei ATCC 18224] >gb\|EEA28948.1\| beta-glucosidase, putative [Penicillium marneffei ATCC 18224] | 1056 | 1056 | 99% | 0.0 |
| XP_002482583.1 | beta-glucosidase, putative [Talaromyces stipitatus ATCC 10500] >gb\|EED12954.1\| beta-glucosidase, putative [Talaromyces stipitatus ATCC 10500] | 1043 | 1043 | 99% | 0.0 |
| XP_002378175.1 | beta-glucosidase, putative [Aspergillus flavus NRRL3357] >gb\|EED51468.1\| beta-glucosidase, putative [Aspergillus flavus NRRL3357] | 983 | 983 | 99% | 0.0 |
| XP_001559200.1 | hypothetical protein BC1G_02364 [Botryotinia fuckeliana B05.10] >gb\|EDN31214.1\| hypothetical protein BC1G_02364 [Botryotinia fuckeliana B05.10] | 923 | 923 | 99% | 0.0 |
| XP_001589644.1 | hypothetical protein SS1G_09366 [Sclerotinia sclerotiorum 1980] >gb\|EDN93499.1\| hypothetical protein SS1G_09366 [Sclerotinia sclerotiorum 1980 UF-70] | 911 | 911 | 99% | 0.0 |
| CBX93517.1 | hypothetical protein [Leptosphaeria maculans] | 882 | 882 | 98% | 0.0 |
| XP_001805834.1 | hypothetical protein SNOG_15694 [Phaeosphaeria nodorum SN15] >gb\|EAT77069.2\| hypothetical protein SNOG_15694 [Phaeosphaeria nodorum SN15] | 848 | 848 | 99% | 0.0 |

- FIGURE 39 –

NCBI Blastn of BGL4 gDNA:

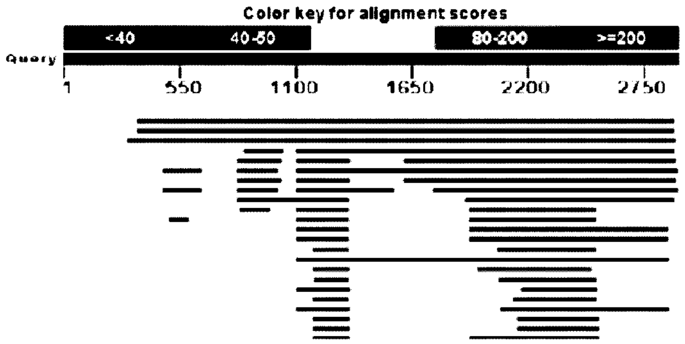

Sequences producing significant alignments:

| Accession | Description | Max score | Total score | Query coverage | E value | Max ident |
|---|---|---|---|---|---|---|
| AM270218.1 | Aspergillus niger contig An11c0010, genomic contig | 957 | 957 | 87% | 0.0 | 69% |
| AC197952.1 | Aspergillus niger clone JGIAXAS 9C8, complete sequence | 948 | 948 | 87% | 0.0 | 68% |
| AP007161.1 | Aspergillus oryzae RIB40 DNA, SC012 | 794 | 794 | 89% | 0.0 | 67% |
| XM_001393987.1 | Aspergillus niger CBS 513.88 beta-glucosidase M partial mRNA | 691 | 871 | 74% | 0.0 | 73% |
| XM_002375398.1 | Aspergillus flavus NRRL3357 beta-glucosidase, putative, mRNA | 567 | 842 | 60% | 1e-157 | 74% |
| XM_748015.1 | Aspergillus fumigatus Af293 beta-glucosidase (AFUA_1G17410), partial mRNA | 558 | 745 | 74% | 8e-155 | 72% |
| XM_001727145.1 | Aspergillus oryzae RIB40 beta-glucosidase M, mRNA | 545 | 820 | 60% | 5e-151 | 74% |
| XM_001264011.1 | Neosartorya fischeri NRRL 181 glycosyl hydrolase, putative (NFIA_007920) partial mRNA | 428 | 858 | 68% | 9e-116 | 72% |
| XM_001218667.1 | Aspergillus terreus NIH2624 hypothetical protein (ATEG_10320) partial mRNA | 374 | 603 | 52% | 2e-99 | 69% |
| XM_741903.1 | Aspergillus fumigatus Af293 beta-glucosidase (AFUA_8G02100), partial mRNA | 297 | 487 | 34% | 4e-76 | 72% |
| XM_001261852.1 | Neosartorya fischeri NRRL 181 glycosyl hydrolase, putative (NFIA_095760) partial mRNA | 266 | 492 | 37% | 7e-67 | 72% |
| XM_001400766.2 | Aspergillus niger CBS 513.88 beta-glucosidase M, mRNA | 259 | 343 | 40% | 1e-64 | 68% |
| AM270315.1 | Aspergillus niger contig An14c0080, genomic contig | 259 | 343 | 40% | 1e-64 | 68% |
| XM_360225.2 | Magnaporthe oryzae 70-15 hypothetical protein (MGG_05599) partial mRNA | 208 | 208 | 15% | 2e-49 | 70% |
| BN001304.1 | TPA: TPA_reasm: Aspergillus nidulans FGSC A4 chromosome IV | 197 | 258 | 62% | 3e-46 | 81% |
| XM_003346088.1 | Sordaria macrospora k-hell hypothetical protein (SMAC_06603), mRNA | 178 | 178 | 18% | 3e-40 | 68% |
| XM_002379007.1 | Aspergillus flavus NRRL3357 conserved hypothetical protein, mRNA | 178 | 178 | 16% | 3e-40 | 68% |
| U16259.1 | Pichia capsulata beta-glucosidase (bgln) gene, complete cds | 178 | 271 | 21% | 3e-40 | 70% |
| XM_001823575.1 | Aspergillus oryzae RIB40 beta-glucosidase M, mRNA | 163 | 163 | 13% | 6e-36 | 69% |
| XM_003008798.1 | Verticillium albo-atrum VaMs.102 beta-glucosidase, mRNA | 143 | 143 | 6% | 6e-30 | 77% |

- FIGURE 40 –

NCBI blastn of BGL4 cDNA (without signal seq):

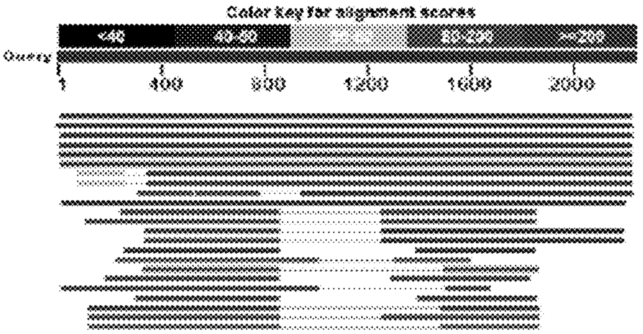

Sequences producing significant alignments:

| Accession | Description | Max score | Total score | Query coverage | E value | Max ident |
|---|---|---|---|---|---|---|
| XM_001392987.1 | Aspergillus niger CBS 513.88 beta-glucosidase M partial mRNA | 1092 | 1092 | 98% | 0.0 | 71% |
| XM_002375398.1 | Aspergillus flavus NRRL3357 beta-glucosidase, putative, mRNA | 984 | 984 | 99% | 0.0 | 70% |
| XM_001727145.1 | Aspergillus oryzae RIB40 beta-glucosidase M, mRNA | 957 | 957 | 98% | 0.0 | 69% |
| XM_001264011.1 | Neosartorya fischeri NRRL 181 glycosyl hydrolase, putative (NFIA_007920) partial mRNA | 946 | 946 | 99% | 0.0 | 69% |
| XM_748015.1 | Aspergillus fumigatus Af293 beta-glucosidase (AFUA_1G17410), partial mRNA | 935 | 935 | 99% | 0.0 | 69% |
| XM_001218867.1 | Aspergillus terreus NIH2624 hypothetical protein (ATEG_10320) partial mRNA | 738 | 738 | 98% | 0.0 | 67% |
| AM270218.1 | Aspergillus niger contig An11c0010, genomic contig | 700 | 769 | 91% | 0.0 | 69% |
| AC197952.1 | Aspergillus niger clone JGIAXA5-9C8, complete sequence | 691 | 759 | 91% | 0.0 | 69% |
| AP007161.1 | Aspergillus oryzae RIB40 DNA, SC012 | 549 | 820 | 78% | 3e-152 | 74% |
| XM_675573.1 | Aspergillus nidulans FGSC A4 hypothetical protein AN7396.2 partial mRNA | 378 | 378 | 97% | 1e-100 | 64% |
| XM_741803.1 | Aspergillus fumigatus Af293 beta-glucosidase (AFUA_8G02100), partial mRNA | 297 | 518 | 54% | 3e-78 | 71% |
| XM_001261852.1 | Neosartorya fischeri NRRL 181 glycosyl hydrolase, putative (NFIA_095780) partial mRNA | 266 | 507 | 60% | 5e-67 | 70% |
| XM_001400766.2 | Aspergillus niger CBS 513.88 beta-glucosidase M, mRNA | 259 | 410 | 65% | 8e-65 | 67% |
| AM270315.1 | Aspergillus niger contig An14c0080, genomic contig | 259 | 410 | 65% | 8e-65 | 67% |
| XM_362225.2 | Magnaporthe oryzae 70-15 hypothetical protein (MGG_05599) partial mRNA | 208 | 208 | 20% | 1e-49 | 70% |
| XM_003008796.1 | Verticillium albo-atrum VaMs.102 beta-glucosidase, mRNA | 203 | 203 | 26% | 5e-48 | 67% |
| XM_001911803.1 | Podospora anserina S mat+ hypothetical protein (PODANSg8883) partial mRNA | 197 | 234 | 48% | 2e-46 | 67% |
| U16259.1 | Pichia capsulata beta-glucosidase (bglN) gene, complete cds | 192 | 370 | 40% | 9e-45 | 70% |
| XM_003346088.1 | Sordaria macrospora k-hell hypothetical protein (SMAC_06603), mRNA | 178 | 178 | 24% | 2e-40 | 68% |
| XM_003052335.1 | Nectria haematococca mpVI 77-13-4 hypothetical protein, mRNA | 178 | 264 | 52% | 2e-40 | 70% |
| XM_002379007.1 | Aspergillus flavus NRRL3357 conserved hypothetical protein, mRNA | 178 | 178 | 20% | 2e-40 | 68% |

- FIGURE 41 –

NCBI Blastx of BGL4 gDNA:

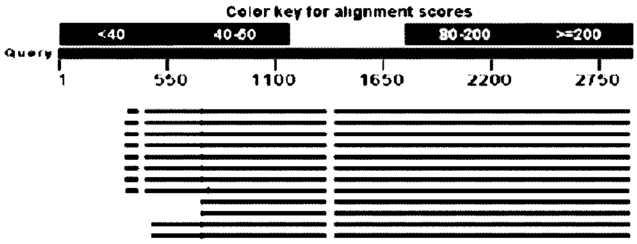

Sequences producing significant alignments:

| Accession | Description | Max score | Total score | Query coverage | E value | Max ident |
|---|---|---|---|---|---|---|
| XP_001394024.1 | beta-glucosidase M [Aspergillus niger CBS 513.88] >sp\|A5ABF5.1\|BGLM_ASPNC RecName: Full=Probable beta-glucosidase M; AltName: Full=Beta-D-glucoside glucohydrolase M; AltName: Full=Cellobiase M; AltName: Full=Gentiobiase M; Flags: Precursor >emb\|CAK48253.1\| unnamed protein product [Aspergillus niger] | 773 | 1175 | 85% | 0.0 | 84% |
| B0XPB8.1 | RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EDP56956.1\| beta glucosidase, putative [Aspergillus fumigatus A1163] | 714 | 1106 | 85% | 0.0 | 86% |
| XP_753108.1 | beta-glucosidase [Aspergillus fumigatus Af293] >sp\|Q4WR62.1\|BGLM_ASPFU RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAL91070.1\| beta-glucosidase, putative [Aspergillus fumigatus Af293] | 714 | 1106 | 85% | 0.0 | 86% |
| XP_001264012.1 | glycosyl hydrolase, putative [Neosartorya fischeri NRRL 181] >sp\|A1D122.1\|BGLM_NEOFI RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAW22115.1\| glycosyl hydrolase, putative [Neosartorya fischeri NRRL 181] | 711 | 1101 | 85% | 0.0 | 81% |
| XP_001218668.1 | hypothetical protein ATEG_10320 [Aspergillus terreus NIH2624] >sp\|Q0C7L4.1\|BGLM_ASPTN RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAU29317.1\| hypothetical protein ATEG_10320 [Aspergillus terreus NIH2624] | 698 | 1093 | 85% | 0.0 | 86% |
| XP_002375439.1 | beta-glucosidase, putative [Aspergillus flavus NRRL3357] >sp\|B8N5S6.1\|BGLM_ASPFN RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EED54167.1\| beta-glucosidase, putative [Aspergillus flavus NRRL3357] | 714 | 1092 | 85% | 0.0 | 77% |
| XP_001727197.1 | beta-glucosidase M [Aspergillus oryzae RIB40] >sp\|Q2UDK7.1\|BGLM_ASPOR RecName: Full=Probable beta-glucosidase M; AltName: Full=Beta-D-glucoside glucohydrolase M; AltName: Full=Cellobiase M; AltName: Full=Gentiobiase M; Flags: Precursor >dbj\|BAE60358.1\| unnamed protein product [Aspergillus oryzae RIB40] | 714 | 1091 | 85% | 0.0 | 77% |
| XP_680665.1 | hypothetical protein AN7396.2 [Aspergillus nidulans FGSC A4] >sp\|Q5AWD4.1\|BGLM_EMENI RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAA61767.1\| hypothetical protein AN7396.2 [Aspergillus nidulans FGSC A4] >tpe\|CBF78465.1\| TPA: beta-glucosidase (Eurofung) [Aspergillus nidulans FGSC A4] | 624 | 974 | 85% | 0.0 | 80% |
| CAK46489.1 | unnamed protein product [Aspergillus niger] | 535 | 811 | 82% | 0.0 | 57% |
| XP_001400803.2 | beta-glucosidase M [Aspergillus niger CBS 513.88] | 525 | 801 | 82% | 0.0 | 57% |
| XP_001261853.1 | glycosyl hydrolase, putative [Neosartorya fischeri NRRL 181] >gb\|EAW19956.1\| glycosyl hydrolase, putative [Neosartorya fischeri NRRL 181] | 521 | 809 | 82% | 0.0 | 58% |

- FIGURE 42 –

NCBI Blastx of BGL4 cDNA (without signal seq):

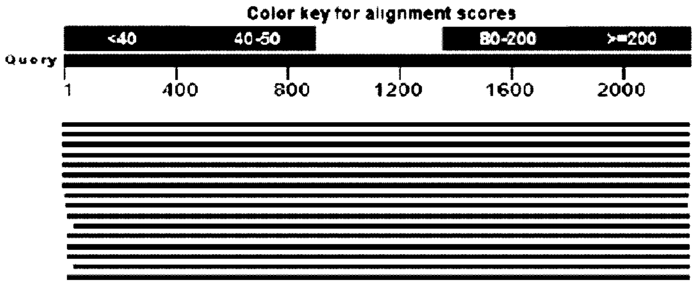

Sequences producing significant alignments:

| Accession | Description | Max score | Total score | Query coverage | E value | Max ident |
|---|---|---|---|---|---|---|
| XP_001394024.1 | beta-glucosidase M [Aspergillus niger CBS 513.88] >sp\|A5ABF5.1\|BGLM_ASPNC RecName: Full=Probable beta-glucosidase M; AltName: Full=Beta-D-glucoside glucohydrolase M; AltName: Full=Cellobiase M; AltName: Full=Gentiobiase M; Flags: Precursor >emb\|CAK48253.1\| unnamed protein product [Aspergillus niger] | 1187 | 1187 | 100% | 0.0 | 78% |
| B0XPB8.1 | RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EDP56956.1\| beta-glucosidase, putative [Aspergillus fumigatus A1163] | 1122 | 1122 | 100% | 0.0 | 74% |
| XP_753108.1 | beta-glucosidase [Aspergillus fumigatus Af293] >sp\|Q4WR62.1\|BGLM_ASPFU RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAL91070.1\| beta-glucosidase, putative [Aspergillus fumigatus Af293] | 1122 | 1122 | 100% | 0.0 | 74% |
| XP_001264012.1 | glycosyl hydrolase, putative [Neosartorya fischeri NRRL 181] >sp\|A1D122.1\|BGLM_NEOFI RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAW22115.1\| glycosyl hydrolase, putative [Neosartorya fischeri NRRL 181] | 1117 | 1117 | 100% | 0.0 | 74% |
| XP_002375439.1 | beta-glucosidase, putative [Aspergillus flavus NRRL3357] >sp\|B8N5S6.1\|BGLM_ASPFN RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EED54167.1\| beta-glucosidase, putative [Aspergillus flavus NRRL3357] | 1108 | 1108 | 100% | 0.0 | 73% |
| XP_001727197.1 | beta-glucosidase M [Aspergillus oryzae RIB40] >sp\|Q2UDK7.1\|BGLM_ASPOR RecName: Full=Probable beta-glucosidase M; AltName: Full=Beta-D-glucoside glucohydrolase M; AltName: Full=Cellobiase M; AltName: Full=Gentiobiase M; Flags: Precursor >dbj\|BAE60358.1\| unnamed protein product [Aspergillus oryzae RIB40] | 1107 | 1107 | 100% | 0.0 | 73% |
| XP_001218668.1 | hypothetical protein ATEG_10320 [Aspergillus terreus NIH2624] >sp\|Q0C7L4.1\|BGLM_ASPTN RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAU29317.1\| hypothetical protein ATEG_10320 [Aspergillus terreus NIH2624] | 1097 | 1097 | 100% | 0.0 | 72% |
| XP_680665.1 | hypothetical protein AN7396.2 [Aspergillus nidulans FGSC A4] >sp\|Q5AWD4.1\|BGLM_EMENI RecName: Full=Probable beta-glucosidase M; AltName: Full=Beta-D-glucoside glucohydrolase M; AltName: Full=Cellobiase M; AltName: Full=Gentiobiase M; Flags: Precursor >gb\|EAA61767.1\| hypothetical protein AN7396.2 [Aspergillus nidulans FGSC A4] >tpe\|CBF78465.1\| TPA: beta-glucosidase (Eurofung) [Aspergillus nidulans FGSC A4] | 985 | 985 | 99% | 0.0 | 66% |
| EFX01027.1 | beta-glucosidase [Grosmannia clavigera kw1407] | 847 | 847 | 99% | 0.0 | 56% |

- FIGURE 43 –

NCBI blastn of beta-tubulin sequence

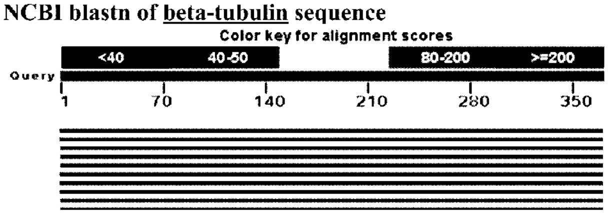

| Accession | Description | Max score | Total score | Query cvrg. | E value | Max ident |
|---|---|---|---|---|---|---|
| HM853553.1 | Aspergillus sp. AS-2011 beta-tubulin gene, partial cds | 684 | 684 | 100% | 0.0 | 100% |
| FR775311.1 | Aspergillus aculeatus partial benA gene for beta-1 and beta-2 tubulin, isolate CCF 108, exons 1-8 | 407 | 407 | 100% | 3e-110 | 87% |
| FJ491689.1 | Aspergillus violaceofuscus strain CBS 119.49 beta-tubulin (benA) gene, partial cds | 405 | 405 | 99% | 1e-109 | 86% |
| FJ491688.1 | Aspergillus sp. CBS 313.89 beta-tubulin (benA) gene, partial cds | 405 | 405 | 99% | 1e-109 | 86% |
| EU159221.1 | Aspergillus sp. JV-2007e strain CBS 121874 beta-tubulin (benA) gene, partial cds | 405 | 405 | 99% | 1e-109 | 86% |
| EU982087.1 | Aspergillus aculeatus strain ATHUM 5028 BenA (benA) gene, partial cds | 401 | 401 | 100% | 1e-108 | 86% |
| EF661107.1 | Aspergillus aculeatus isolate NRRL 2053 beta-tubulin gene, partial cds | 401 | 401 | 100% | 1e-108 | 86% |
| EF661105.1 | Aspergillus aculeatus isolate NRRL 4912 beta-tubulin gene, partial cds | 401 | 401 | 100% | 1e-108 | 86% |
| EU159225.1 | Aspergillus sp. JV-2007e strain CBS 121875 beta-tubulin (benA) gene, partial cds | 399 | 399 | 99% | 5e-108 | 86% |
| EU159223.1 | Aspergillus sp. JV-2007e strain CBS 121873 beta-tubulin (benA) gene, partial cds | 399 | 399 | 99% | 5e-108 | 86% |
| EU159220.1 | Aspergillus sp. JV-2007e strain CBS 121060 beta-tubulin (benA) gene, partial cds | 399 | 399 | 99% | 5e-108 | 86% |
| EU159219.1 | Aspergillus sp. JV-2007e strain CBS 121062 beta-tubulin (benA) gene, partial cds | 399 | 399 | 99% | 5e-108 | 86% |
| EU159218.1 | Aspergillus sp. JV-2007e strain CBS 115570 beta-tubulin (benA) gene, partial cds | 399 | 399 | 99% | 5e-108 | 86% |
| EU159217.1 | Aspergillus sp. JV-2007e strain CBS 121061 beta-tubulin (benA) gene, partial cds | 399 | 399 | 99% | 5e-108 | 86% |
| EF661106.1 | Aspergillus aculeatus isolate NRRL 359 beta-tubulin gene, partial cds | 396 | 396 | 100% | 6e-107 | 86% |
| AY585538.1 | Aspergillus aculeatus strain CBS 62078 beta tubulin-like gene, partial sequence | 396 | 396 | 100% | 6e-107 | 86% |
| AY820020.1 | Aspergillus aculeatus strain CBS 62078 beta-tubulin-like gene, partial sequence | 396 | 396 | 100% | 6e-107 | 86% |
| EU159227.1 | Aspergillus sp. JV-2007e strain CBS 121871 beta-tubulin (benA) gene, partial cds | 388 | 388 | 99% | 1e-104 | 86% |
| EU159226.1 | Aspergillus sp. JV-2007e strain CBS 121872 beta-tubulin (benA) gene, partial cds | 388 | 388 | 99% | 1e-104 | 86% |
| EU159224.1 | Aspergillus sp. JV-2007e strain CBS 121877 beta-tubulin (benA) gene, partial cds | 388 | 388 | 99% | 1e-104 | 86% |
| EU159222.1 | Aspergillus sp. JV-2007e strain CBS 121876 beta-tubulin (benA) gene, partial cds | 388 | 388 | 99% | 1e-104 | 86% |
| EF661104.1 | Aspergillus japonicus isolate NRRL 35541 beta-tubulin gene, partial cds | 359 | 359 | 100% | 8e-96 | 84% |

- FIGURE 44 –

NCBI blastn of calmodulin sequence

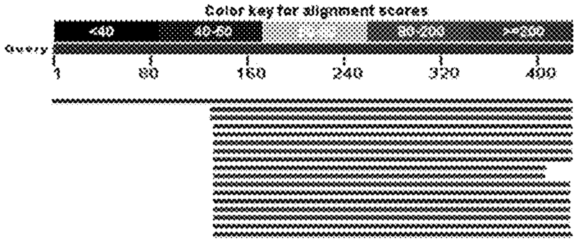

| Accession | Description | Max score | Total score | Query cvrg | E value | Max ident |
|---|---|---|---|---|---|---|
| HM853554.1 | Aspergillus sp. AS-2011 calmodulin gene, partial cds | 789 | 789 | 100% | 0.0 | 100% |
| FN594549.1 | Aspergillus homomorphus partial cam gene for calmodulin, strain CBS 101889 | 366 | 366 | 69% | 6e-98 | 89% |
| AM887865.1 | Aspergillus homomorphus partial cam gene for calmodulin, strain ITEM 7556, exons 2-3 | 366 | 366 | 69% | 6e-98 | 89% |
| HM055489.1 | Aspergillus aculeatus calmodulin (cmdA) gene, partial cds | 359 | 359 | 69% | 9e-96 | 88% |
| EF661146.1 | Aspergillus aculeatus isolate NRRL 359 calmodulin gene, partial cds | 359 | 359 | 69% | 9e-96 | 88% |
| EF661147.1 | Aspergillus aculeatus isolate NRRL 4912 calmodulin gene, partial cds | 353 | 353 | 69% | 4e-94 | 88% |
| AM886693.1 | Aspergillus aculeatus partial cam gene for calmodulin, strain CBS 621.78, exons 2-3 | 353 | 353 | 69% | 4e-94 | 88% |
| AM419750.1 | Aspergillus aculeatus partial cam gene for calmodulin, strain ITEM 7038 | 348 | 348 | 69% | 2e-92 | 88% |
| FJ491695.1 | Aspergillus sp. CBS 313.89 calmodulin gene, partial cds | 331 | 331 | 64% | 2e-87 | 88% |
| FJ491701.1 | Aspergillus sp. CBS 119.49 calmodulin gene, partial cds | 329 | 329 | 63% | 7e-87 | 88% |
| HM104687.1 | Eurotium repens calmodulin gene, partial cds | 263 | 263 | 68% | 8e-67 | 82% |
| FR751446.1 | Eurotium repens partial caM gene for calmodulin, culture collection CCF<CZE>:4011, exons 1-4 | 263 | 263 | 68% | 8e-67 | 82% |
| EF652007.1 | Eurotium pseudoglaucum isolate NRRL 40 calmodulin gene, partial cds | 263 | 263 | 68% | 8e-67 | 82% |
| EF652006.1 | Eurotium repens isolate NRRL 17 calmodulin gene, partial cds | 263 | 263 | 68% | 8e-67 | 82% |
| EF652005.1 | Eurotium repens isolate NRRL 13 calmodulin gene, partial cds | 263 | 263 | 68% | 8e-67 | 82% |
| EF652008.1 | Aspergillus reptans isolate NRRL 25865 calmodulin gene, partial cds | 257 | 257 | 68% | 4e-65 | 82% |
| FJ530972.1 | Aspergillus malodoratus strain CBS 490.65 calmodulin gene, partial cds | 255 | 255 | 69% | 1e-64 | 82% |
| EF669696.1 | Aspergillus malodoratus isolate NRRL 5083 calmodulin gene, partial cds | 255 | 255 | 69% | 1e-64 | 82% |
| FR751433.1 | Aspergillus terreus partial caM gene for calmodulin, culture collection CCF<CZE>:2539, exons 1-5 | 246 | 246 | 68% | 8e-62 | 82% |
| FR751432.1 | Aspergillus terreus partial caM gene for calmodulin, culture collection CCF<CZE>:2911, exons 1-5 | 246 | 246 | 68% | 8e-62 | 82% |
| EU147531.1 | Aspergillus terreus strain CBS503.65 calmodulin gene, partial sequence | 241 | 241 | 67% | 4e-60 | 82% |
| EF669538.1 | Aspergillus terreus isolate NRRL 1923 calmodulin gene, partial cds | 241 | 241 | 67% | 4e-60 | 82% |
| FJ491592.1 | Aspergillus kanagawaensis strain IBT 22045 calmodulin gene, partial cds | 239 | 239 | 69% | 1e-59 | 81% |
| EF652126.1 | Aspergillus gorakhpurensis isolate NRRL 3649 calmodulin gene, partial cds | 239 | 239 | 68% | 1e-59 | 81% |
| EF661258.1 | Aspergillus parvulus isolate NRRL 2667 calmodulin gene, partial cds | 239 | 239 | 69% | 1e-59 | 81% |
| EF661257.1 | Aspergillus parvulus isolate NRRL 4994 calmodulin gene, partial cds | 239 | 239 | 69% | 1e-59 | 81% |
| EF661256.1 | Aspergillus parvulus isolate NRRL 5023 calmodulin gene, partial cds | 239 | 239 | 69% | 1e-59 | 81% |
| EF661255.1 | Aspergillus parvulus isolate NRRL 4220 calmodulin gene, partial cds | 239 | 239 | 69% | 1e-59 | 81% |
| FN594581.1 | Aspergillus carbonarius partial cam gene for calmodulin, strain MUCL 30479 | 237 | 237 | 68% | 5e-59 | 81% |
| EF661168.1 | Aspergillus carbonarius isolate NRRL 4849 calmodulin gene, partial cds | 237 | 237 | 68% | 5e-59 | 81% |

- FIGURE 45 -

NCBI blastn of ITS sequence

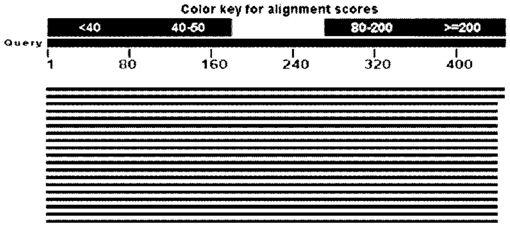

| Accession | Description | Max score | Tot. score | Query cvrg. | E val. | Max ident. |
|---|---|---|---|---|---|---|
| HM853552.1 | Aspergillus sp. AS-2011 18S ribosomal RNA gene, partial sequence; internal transcribed spacer 1, 5.8S ribosomal RNA gene, and internal transcribed spacer 2, complete sequence; and 28S ribosomal RNA gene, partial sequence | 828 | 828 | 100% | 0.0 | 100% |
| DQ092542.1 | Aspergillus sp. CCN27 18S ribosomal RNA gene, partial sequence; internal transcribed spacer 1, 5.8S ribosomal RNA gene, and internal transcribed spacer 2, complete sequence; and 28S ribosomal RNA gene, partial sequence | 547 | 547 | 100% | 2e-152 | 89% |
| JF793537.1 | Aspergillus japonicus strain F80 18S ribosomal RNA gene, internal transcribed spacer 1, 5.8S ribosomal RNA gene, internal transcribed spacer 2, and 28S ribosomal RNA gene, complete sequence | 538 | 538 | 98% | 1e-149 | 89% |
| HQ443257.1 | Aspergillus japonicus strain SFLs10 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| JF439460.1 | Aspergillus aculeatus isolate F36 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| JF770435.1 | Aspergillus japonicus isolate AJP01 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| FR733805.1 | Aspergillus japonicus 18S rRNA gene (partial), ITS1, 5.8S rRNA gene, ITS2 and 28S rRNA gene (partial), culture collection CCF<CZE>:4079 | 538 | 538 | 98% | 1e-149 | 89% |
| HM595495.1 | Aspergillus aculeatus isolate M18 internal transcribed spacer 1, partial sequence; 5.8S ribosomal RNA gene and internal transcribed spacer 2, complete sequence; and 28S ribosomal RNA gene, partial sequence | 538 | 538 | 98% | 1e-149 | 89% |
| HM537074.1 | Fungal endophyte sp. g105 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| HM140184.1 | Aspergillus aculeatus strain RCEF4894 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| HM101061.1 | Fungal sp. FE-7 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| HM101039.1 | Fungal sp. FB-5 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| GU290041.1 | Aspergillus sp. YN1 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |
| FJ525443.1 | Aspergillus aculeatus isolate CRI 323-04 18S ribosomal RNA gene, partial sequence; internal transcribed spacer 1, 5.8S ribosomal RNA gene, and internal transcribed spacer 2, complete sequence; and 28S ribosomal RNA gene, partial sequence | 538 | 538 | 98% | 1e-149 | 89% |

*ASPERGILLUS* CONTAINING BETA-GLUCOSIDASE, BETA-GLUCOSIDASES AND NUCLEIC ACIDS ENCODING THE SAME

CROSS-REFERENCE TO RELATED APPLICATIONS

The present application is a divisional application of U.S. patent application Ser. No. 13/813,031, filed Apr. 19, 2013 and titled "*ASPERGILLUS* CONTAINING BETA-GLUCOSIDASE, BETA-GLUCOSIDASES AND NUCLEIC ACIDS ENCODING THE SAME" ("the '031 Application") The '031 Application is a national stage application of Patent Application Number PCT/DK2011/050296, filed Aug. 1, 2011 and titled "*ASPERGILLUS* CONTAINING BETA-GLUCOSIDASE, BETA-GLUCOSIDASES AND NUCLEIC ACIDS ENCODING THE SAME" ("the PCT Application"). The PCT Application claims priority to Danish Patent Application Number PA201070347, filed Jul. 30, 2010 ("the Danish Application"). The '031 Application, the PCT Application, and the Danish Application are hereby fully incorporated by reference.

FIELD OF INVENTION

The present invention relates to an *Aspergillus* strain AP, *Aspergillus saccharolyticus*, producing a superior novel beta-glucosidase enzyme for efficient saccharification of lignocellulosic biomasses.

BACKGROUND OF INVENTION

Exploitation of lignocellulosic biomasses for production of biofuels, biochemicals, and pharmaceuticals is alternative to the world's limited fossil resources. Bio refineries should replace oil refineries, producing the same products, but using renewable resources: lignocellulosic biomasses. Lignocellulosic biomasses mainly consist of cellulose, hemicelluloses, and lignin, with different distribution of each component depending on the specific plant species, from which it is derived. Cellulose is of great interest in terms of creating a sugar platform for biofuels and chemicals as its hydrolysis product, glucose, can readily be fermented into ethanol or converted into high value chemicals. Cellulose is a polymer of the simple sugar glucose covalently bonded by beta-1,4-glycosidic linkages. Many microorganisms produce enzymes that hydrolyze beta-linked glucans. These enzymes include endoglucanases, cellobiohydrolases, and beta-glucosidases. The complete hydrolysis of cellulose involves the synergistic action of cellobiohydrolases (EC 3.2.1.91), endoglucanases (EC 3.2.1.4), and beta-glucosidases (EC 3.2.1.21). The cellobiohydrolases are capable of degrading the crystalline parts of cellulose by cleaving off cellobiose molecules from the ends of the cellulose chains. The endoglucanases digest the cellulose polymer at random locations, hydrolyzing glucosidic bonds of the more amorphous regions of the cellulose, decreasing the degree of polymerization and opening it to attack by cellobiohydrolases by creating more free ends for attack by cellobiohydrolases. Finally, the beta-glucosidases act in the liquid phase hydrolyzing mainly cellobiose (a water-soluble beta-1,4-linked dimer of glucose) to glucose, but also to some extent cellodextrins, sugars with a low degree of polymerization.

Historically, enzymes from *Trichoderma reesei* and *Aspergillus niger* are known as a good match for the hydrolysis of cellulose; *T. reesei* enzymes mainly contributing with cellobiohydrolase and endoglucanase activity and *A. niger* enzymes with beta-glucosidase activity (Sternberg D et al. Can J Microbiol 1977; 2:139-47). Beta-glucosidases are of key importance as they are needed to supplement the cellobiohydrolase and endoglucanase activities for final glucose release and at the same time decreasing the accumulation of cellobiose and shorter cellooligmers that are known as product inhibitors for the cellobiohydrolases (Zhang Y-P et al. Biotechnol Adv 2006; 5:452-81). Especially efficient beta-glucosidases, that are not themselves easily inhibited by their substrate, glucose, are of great interest. Currently, most commercial cellulase preparations are produced by *T. reesei*, e.g. Celluclast 1.5 L (Novozymes A/S), which has to be supplemented with extra beta-glucosidase activity from another source, e.g. Novozym 188 (Novozymes A/S), in order to improve cellulose hydrolysis. However, the commercial available beta-glucosidases have relatively low long-term temperature stability. Robustness, thermostability and substrate specificity are very important characteristics for enzymes to be applied in industrial processes.

The conversion of cellulosic feedstocks into bioethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily processed, for example fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is extremely undesirable for ethanol production. Other than biofuels, the monomeric sugars (including glucose) produced by enzymatic hydrolysis in the biorefinery will be used as a platform for biochemicals, plastics, pharmaceuticals, etc.

Cellobiose accumulation has been a major problem in enzymatic hydrolysis because cellulase-producing microorganisms produce little beta-glucosidase. The low amount of beta-glucosidase results in a shortage of capacity to hydrolyze the cellobiose to glucose. Several approaches have been used to increase the amount of beta-glucosidase in cellulose conversion to glucose.

Thus it would be an advantage in the art to provide beta-glucosidases with improved properties for converting cellulosic materials to polysaccharides, cellodextrins, disaccharides and monosaccharides. Improved properties include altered temperature-dependent activity profiles, thermostability, pH activity, pH stability, and substrate specificity.

SUMMARY OF INVENTION

The present invention relates to the identification of a novel and improved beta-glucosidase producing strain of the fungus *Aspergillus*, namely *Aspergillus saccharolyticus*, which is efficient in the degradation of lignocellulosic biomasses into glucose for production of biofuels, biochemical and pharmaceuticals. Several enzymes of the newly identified strain are efficient in degradation of lignocellulosic biomasses. In particular one enzyme has been identified and characterised as having improved beta-glucosidase activity. The identified beta-glucosidase has improved thermal stability, while maintaining its activity at a high level for a prolonged period of time compared to other fungal beta-glucosidases. This makes it a superior choice for degradation of lignocellulosic material.

In one aspect, the present invention relates to an isolated polypeptide comprising a. an amino acids consisting of the SEQ NO: 3, 4, 7, 10, or 13, b. a biologically active sequence variant of SEQ NO: 3, 4, 7, 10, or 13, wherein the variant has at least 92% sequence identity to said SEQ NO: 3, 4, 7, 10, or 13, or c. a biologically active fragment of at least 30 consecutive amino acids of any of a) through b), wherein said fragment is a fragment of SEQ ID NO: 3, 4, 7, 10, or 13.

In a preferred embodiment the polypeptide is purified from *Aspergillus saccharolyticus*, such as deposit no.: CBS 127449. The polypeptide is capable of degrading or converting lignocellulosic material that may be obtained from various sources. In a preferred embodiment the polypeptide of the present invention is capable of hydrolyzing a β1-4 bond linking two glucose or glucose-substituted molecules. A second aspect of the invention relates to an isolated polynucleotide comprising a nucleic acid or its complementary sequence being selected from the group consisting of a. a polynucleotide sequence encoding a polypeptide consisting of an amino acid sequence SEQ ID NO: 3, 4, 7, 10, or 13, b. a polynucleotide sequence encoding a biologically active sequence variant of the amino acid sequence, wherein the variant has at least 92% sequence identity to said SEQ ID NO 3, 4, 7, 10, or 13, and c. a polynucleotide sequence encoding a biologically active fragment of at least 30 contiguous consecutive amino acids of any of a) through b), wherein said fragment is a fragment of SEQ ID NO 3, 4, 7, 10, or 13 or d. SEQ ID NO.: 1, 2, 5, 6, 8, 9, 11, 12, or 29, or fragments of at least 90 contiguous nucleotides thereof, or e. a polynucleotide comprising a nucleic acid sequence having at least 88% identity to SEQ ID NO: 1, 2, 5, 6, 8, 9, 11, 12 or 29, or fragments of at least 90 contiguous nucleotides thereof or f. a polynucleotide hybridising to SEQ ID NO: 1, 2, 5, 6, 8, 9, 11, 12, or 29, or fragments of at least 30 contiguous nucleotides thereof, and g. a polynucleotide complementary to any of a) to f).

The polynucleotide may be used for cloning purposes and for production of the polypeptide of the invention. Thus, in a third aspect, the present invention also relates to a recombinant nucleic acid vector comprising a polynucleotide of the invention.

It is appreciated that the polynucleotide and/or the recombinant nucleic acid vector of the present invention may be introduced into host cells. Accordingly, the invention in a fourth aspect pertains to a recombinant host cell comprising a polynucleotide of the present invention and/or a nucleic acid vector of the invention.

A fifth aspect of the invention relates to an isolated microorganism comprising a polypeptide of the invention, a polynucleotide of the invention and/or a recombinant nucleic acid vector of the invention. The isolated microorganism is in one preferred embodiment the newly discovered strain *Aspergillus saccharolyticcus* of the invention or progeny thereof.

A sixth aspect relates to a method of producing a polypeptide as disclosed in the present invention comprising a. cultivating a microorganism, where said microorganism produces said polypeptide, b. recovering the polypeptide from said microorganism.

The microorganism may thus comprise a polynucleotide of the invention and/or a recombinant nucleic acid vector of the invention. The microorganism may be any microorganism suitable for the purpose. In a preferred embodiment, wherein microorganism is *Aspergillus*, and particularly *Aspergillus saccharolyticcus* or progeny thereof.

According to the invention the polypeptide, recombinant host cell and/or microorganism may be used in a composition. Thus, a seventh aspect related to a composition comprising at least one polypeptide of the invention, at least one recombinant host cell of the invention and/or at least one microorganism of the invention.

It is further appreciated that the polypeptide, recombinant nucleic acid vector, recombinant host cell, microorganism and/or composition of the present invention may be combined with other components. Thus, a further aspect pertains to a kit-of parts comprising at least one polypeptide of the invention, at least one recombinant nucleic acid vector of the invention, at least one recombinant host cell of the invention, at least one isolated microorganism of the invention and/or at least one composition of the invention, and at least one additional component. An additional component is typically enzymes that aid in the degradation or conversion of biomass for example cellulases, endogluconase, cellobiohydrolase, beta-glucosidase, hemicellulase, esterase, laccase, protease and/or peroxidise.

The invention in yet a further aspect relates to a method for degrading or converting a lignocellulosic material, said method comprising a) incubating said lignocellulosic material with at least one polypeptide of the invention, at least one microorganism of the invention, at least one recombinant host of the invention, at least one composition of the invention and/or at least one kit-of parts of the invention and b) recovering the degraded lignocellolosic material.

In a further aspect the invention pertains to a method for fermenting a cellulosic material, said method comprising a. treating the cellulosic material with at least one polypeptide of the invention, at least one recombinant host cell of the invention, at least one microorganism of the invention, at least one composition of the invention, at least one kit-of parts of the invention, and b. incubating the treated cellulosic material with one or more fermenting microorganisms.

c. obtaining at least one fermentation product.

In addition to the aspects mentioned above, the present invention also pertains to the following related aspects. In one related aspect, the invention relates to an isolated microorganism of the species *Aspergillus saccharolyticus*, in particular the microorganism as deposited in the Centraalbereau voor Schimmelcultures (CBS) and having accession number CBS 127449, or a descendant or a functional mutant thereof.

In another aspect, the present invention relates to an isolated polypeptide identified as a beta-glucosidase comprising a. an amino acid sequence selected from SEQ NO: 3, 4, 7, 10, or 13 b. a biologically active sequence variant of any of SEQ NO: 3, 4, 7, 10, or 13, wherein said variant has at least 92% sequence identity to said SEQ NO: 3, 4, 7, 10, or 13, or c. a biologically active fragment of at least 30 consecutive amino acids of any of the amino acid sequences of a) through b.

The polypeptide is for example purified from *Aspergillus saccharolyticus*, such as deposit no.: CBS 127449, but it may also be heterologously expressed from a recombinant host cell and purified therefrom. The polypeptide is capable of hydrolyzing cellobiose and/or cellodextrins, by hydrolyzing a 131-4 glucose-glucose linkage.

The invention also pertains to an isolated polynucleotide comprising a nucleic acid or its complementary sequence being selected from the group consisting of a. a polynucleotide sequence encoding a polypeptide consisting of an amino acid sequence SEQ ID NO: 3, 4, 7, 10, or 13
b. a polynucleotide sequence encoding a biologically active sequence variant of the amino acid sequence, wherein the variant has at least 92% sequence identity to said SEQ ID NO: 3, 4, 7, 10, or 13 and
c. a polynucleotide sequence encoding a biologically active fragment of at least 30 consecutive amino acids of any of the amino acid sequences of a) through b), or
d. SEQ ID NO.: 1, 2, 5, 6, 8, 9, 11, 12, 29, or fragments of at least 90 contiguous nucleotides thereof. or
e. a polynucleotide comprising a nucleic acid sequence having at least 89% identity to SEQ ID NO: 1, 2, 5, 6, 8, 9, 11, 12, 14, 15, 16, 17, 29 or fragments of at least 30 contiguous nucleotides thereof, or
f. a polynucleotide hybridising to SEQ ID NO.: 1, 2, 5, 6, 8, 9, 11, 12, 14, 15, 16, 17, 29, or fragments of at least 30 contiguous nucleotides thereof, and
g. a polynucleotide complementary to any of a) to f).

The invention also relates to a recombinant nucleic acid vector comprising a polynucleotide of the present invention.

Moreover, the invention relates to a host cell and/or an *Aspergillus saccharolyticus* microorganism or a descendant or functional mutant thereof, which comprises a polypeptide, a polynucleotide and/or a recombinant nucleic acid vector according to the invention.

The invention also pertains to a method of producing a polypeptide, said method comprising a. cultivating a host cell and/or a microorganism of the invention, and b. recovering said polypeptide from said microorganism.

Furthermore, the invention encompass a composition comprising a polypeptide, a host cell and/or a microorganism of the invention, and the invention also pertains to a kit-of parts comprising such a composition and at least one additional component. The additional component is for example selected from the group consisting of cellulases, endogluconase, cellobiohydrolase, beta-glucosidase, hemicellulase, esterase, laccase, protease and peroxidise.

In one important aspect, the invention relates to a method of degrading or converting a lignocellulosic material, said method comprising incubating said lignocellulosic material with a composition or a kit-of parts of the invention.

DESCRIPTION OF DRAWINGS

FIG. 1. Extracellular beta-glucosidase activity of screened fungi grown in simple submerged fermentation. pNPG was used as substrate in the assays, with one unit (U) of enzyme activity defined as the amount of enzyme needed to hydrolyze 1 umol pNPG in 1 minute.

FIG. 2. Neighbor-joining phylogenetic tree based on ITS1 region sequence data of black *Aspergillus*, including strain AP/*Aspergillus saccharolyticus*, and using *A. flavus* as out group. Numbers above the branches are bootstrap values. Bar, 0.02 substitutions per nucleotide.

FIG. 3. Beta-glucosidase activity of extracts from selected Aspergilli grown in simple submerged fermentation (*=type strain). One unit (U) of enzyme activity is defined as the amount of enzyme needed to hydrolyze 1 umol pNPG in 1 minute.

FIG. 4. pH profile. Beta-glucosidase activity of Strain AP/*Aspergillus saccharolyticus* and Novoym 188 at different pH measured on pNPG. Endoglucanase activity of Celluclast 1.5 L at different pH measured on AZO-CMC.

FIG. 5. Product inhibition; remaining beta-glucosidase activity at different inhibitor (glucose) concentrations relative to activity measured without inhibitor. A: pNPG as substrate, activity measured by release of pNP. B: cellobiose as substrate, activity measured by decrease in cellobiose concentration.

FIG. 6. Time course of thermal inactivation of the beta-glucosidases of (A) strain AP/*Aspergillus saccharolyticus*, (B) Novozym 188, and (C) Cellic CTec. Thermostability is evaluated based on the remaining activity after 0-4 hours of incubation at different temperatures relative to the activity without incubation.

FIG. 7. Hydrolysis of cellohexaose by Strain AP/*Aspergillus saccharolyticus* extract, Novozym 188, Celluclast 1.5 L, and Cellic CTec showing a clear difference in the mode of action.

FIG. 8. Hydrolysis of bagasse using different enzyme ratios of Strain AP/*Aspergillus saccharolyticus* or Novozym 188 relative to Celluclast 1.5 L.

FIG. 9. Neighbor-joining phylogenetic tree based on partial calmodulin gene sequence data for *Aspergillus* section *Nigri*. Numbers above the branches are bootstrap values. Only values above 70% are indicated. Bar, 0.02 substitutions per nucleotide.

FIG. 10. Neighbor-joining phylogenetic tree based on ITS sequence data for *Aspergillus* section *Nigri*. Numbers above the branches are bootstrap values. Only values above 70% are indicated. Bar, 0.02 substitutions per nucleotide.

FIG. 11. Neighbor-joining phylogenetic tree based on partial beta-tubulin gene sequence data for *Aspergillus* section *Nigri*. Numbers above the branches are bootstrap values. Only values above 70% are indicated. Bar, 0.02 substitutions per nucleotide.

FIG. 12. Universally Primed-PCR analysis using each of the two UP primers, L45 and L15/AS19. Loaded in lanes: 1&2) *A. saccharolyticus* sp. nov. CBS 127449$^T$, 3) *A. aculeatinus* CBS 121060$^T$, 4) *A. ellipticus* CBS 707.79$^T$, 5) *A. homomorphus* CBS 101889$^T$, 6) *A. niger* CBS 554.65$^T$, 7) *A. uvarum* CBS 121591$^T$, 8) *A. auleatus* CBS 172.66$^T$, 9) *A. japonicus* CBS 114.51$^T$ FIG. 13. Extrolite profile from YES agar (14 days 25° C.) of *A. saccharolyticus* sp. nov. CBS 127449$^T$. Above is the $ESI^+$ trace (m/z 100-900) and below the UV trace (200-700 nm, 0.05 min ahead of $ESI^+$). Mono isotopic masses ($M_m$) of major peaks are inserted. The UV spectrum of two related compounds, ACU-1 and ACU-2, with identical UV spectra is also inserted.

FIG. 14. *A. saccharolyticus* sp. nov. CBS 127449$^T$. A) conidia, B-C) conidial heads, D-H) Three-point inoculation on CREA, CYA, CYA 37° C., MEA, and CYAS, respectively, incubated 7 days FIG. 15. *A. saccharolyticus* sp. nov. CBS 127449$^T$ three point inoculation on CYA, incubation at different temperatures, growth observation day 7.

FIG. 16. Sketch of the cloning vector, pAN7-1 modified with a cassette of RP27 promoter, beta-glucosidase gene bgl1, his-tail, and beta-tubulin terminator inserted at the PciI restriction site.

FIG. 17. Beta-glucosidase activity and protein content of the different fractions from ion exchange, and SDS-page 4-12% of fractions 14-23 with high beta-glucosidase activity. Fractions 2-6 are flow through from the load, fractions 7-8 are wash prior to gradient elution, fractions 9-38 are gradient elution, and fractions 39-45 are final column stripping.

FIG. 18. SDS-page 12-20%, lane 1) *A. cellulolyticus* raw extract, lane 2) fraction #15 from the ion exchange fractionation, lane 3) His-tag purified BGL1

FIG. 19. Alignment of proposed active site region (boxed) of different aspergilli GH3 beta-glucosidases, the GenBank accession number is given in parenthesis FIG. 20. A) Substrate saturation plot where enzyme activity is related to substrate concentration with the two substrates, pNPG and cellobiose. B) Relative beta-glucosidase activity at different inhibitor concentrations with a substrate concentration of 5 mM pNPG.

FIG. 21. A) Thermostability of BGL 1 incubated at different temperatures for different time period followed by assaying at 50° C., pH 4.8, 10 min reactions. $TR_{1/2}$=half-life, calculated for temperatures above 60° C. B) pH profile of BGL1 assayed at 50° C., varying pH, 10 min reactions.

FIG. 22. Snap shot at different time points of the hydrolysis of cellohexaose for analysis of the degradation pattern. G1=glucose, G2=cellobiose, G3=cellotriose, G4=cellotetraose, G5=cellopentaose, G6=cellohexaose.

FIG. 23. Homology model of the catalytic module of beta-glucosidase from *Aspergillus saccharolyticus*. A. Ribbon cartoon representation of the catalytic module showing the important residues for catalysis (in royal-blue) and substrate/product binding (in spring-green). Glucose (in gray) is modeled into the catalytic site. The part of the loop marked ‘Y’ is not modeled. B. Stereo diagram illustrating the comparison of beta-glucosidase homology model of *A. saccharolyticus* (in steel-blue) with the template structure from *T. neapolitana* (PDB entry 2X41) (in orange-red). The catalytic nucleophile (D261) and the acid/base (E490) are shown in gold.

FIG. 24. NCBI blastn of BGL1 gDNA, closest identity 74%

FIG. 25. NCBI blastn of BGL1 cDNA without signal sequence, closest identity 84%

FIG. 26. NCBI blastx of BGL1 gDNA, closest identity 96%

FIG. 27. NCBI blastx of BGL1 cDNA, without signal sequence, closest identity 91%

FIG. 28. NCBI blastp of BGL1 polypeptide, without signal sequence, closest identity 91%

FIG. 29. NCBI blastn of BGL2 gDNA, closest identity 78%

FIG. 30. NCBI blastn of BGL2 cDNA, without signal sequence, closest identity 78%

FIG. 31. NCBI blastx of BGL2 gDNA, closest identity 87%

FIG. 32. NCBI blastx of BGL2 cDNA, closest identity 87%

FIG. 33. NCBI blastp of BGL2 polypeptide, without signal sequence, closest identity 73%

FIG. 34. NCBI blastn of BGL3 gDNA, closest identity 88%

FIG. 35. NCBI blastn of BGL3 cDNA, without signal sequence, closest identity 84%

FIG. 36. NCBI blastx of BGL3 gDNA, closest identity 92%

FIG. 37. NCBI blastx of BGL3 cDNA, without signal sequence, closest identity 75%

FIG. 38. NCBI blastp of BGL3 polypeptide, without signal sequence, closest identity 75%

FIG. 39. NCBI blastn of BGL4 gDNA, closest identity 77%

FIG. 40. NCBI blastn of BGL4 cDNA, without signal sequence, closest identity 71%

FIG. 41. NCBI blastx of BGL4 gDNA, closest identity 86%

FIG. 42. NCBI blastx of BGL4 cDNA, without signal sequence, closest identity 78%

FIG. 43. NCBI blastn of beta-tubulin partial coding sequence, SEQ ID NO: 14, closest identity 87%

FIG. 44. NCBI blastn of calmodulin partial coding sequence, SEQ ID NO: 15, closest identity 89% and FIG. 45. NCBI blastn of ITS partial coding sequence, SEQ ID NO: 16, closest identity 89%.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms “a,” “an” and “the” include plural referents unless the context clearly dictates otherwise. Definition of standard chemistry terms may be found in reference works, including Carey and Sundberg (1992) “Advanced Organic Chemistry $3^{rd}$ Ed.” Vols. A and B, Plenum Press, New York. The practice of the present invention will employ, unless otherwise indicated, conventional methods of mass spectroscopy, protein chemistry, biochemistry, and recombinant DNA techniques, within the skill of the art. The term AP, *Aspergillus* AP as found herein is meant to refer to *Aspergillus saccharolyticus.*

Amino Acids and Nucleic Acids

Throughout the description and claims the three letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a polypeptide of the invention exists as the free carboxylic acid, this may also be specified as “—OH”. The N-terminal amino acid of a polypeptide comprise a free amino-group, this may also be specified as “H—”.

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp. Glu, Lys, Arg, His, Aib, Nal, Sar, Orn, Lysine analogues DAP and DAPA.

Nucleic acid is meant to encompass DNA and RNA as well as derivatives thereof such as peptide nucleic acids (PNA) or locked nucleic acids (LNA) throughout the description.

Gene product refers to any transcriptional or translational product of a gene. A transcriptional product comprises any RNA-species, which is transcribed from the specific gene, such as pre-RNA, mRNA, tRNA, miRNA, spliced and nonspliced RNA. Thus, a transcriptional gene product of the present invention comprises any RNA-species encoded by or comprising a sequence selected from any β-glucosidase gene. For example, a transcriptional gene product of the present invention comprises any RNA-species encoded by or comprising a sequence selected from any of SEQ ID NO: 1, 2, 5, 6, 8, 9, 11, or 12. The transcript may be bound by RNA-binding proteins and, thus, packaged into a ribonucleoprotein (RNP), for example an mRNP molecule.

A translational gene product of the present invention comprises any peptide or polypeptide encoded by the gene or a fragment thereof. Thus, a "polypeptide encoded by a gene of the present invention" is comprised in the terms "gene product", or "translational gene product". A translational gene product of the present invention comprises any polypeptide-species encoded by a sequence selected from any β-glucosidase. For example, a gene product or translational gene product of the present invention comprises any polypeptide-species encoded by a sequence selected from any of SEQ ID NO: 1, 2, 5, 6, 8, 9, 11, 12, or the complement thereof or part thereof or any sequence which is at least 70%, such as at least 80%, for example at least 90% identical to any of said sequences or part thereof.

Fragments or parts of a polypeptide or polynucleotide refers to a fragment, piece, or sub-region of a nucleic acid or protein molecule whose sequence is disclosed herein, such that the fragment comprising 5, 10, 15, 20 or more amino acids, or 5, 10, 15, 30, 45, 60 or more nucleotides that are contiguous in the parent protein or nucleic acid compound. When referring to a nucleic acid sequence, "fragment thereof" or "part thereof" refers to 5, 10, 15, 30, 45, 60 or more contiguous nucleotides, derived from the parent nucleic acid sequence, and also, owing to the genetic code, to the complementary sequence. For example, if the fragment entails the sequence 5'-AGCTAG-3', then "fragment thereof" would also include the complementary sequence, 3'-TCGATC-5'. Thus, the terms "fragment thereof" or "part thereof" as used herein in relation to an amino acid sequence refers to any portion of the given amino acid sequence which has the same activity as the complete amino acid sequence. Fragments will suitably comprise at least 30 and preferably at least 35 consecutive amino acids from the basic sequence. Fragments or parts of the polypeptide include deletion mutants and polypeptides where small regions of the polypeptides are joined together. The fragments should contain an epitope, and preferably contain at least one antigenic region.

The terms "fragment thereof" or "part thereof" as used herein in relation to a nucleic acid or polynucleotide sequence refers to any portion of the given polynucleotide sequence which serves a relevant purpose. In an oligonucleotide primer or probe comprising a fragment or part of a given basic sequence, the fragment or part should comprise enough nucleotides to support specific binding of the oligonucleotide primer or probe to its target. Such fragments typically comprise or consist of at least 5 nucleotides, such as at least 10, 15, or at least 20 consecutive nucleotides. With respect to a nucleic acid sequence encoding a polypeptide, wherein the nucleic acid sequence comprises or consists of a fragment or part of a basic nucleic acid, the fragment or part should comprise or consist of a nucleic acid sequence, which encodes a polypeptide with an activity which corresponds to the activity of the basic protein. Such fragments or parts will typically comprise at least 15, preferably at least 30 and more preferably at least 60 consecutive bases from the basic sequence.

Cellulosic ethanol is a biofuel produced from wood, grasses, or the non-edible parts of plants. It is a type of biofuel produced from lignocellulose, a structural material that comprises much of the mass of plants. Lignocellulose is composed mainly of cellulose, hemicellulose and lignin.

Beta-glucosidase is defined herein as a beta-D-glucoside glycohydrolase (E.C. 3.2.1.21) which catalyses the hydrolysis of terminal non-reducing beta-D-glucose residues with release of beta-D-glucose.

Extract is used herein for any extraction of a microorganism and/or host cell of the present invention. The extract preferably comprise a polypeptide and/or polynucleotide of the present invention. The extract may be prepared by opening the cells by lysis or chemical shear, and extracting the desired components in a suitable buffer.

Broth is used herein to describe a medium, which has been used for the culturing of a microorganism and/or host cell of the present invention. The broth is preferably a liquid culture broth, and the broth preferably comprise metabolites and/or other secreted components of the cultured microorganism and/or host cell, for example polypeptides of the present invention.

Lignocellulosic Material

The present invention refers to a newly identified strain of *Aspergillus*, strain AP, *Aspergillus saccharolyticus*, and the polypeptide of the present invention harbouring polypeptides that have improved qualities in the conversion or degradation of lignocellulosic material. Thus, the invention relates to the newly discovered strain, extracts, broths and polypeptides isolated from the strain, such as BGL1-4, that can be used in the conversion or degradation of lignocellulosic material. The invention also provides methods for degradation and/or conversion of lignocellulosic material. The origin of the lignocellulosic material of the present invention is preferably biomass in the form of low-cost by-products from gardening, agriculture, forestry, the timber industry and the like; thus, for example, materials such as straw, maize stems, forestry waste (log slash, bark, small branches, twigs and the like), sawdust and wood-chips are all materials which can be degraded or converted to lower order sugars, such as monosaccharide sugars according to the present invention. Thus, according to the present invention the lignocellulosic material may be obtained from agricultural residues such as straw, maize stems, corn fibers and husk, forestry waste such as sawdust and/or wood-chips, and/or from energy crops such as willow, yellow poplar and/or switch grass. Thus, the lignocellulosic material may be obtained from for example, but not limited to, straw, maize stems, corn fibers, husk, sawdust, wood-chips, willow, yellow poplar and/or switch grass. A cellulosic material to be used in accordance with the present invention is any available carbon source such as for example biomass, including plant biomass and complex plant biomass, such as e.g. plant cell wall constituents. The polypeptide, recombinant host cells, and/or microorganisms (*Aspergillus saccharolyticus*) of the present invention is preferably capable of degrading one or more plant cell wall constituents selected from the group consisting of cellulose, hemicellulose, pectin, and lignin. Accordingly, the carbon source preferably comprises at least one of, preferably at least two of, more preferably at least three of, yet more preferably all of the plant cell wall constituents selected from the group consisting of cellulose, hemicellulose, pectin, and lignin. Thus, the microorganism is preferably capable of degrading at least one or more selected from the group consisting of cellulose, hemicellulose, cellobiose, cellodextrin and pectin, more preferably from the group consisting of cellobiose and cellodextrin, More preferably, the microorganism of the present invention, extracts thereof, and/or the polypeptide of the present invention is at least capable of degrading icellobiose. In another preferred embodiment, the microorganism of the present invention, extracts thereof, and/or the polypeptide of the present invention is capable of degrading cellodextrin.

Cellulose is the structural component of the primary cell wall of green plants, many forms of algae and the oomycetes. Some species of bacteria secrete it to form biofilms. Cellulose is the most common organic compound on Earth. About 33 percent of all plant matter is cellulose (the cellulose content of cotton is 90 percent and that of wood is 40-50 percent). Cellulose is a polysaccharide consisting essentially of polymerized glucose monomer units, in general cellulose is a linear chain of D-glucose monomer units linked by β-(1→4) bonds. The cellulose polysaccharide preferably consists of in the range of 300 to 15,000, for example in the range of 500 to 10,000 glucose monomer units. The enzymes utilized to cleave the glycosidic linkage in cellulose are glycoside hydrolases including endo-acting cellulases (glucanases) and exo-acting glucosidases. Such enzymes are usually secreted as part of multienzyme complexes that may include dockerins and cellulose binding modules.

Cellobiose is a disaccharide with the formula $[HOCH_2CHO(CHOH)_3]_2O$. The molecule is derived from the condensation of two glucose molecules linked in a β(1→4) bond.

Cellodextrin is classified by its degree of polymerization (DP) which indicates the number of linked glucose monomers it contains. Each glucose monomer is linked via a beta-1,4 glycosidic bond. The most common cellodextrins are cellobiose (DP=2)
cellotriose (DP=3)
cellotetrose (DP=4)
cellopentose (DP=5)
cellohexose (DP=6)

Thus, in a preferred embodiment the beta-glucosidase of the present invention is capable of degrading or converting a lignocellulosic material, preferably cellobiose and/or cellodextrin, recovering degraded lignocellulosic material in the form of glucose monomers.

Hemicellulose is the term used to denote non-cellulosic polysaccharides associated with cellulose in plant tissues. Hemicellulose frequently constitutes about 20-35% w/w of lignocellulosic materials, and the majority of hemicelluloses consists predominantly of polymers based on pentose (five-carbon) sugar units, such as D-xylose and D-arabinose units, although more minor proportions of hexose (six-carbon) sugar units, such as D-glucose and D-mannose units, are generally also present.

Lignin, which is a complex, cross-linked polymer based on variously substituted p-hydroxyphenylpropane units, generally constitutes about 10-30% w/w of lignocellulosic materials. It is believed that lignin functions as a physical barrier to the direct bioconversion (e.g. by fermenting microorganisms) of cellulose and hemicellulose in lignocellulosic materials which have not been subjected to some kind of pre-treatment process (which may very suitably be a wet-oxidative process as described in relation to the present invention) to disrupt the structure of lignocellulose.

To minimise the production cost of generating a sugar platform in the biorefinery for biofuel and chemicals produced from biomass it is important to use biomass in the form of low-cost by-products from gardening such as garden refuse, waste materials from agriculture, forestry, the timber industry and the like. Thus, processes of the invention are applicable to any kind of cellulose-containing lignocellulosic materials, Relevant materials thus include wooden or non-wooden plant material in the form of stem, stalk, shrub, foliage, bark, root, shell, pod, nut, husk, fibre, vine, straw, hay, grass, bamboo or reed, singularly or in a mixture.

Preferred lignocellulosic materials in the context of the invention include but are not limited to wood (both softwood and hardwood), straw, corn stovers and so-called hulls. Wood employed in the context of the invention is generally heartwood (duramen) and/or outer wood (secondary xylem) derived from trunks, stems and/or branches of deciduous or evergreen trees or shrubs, Wood from the roots of such trees or shrubs may also be of value.

Useful sources of wood include numerous species of various genera of coniferous and broad-leaved trees/shrubs. Among conifers may be mentioned the following: Pinaceae, including pines (*Pinus* spp., such as *Pinus sylvestris*), silver firs (*Abies* spp., such as *Abies alba*), spruces (*Picea* spp., such as *Picea abies*), larches (*Larix* and *Pseudolarix* spp., such as *Larix decidua* and *L. kaempfen*) and Douglas fir (*Pseudotsuga menziesii*). Among broadleaves may be mentioned the following: Betulaceae, including birches (*Betula* spp., such as *Betula pendufa*); and Fagaceae, including beeches (*Fagus* spp., such as *Fagus sylvatica*) and oaks (*Quercus* spp., such as *Quercus robur*).

Useful sources of straw include in particular cereals (cereal grasses), i.e. gramineous plants which yield edible grain or seed. Straw from, for example, oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g. species of *Digitaria, Panicum, Paspalum, Pennisetum* or *Setana*), *sorghum* (*Sorghum* spp., including *S. bicolor* var. *durra* (also referred to as "*durra*") and *milo*), buckwheat (*Fagopyrum* spp., such as *F. esculentum*) and maize (also referred to as corn (*Zea mays*), including sweetcorn) is well suited for treatment according to the process of the invention.

As employed herein, the term "hull" generally denotes the outer covering, rind, shell, pod or husk of any fruit or seed, but the term as employed herein also embraces, for example, the outer covering of an ear of maize. Relevant hulls include hulls selected among the following: hulls from oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g. species of *Digiftaa, Panicum, Paspalum, Pennisetum* or *Setaria*), *sorghum* (*Sorghum* spp., including *S. bicolor* var. *durra* and *milo*), buckwheat (*Fagopyrum* spp., such as *F. esculentum*), maize [also known as corn (*Zea mays*), including sweetcorn], corn cob, rape-seed (from *Brassica* spp., such as *B. napus, B. napus* subsp. *rapifera* or *B. napus* subsp. *oleifera*), cotton-seed (from *Gossypium* spp., such as *G. heraceum*), almond (*Prunus dulcis*, including both sweet and bitter almond) and sunflower seed (*Helianthus* spp., such as *H. annuus*).

Hulls of cereals, including not only those mentioned among the above, but also hulls of cereals other than those mentioned among the above, are generally of interest in the context of the invention, and preferred hulls, such as oat hulls and barley hulls, belong to this category. In this connection it may be mentioned by way of example that oat hulls are often available in large quantities at low cost as a by-product of oat-processing procedures for the production of oatmeal, porridge oats, rolled oats and the like; thus, a total of around 75,000 tons of oat hulls is produced per year as a by-product of oat-processing in Denmark, Norway and Sweden together with northern Germany.

Other types of hulls of relevance in relation to processes of the invention include, for example, palm shells, peanut shells, coconut shells, other types of nut shells, and coconut husk.

It should be noted that the native physical form, bulk and/or dimensions of lignocellulosic materials such as wood, straw, hay and the like will generally necessitate, or at least make it desirable, to carry out comminution of the material (e.g. by milling, abrading, grinding, crushing, chopping, chipping or the like) to some extent in order to obtain particles, pieces, fibres, strands, wafers, flakes or the like of material of sufficiently small size and/or sufficiently high surface area to mass ratio to enable degradation of the material to be performed satisfactorily. In the case of wood, material of suitable dimensions will often be available as a waste product in the form of sawdust, wood chips, wood flakes, twigs and the like from sawmills, forestry and other commercial sources.

In contrast, numerous types of hulls, e.g. cereal grain or seed hulls in general, including oat hulls as employed in the working examples reported herein, have in their native form sufficiently small dimensions and a sufficiently high surface area to mass ratio to enable them to be used directly, without prior comminution, as lignocellulosic materials in a process according to the present invention.

According to the present invention, a microorganism, an extract or broth from the microorganism, or a polypeptide is considered capable of degrading cellulose and/or cellodextrins, such as cellobiose, when it is capable of degrading at least 50%, preferably at least 60%, more preferably at least 70%, yet more preferably at least 80%, yet more preferably at least 90% of provided cellulose and/or cellodextrins, such as cellobiose to monomers or oligomers of glucose, wherein oligomers of glucose consists of in the range of 2 to 8 glucosidic monomers. The microorganism may be capable of further degrading glucose or oligomers of glucose and for example use said glucose as carbon source for growth and/or acid or acid derivative synthesis.

Hemicellulose may comprise monosaccharide units selected from the group consisting of glucose, xylose, mannose, galactose, rhamnose and arabinose, more preferably hemicellulose comprises at least glucose and xylose. In general the hemicellulose polysaccharide consists of in the range of 100 to 300, such as 150 to 250 monosaccharide monomer units.

According to the present invention, a microorganism, an extract or broth from the microorganism, or a polypeptide is considered capable of degrading hemicellulose, when it is capable of degrading at least 50%, preferably at least 60%, more preferably at least 70%, yet more preferably at least 80%, yet more preferably at least 90% of provided hemicellulose to monosaccharide monomers or oligosaccharides, wherein oligosaccharides consists of in the range of 2 to 8 monosaccharide monomers. The nature of said monosaccharide monomers depend on the particular hemicellulose, but may in general be selected from the group consisting of glucose, xylose, mannose, galactose, rhamnose and arabinose. The microorganism may be capable of further degrading said monosaccharides or oligosaccharides and for example use said monosaccharides or oligosaccharides as carbon source for growth and/or acid or acid derivative synthesis. Thus, it is preferred that in addition to the capability of degrading hemicellulose, the genetically modified microorganisms of the present invention also are capable of degrading one or more selected from the group consisting of glucose, xylose, mannose, galactose, rhamnose and arabinose, in particular it is preferred that the genetically modified microorganisms of the present invention at least are capable of further degrading glucose and xylose and for example use said monosaccharide as carbon source for growth and/or acid or acid derivative synthesis.

Pectin is a polysaccharide consisting of different monosaccharide monomer units, wherein at least some the monosaccharides may be sugar acids. Thus, pectin may be considered a heteropolysaccharide. Preferably, pectin according to the present invention may comprise monosaccharide units selected from the group consisting of galacturonic acid, rhamnose, xylose, galactose and arabinose, more preferably pectin comprises at least galacturonic acid and rhamnose. The galacturonic acid may be esterified, for example with a short alkyl-, preferably methyl-group. The galacturonic acid may also be present in the form of a salt, with any useful cation, for example sodium, potassium or calcium. In general pectin has a size of in the range of 60 to 130,000 g/mol.

According to the present invention, a microorganism, an extract from the microorganism, or a polypeptide is considered capable of degrading pectin, when it is capable of degrading at least 50%, preferably at least 60%, more preferably at least 70%, yet more preferably at least 80%, yet more preferably at least 90% of provided pectin to monosaccharides or oligosaccharides, wherein oligosaccharides consists of in the range of 2 to 8 monosaccharides. The monosaccharides may for example be sugars, sugar acids or esters or salts thereof. Thus, the monosaccharides may for example be selected from the group consisting of galacturonic acid, rhamnose, xylose, galactose and arabinose. The microorganism may be capable of further degrading the monosaccharides and/or oligosaccharides and for example use said monosaccharides and/or oligosaccharides as carbon source for growth and/or acid or acid derivative synthesis.

Lignin is a large polymer which is abundant in plant biomass and it is an integral part of the cell walls of plants. Lignins are very diverse in structure and according to the present invention lignin may be any naturally occurring lignin. Preferably, lignin comprises one or more different monomer units (also referred to as monolignol) selected from the group consisting of p-coumaryl alcohol, coniferyl alcohol, sinapyl alcohol and any of the aforementioned substituted with one or more lower alkoxy, preferably methoxy. Preferably, said monomer units are incorporated into the lignin polymer in the form of phenylpropanoid p-hydroxyphenyl, guaiacyl, syringal and any of the aforementioned substituted with one or more lower alkoxy, preferably methoxy, respectively. In addition to the aforementioned monomer units, lignin may comprise other monolignols. Lignin may be covalently linked to hemicellulose and/or cellulose. In particular, lignin may be covalently bonded to hemicellulose via infrequent linkages to the hemicellulose chains. Alternatively, lignin may be associated with hemicellulose and/or cellulose for example through hydrogen bonding. A complex (covalently bound and/or associated by means of hydrogen bonding) of lignin, hemicellulose and cellulose is also referred to as lignocellulosic complexes herein.

According to the present invention, a microorganism or a polypeptide is considered capable of degrading lignin, when it is capable of degrading at least 40%, preferably at least 50%, more preferably at least 60%, yet more preferably at least 65%, for example at least 70%, such as at least 80% of provided lignin to mono components derived from lignins or to oligomers of in the range of 2 to 8 monolignols. The microorganism may be capable of further degrading said monolignols or said oligomers and for example use said monolignols as carbon source for growth and/or acid or acid derivative synthesis.

The carbon source preferably comprises at least one, preferably at least two, more preferably at least three, even more preferably at least four, for example all of the plant cell wall constituents selected from the group consisting of cellulose, hemicellulose, cellobiose, cellodextrin and pectin. Thus, the microorganism is preferably capable of degrading at least one or more selected from the group consisting of cellulose, hemicellulose, cellobiose, cellodextrin and pectin, more preferably from the group consisting of cellobiose and cellodextrin. More preferably, the microorganism of the present invention, extracts thereof, polypeptide of the present invention is at least capable of degrading cellobiose. In another preferred embodiment, the microorganism of the present invention, extracts thereof, polypeptide of the present invention is capable of degrading cellodextrin. Aforementioned plant cell wall constituents may be provided in a purified form or a partly purified form, however, frequently they will be provided in the form of plant biomass (see below).

In addition to the plant cell wall constituents the carbon source may comprise other components, in particular it is comprised within the scope of the present invention that the carbon source may comprise additional polysaccharides, such as e.g. starch. The carbon source may also comprise chitin. Starch is a polysaccharide consisting essentially of polymerized glucose monomer units. Starch is in general made up by a mixture of amylose and amylopectin. Amylose is a polymer of glucose linked mainly by $\alpha(1\rightarrow4)$ bonds and amylopectin is a branched polymer of glucose linked in a linear way with $\alpha(1\rightarrow4)$ bonds and with branching taking place with $\alpha(1\rightarrow6)$ bonds occurring approximately at every 24 to 30 glucose units.

In one embodiment of the invention where the carbon source further comprises a polysaccharide as e.g. starch, the microorganism is capable of degrading at least 50%, preferably at least 60%, more preferably at least 70%, yet more preferably at least 80%, yet more preferably at least 90% of provided polysaccharide as e.g. starch to monomers or oligomers of glucose, wherein oligomers of glucose consists of in the range of 2 to 8 glucosidic monomers. The microorganism may be capable of further degrading glucose or oligomers of glucose and for example use said glucose as carbon source for growth and/or acid or acid derivative synthesis.

In a very preferred embodiment of the invention the carbon source is a complex carbon source, such as a carbon source comprising complex plant material, wherein said complex plant material may be plant biomass. In particular crude plant biomass is considered a complex plant material according to the present invention. In particular for industrial scale production of microbial oil for example for preparing bioethanol it is preferred that the carbon source is plant biomass. In this way, the methods of the present invention may serve to substitute conventional oil refineries by producing similar or identical products on the basis of plant biomass in stead of oil. Said plant biomass is readily available in the form of agricultural or forestry wastes. In general agricultural or forestry wastes comprise or more preferably even consist mainly of lignocellulosic complexes and starch. Thus, the carbon source may be plant biomass for example wood residues, paper waste, agricultural residues or energy crops, which all comprises one or more plant cell wall constituents. Wood residues may for example be forestry waste, saw mill waste and/or paper mill waste. Paper waste may be any discarded paper, such as discarded paper collected from households and/or businesses, such as industry. Agricultural residues may be any plant material obtained as a product of agriculture, and thus agricultural residues may for example be any cultivated plant or parts thereof. Preferably, agricultural residues is agricultural waste, such as waste from cereal crops, for example stalks, straw and/or leaves from cereal crops, wherein cereal crops for example may be selected from the group consisting of barley, wheat, millet, maize, rice, *sorghum*, oats, rye, triticale, buckwheat, fonio and quinoa. Agricultural waste may also be bagasse, for example bagasse from sugar production, such as sugar cane bagasse. Agricultural waste may also be waste from the production of vegetable oils, such as soybean oil, palm oil, peanut oil, rape seed oil, olive oil, grape seed oil or sunflower oil, preferably waste from production of palm oil, Waste from oil production, such as palm oil production may include fibers, kernel shells and/or oil mill effluent. Energy crops includes any plant grown for exploitation of its energy content and are thus typically densely planted, high yielding crop species. Non-limiting examples include miscanthus, salix, populus, maize, sudangrass, millet, or white sweetclover. The carbon source may also be other organic waste, for example organic waste collected from house holds and/or industry. The carbon source may also be a mixture of one or more of the aforementioned.

In one embodiment it is preferred that the carbon source is not a plant product, which may be used for food or feed production. Preferably, the carbon source is not a plant product which may be used for food production.

The degradation of lignocellulosic complexes has been described for example in Kirk, T. K. and Cullen, D. in: Environmentally Friendly Technologies for the Pulp and Paper Industry; Young, R. A. and Akthar, M. eds. (1998) John Wiley & Sons ISBN 0-471-15770-8. Plant cell walls are a composite material having constituent parts for example cellulose, hemicellulose, lignin and pectin. With the exception of lignin these materials are polymerized carbohydrates with either C6 or C5-sugars or sugar acids as monomeric units. The long chains are branched at specific positions of the chains of the polymer.

The entire structure is rendered compact and semi-crystalline by crosslinking of the different polymer structures and by hydrogen-bonds giving the plant cell not only a turgor-resistant cell wall but also a barrier of defense against plant pathogens.

For any given process, such as an industrial process which uses a heterogeneous plant biomass as carbon source for the growth of the microorganism it is preferred that the enzymatic profile of the organism permits the degradation of a maximum of the available energy sources present in the given biomass. Thus, the preferred microorganism to be employed with the methods according to the present invention preferably are able to grow equally well on all major plant biomass constituents such as cellulose, hemi-cellulose, pectin, and lignin In one embodiment the carbon source is pretreated. This is in particular relevant when the carbon source is a complex plant material, such as any of the complex plant materials described herein above.

The carbon source, such as the complex plant material can be pretreated. Such pretreatments could be treatment with cellular extracts. It could be treatment with chemicals for example acids, alkali or oxygen, such as acid or alkali treatment of wood for wood saccharification. The pretreatment may also be a heat treatment. Said heat treatment may be performed alone (e.g. as in wood distillation) or in combination with acid, alkali and oxygen treatment. Such methods are for example used in the paper industry to separate cellulose from other wood constituents.

In one embodiment of the invention the carbon source is pretreated with enzymes capable of degrading lignocellulosic material extracted or purified from microorganisms, for example microorganisms like *Chrysosporium, Trichoderma, Aspergillus, Fusarium* and *Pencillium*. Preferably a complex carbon source containing one or more of cellulose, cellobiose, cellodextrin and/or pectin is pretreated with a multi-enzyme product comprising enzymes e.g. selected from hemicellulases and cellulases, prepared as described by Magnuson et al in WO 2008/008793, which is hereby incorporated by reference.

Polypeptide

The present invention relates to polypeptides with beta-glucosidase activity. Thus, the polypeptides provided herein are capable of hydrolyzing a glycosidic linkage in a polysaccharide. In specific embodiment, the polypeptide or a biologically active fragment thereof is encoded by a gene selected from the group consisting of SEQ ID NO: 1, 2, 5, 6, 8, 9, 11 and 12.

Thus the present invention relates in one aspect to an isolated polypeptide comprising
   a. an amino acid sequence consisting of SEQ NO: 3, 4, 7, 10, or 13,
   b. a biologically active sequence variant of SEQ NO: 3, 4, 7, 10, or 13, wherein the variant has at least 92% sequence identity to said SEQ NO: 3, 4, 7, 10, or 13, or
   c. a biologically active fragment of at least 30 consecutive amino acids of any of a) through b), wherein said fragment is a fragment of SEQ ID NO: 3, 4, 7, 10, or 13.

In a preferred embodiment the polypeptide originates from or is purified from *Aspergillus saccharolyticus*, characterised as deposit no.: CBS 127449$^T$.

The polypeptide of the invention has beta-glucosidase activity, and thus, the polypeptide of the invention is capable of hydrolyzing a β1-4 glucose-glucose linkage. Accordingly, the isolated polypeptide is capable of hydrolyzing cellobiose and/or other cellodextrins, such as cellotriose (DP=3), cellotetrose (DP=4), cellopentose (DP=5), or cellohexose (DP=6). The cellobiose and/or cellodextrins is preferably obtained from a lignocellulosic material originating from agricultural residues such as straw, maize stems, corn fibers and husk, forestry waste such as sawdust and/or wood-chips, and/or from energy crops such as willow, yellow poplar and/or switch grass.

The catalytic activity of the betaglucosidase (BGL) polypeptides of the present invention is higher, and more robust in terms of thermostability, pH activity, and pH stability than conventional BGL enzymes. For example, in one embodiment, a BGL polypeptide of the invention, such as the BGL1 polypeptide, has a specific activity, Vmax, of at least 20, such as at least 30, for example at least 40, for example at least 50, such as at least 60 U/mg with cellobiose as substrate in hydrolysis. Preferably, the BGL polypeptide has a specific activity, Vmax, of at least 40, such as at least 45 U/mg with cellobiose as substrate in hydrolysis.

The half-life of the beta-glucosidase activity at 60° C. of a BGL polypeptide of the invention, such as the BGL1 polypeptide, is preferably at least 100 minutes, such as at least 150, such as at least 180, or at least 190, such as at least 200 minutes. In a preferred embodiment, the half-life of the beta-glucosidase activity at 60° C. is at least 200 minutes, such as at least 300 minutes, for example at least 400 minutes, such as at least 430, 440, or at least 450 minutes.

In one embodiment, at least 30%, such as at least 40, 50, 60, such as at least 70% of the beta-glucosidase activity of said polypeptide remains after 4 hours of incubation at 60° C. In a more preferred embodiment, at least 60%, such as at least 65% of the beta-glucosidase activity of said polypeptide remains after 4 hours of incubation at 60° C.

The polypeptide of the present invention may be a fragment of SEQ ID NO: 3, 7, 10, 13, wherein the polypeptide fragment is devoid of the signal peptide, wherein said polypeptide for example for BGL1 is SEQ ID NO: 4. The position of the signal peptides for BGL1-4 are indicated in the sequences herein below.

Biologically Active Variant of Polypeptides

A biologically active variant of a polypeptide of a given sequence within the present invention is a polypeptide sharing at least some sequence identity with the given sequence and which shares at least one function. For enzymes, that function is preferably the capability to catalyse the reaction catalysed by the particular enzyme.

Evolutionary conservation between polypeptides of different closely related species, e.g. assessed by sequence alignment, can also be used to pinpoint the degree of evolutionary pressure on individual residues. Preferably, polypeptide sequences from at least 2, preferably at least 3, more preferably at least four different species where the function of the polypeptide is conserved are compared, for example from different species of fungi. Conserved residues are more likely to represent essential amino acids that cannot easily be substituted than residues that change between species. For example, such an alignment may be performed using ClustalW from EMBL-EBI. It is evident from the above that a reasonable number of modifications or alterations of a polypeptide sequence does not interfere with the activity of a given polypeptide. Thus, preferably, functional homologues of a given polypeptide comprise all residues, which are conserved between at least 4, such as at least 3, for example at least 2 different species. Functional homologues may thus comprise one or more amino acid substitutions at residues, which are not conserved between at least 4, such as at least 3, for example at least 2 different species.

Functional homologues may also be identified by DNA shuffling such as for example described in WO 95/22625, Stemmer, W. and Crameri: A DNA Mutagenesis by Random Fragmentation and Reassembly, and be prepared by conventional molecular biology techniques.

Biologically active as described herein means that the polypeptide, variant or fragment thereof is able to degrade or convert lignocellulosic material, preferably cellobiose, into monomeric glucose units. The ability to degrade or convert lignocellulosic material is determined in a beta-glucosidase assay. In this work specific activity is defined as units per amount of total protein.

Biologically active variants may also be defined with reference to the biological assays described in the examples. A preferred biological activity is the ability of the polypeptide to act as a beta-glucosidase, being capable of hydrolysing a glycosidic linkage in a polysaccharide, see elsewhere herein.

As used herein "variant" refers to polypeptides or proteins which are homologous to a polypeptide, for example beta-glucosidase/BGL-genes (such as BGL1, SEQ ID NO.: 3, BGL2: SEQ ID NO: 7, BGL3, SEQ ID NO: 10, and BGL4, SEQ ID NO: 13), but which differs from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide.

A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Within the meaning of the term "conservative amino acid substitution" as applied herein, one amino acid may be substituted for another within the groups of amino acids indicated herein below:

Lower Levels of Similarity:

Polarity:

i) Amino acids having polar side chains (Asp, Glu, Lys, Arg, His, Asn, Gln, Ser, Thr, Tyr, and Cys)

ii) Amino acids having non-polar side chains (Gly, Ala, Val, Leu, Ile, Phe, Trp, Pro, and Met)

Hydrophilic or Hydrophobic:

iii) Hydrophobic amino acids (Ala, Cys, Gly, Ile, Leu, Met, Phe, Pro, Trp, Tyr, Val)

iv) Hydrophilic amino acids (Arg, Ser, Thr, Asn. Asp, Gln, Glu, His, Lys)

Charges:

v) Neutral amino acids (Ala, Asn. Cys, Gln, Gly, Ile, Leu, Met, Phe, Pro, Ser, Thr, Trp, Tyr, Val)

vi) Basic amino acids (Arg. His, Lys)

vii) Acidic amino acids (Asp, Glu)

High Level of Similarity:

viii) Acidic amino acids and their amides (Gln, Asn, Glu, Asp)

ix) Amino acids having aliphatic side chains (Gly, Ala Val, Leu, Ile)

x) Amino acids having aromatic side chains (Phe, Tyr, Trp)

xi) Amino acids having basic side chains (Lys, Arg, His)

xii) Amino acids having hydroxy side chains (Ser. Thr)

xiii) Amino acids having sulphor-containing side chains (Cys. Met).

Substitutions within the following groups ('strong' conservation group) are to be regarded as conservative substitutions within the meaning of the present invention

-STA, NEQK, NHQK, NDEQ, QHRK, MILV, MILF, HY, FYW.

Substitutions within the following groups ('weak' conservation group) are to be regarded as semi-conservative substitutions within the meaning of the present invention

-CSA, ATV, SAG, STNK, STPA, SGND, SNDEQK, NDEQHK, NEQHRK, VLIM, HFY.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

Both standard and non standard amino acid residues described herein can be in the "D" or or "L" isomeric form.

It is contemplated that a functional equivalent according to the invention may comprise any amino acid including non-standard amino acids. In preferred embodiments a functional equivalent comprises only standard amino acids.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Suitably variants of SEQ ID NO: 3, 4, 7, 10, and 13 are variants having at least 73%, such as at least 74%, for example at least 75%, such as at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with any one of SEQ ID No: 3, 4, 7, 10, and 13 or fragments thereof, such as fragments of at least 30 amino acids, for example any fragments of 30-300 amino acids or 300-600, or 600-850 amino acids.

Suitably variants are variant(s) of SEQ ID NO: 4, which is a preferred fragment of SEQ ID NO: 3 are variants having at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 4, or fragments thereof, such as fragments of at least 30 amino acids, for example any fragments of 30-300 amino acids or 300-600, or 600-850 amino acids.

Suitably variants are variant(s) of BGL1 are variants having at least 91%, such as preferably at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 3 or fragments thereof, such as fragments of at least 30 amino acids, for example any fragments of 30-300 amino acids or 300-600, or 600-850 amino acids. One suitable variant of BGL1 is a variant devoid of the signal peptide. Thus in one embodiment, the polypeptide of the present invention has at least 91%, such as preferably at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with amino acids 20-860 of SEQ ID No: 3, which corresponds to SEQ ID NO: 4, or fragments thereof, such as fragments of at least 30 amino acids, for example any fragments of 30-300 amino acids or 300-600, or 600-850 amino acids.

Suitably variants are variant(s) of BGL2 are variants having at least 73%, such as preferably at least 74%, for example at least 75%, such as at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 7, or fragments thereof, such as fragments of at least 30 amino acids, for example any fragments of 30-300 amino acids or 300-600, or 600-850 amino acids. One suitable variant of BGL2 is a variant devoid of the signal peptide. Thus in one embodiment, the polypeptide of the present invention has at least 73%, such as preferably at least 74%, for example at least 75%, such as at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with amino acids 21-866 of SEQ ID No: 7, or fragments thereof, such as fragments of at least 30 amino acids, for example any fragments of 30-300 amino acids or 300-600, or 600-850 amino acids.

Suitably variants are variant(s) of BGL3 are variants having at least 75%, such as preferably at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 10 or fragments thereof, such as fragments of at least 30 amino acids, for example any fragments of 30-300 amino acids or 300-600, or 600-850 amino acids. One suitable variant of BGL3 is a variant devoid of the signal peptide. Thus in one embodiment, the polypeptide of the present invention has at least at least 75%, such as preferably at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with amino acids 21-722 of SEQ ID No: 10 or fragments thereof, such as fragments of at least 30 amino acids, for example any fragments of 30-300 amino acids or 300-600, or 600-850 amino acids.

Suitably variants are variant(s) of BGL4 are variants having at least 78%, such as preferably at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 13 or fragments thereof, such as fragments of at least 30 amino acids, for example any fragments of 30-300 amino acids or 300-600, or 600-850 amino acids. One suitable variant of BGL4 is a variant devoid of the signal peptide. Thus in one embodiment, the polypeptide of the present invention has at least at least 78%, such as preferably at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with amino acids 20-766 of SEQ ID No: 13 or fragments thereof, such as fragments of at least 30 amino acids, for example any fragments of 30-300 amino acids or 300-600, or 600-850 amino acids.

The polypeptide fragment according to the invention is a fragment, wherein the fragment has a stretch of at least 30 consecutive amino acids and contains less than 860 amino acids residues of SEQ ID NO: 3, or at least 30 consecutive amino acids and less than 866 amino acids residues of SEQ ID NO: 7, or at least 30 consecutive amino acids and less than 722 amino acids residues of SEQ ID NO: 10, or at least 30 consecutive amino acids and less than 766 amino acids residues of SEQ ID NO: 13. So in general, a polypeptide fragment according to the invention is a fragment, wherein the fragment has a stretch of at least 30 consecutive amino acids and contains less than 800 consecutive amino acid residues of any one of SEQ ID NO: 3, 4, 7, 10, and 13, such as less than 800 consecutive amino acid residues, such as less than 795 consecutive amino acid residues, e.g. less than 790 consecutive amino acid residues, such as less than 785 consecutive amino acid residues, e.g. less than 780 consecutive amino acid residues, such as less than 770 consecutive amino acid residues, e.g. less than 760 consecutive amino acid residues, such as less than 750 consecutive amino acid residues, e.g. less than 745 consecutive amino acid residues, such as less than 740 consecutive amino acid residues, e.g. less than 735 consecutive amino acid residues, such as less than 730 consecutive amino acid residues, e.g. less than 725 consecutive amino acid residues, such as less than 720 consecutive amino acid residues, such as less than 715 consecutive amino acid residues, e.g. less than 390 consecutive amino acid residues, such as less than 710 consecutive amino acid residues, e.g. less than 705 consecutive amino acid residues, such as less than 700 consecutive amino acid residues. e.g. less than 690 consecutive amino acid residues, such as less than 685 consecutive amino acid residues, e.g. less than 680 consecutive amino acid residues, such as less than 675 consecutive amino acid residues, e.g. less than 670 consecutive amino acid residues, such as less than 650 consecutive amino acid residues, e.g. less than 645 consecutive amino acid residues, such as less than 640 consecutive amino acid residues, e.g. less than 635 consecutive amino acid residues, such as less than 630 consecutive amino acid residues, e.g. less than 625 consecutive amino acid residues, such as less than 620 consecutive amino acid residues, such as less than 615 consecutive amino acid residues, such as less than 610 consecutive amino acid residues, e.g. less than 605 consecutive amino acid residues, such as less than 600 consecutive amino acid residues, e.g. less than 590 consecutive amino acid residues, such as less than 585 consecutive amino acid residues. e.g. less than 580 consecutive amino acid residues, such as less than 575 consecutive amino acid residues, e.g. less than 570 consecutive amino acid residues, such as less than 565 consecutive amino acid residues, such as less than 560 consecutive amino acid residues, e.g. less than 555 consecutive amino acid residues, such as less than 550 consecutive amino acid residues, e.g. less than 545 consecutive amino acid residues, such as less than 540 consecutive amino acid residues, e.g. less than 535 consecutive amino acid residues, such as less than 530 consecutive amino acid residues, e.g. less than 525 consecutive amino acid residues, such as less than 520 consecutive amino acid residues, such as less than 515 consecutive amino acid residues, e.g. less than 490 consecutive amino acid residues, such as less than 485 consecutive amino acid residues, e.g. less than 480 consecutive amino acid residues, such as less than 475 consecutive amino acid residues, e.g. less than 470 consecutive amino acid residues, such as less than 465 consecutive amino acid residues, such as less than 460 consecutive amino acid residues, e.g. less than 455 consecutive amino acid residues, such as less than 450 consecutive amino acid residues, e.g. less than 445 consecutive amino acid residues, such as less than 440 consecutive amino acid residues, e.g. less than 435 consecutive amino acid residues, such as less than 430 consecutive amino acid residues, e.g. less than 425 consecutive amino acid residues, such as less than 420 consecutive amino acid residues, such as less than 415 consecutive amino acid residues, such as less than 410 consecutive amino acid residues, e.g. less than 405 consecutive amino acid residues, such as less than 400 consecutive amino acid residues, e.g. less than 410 consecutive amino acid residues of, such as less than 400 consecutive amino acid residues, such as less than 395 consecutive amino acid residues, e.g. less than 390 consecutive amino acid residues, such as less than 385 consecutive amino acid residues, e.g. less than 380 consecutive amino acid residues, such as less than 370 consecutive amino acid residues, e.g. less than 360 consecutive amino acid residues, such as less than 350 consecutive amino acid residues, e.g. less than 345 consecutive amino acid residues, such as less than 340 consecutive amino acid residues, e.g. less than 335 consecutive amino acid residues, such as less than 330 consecutive amino acid residues, e.g. less than 325 consecutive amino acid residues, such as less than 300 consecutive amino acid residues, e.g. less than 295 consecutive amino acid residues, such as less than 290 consecutive amino acid residues, e.g. less than 285 consecutive amino acid residues, such as less than 280 consecutive amino acid residues, e.g. less than 275 consecutive amino acid residues, such as less than 270 consecutive amino acid residues, e.g. less than 265 consecutive amino acid residues, such as less than 260 consecutive amino acid residues, such as less than 255 consecutive amino acid residues, e.g. less than 250 consecutive amino acid residues, such as less than 245 consecutive amino acid residues, e.g. less than 240 consecutive amino acid residues, such as less than 235 consecutive amino acid residues, e.g. less than 230 consecutive amino acid residues, such as less than 225 consecutive amino acid residues, such as less than 220 consecutive amino acid residues, such as less than 215 consecutive amino acid residues, e.g. less than 210 consecutive amino acid residues, such as less than 205 consecutive amino acid residues, e.g. less than 200 consecutive amino acid residues, such as less than 195 consecutive amino acid residues, e.g. less than 190 consecutive amino acid residues, such as less than 185 consecutive amino acid residues, e.g. less than 180 consecutive amino acid residues, such as less than 175 consecutive amino acid residues, e.g. less than 170 consecutive amino acid residues, such as less than 165 consecutive amino acid residues, e.g. less than 160 consecutive amino acid residues, such as less than 155 consecutive amino acid residues, e.g. less than 150 consecutive amino acid residues, such as less than 145 consecutive amino acid residues, e.g. less than 140 consecutive amino acid residues, such as less than 135 consecutive amino acid residues, e.g. less than 130 consecutive amino acid residues, such as less than 125 consecutive amino acid residues, e.g. less than 120 consecutive amino acid residues, such as less than 115 consecutive amino acid residues, e.g. less than 110 consecutive amino acid residues, such as less than 105 consecutive amino acid residues, e.g. less than 100 consecutive amino acid residues, such as less than 95 consecutive amino acid residues, e.g. less than 90 consecutive amino acid residues, such as less than 85 consecutive amino acid residues, e.g. less than 80 consecutive amino acid residues, such as less than 75, e.g. less than 60 consecutive amino acid residues, such as less than 50 consecutive amino acids, e.g. less than 40 consecutive amino acids of SEQ ID NO: 3, 4, 7, 10, and 13.

The polypeptide variant according to the present invention, is a variant of SEQ ID NO: 3, 4, 7, 10, and 13 having at least 73%, such as preferably at least 74%, for example at least 75%, such as at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as preferably at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity to any one of said SEQ ID NO: 3, 4, 7, 10 and 13, or a fragment thereof. The polypeptide according to the present invention is a variant, wherein the polypeptide variant fragment contains less than 99.5%, such as less than 98%, e.g. less than 97%, such as less than 96%, e.g. less than 95%, such as less than 94%, e.g. less than 93% of the amino acid residues of any one of SEQ ID NO: 3, 4, 7, 10 and 13, or a fragment thereof.

In one embodiment of the present invention the polypeptide variant fragment contains less than 810 consecutive amino acid residues of any one of SEQ ID NO: 3, 4, 7, 10 and 13, or a fragment thereof, such as less than 800 consecutive amino acid residues, such as less than 795 consecutive amino acid residues, e.g. less than 790 consecutive amino acid residues, such as less than 785 consecutive amino acid residues, e.g. less than 780 consecutive amino acid residues, such as less than 770 consecutive amino acid residues, e.g. less than 760 consecutive amino acid residues, such as less than 750 consecutive amino acid residues, e.g. less than 745 consecutive amino acid residues, such as less than 740 consecutive amino acid residues, e.g. less than 735 consecutive amino acid residues, such as less than 730 consecutive amino acid residues, e.g. less than 725 consecutive amino acid residues, such as less than 720 consecutive amino acid residues, such as less than 715 consecutive amino acid residues, e.g. less than 390 consecutive amino acid residues, such as less than 710 consecutive amino acid residues, e.g. less than 705 consecutive amino acid residues, such as less than 700 consecutive amino acid residues, e.g. less than 690 consecutive amino acid residues, such as less than 685 consecutive amino acid residues, e.g. less than 680 consecutive amino acid residues, such as less than 675 consecutive amino acid residues, e.g. less than 670 consecutive amino acid residues, such as less than 650 consecutive amino acid residues, e.g. less than 645 consecutive amino acid residues, such as less than 640 consecutive amino acid residues, e.g. less than 635 consecutive amino acid residues, such as less than 630 consecutive amino acid residues, e.g. less than 625 consecutive amino acid residues, such as less than 620 consecutive amino acid residues, such as less than 615 consecutive amino acid residues, such as less than 610 consecutive amino acid residues, e.g. less than 605 consecutive amino acid residues, such as less than 600 consecutive amino acid residues, e.g. less than 590 consecutive amino acid residues, such as less than 585 consecutive amino acid residues, e.g. less than 580 consecutive amino acid residues, such as less than 575 consecutive amino acid residues, e.g. less than 570 consecutive amino acid residues, such as less than 565 consecutive amino acid residues, such as less than 560 consecutive amino acid residues, e.g. less than 555 consecutive amino acid residues, such as less than 550 consecutive amino acid residues, e.g. less than 545 consecutive amino acid residues, such as less than 540 consecutive amino acid residues, e.g. less than 535 consecutive amino acid residues, such as less than 530 consecutive amino acid residues, e.g. less than 525 consecutive amino acid residues, such as less than 520 consecutive amino acid residues, such as less than 515 consecutive amino acid residues, e.g. less than 490 consecutive amino acid residues, such as less than 485 consecutive amino acid residues, e.g. less than 480 consecutive amino acid residues, such as less than 475 consecutive amino acid residues, e.g. less than 470 consecutive amino acid residues, such as less than 465 consecutive amino acid residues, such as less than 460 consecutive amino acid residues, e.g. less than 455 consecutive amino acid residues, such as less than 450 consecutive amino acid residues, e.g. less than 445 consecutive amino acid residues, such as less than 440 consecutive amino acid residues, e.g. less than 435 consecutive amino acid residues, such as less than 430 consecutive amino acid residues, e.g. less than 425 consecutive amino acid residues, such as less than 420 consecutive amino acid residues, such as less than 415 consecutive amino acid residues, such as less than 410 consecutive amino acid residues of any one of SEQ ID NO: 3, 4, 7, 10 and 13, or a fragment thereof, such as less than 400 consecutive amino acid residues, such as less than 395 consecutive amino acid residues, e.g. less than 390 consecutive amino acid residues, such as less than 385 consecutive amino acid residues, e.g. less than 380 consecutive amino acid residues, such as less than 370 consecutive amino acid residues, e.g. less than 360 consecutive amino acid residues, such as less than 350 consecutive amino acid residues, e.g. less than 345 consecutive amino acid residues, such as less than 340 consecutive amino acid residues, e.g. less than 335 consecutive amino acid residues, such as less than 330 consecutive amino acid residues, e.g. less than 325 consecutive amino acid residues, such as less than 300 consecutive amino acid residues, e.g. less than 295 consecutive amino acid residues, such as less than 290 consecutive amino acid residues, e.g. less than 285 consecutive amino acid residues, such as less than 280 consecutive amino acid residues, e.g. less than 275 consecutive amino acid residues, such as less than 270 consecutive amino acid residues, e.g. less than 265 consecutive amino acid residues, such as less than 260 consecutive amino acid residues, such as less than 255 consecutive amino acid residues, e.g. less than 250 consecutive amino acid residues, such as less than 245 consecutive amino acid residues, e.g. less than 240 consecutive amino acid residues, such as less than 235 consecutive amino acid residues, e.g. less than 230 consecutive amino acid residues, such as less than 225 consecutive amino acid residues, such as less than 220 consecutive amino acid residues, such as less than 215 consecutive amino acid residues, e.g. less than 210 consecutive amino acid residues, such as less than 205 consecutive amino acid residues, e.g. less than 200 consecutive amino acid residues, such as less than 195 consecutive amino acid residues, e.g. less than 190 consecutive amino acid residues, such as less than 185 consecutive amino acid residues, e.g. less than 180 consecutive amino acid residues, such as less than 175 consecutive amino acid residues, e.g. less than 170 consecutive amino acid residues, such as less than 165 consecutive amino acid residues. e.g. less than 160 consecutive amino acid residues, such as less than 155 consecutive amino acid residues, e.g. less than 150 consecutive amino acid residues, such as less than 145 consecutive amino acid residues, e.g. less than 140 consecutive amino acid residues, such as less than 135 consecutive amino acid residues, e.g. less than 130 consecutive amino acid residues, such as less than 125 consecutive amino acid residues, e.g. less than 120 consecutive amino acid residues, such as less than 115 consecutive amino acid residues, e.g. less than 110 consecutive amino acid residues, such as less than 105 consecutive amino acid residues, e.g. less than 100 consecutive amino acid residues, such as less than 95 consecutive amino acid residues, e.g. less than 90 consecutive amino acid residues, such as less than 85 consecutive amino acid residues, e.g. less than 80 consecutive amino acid residues, such as less than 75, e.g. less than 60 consecutive amino acid residues, such as less than 50 consecutive amino acids, e.g. less than 40 consecutive amino acids of any one of SEQ ID NO: 3, 4, 7, 10 and 13, or a fragment thereof.

The term "fragment thereof" may refer to any portion of the given amino acid sequence of any one of SEQ ID NO: 3, 4, 7, 10 and 13. Fragments may comprise more than one portion from within a full-length protein (such as SEQ ID NO: 3, 7, 10, or 13), joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these. The deletion and/or the addition may—independently of one another—be a deletion and/or an addition within a sequence and/or at the end of a sequence.

A biologically active variant may be a deletion mutant of any one of SEQ ID NO: 3.4, 7, 10 and 13, sharing at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity to any one of SEQ ID NO: 3, 4, 7, 10 and 13.

Deletion mutants suitably comprise at least 20 or 40 consecutive amino acid and more preferably at least 80 or 100 consecutive amino acids in length. Accordingly such a fragment may be a shorter sequence of the sequence as identified by any one of SEQ ID NO: 3, 4, 7, 10 and 13, comprising at least 20 consecutive amino acids, for example at least 30 consecutive amino acids, such as at least 40 consecutive amino acids, for example at least 50 consecutive amino acids, such as at least 60 consecutive amino acids, for example at least 70 consecutive amino acids, such as at least 80 consecutive amino acids, for example at least 90 consecutive amino acids, such as at least 95 consecutive amino acids, such as at least 100 consecutive amino acids, such as at least 105 amino acids, for example at least 110 consecutive amino acids, such as at least 115 consecutive amino acids, for example at least 120 consecutive amino acids, wherein said deletion mutants preferably share at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with full length any one of SEQ ID NO: 3, 4, 7, 10 and 13.

It is preferred that biological active variant of any one of SEQ ID NO: 3, 4, 7, 10 and 13 comprises at the most 860, preferably at the most 850, more preferably at the most 840, even more preferably at the most 820, yet more preferably at the most 810, such as at the most 800, for example at the most 790, more preferably at the most 780, even more preferably at the most 770, at the most 760, preferably at the most 750, more preferably at the most 740, even more preferably at the most 720, yet more preferably at the most 710, such as at the most 700, for example at the most 690, more preferably at the most 680, even more preferably at the most 670, at the most 660, preferably at the most 650, more preferably at the most 640, even more preferably at the most 620, yet more preferably at the most 610, such as at the most 600, for example at the most 590, more preferably at the most 580, even more preferably at the most 570, at the most 560, preferably at the most 550, more preferably at the most 540, even more preferably at the most 520, yet more preferably at the most 510, such as at the most 500, for example at the most 490, more preferably at the most 480, even more preferably at the most 470, at the most 460, preferably at the most 450, more preferably at the most 440, even more preferably at the most 420, yet more preferably at the most 410, such as at the most 400, even more preferably at the most 300, yet more preferably at the most 200, such as at the most 175, for example at the most 160, such as at the most 150 amino acids, for example at the most 140 amino acids.

It is appreciated that a person skilled in the art will know how to make and assess 'conservative' amino acid substitutions, by which one amino acid is substituted for another with one or more shared chemical and/or physical characteristics. Conservative amino acid substitutions are less likely to affect the functionality of the protein.

SEQ ID NO: 3 defines the BGL1 polypeptide of the present invention. The signal peptide is underlined.

SEQ ID NO: 3

MRLSWLEAAALTAASVVSADELAFASPFYPSPWANGQGEWADAYKRAVDIVSQMTL

DEKVNLTTGTGWELEKCVGQTGGVPRLDIGGMCLQDSPLGVRDSDYNSGFPAGVNV

AATWDRKLAYLRGQAMGQEFSDKGVDVQLGPAAGPLGRSPDGGRNWEGFSPDPAL

TGVLFAETIKGIQDAGVIATAKHYILNEQEHFRQVSEAAGYGFNISDTISSNIDDKTIHEM

YLWPFADAVRAGVGAVMCSYNQINNSYACQNSYTLNKLLKSELGFQGFVMS*D*WGAH

-continued

HSGVGSALAGLDMSMPGDVSFDSATSFWGTNLTVAVLNGTVPQWRVDDMAVRIMA

AYYKVGRDRLYQPPNFSSWTRDEYGFKYYYSQEGPYEKVNQYVNVQRNHSEVIRKV

GADSTVLLKNNNALPLTGKERKVALIGEDAGSNAYGANGCSDRGCDNGTLAMAWGS

GTAEFPYLVTPEQAIQAEVLKNKGSTYTITDNWALSQVEALAKTASVSLVFVNADSG*E*

GYISVDGNEGDRNNLTLWKNGDNLIKATASNCNNTIVVIHSVGAVLVDEWYDHPNVTA

ILWAGLPGQESGNSLADVLYGRVNPGGKTPFTWGKTRASYGDYLVREPNNGHGAPQ

DNFSEGVFIDYRGFDKRNETPIYEFGHGLSYTTFNYSGLQVEVLNTSSSTPVATQTKP

APTFGEIGNASDYLYPEGLDRITAFIYPWLNSTDLKESSGDPDYGVDTAKYIPAGATNS

SAQPVLPAGGGFGGNPRLYDELIRVSVTVKNTGRVTGDAVPQLYVSLGGPNEPKVVL

RQFDRITLRPSEETVWTTTLTRRDLSNWDVAAQDWVITSYPKKVHVGSSSRQLPLHA

ALPKVQ

SEQ ID NO: 4 is the amino acid sequence of the BGL1 polypeptide without signal peptide.

SEQ ID NO: 4

DELAFASPFYPSPWANGQGEWADAYKRAVDIVSQMTLDEKVNLTTGTGW

ELEKCVGQTGGVPRLDIGGMCLQDSPLGVRDSDYNSGFPAGVNVAATWD

RKLAYLRGQAMGQEFSDKGVDVQLGPAAGPLGRSPDGGRNWEGFSPDPA

LTGVLFAETIKGIQDAGVIATAKHYILNEQEHFRQVSEAAGYGFNISDT

ISSNIDDKTIHEMYLWPFADAVRAGVGAVMCSYNQINNSYACQNSYTLN

KLLKSELGFQGFVMS*D*WGAHHSGVGSALAGLDMSMPGDVSFDSATSFW

GTNLTVAVLNGTVPQWRVDDMAVRIMAAYYKVGRDRLYQPPNFSS

WTRDEYGFKYYYSQEGPYEKVNQYVNVQRNHSEVIRKVGADSTVLLK

NNNALPLTGKERKVALIGEDAGSNAYGANGCSDRGCDNGTLAMAWGS

GTAEFPYLVTPEQAIQAEVLKNKGSTYTITDNWALSQVEALAKTASV

SLVFVNADSG*E*GYISVDGNEGDRNNLTLWKNGDNLIKATASNCNNTI

VVIHSVGAVLVDEWYDHPNVTAILWAGLPGQESGNSLADVLYGRVNP

GGKTPFTWGKTRASYGDYLVREPNNGHGAPQDNFSEGVFIDYRGFDK

RNETPIYEFGHGLSYTTFNYSGLQVEVLNTSSSTPVATQTKPAPTFG

EIGNASDYLYPEGLDRITAFIYPWLNSTDLKESSGDPDYGVDTAKYIPA

GATNSSAQPVLPAGGGFGGNPRLYDELIRVSVTVKNTGRVTGDAVPQLY

VSLGGPNEPKVVLRQFDRITLRPSEETVWTTTLTRRDLSNWDVAAQDWV

ITSYPKKVHVGSSSRQLPLHAAPKVQ

For the sequence shown above, amino acid residues shown in bold are involved in substrate binding Residues in italics are D (catalytic nucleophil) and E (catalytic acid residue). The amino acids that are underlined by ' . . . ' constitute the catalytic domain of the beta-glucosidase polypeptide BGL1. Within this region of the catalytic domain it is preferred that the amino acids are not changed. In another embodiment the amino acids of the region of the catalytic domain if changed are only substituted with conservative amino acids as described herein. In a preferred embodiment variants are variants, wherein variation is occurs outside amino acids D261 and/or E490. In another preferred embodiment variants are variants, wherein variation occurs outside the catalytic domain. In a more preferred embodiment variants, are variants, wherein variation occurs outside amino acids selected from the group consisting of D73, R137, R181, H171, Y229, M226, L122, W262, W49 and V55. It is appreciated that any single of the amino acids of the group constitutes separate preferred embodiments. Thus, variants are variants, wherein variation occurs outside amino acids D73, R137, R181, H171, Y229, M226, L122, W262, W49 or V55.

Measuring Activity of the Polypeptide

Specific beta-glucosidase activity was measured using two different substrates, pNPG and cellobiose. The assay using 5 mM p-nitrophenyl-beta-D-glucopyranoside (pNPG) (Sigma) as substrate for measuring beta-glucosidase activity was in 50 mM Na-Citrate buffer pH 4.8, 15 μl sample and 150 μl substrate was incubated at 50° C. for 10 min in 200 μl PCR tubes in a thermocycler (Biorad); 30 μl of the reaction was transferred to a microtiter plate already containing 50 μl 1M Na2CO3 for termination of the reaction. Absorbance was read at 405 nm in a plate reader (Dynex technology revalation 4.25). pNP (Sigma) was used to prepare a standard curve. One unit (U) of enzyme activity was defined as the amount of enzyme needed to hydrolyze 1 μmol pNPG in 1 minute. Protein quantification was done using the Pierce BCA protein assay kit microplate procedure according to manufacturer's instructions (Pierce Biotechnology); enzyme samples were assayed at different concentrations in triple determination to ensure substrate saturation in the assay.

The assay using 6 mM cellobiose was in 50 mM NaCitrate buffer pH 4.8 and was performed as follows: 15 μl sample and 150 μl substrate was incubated at 50° C. for 10 min in PCR tubes in a thermocycler (Bioread); 50 μl of the reaction was transferred to a HPLC vial already containing 1 ml 100 mM NaOH for termination of the reaction. The glucose concentration was measured by ion exchange chromatography at Dionex ICS3000 chromatography system equipped with an amperometric detector using a gold working electrode and an Ag/AgCl pH reference electrode, acquiring and interpreting data with the Chromeleon software (Dionex). 10 μl samples were run on a CarboPac PA1 column with 100 mM NaOH as eluent A and 0.5 M NaAcetate in 100 mM NaOH as eluent B, run at a flow rate of 1 ml/min. Gradient elution was performed: 0-20% eluent B (0.5M NaAcetate in 100 mM NaOH) in 13 min followed by 2 min washing with 50% eluent B and 5 min re-equilibrating with 100% eluent A (100 mM NaOH). Samples were assayed at different concentrations in triple determination to ensure substrate saturation in the assay.

For beta-glucosidase activity screening, three 0.5×0.5 cm squares were cut from PDA plates with 7 days old single fungal strains and incubated in liquid culture of 20 g/l wheat bran (Finax), 20 g/l corn steep liquor (Sigma), 3 g/l NaNO3, 1 g/l K2HPO4, 0.5 g/l KCl, 0.5 g/l MgSO47H2O, 0.01 g/l FeSO47H2O in a Falcon tube set-up with 10 ml of media shaking (180 rpm) at room temperature for another 7 days. The samples were centrifuged at 10,000 rpm for 10 min and the supernatants assayed for beta-glucosidase activity and protein content.

Enzymatic Activity of the Polypeptide

The polypeptide of the present invention has good thermostability compared to known beta-glucosidases. This makes the polypeptide suitable for incubation at higher temperatures than normally employed for degrading or converting lignocellulosic material into glucose due to the intolerance of increased temperatures by other enzymes present in the degradation cocktail as a cocktail of enzymes may be employed in order to obtain a complete hydrolysis of lignocellulosic material. It is appreciated that the beta-glucosidase polypeptide of the present invention is hydrolyzing a β1-4 glucose-glucose linkage In one embodiment the incubation temperature is in the range of 35° C. to 65° C., such as 40° C., preferably 41° C., more preferably 42° C., preferably 43° C., more preferably 44° C., preferably 45° C., more preferably 46° C., preferably 47° C., more preferably 48° C., preferably 49° C., more preferably 50° C. However, the incubation temperature may also be higher such as 51° C., for example 52° C., such as 53° C., for example 54° C., such as 55° C., for example 56° C., such as 58° C., for example 59° C., such as 60° C., for example 61° C., such as 62° C. for example 63° C., such as 64° C., for example 65° C., such as 66° C. for example 67° C.

The activity of the polypeptides of the present invention is maintained to a large extent even at elevated incubation temperatures. Thus, at 62° C. the activity of said polypeptide is 50% after 2 hours incubation.

The half life of the polypeptides of the present invention is preferably at least 1 hr at the selected temperature for incubation, preferably at least 1.5 hrs. more preferably at least 2 hrs, preferably at least 2.5 hrs, more preferably at least 3 hrs, preferably at least 3.5 hrs, more preferably at least 4 hrs, preferably at least 5.5 hrs, more preferably at least 6 hrs, preferably at least 6.5 hrs, more preferably at least 7 hrs, preferably at least 8 hrs, more preferably at least 9 hours, preferably at least 12 hours, more preferably at least 24 hours, preferably at least 2 days at 40° C.

The half life of the polypeptides of the present invention is preferably at least 1 hr at the selected temperature for incubation, preferably at least 1.5 hrs, more preferably at least 2 hrs, preferably at least 2.5 hrs, more preferably at least 3 hrs, preferably at least 3.5 hrs, more preferably at least 4 hrs, preferably at least 5.5 hrs, more preferably at least 6 hrs, preferably at least 6.5 hrs, more preferably at least 7 hrs, preferably at least 8 hrs, more preferably at least 9 hours, preferably at least 12 hours, more preferably at least 24 hours, preferably at least 2 days at 45° C.

The half life of the polypeptides of the present invention is preferably at least 1 hr at the selected temperature for incubation, preferably at least 1.5 hrs, more preferably at least 2 hrs, preferably at least 2.5 hrs, more preferably at least 3 hrs, preferably at least 3.5 hrs. more preferably at least 4 hrs. preferably at least 5.5 hrs, more preferably at least 6 hrs, preferably at least 6.5 hrs, more preferably at least 7 hrs, preferably at least 8 hrs, more preferably at least 9 hours, preferably at least 12 hours, more preferably at least 24 hours at 50° C.

The half life of the polypeptides of the present invention is preferably at least 1 hr at the selected temperature for incubation, preferably at least 1.5 hrs, more preferably at least 2 hrs, preferably at least 2.5 hrs, more preferably at least 3 hrs, preferably at least 3.5 hrs, more preferably at least 4 hrs, preferably at least 5.5 hrs, more preferably at least 6 hrs, preferably at least 6.5 hrs, more preferably at least 7 hrs, preferably at least 8 hrs, more preferably at least 9 hours, preferably at least 12 hours at 55° C.

The half life of the polypeptides of the present invention is preferably at least 1 hr at the selected temperature for incubation, preferably at least 1.5 hrs, more preferably at least 2 hrs, preferably at least 2.5 hrs, more preferably at least 3 hrs, preferably at least 3.5 hrs, more preferably at least 4 hrs, preferably at least 5.5 hrs, more preferably at least 6 hrs at 60° C.

The half life of the polypeptides of the present invention is preferably at least 1 hr at the selected temperature for incubation, preferably at least 1.5 hrs, more preferably at least 2 hrs, preferably at least 2.5 hrs at 62° C.

The half life of the polypeptides of the present invention is preferably at least 1 hr at the selected temperature for incubation at 65° C.

The half life of the polypeptides of the present invention is preferably at least 30 min, preferably at least 1 hr at the selected temperature for incubation at 66° C.

In particular, when the polypeptide of the invention is SEQ ID NO: 3, 4, or any functional fragment or variant thereof, as described elsewhere herein, the half-life of the beta-glucosidase activity at 60° C. is at least 200 minutes, for example 300 minutes, such as at least 360 minutes. Furthermore, when the polypeptide of the invention is SEQ ID NO: 3, 4, or any functional fragment or variant thereof, as described elsewhere herein, at least 50% of the beta-glucosidase activity of said polypeptide remains after 4 hours, such as 5 hours, for example after 6 hours of incubation at 60° C.

Also, when the polypeptide of the invention is SEQ ID NO: 3, 4, or any functional fragment or variant thereof, as described elsewhere herein, the specific activity, Vmax, of at least 40 U/mg with cellobiose as substrate in hydrolysis.

The activity of the enzyme in degrading or converting lignocellulosic material at temperatures as described herein incubating the enzyme with the cellulosic material for 2 hrs is at least 20%, preferably at least 30%, more preferably at least 40%, preferably at least 50%, more preferably at least 60%, preferably at least 70%, more preferably at least 80%, preferably at least 90%, more preferably at least 95% of the activity at the starting activity.

In another embodiment, the activity of the enzyme in degrading or converting lignocellulosic material at elevated temperatures incubating the enzyme with the cellulosic material for 3 hrs is at least 20%, preferably at least 30%, more preferably at least 40%, preferably at least 50%, more preferably at least 60%, preferably at least 70%, more preferably at least 80%, preferably at least 90%, more preferably at least 95% of the activity at the starting activity.

In a further embodiment, the activity of the enzyme in degrading or converting lignocellulosic material at elevated temperatures incubating the enzyme with the cellulosic material for 4 hrs is at least 20%, preferably at least 30%, more preferably at least 40%, preferably at least 50%, more preferably at least 60%, preferably at least 70%, more preferably at least 80%, preferably at least 90%, more preferably at least 95% of the activity at the starting activity.

In yet a further embodiment, the activity of the enzyme in degrading or converting lignocellulosic material at elevated temperatures incubating the enzyme with the cellulosic material for 5 hrs is at least 20%, preferably at least 30%, more preferably at least 40%, preferably at least 50%, more preferably at least 60%, preferably at least 70%, more preferably at least 80%, preferably at least 90%, more preferably at least 95% of the activity at the starting activity.

In another embodiment, the activity of the enzyme in degrading or converting lignocellulosic material at elevated temperatures incubating the enzyme with the cellulosic material for 6 hrs is at least 20%, preferably at least 30%, more preferably at least 40%, preferably at least 50%, more preferably at least 60%, preferably at least 70%, more preferably at least 80%, preferably at least 90%, more preferably at least 95% of the activity at the starting activity.

The polypeptides of the present invention is capable of degrading at least 20% lignocellulosic material, preferably at least 30%, more preferably at least 40%, preferably at least 50%, more preferably at least 60%, preferably at least 70%, more preferably at least 80%, preferably at least 90%, more preferably at least 95% of the lignocellulosic material over a time span of at the most 7 days.

The mentioned activities and incubation temperatures are performed at pH in the range of pH 3 to pH 6, preferably in the range of pH 3.5 to pH 5.5, more preferably in the range of pH 4 to pH 5, preferably in the range of pH 4.5 to pH 5.

In a preferred embodiment the pH used for incubation when degrading or converting a lignocellulosic material is at pH 4.8

It is appreciated that the lignocellulosic material is in one embodiment cellulose, in particular cellobiose, cellodextrins as defined elsewhere herein. The lignocellulosic material may be obtained from any plant biomass source, for example straw, maize stems, forestry waste, sawdust and/or woodchips.

Polynucleotide

The present invention relates in one aspect to an isolated polynucleotide comprising a nucleic acid or its complementary sequence being selected from the group consisting of a. a polynucleotide sequence encoding a polypeptide consisting of an amino acid sequence SEQ ID NO: 3, 4, 7, 10, or 13.
b. a polynucleotide sequence encoding a biologically active sequence variant of the amino acid sequence, wherein the variant has at least 92% sequence identity to said SEQ ID NO: 3, 4, 7, 10, or 13, and
c. a polynucleotide sequence encoding a biologically active fragment of at least 30 consecutive amino acids of any of a) through b), wherein said fragment is a fragment of SEQ ID NO 3, 4, 7, 10, or 13 or
d. SEQ ID NO.: 1, 2, 5, 6, 8.9, 11, 12, 29, or fragments of at least 30 contiguous nucleotides therefor
e. a polynucleotide comprising a nucleic acid sequence having at least 70% identity to SEQ ID NO: 1, 2, 5, 6, 8, 9, 11, 12, 29 or fragments of at least 30 contiguous nucleotides thereof, or
f. a polynucleotide hybridising to SEQ ID NO.: 1, 2, 5, 6, 8, 9, 11, 12, or 29, or fragments of at least 90 contiguous nucleotides thereof, and
g. a polynucleotide complementary to any of a) to f).

In one embodiment, the polynucleotide of the present invention is selected from the group consisting of a. a polynucleotide encoding an amino acid sequence consisting of SEQ ID NO.: 3 or
b. a polynucleotide sequence encoding a biologically active sequence variant of the amino acid sequence, wherein the variant has at least 92% sequence identity to said SEQ ID NO.: 3 and
c. a polynucleotide sequence encoding a biologically active fragment of at least 30 consecutive amino acid of any of a) trough b), wherein said fragment is a fragment of SEQ ID NO.: 3.

In another preferred embodiment of the invention, the polynucleotide is SEQ ID NO.: 1 or 2.

In another preferred embodiment of the invention the polynucleotide is a polynucleotide comprising a nucleic acid having 70% sequence identity to SEQ ID NO.: 1 or 2.

In yet another preferred embodiment of the invention the polynucleotide is capable of hybridising to a polynucleotide having the sequence of SEQ ID NO.: 1 or 2.

In a further, preferred embodiment of the invention the polynucleotide is complementary to i) a polynucleotide encoding an amino acid sequence consisting of SEQ ID No. 3 or
ii) a polynucleotide encoding a biologically active sequence variant of the amino acid sequence, wherein the variant has at least 70% sequence identity to said SEQ ID NO. 3, and
iii) a polynucleotide encoding a biologically active fragment of at least 30 consecutive amino acids of any of a) through b), wherein said fragment is a fragment of SEQ ID NO 3.

Thus, in one embodiment the polynucleotide of the present invention is complementary to SEQ ID NO.:1 or 2. In another preferred embodiment the polynucleotide of the present invention is complementary to a polynucleotide encoding an amino acid sequence consisting of SEQ ID NO.: 3.

However, the polynucleotide of the invention is in another embodiment complementary to a polynucleotide comprising a nucleic acid having 70% sequence identity to SEQ ID NO.: 1 or 2.

The polynucleotide may comprise the nucleotide sequence of a naturally occurring allelic nucleic acid variant.

The polynucleotide of the invention may encode a variant polypeptide, wherein the variant polypeptide has the polypeptide sequence of a naturally occurring polypeptide variant.

The nucleic acid sequence of the polynucleotide may differ by a single nucleotide from a nucleic acid sequence selected from the group consisting of SEQ ID NO: 1, 2, 5, 6, 8, 9, 11, 12 or 29. However, the polynucleotide may also differ from a nucleic acid sequence selected from the group consisting of SEQ ID NO: 1, 2, 5, 6, 8, 9, 11, 12 or 29 by 2, 3, 4, 5, 6, 7, 8, 9, 10, or more nucleotides.

In one embodiment, the nucleic acid sequence of the polynucleotide has at least 70% sequence identity such as preferably at least 71% sequence identity, more preferably e.g. at least 72% sequence identity, such as more preferably at least 73% sequence identity, e.g. more preferably at least 74% sequence identity, more preferably such as at least 75% sequence identity, more preferably e.g. at least 76% sequence identity, more preferably such as at least 77% sequence identity, more preferably e.g. at least 78% sequence identity, more preferably such as at least 79% sequence identity, such as preferably 80% sequence identity, such as preferably at least 81% sequence identity, more preferably e.g. at least 82% sequence identity, such as more preferably at least 83% sequence identity, e.g. more preferably at least 84% sequence identity, more preferably such as at least 85% sequence identity, more preferably e.g. at least 86% sequence identity, more preferably such as at least 87% sequence identity, more preferably e.g. at least 88% sequence identity, more preferably such as at least 89% sequence identity, more preferably e.g. at least 90% sequence identity, more preferably such as at least 91% sequence identity, more preferably e.g. at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity to a nucleotide sequence selected from the group consisting of SEQ ID No. 1, 2, 5, 6, 8, 9, 11, 12 and 29.

In a preferred embodiment the encoded polypeptide has at least 73%, such as preferably at least 74%, for example at least 75%, such as at least 76%, such as at least 77%, for example at least 78%, such as at least 79%, such as at least 80%, for example at least 81%, such as at least 82%, such as at least 83%, for example at least 84%, such as at least 85%, such as at least 86%, for example at least 87%, such as at least 88%, such as at least 89%, for example at least 90%, such as at least 91%, such as at least 92% sequence identity, such as at least 93% sequence identity, more preferably e.g. at least 94% sequence identity, more preferably such as at least 95% sequence identity, more preferably e.g. at least 96% sequence identity, more preferably such as at least 97% sequence identity, more preferably e.g. at least 98% sequence identity, more preferably such as at least 99% sequence identity, more preferably e.g. at least 99.5% sequence identity with SEQ ID No: 3, 4, 7, 10, or 13, more preferably at least 93%, more preferably at least 94%, more preferably at least 95%, more preferably at least 96% more preferably at least 96%, more preferably at least 97%, more preferably at least 98%, more preferably at least 99% sequence identity to SEQ ID No. 3, 4, 7, 10, or 13, more preferably wherein said polypeptide has the sequence of SEQ ID No. 3, 4, 7, 10, or 13.

In one embodiment, the isolated polynucleotide of the invention comprises a nucleic acid sequence having at least 70%, preferably at least 71%, more preferably at least 72%, preferably at least 73%, more preferred at least 74%, more preferred at least 75%, preferably at least 76%, more preferably at least 77%, preferably at least 78%, more preferred at least 79%, more preferred at least 80%, preferably at least 81%, more preferably at least 82%, preferably at least 83%, more preferred at least 84%, more preferred at least 85%, preferably at least 86%, more preferably at least 87%, preferably at least 88%, more preferred at least 89%, more preferred at least 90%, preferably at least 91%, more preferably at least 92%, preferably at least 93%, more preferred at least 94%, more preferred at least 95%, preferably at least 96%, more preferably at least 97%, preferably at least 98%, more preferred at least 99% sequence identity to the polynucleotide sequence presented as any one of SEQ ID NO: 1, 2, 5, 6, 8, 9, 11, 12 and 29.

In one embodiment, the isolated polynucleotide of the invention comprises a nucleic acid sequence having at least 70%, preferably at least 71%, more preferably at least 72%, preferably at least 73%, more preferred at least 74%, more preferred at least 75%, preferably at least 76%, more preferably at least 77%, preferably at least 78%, more preferred at least 79%, more preferred at least 80%, preferably at least 81%, more preferably at least 82%, preferably at least 83%, more preferred at least 84%, more preferred at least 85%, preferably at least 86%, more preferably at least 87%, preferably at least 88%, more preferred at least 89%, more preferred at least 90%, preferably at least 91%, more preferably at least 92%, preferably at least 93%, more preferred at least 94%, more preferred at least 95%, preferably at least 96%, more preferably at least 97%, preferably at least 98%, more preferred at least 99% sequence identity to the polynucleotide sequence presented as SEQ ID NO: 1 and/or 2. The polynucleotide is even more preferred at least 75%, such as at least 76%, for example at least 77, 78, 79 or at least 80% identical to SEQ ID NO: 1 or 29, or any fragment of at least 30 amino acids thereof, and/or at least 85%, such as at least 86%, for example at least 87, 88.89 or at least 90% identical to SEQ ID NO: 2, or any fragment of at least 30 nucleotides thereof.

In another preferred embodiment, the polynucleotide is even more preferred at least 79%, such as at least 80%, for example at least 81, 82, 82 or at least 85% identical to SEQ ID NO: 5, or any fragment of at least 30 nucleotides thereof, and/or at least 79%, such as at least 80%, for example at least 81, 82, 83 or at least 85% identical to SEQ ID NO: 6, or any fragment of at least 30 nucleotides thereof.

In another preferred embodiment, the polynucleotide is even more preferred at least 89%, such as at least 90%, for example at least 91, 92, 93 or at least 95% identical to SEQ ID NO: 8, or any fragment of at least 30 nucleotides thereof, and/or at least 85%, such as at least 86%, for example at least 87, 88, 89 or at least 90% identical to SEQ ID NO: 9, or any fragment of at least 30 nucleotides thereof.

In another preferred embodiment, the polynucleotide is even more preferred at least 78%, such as at least 79%, for example at least 79, 80, 81 or at least 82% identical to SEQ ID NO: 11, or any fragment of at least 30 nucleotides thereof, and/or at least 72%, such as at least 73%, for example at least 74, 75, 76, 77, 78, 79 or at least 80%, identical to SEQ ID NO: 12, or any fragment of at least 30 nucleotides thereof.

In yet another embodiment the polynucleotide is capable of hybridizing to the nucleic acid selected from the group consisting of SEQ ID NO: 1, 2, 5, 6, 8, 9, 11, 12 and 29, or a fragment hereof, under stringent conditions as described below.

A portion of the polynucleotide may hybridize under stringent conditions to a nucleotide probe corresponding to at least 10 consecutive nucleotides of a nucleotide sequence selected from the group consisting of SEQ ID NO: 1, 2, 5, 6, 8, 9, 11, 12 and 29, or a fragment hereof.

In yet another embodiment, the invention relates to polynucleotides having nucleic acid sequences (e. g., DNA, RNA) that hybridise to nucleic acids encoding a beta-glucosidase BGL polypeptide. In particular, nucleic acids which hybridize to SEQ ID NO: 1, 2, 5, 6, 8, 9, 11, 12 or 29 under high, moderate or reduced stringency conditions as described above.

In another embodiment, the invention relates to an RNA counterpart of the DNA nucleic acid encoding a beta-glucosidase BGL. In particular, it relates to RNA counterparts of SEQ ID NO: 1, 2, 5, 6, 8, 9, 11, 12 or 29.

It is appreciated that the polynucleotide of the present invention is DNA, RNA, LNA or PNA.

Heterologous Nucleic Acid Sequence

The microorganism and/or the host cell of the present invention may comprise one or more additional sequences, such as heterologous nucleic acid sequences, which are not native to the microorganism and/or host cell, but has for example been inserted by recombinant gene transfection technologies.

For example, a genetically modified host cell and/or microorganism according to the invention may comprise one or more additional heterologous nucleic acid sequences in addition to a polynucleotide encoding a beta-glucosidase polypeptide of the present invention. Such sequences may encode additional components as described herein below, including for example endoglucanase and/or cellobiohydrolase. However, the additional sequence may also be operably linked to the beta-glucosidase gene of the invention, and direct the expression thereof.

Accordingly, in the host cell and/or microorganism, a beta-glucosidase gene may be operably linked to an additional sequence directing the expression thereof. In this case, it is preferred that the additional sequence is capable of directing expression of the beta-glucosidase gene in the particular host cell and/or microorganism. If a heterologous nucleic acid sequence comprises more than one beta-glucosidase gene the expression of all of said beta-glucosidase genes may be directed by one second sequence, it is however preferred that each beta-glucosidase gene comprised within a genetically modified host microorganism is operably linked to one such additional sequence, which directs expression of said beta-glucosidase gene. It is preferred that the additional sequence comprises or even more preferably consists of a promoter sequence capable of directing expression in the particular host microorganism. The skilled person will in general be able to identify and provide promoter sequences useful in a particular host microorganism.

The additional sequence may thus be a constitutive promoter or an externally inducible promoter. In embodiments of the invention, wherein the host microorganism is a fungus, and in particular when the host microorganism is selected from species of *Phanerochaete*, such as *P. chrysosporium*; or *Trichoderma, Fusarium* or *Aspergillus*, then the additional sequence may for example be selected from the group consisting of GPD-1 (Glyceraldehyd-Dehydrogenase), CBH1-1 (Cellobiohydrolase), and G-6-P-DH (Glucose-6-phosphate Dehydrogenase) promoters (see specifics regarding these promoters in the Examples herein below).

The additional sequence may also be an externally inducible promoter, i.e. any promoter which may be controlled by external factors, such as temperature or concentration of solutes in the surroundings, or an internally inducible promoter, such as e.g. internally inducible by a metabolite reaching a threshold value. Preferred externally inducible promoters are such promoters which are responsive to the concentration of a solute in the surroundings, such as in the culture medium or in the provided substrate. Very preferred inducible promoters are such promoters, which are activated by low levels or more preferably absence of a nutrient, such as a nutrient selected from the group consisting of nitrogen, phosphate, potassium, magnesium, sulfur and iron. Yet more preferably, the inducible promoter is activated by low levels of and/or absence of nitrogen. A non-limiting example of such a promoter is LG2 (Ligninperoxidase H8 from *P. chrysosporium*) (see also examples herein below) The LG2 promoter is in particularly useful, when the host microorganism is a fungus, such as *P. chrysosporium* or *Aspergillus*.

In some embodiments of the invention, the heterologous nucleic acid sequence inserted in a host cell or microorganism of the present invention, does not comprise a second sequence, as described herein above. In these embodiments it is preferred that expression of the heterologous gene, such as a beta-glucosidase gene or other additional component as described herein below, including for example endoglucanase and/or cellobiohydrolase is directed by a sequence endogenous to the host microorganism, such as an endogenous promoter. This may be achieved by inserting the heterologous gene, such as the beta-glucosidase gene, just downstream of an endogenous promoter, for example by replacement by recombination. For this purpose the heterologous nucleic acid sequence preferably comprises flanking sequences (see more details below).

In addition to said heterologous gene, such as beta-glucosidase gene and optionally said second sequence, the heterologous nucleic acid sequence may comprise flanking regions. This is in particularly the case when it is desired that the heterologous sequence is comprised in a specific position in the genome of the host cell and/or microorganism of the invention. Each flanking sequence preferably comprises a sequence of in the range of 200 to 2000, more preferably in the range of 200 to 1000 base pairs, wherein said flanking sequence is at least 70%, preferably at least 80%, more preferably at least 90%, yet more preferably at least 95%, even more preferably at least 98%, yet more preferably at least 100% identical to the sequence of the host cell or microorganism genome, where it is desirable that the heterologous nucleic acid sequence is inserted. In general the heterologous nucleic acid sequence comprises a 5' and a 3' flanking sequence, wherein the 5' flanking sequence also is positioned 5' to the 3' flanking sequence within the genome of the host cell or microorganism. Preferably, a heterologous nucleic acid sequence comprising flanking regions will be inserted into the genome of the host cell or microorganism by recombination. Non-limiting examples of flanking sequences are given in the Examples herein below.

It is also comprised within the present invention that the heterologous nucleic acid sequence does not comprise flanking sequences, in which case the heterologous nucleic acid sequence may be inserted randomly into the genome of the host cell or microorganism.

In addition to gene encoded by the heterologous sequence, such as a beta-glucosidase gene and the optional additional sequence and/or flanking sequences, the heterologous nucleic acid may comprise one or more terminator sequences. In general the heterologous nucleic acid comprises at most one terminator sequence operably linked to each first sequence. The skilled person will be able to identify suitable terminator sequences useful in any given host cell or microorganism. In embodiments wherein the host cell is a fungus, the terminator sequence may for example be selected from the group consisting of trpC (Indole-3-glycerolphosphate synthase), GDP-(Glyceraldehyde phosphate dehydrogenase), CBH1-2 (Cellobiohydrolase)-terminator.

Further, in addition to gene encoded by the heterologous sequence, such as a beta-glucosidase gene of the present invention and the optional additional sequence and/or flanking sequences and/or terminator, the heterologous nucleic acid may comprise one or more selection markers, preferably one selection marker. When a genetically modified host cell or microorganism comprises more than one heterologous nucleic acid sequence, then it is preferred that each heterologous nucleic acid sequence comprises different selection markers. The skilled person will be able to identify suitable selection markers useful in any given host cell and/or microorganism. In embodiments wherein the host cell or microorganism is a fungus, such as *Phanerochaete* (such as *P. chrysosporium*), *Trichoderma, Fusarium* or *Aspergillus* (such as *Aspergillus saccharolyticus*) then the selection markers may for example be selected from the group consisting of Phleomycin binding protein (providing resistance to Phleomycin), Neomycin phosphotransferase (providing resistance to Kanamycin), Hygromycin resistance factor (providing resistance to hygromycin), NCBI Blast of icidine-aminase (providing resistance to NCBI Blast of icidine) and Bialaphois resistance factor (providing resistance to Bialaphos).

Recombinant Vector Construct

The present invention also relates to recombinant expression vectors comprising a nucleotide sequence encoding a polypeptide of the present invention, a promoter, and transcriptional and translational stop signals. The various nucleotide and control sequences described above may be joined together to produce a recombinant expression vector which may include one or more convenient restriction sites to allow for insertion or substitution of the nucleotide sequence encoding the variant at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HISS, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrg (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

The vector may be an autonomously replicating vector, i.e., a vector which exists as an extrachromosomal entity, the replication of which is distinct from chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain an element(s) that permits integration of the vector into the host cell's genome or autonomous replication of the vector in the cell independent of the genome.

For integration into the host cell genome, the vector may rely on the nucleotide sequence encoding the variant or any other element of the vector for integration of the vector into the genome by homologous or random recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the Integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes functioning temperature sensitive in the host cell (see, e.g., Ehrlich, 1978*, Proceedings of the National Academy of Sciences USA* 75: 1433). Examples of a plasmid replicator useful in a filamentous fungal cell are AMA1 and ANSI (Gerns et al., 1991*, Gene* 98:61-67; Cullen et al., 1987*, Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a nucleotide sequence of the present invention may be inserted into the host cell to increase production. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see Sambrook et al., 1989, supra).

In one aspect, the present invention relates to an isolated recombinant nucleic acid vector comprising at least one isolated polynucleotide comprising a nucleic acid or its complementary sequence being selected from the group consisting of a. a polynucleotide sequence encoding a polypeptide consisting of an amino acid sequence SEQ ID NO: 3, 4, 7, 10, and 13,
b. a polynucleotide sequence encoding a biologically active sequence variant as defined herein above, for example a varian having at least 92% sequence identity to any one of said SEQ ID NO: 3, 4, 7, 10, and 13, and c. a polynucleotide sequence encoding a biologically active fragment of at least 30 consecutive amino acids of any of the amino acid sequences of a) through b), or
d. SEQ ID NO.: 1, 2, 5, 6, 8, 9, 11, or 12, 29, or
e. a polynucleotide comprising a nucleic acid sequence having at least 70% identity to SEQ ID NO: 1, 2, 5, 6, 8, 9, 11, 12, or 29, or
f. a polynucleotide hybridising to SEQ ID NO.: 1, 2, 5, 6, 8, 9, 11, 12 or 29, and
g. a polynucleotide complementary to any of a) to f).

In a preferred embodiment, the nucleic acid vector comprises at least one polynucleotide comprising a nucleic acid sequence selected from the group consisting of:

a. a polynucleotide encoding an amino acid sequence consisting of SEQ ID NO.: 3 or
b. a polynucleotide sequence encoding a biologically active sequence variant of the amino acid sequence, wherein the variant has at least 92% sequence identity to said SEQ ID NO.: 3 and
c. a polynucleotide sequence encoding a biologically active fragment of at least 30 consecutive amino acid of any of the amino acid sequences of a) trough b)
d. a polynucleotide comprising a nucleic acid sequence having at least 70% identity to SEQ ID NO: 1 or 2, or
e. a polynucleotide hybridising to SEQ ID NO.: 1 or 2, and
f. a polynucleotide complementary to any of a) to f).

The specific choice of a vector backbone of the present invention depends on the choice of the microorganism for expression of a polypeptide of the present invention. For example, the vector is a prokaryotic expression vector or a eukaryotic expression vector. Thus, in one embodiment, the present invention relates to an isolated eukaryotic expression vector comprising at least one nucleic acid sequence encoding at least one β-glucosidase polypeptide of the present invention, or a biologically active fragment thereof.

Numerous vectors are available and the skilled person will be able to select a useful vector for the specific purpose. The vector may, for example, be in the form of a plasmid, cosmid, viral particle, yeast vector or artificial chromosome. In a preferred embodiment, a vector for fungal expression of the polynucleotide in a fungal cell such as *Aspergillus*, for example the *Aspergillus* AP, *Aspergillus saccharolyticus*, or *Trichoderma, Fusarium.*

The appropriate polynucleotide sequence may be inserted into the vector by a variety of procedures, for example, DNA may be inserted into an appropriate restriction endonuclease site(s) using techniques well known in the art. Apart from the polynucleotide according to the invention, the vector may furthermore comprise one or more of a signal sequence, an origin of replication, one or more marker genes, an enhancer element, a promoter, and a transcription termination sequence. The vector may also comprise additional sequences, such as enhancers, poly-A tails, linkers, polylinkers, operative linkers, multiple cloning sites (MCS), STOP codons, internal ribosomal entry sites (IRES) and host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989).

The plasmid or plasmids used for preparing the beta-glucosidase of the present invention, in particular for producing BGL (such as SEQ ID NO; 3, 4, 7, 10 or 13) may be any plasmid or vector that may be subjected to recombinant DNA procedures. The plasmid comprising a polynucleotide sequence encoding a beta-glucosidase may be prepared by ligating the nucleotide sequence into a suitable plasmid, or by any other suitable method. The plasmid preferably contains one or more selectable markers described herein which permit easy selection of transformed cells. The choice of plasmid will often depend on the host cell into which it is to be introduced.

In the present invention, the plasmid may be an autonomously replicating plasmid, i.e. a plasmid which exists as an extrachromosomal entity, the replication of which is distinct from chromosomal replication.

The plasmid is preferably an expression vector in which the nucleotide sequence in question is operably linked to additional segments required for transcription of the DNA. In general, the expression vector is derived from a plasmid, a cosmid or a bacteriophage, or may contain elements of any or all of these. For purposes of the present invention, the terms "plasmid" and "vector" are used interchangeably.

The present invention also relates to nucleic acid constructs comprising a polynucleotide sequence encoding the beta-glucosidase of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of a polypeptide of the present invention. The term "coding sequence" is defined herein as a nucleotide sequence which directly specifies the amino acid sequence of its protein product. The boundaries of a genomic coding sequence are generally determined by the ATG start codon (eukaryotes), or alternative start codons such as GTG and TTG, located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleotide sequences.

An isolated nucleotide sequence encoding the polypeptides of the present invention, preferably a beta-glucosidase polypeptide BGL may be manipulated in a variety of ways to provide for expression of the variant. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components which are necessary or advantageous for the expression of the polypeptides, in particular a beta-glucosidase polypeptide BGL of the present invention. Each control sequence may be native or foreign to the nucleotide sequence encoding BGL. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding the polypeptides of the present invention, in preferred embodiment the beta-glucosidase BGL. The term "operably linked" is defined herein as a configuration in which a control sequence is appropriately placed at a position relative to the coding sequence of the nucleotide sequence such that the control sequence directs the expression of the polypeptides.

The control sequence may be an appropriate promoter sequence, which is recognized by a host cell for expression of the nucleotide sequence. The promoter sequence contains transcriptional control sequences which mediate the expression of polypeptides of the present invention, in particular the beta-glucosidase polypeptide BGL. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

In one embodiment, at least one control sequence obtained from *Aspergillus* is employed, and in a preferred embodiment, one or more control sequences are obtained from a microorganism of the present invention, in particular *Aspergillus saccharolyticus.*

Promoters for directing the transcription of the polynucleotides of the present invention is for example obtained from *Aspergillus*, most preferred from a microorganism of the present invention, such as *Aspergillus saccharolyticus*. Other examples of suitable promoters for directing the transcription of the polynucleotides of the present invention in a filamentous fungal host cell are obtained from *Aspergillus saccharolyticus*, or promoters obtained from the genes for *Aspergillus oryzae* TAKA amylase. *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenalum* amyloglucosidase, *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); *Magnaporta grisea* ribosomal promoter or equivalents thereof; and also mutant, truncated, and hybrid promoters thereof.

In a yeast host, useful promoters are obtained from the genes for *Saccharomyces cerevisiae enolase* (ENO-1). *Saccharomyces cerevisiae* galactokinase (GAL1), *Saccharomyces cerevisiae* alcohol dehydrogenase/glyceraldehyde3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al, 1992*, Yeast* 8: 423-488.

The control sequence may also be a suitable transcription terminator sequence, which is recognized by a host cell to terminate transcription. The terminator sequence is operably linked to the 3'-terminus of the nucleotide sequence encoding the polypeptide, in particular the beta-glucosidase polypeptide BGL. Any terminator which is functional in the host cell of choice may be used in the present invention.

Terminators are for example obtained from *Aspergillus*, most preferred from a microorganism of the present invention, such as *Aspergillus saccharolyticus*. For example, preferred terminators for filamentous fungal host cells are obtained from *Aspergillus saccharolyticus*, or the genes for *Aspergillus oryzae* TAKA amylase, *Aspergillus niger* glucoamylase, *Aspergillus nidulans* anthranilate synthase, *Aspergillus niger* alphaglucosidase, *Fusarium oxysporum* trypsin-like protease, or *Neurospora crassa* beta-tubulin terminator.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleotide sequence encoding the beta-glucosidase polypeptide BGL. Any leader sequence that is functional in the host cell of choice may be used in the present invention.

Leaders are for example obtained from *Aspergillus*, most preferred from a microorganism of the present invention, such as *Aspergillus saccharolyticus*. Preferred leaders for filamentous fungal host cells are obtained from *Aspergillus saccharolyticus*, or the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO1). *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and which, when transcribed, is recognized by the host cell as a signal to add polyadenosine residues to transcribed mRNA. Any polyadenylation sequence which is functional in the host cell of choice may be used in the present invention.

Polyadenylation sequences are for example obtained from *Aspergillus*, most preferred from a microorganism of the present invention, such as *Aspergillus saccharolyticus*. Preferred polyadenylation sequences for filamentous fungal host cells are obtained from *Aspergillus saccharolyticus*, or from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995*, Molecular Cellular Biology* 15: 5983-5990.

The control sequence may also be a signal peptide coding region that codes for an amino acid sequence linked to the amino terminus of the polypeptides of the present invention, in particular the beta-glucosidase polypeptide BGL, where BGL is free of its signal peptide (e.g. SEQ ID NO 4 for BGL1) and directs the encoded polypeptide into the cell's secretory pathway. The 5'-end of the coding sequence of the nucleotide sequence may inherently contain a signal peptide coding region naturally linked in translation reading frame with the segment of the coding region which encodes the secreted beta-glucosidase polypeptide(s). Alternatively, the 5'-end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the beta-glucosidase polypeptides of the present invention. However, any signal peptide coding region which directs the expressed polypeptide into the secretory pathway of a host cell of choice may be used in the present invention.

Signal peptide sequences are for example obtained from *Aspergillus*, most preferred from a microorganism of the present invention, such as *Aspergillus saccharolyticus*. Effective signal peptide coding regions for filamentous fungal host cells are the signal peptide coding regions obtained from *Aspergillus saccharolyticus* (cf. SEQ ID NO: 3, 7, 10, 13, initial bold sequence), or from the genes for *Aspergillus oryzae* TAKA amylase. *Aspergillus niger* neutral amylase, *Aspergillus niger* glucoamylase, *Rhizomucor miehei* aspartic proteinase, *Humicola insolens* Cel45A cellulase, and *Humicola lanuginosa* lipase. Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of the polypeptides of the present invention. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptides of the present invention relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding polypeptides of the present invention, in particular the beta-glucosidase polypeptide BGL, would be operably linked with the regulatory sequence.

By having the polynucleotide positioned in a vector the polynucleotide can easily be stored, amplified, modified and expressed.

Microorganism and Host Cell

The present invention also encompasses any microorganism, which comprises a polypeptide or nucleic acid sequence or vector of the present invention, in particular, the host organism is a microorganism, which comprise a beta-glucosidase of the invention, or at least one polynucleotide encoding same or a biological active part thereof. The host organism may be the natural host of the native beta-glucosidase polypeptide, such as *Aspergillus* AP (*Aspergillus saccharolyticus*), or the host microorganism may be a genetically modified microorganism, wherein a polypeptide of the present invention has been introduced by transgenesis. Thus, one aspect of the present invention relates to an isolated microorganism comprising a polypeptide as defined elsewhere herein, a polynucleotide as defined herein and/or a recombinant nucleic acid vector as defined herein.

Preferably the microorganism, host organism, and/or polypeptide of the present invention is capable of degrading one or more plant cell wall constituents such as lignocellolosic material. In a preferred embodiment the lignocellulosic material is selected from the group consisting of cellulose, hemicellulose, cellobiose, cellodextrin and pectin, more preferably, the host microorganism is capable of degrading at least two plant cell wall constituents selected from the group consisting of cellulose, hemicellulose, cellobiose, cellodextrin and pectin, yet more preferably the host organism is capable of degrading at least three plant cell wall constituents selected from the group consisting of cellulose, hemicellulose, cellobiose, cellodextrin and pectin, even more preferably the host microorganism is capable of degrading all of cellulose, hemicellulose, cellobiose, cellodextrin and pectin.

It is thus preferred that the microorganism, host organism and/or polypeptide of the present invention is capable of degrading at least one plant cell wall constituent selected from the group consisting of cellulose, hemicellulose, cellobiose, cellodextrin and pectin, more preferably the host microorganism is capable of degrading at least one plant cell wall constituent selected from the group consisting of cellobiose and cellodextrin, yet more preferably, the host organism is capable of degrading cellobiose.

Accordingly, it is very preferred that the microorganism, host organism and/or polypeptide of the present invention is capable of degrading lignocellulosic material as described herein. Preferably, the microorganism, host organism and/or polypeptide of the present invention is capable of degrading at least 40%, more preferably at least 50%, even more preferably at least 60%, yet more preferably at least 65%, and most preferably at least 90% of the lignocellulosic material content of any given carbon source (preferably wood residuals or agricultural residuals), within a time span of at the most 6 months, preferably at the most 5 months, yet more preferably at the most 4 month, yet more preferably at the most 3 months, even more preferably at the most 2 months, yet more preferably at the most 1 month, yet more preferably at the most 1 week, and most preferably at the most 3 days.

In addition, it is preferred that the host organism of the present invention is capable of degrading one or more additional components of plant biomass, such as for example polymerized carbon sources, structural or non-structural carbohydrates, in particular it is preferred that the host organism is capable of degrading polysaccharides, such as e.g. cellulose, in plant biomass. Preferably at least 50%, more preferably at least 60%, yet more preferably at least 70%, even more preferably at least 80%, further preferred at least 90% of the one or more additional components of plant biomass, such as all polysaccharides in plant biomass, preferably within a time span of at the most 6 months, preferably at the most 3 months, yet more preferably at the most 1 month, yet more preferably at the most 20 days, even more preferably at the most 3 days.

Thus, it is preferred that the microorganism, host organism and/or polypeptide of the present invention is capable of degrading at least 50%, more preferably at least 60%, yet more preferably at least 70%, even more preferably at least 80% of any given plant, more preferably at least 90% biomass comprising lignocellulosic material as determined in reference to dry weight, preferably within a time span of at the most 6 months, preferably at the most 3 months, yet more preferably at the most 1 month, yet more preferably at the most 20 days, even more preferably at the most 3 days.

In addition it is preferred that the microorganism, host organism and/or polypeptide of the present invention is capable of degrading and assimilating at least 50%, more preferably at least 60%, yet more preferably at least 70%, even more preferably at least 80% of any given plant biomass as determined by carbon content, preferably within a time span of at the most 6 months, preferably at the most 3 months, yet more preferably at the most 1 month, yet more preferably at the most 20 days, even more preferably at the most 10 days, and most preferred at the most 3 days.

When mentioned herein that the genetically modified microorganism, or the host organism, is capable of degrading one or more plant cell wall constituents it is furthermore preferred that the genetically modified microorganism, or the host organism, is capable of degrading and assimilating the breakdown products of one or more plant cell wall constituents selected from the group consisting of cellulose, hemicellulose, cellobiose, cellodextrin and pectin.

When used herein the term assimilating means capable of degrading and utilizing the breakdown products of a carbon source in the metabolisme, preferably anabolism, of biomolecules, such as e.g. acids and acid derivatives, and preferably in the anabolism of "microbial oil" or biochemicals and bioproducts produced through biorefinery for substitution of products produced by oil in oil refineries.

Thus, it is preferred that the host organism expresses and secretes as complete a set of enzymes as possible for the degradation of the biomass as defined above. Thus, a host organism capable of degrading lignocellulosic material in general expresses and secretes all enzymes required for degradation of lignin. Preferred host microorganisms are capable of degrading lignin in its entirety and it is preferred that such host microorganisms comprise one or more enzymes selected from the group consisting of lignin peroxidases (also referred to as ligninase), manganese peroxidase, and laccase. Particularly useful is the combined action of a set of enzymes from *Phanerochaete crysosporium* having as main constituents a lignin peroxidase, a manganese peroxidase and a laccase activity, or enzymes from *Trichoderma, Aspergillus* or *Fusarium.*

The same applies for the other polysaccharide and/or other plant cell wall constituents mentioned herein above. Thus, more preferably, the host microorganism expresses and secretes all enzymes for the degradation of all of cellulose, hemicellulose, cellobiose, cellodextrin and/or pectin, and any other structural or non-structural carbohydrate, such as polysaccharides. The enzyme mixtures that may be involved in degradation of various polysaccharides and/or plant cell wall constituents are reviewed by Evans and Hedge (Evans, C. S. and Hedger J. N. in Gadd, G. M. ed.: in Fungi in Bioremediation; Cambridge University Press, (2001) p 1-24; ISBN 0-521-781191). Preferably, the host microorganism expresses and preferably secretes a set of carbohydrolases.

*Aspergillus saccharolyticus*

In one important aspect, the present invention relates to a microorganism, such as an isolated microorganism, of the species *Aspergillus saccharolyticus*. The novel *Aspergillus* strain of the present invention has been named *Aspergillus saccharolyticus* A. Sørensen, P. Lübeck et Frisvad sp. nov.

*Aspergillus saccharolyticus* (sac.ca'ro.ly'ti.cus. N.L. masc. adj. *saccharolyticus*, being able to degrade cellobiose and cellodextins).

In particular, the invention relates to a microorganism as deposited in the Centraalbereau voor Schimmelcultures (CBS) and having accession number CBS 127449. The invention also relates to any descendant or a functional mutant of said microorganism. Thus, in any context of the present invention, any reference to the microorganism, also relates to any descendant or a functional mutant of said microorganism.

In particular, the microorganism, descendant or a functional mutant thereof is capable of hydrolyzing a β1-4 glucose-glucose linkage. Thus, the microorganism of the invention, including said descendant or functional mutant thereof, comprises at least one beta-glucosidase (BGL) polypeptide and/or a gene endoding said polypeptide. However, the microorganism may comprise at least two, such as at least three, for example at least four beta-glucosidase (BGL) polypeptides and/or a genes endoding these. In particular, the microorganism, descendant or a functional mutant thereof may also comprise multiple copies of each beta-glucosidase (BGL) polypeptide and/or a gene endoding said polypeptide. For example, the microorganism, descendant or a functional mutant thereof, in one embodiment comprise comprise at least 2 copies of said one or more genes encoding said BGL polypeptide, for example at least 5, or at least 10, such as more than 20, 30, 40, or more than 50 copies of said one or more genes.

For example, the microorganism, *Aspergillus saccharolyticus*, comprise at least one beta-glucosidase (BGL) polypeptide, which is selected from the group consisting of BGL1 (SEQ ID NO: 3 or 4), BGL2 (SEQ ID NO: 7), BGL3 (SEQ ID NO: 10) and BGL4 (SEQ ID NO: 13).

In another example, the microorganism, *Aspergillus saccharolyticus*, comprise at least one nucleotide sequence encoding a beta-glucosidase (BGL) polypeptide, which is selected from the group consisting of BGL1 (SEQ ID NO: 3 or 4), BGL2 (SEQ ID NO: 7). BGL3 (SEQ ID NO: 10) and BGL4 (SEQ ID NO: 13). For example, the microorganism, *Aspergillus saccharolyticus*, comprise at least one nucleotide sequence, which is selected from the group consisting of SEQ ID NO: 1, 2, 5, 6, 8, 9, 11, 12, 14, 15, 16, and/or 29, and/or any fragment of at least 30 nucleotides thereof.

In one embodiment, the microorganism, descendant or functional mutant thereof, comprise an ITS nucleic acid sequence, which is at least 89% identical to SEQ ID NO: 16 or any fragment thereof as defined elsewhere herein. However in a preferred embodiment, the microorganism, descendant or functional mutant thereof, comprise an ITS nucleic acid sequence, which is at least 90%, such as at least 91%, such as at least 92%, such as at least 93%, more preferably e.g. at least 94%, more preferably such as at least 95%, more preferably e.g. at least 96%, more preferably such as at least 97%, more preferably e.g. at least 98%, more preferably such as at least 99%, more preferably e.g. at least 99.5% with SEQ ID NO: 16, or any fragment thereof as defined elsewhere herein.

In one embodiment, the microorganism, descendant or functional mutant thereof, comprise a Calmodulin nucleic acid sequence, which is at least 89% identical to SEQ ID NO: 15 or any fragment thereof as defined elsewhere herein. However in a preferred embodiment, the microorganism, descendant or functional mutant thereof, comprise a Calmodulin nucleic acid sequence, which is at least 90%, such as at least 91%, such as at least 92%, such as at least 93%, more preferably e.g. at least 94%, more preferably such as at least 95%, more preferably e.g. at least 96%, more preferably such as at least 97%, more preferably e.g. at least 98%, more preferably such as at least 99%, more preferably e.g. at least 99.5% identical with SEQ ID NO: 15, or any fragment thereof as defined elsewhere herein.

In one embodiment, the microorganism, descendant or functional mutant thereof, comprise a beta-tubulin nucleic acid sequence, which is at least 87% identical to SEQ ID NO: 14, or any fragment thereof as defined elsewhere herein. However in a preferred embodiment, the microorganism, descendant or functional mutant thereof, comprise a beta-tubulin nucleic acid sequence, which is at least 88%, such as at least 89%, such as at least 90%, such as at least 91%, such as at least 92%, such as at least 93%, more preferably e.g. at least 94%, more preferably such as at least 95%, more preferably e.g. at least 96%, more preferably such as at least 97%, more preferably e.g. at least 98%, more preferably such as at least 99%, more preferably e.g. at least 99.5% identical with SEQ ID NO: 14, or any fragment thereof as defined elsewhere herein.

In a preferred embodiment, the the microorganism, descendant or functional mutant thereof, comprise a nucleic acid sequence at least 90% identical to SEQ ID NO: 16, a nucleic acid sequence at least 90% identical to SEQ ID NO: 15, and a nucleic acid sequence at least 88% identical to SEQ ID NO: 14.

Based on morphology, the microorganism of the invention (*Aspergillus saccharolyticus*) is related to *A. japonicus* or *A. aculeatus*. However, extrolite profiles and DNA sequencing data show that *Aspergillus saccharolyticus* is clearly different from all known species. *A. saccharolyticus* is not related to other black aspergilli based on comparing sequence data of parts of the beta-tubulin and calmodulin genes as well as the ITS region, using *A. flavus* as the out group.

Phylogeny

Based on the phylogenetic analysis of the ITS and calmodulin gene sequence data, *A. saccharolyticus* belongs to the clade with *A. homomorphus, A. aculeatinus, A. uvarum, A. japonicus*, and both *A. aculeatus* strains, while for the beta-tubulin gene sequence data *A. saccharolyticus* clusters with *A. homomorphus, A. aculeatinus, A. uvarum*, and *A. aculeatus* CBS 114.80. The separate grouping in the beta-tubulin tree of *A. japonicus* and *A. aculeatus* CBS 172.66T has consistently been shown in other publications that have used these exact strain sequences (Noonim et al., 2008, Samson et al., 2007, Varga et al., 2007, de Vries et al., 2005, Samson et al., 2004b). The separate grouping is due to the two aspergilli having one less intron in the beta-tubulin gene compared to the other *Nigri* species. For all three loci, *A. saccharolyticus* is placed on its own branch far from the other species in the clade supported by the majority-rule consensus analysis for all three loci and high bootstrap values for the beta-tubulin and calmodulin loci, but low bootstrap value (51%) for the ITS locus. Sequence alignment shows that amongst the species from series *Aculeata* and *Homomorpha* (Frisvad et al., 2007) that are phylogenetically closely related to *A. saccharolyticus*, interspecific sequence divergences are 50.7%, 7.1%, and 5.7% for the ITS, calmodulin, and beta-tubulin regions, respectively.

Meanwhile, the interspecific sequence divergences in the ITS, calmodulin, and beta-tubulin region between *A. saccharolyticus* and the other species in the clade are on average 12.9±0.6%, 20±0.5%, and 15.4±1.2%, respectively. The variation in sequence data between *A. saccharolyticus* and *A. homomorphus* is the same as the variation between *A. homomorphus* and the smaller clade(s) of *A. aculeatinus, A. uvarum, A. japonicus*, and both *A. aculeatus* strains. Searching the NCBI database does not give any closer genetic match with respect to *A. saccharolyticus.*

UP-PCR Fingerprinting

The microorganism of the invention, *A. saccharolyticus*, may be distinguished from other black aspergilli by Universally Primed-PCR analysis using each of the two UP primers, L45 and L15/AS19. UP-PCR is a PCR fingerprinting method that has demonstrated its applicability in different aspects of mycology. These applications constitute analysis of genome structures. Identification of species, analysis of population and species diversity, revealing of genetic relatedness at infra- and inter-species level, and identification of UP-PCR markers at different taxonomic levels (strain, group and/or species) (Lübeck & Lübeck, 2005). Different Aspergilli: *A. saccharolyticus. A. aculeatinus, A. ellipticus, A. homomorphus, A. niger, A. uvarum, A. aculeatus* and *A. japonicus*, produced a unique banding profile, and do not share any bands.

Enzyme Activity

The microorganism of the invention preferably comprise a beta-glucosidase activity, and the betaglucosidase activity may be isolated or obtained from an extract of the microorganism or from the incubation broth of the microorganism, after letting the microorganism incubate in the broth for a certain period. In one embodiment, the microorganism of the invention is characterized in that an extract and/or incubation broth of said microorganism, descendant or functional mutant thereof, has a beta-glucosidase activity of at least 5 U/mg of total protein. For example, an extract and/or incubation broth of said microorganism, descendant or functional mutant thereof, has a beta-glucosidase activity, wherein the half-life of said beta-glucosidase activity at 60° C. is at least 200 minutes. Also, in one example, an extract and/or incubation broth of said microorganism, descendant or functional mutant thereof, has a betaglucosidase activity, wherein at least 50% of said beta-glucosidase activity remains after 4 hours of incubation at 60° C.

Morphology

*Aspergillus saccharolyticus* is characterised by the following features: Colony diameter at 7 days: CYA at 25° C.: 58-62 mm, at 37° C.: 7-14 mm; CYAS: 11.14 mm; YES: 75-80 mm; OA: 39-42 mm; CY20S: 42-54 mm; CY40S: 43-54 mm; MEA: 35-37 mm; CREA 30-34 mm, poor growth, good acid production, colony first white then dark brown to black. Exudates absent, reverse cream-coloured to light greyish olive brown on CYA and light brown on YES. Conidial heads globose; stipes 200-850×5-7 μm, walls thick, smooth; vesicles 25-40 μm diam, globose; uniseriate, phialides flask shaped with a short broad collulum, 5.5-7 μm; conidia mostly globose, but some are subglobose, 5-6.2 μm, distinctly echinulate, with long sharp discrete spines, the spines being 0.6-0.8 μm long. Sclerotia have not been observed.

The type strain CBS 127449$^T$ (=IBT 28509$^T$) was isolated from under a toilet seat made of treated oak wood, Gentofte, Denmark.

Further characteristics of *Aspergillus saccharolyticus* are described in example 2.

Host Cells

The present invention also relates to a recombinant host cell, comprising a polynucleotide sequence encoding a beta-glucosidase polypeptide as described elsewhere herein and/or a recombinant nucleic acid vector as described herein. The recombinant host cell comprises a recombinant nucleic acid vector comprising a polynucleotide of the present invention is introduced into a host cell so that the vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may also be any suitable host microorganism. Accordingly, preferably the host cell may be selected from host microorganisms belonging to a phylum selected from the group consisting of yeasts, fungi, bacteria, algae or plants. However, the host cell may be any prokaryote or eukaryote, such as a mammalian, insect, plant, or fungal cell.

Host microorganisms capable of degrading cellulose preferably express and secrete one or more glycoside hydrolases, such as endo-acting or exo-acting cellulases. These enzymes may be part of a multienzyme complex, such as a cellulosome. Host microorganisms that are capable of degrading starch preferably comprise amylases. In a very preferred embodiment the host microorganism comprises a secretome, such as a cellulose-induced secretome, which preferably may be composed of glycosyl-hydrolases, such as a total of in the range of 15 to 50, such as around 32, for example 32 glycosyl-hydrolases. In addition, the host microorganism preferably contains endoglucanases and/or cellobiohydrolases for cellulose degradation. Additionally, the host microorganism preferably comprises endoxylanases, alpha-galactosidases and/or other enzymes involved in the degradation of hemicelluloses.

If the host microorganism does not endogenously comprise genes encoding some or all of the enzymes for degradation of desired polysaccharides and/or plant cell wall constituents, the enzyme(s) may be introduced into the host microorganism by genetic modification.

In one embodiment, the host microorganism is an organism with a yeast-like growth behavior, such as yeast, for example *Saccharomyces cerevisiae*. Preferably, said yeast is capable of degrading polysaccharides, such as starch, comprises the enzymatic apparatus to grow on carbon sources such as, for example, fruit juices or starch containing substrates. In another less preferred embodiment the host microorganism is a bacteria, such as a bacteria capable of degrading at least one, preferably at least two, more preferably at least three, even more preferably at least four, yet more preferably all of the plant cell wall constituents selected from the group consisting of cellulose, hemicellulose, pectin, and lignin.

In a very preferred embodiment of the invention the host microorganism is a fungus, more preferably a filamentous fungus. Filamentous fungi particularly useful as host microorganisms within the scope of the present invention are filamentous fungi capable of degrading and assimilating the breakdown products of the lignocellulosic matter from the plant biomass, preferably the natural habitat of said filamentous fungi is decaying plant material. Examples of useful host organisms having as natural habitat decaying plant material include white rot, red rot and soft rot fungi together with fungi like *Penicillium, Aspergillus, Fusarium, Trichoderma* and *Neurospora*. Preferred host microorganisms are fungi capable of hyphal growth that can penetrate into the lignocellulosic matter, usually with the help of secreted carbohydrolases.

Many fungi have specialized in the degradation of a fraction of the polysaccharides and/or plant cell wall constituents from plant biomass such as for example cellulose or hemicellulose. Thus, in one embodiment, the host microorganism is a fungus specialized in the degradation of a fraction of the polysaccharides and/or plant cell wall constituents from plant biomass such as for example cellulose or hemicellulose. However, more preferably the host microorganism is a fungus capable of degrading most of the polysaccharides and plant cell wall constituents present in plant biomass.

Thus, the host microorganism may be any fungus having the ability to degrade any plant cell wall constituents, in particular lignocellosic material e.g. any structural or non-structural polysaccharide as described herein above, in particular the host microorganism may be any fungus capable of growing on one or more constituents of plant biomass such as starch, pectin, cellulose, hemicellulose, cellobiose, cellodextrin or lignin. Accordingly, the host organism may be a filamentous fungus which has the capacity to use one or more plant cell wall constituents as carbon source. Examples of useful fungi are given in Evans and Hedge (Evans, C. S. and Hedger J. N. in Gadd, G M ed.: in Fungi in Bioremediation; Cambridge University Press, (2001) p 1-24; ISBN 0-521-781191). In one embodiment, the host microorganism is a fungus selected from the group consisting of white-rot, red-rot and soft-rot fungi. The host cell may also in a preferred embodiment be selected from Ascomycetes. Thus, for example, the host microorganism may be a fungus selected from the group consisting of fungi of the genus *Trichoderma, Trametes, Aspergillus, Fusarium* and *Penicillium.*

In a very preferred embodiment of the invention the host microorganism is a fungus capable of degrading at least one, preferably at least two, more preferably at least three, yet more preferably at least four, more preferably all of the plant cell wall constituents selected from cellulose, hemicellulose, cellobiose, cellodextrin and pectin. Thus, it is preferred that the host microorganism is a fungus which is capable of degrading at least cellobiose, preferably at least cellobiose and cellodextrin, more preferably all of cellulose, hemicellulose, cellobiose, cellodextrin and pectin.

Therefore, in one embodiment of the present invention the host microorganism is a fungus of the Phanerochaetaceae family, more preferably a fungus belonging to the *Phanerochaete* genus, even more preferably, a fungus selected from the group consisting of *Phanerochaete alfantospora, Phanerochaete arizonica, Phanerochaete chrysosporium, Phanerochaete aveilanea, Phanerochaete burtii, Phanerochaete carnosa, Phanerochaete chrysorhizon, Phanerochaete radicata, Phanerochaete salmonicolor, Phanerochaete tuberculata, Phanerochaete velutina* and *Phanerochaete chrysosporium*. In one preferred embodiment the host microorganism is a white rot fungus. The advantage of using for example white-rot fungi is i.a. the ability of these fungi to degrade lignin, which supports the betaglucosidase activity of the polypeptides of the present invention.

More preferably, the host microorganism is, for example of the strain RP 78. This fungus has the enzymatic capacity to degrade cellulose, hemi-cellulose, lignin, and pectin.

*P. chrysosporium* is in general capable of achieving high conversion rates in biomass degradation and therefore *P.*

*chrysosporium* is particularly useful as a host microorganism for industrial scale application of the methods according to the present invention. For example, cultivating *P. chrysosporium* in industrial scale may be performed by solid state fermentation, for example essentially as described by Kumar, A. G. et al. (2006) Bioresource Technology p. 1521-1528). Using this process *P. chrysosporium* was capable of degrading 65% of lignin content of *Achra zapota* leaves in 28 days.

In another highly preferred embodiment, the host cell is selected from Ascomycetes. In a most preferred embodiment, the host cell is selected from *Trichoderma* and *Aspergillus*

In one embodiment, the microorganism or host cell/organism is a fungus, such as *Aspergillus*, and in a specific embodiment, the host of *Aspergillus* AP/*Aspergillus saccharolyticus*, which is the natural host for the beta-glucosidases identified by SEQ ID NO: 3, 7, 10, and 13.

The host cell may be any fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge. UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (NCBI Blast of omycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacterial. Symposium Series* No. 9, 1980).

In a more preferred embodiment, the yeast host cell is a *Candida, Hansenula, Kluyveromyces, Pichia, Saccharomyces. Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is, but not limited to, an *Acremonium, Aspergillus, Fusarium, Humicola, Mucor, Mycellophthora, Neurospora, Penicillium, Thielavia, Tolypocladium*, or *Trichoderma* cell.

In a most preferred embodiment, the filamentous fungal host cell is an *Aspergillus awamori, Aspergillus foetidus, Aspergillus japonicus, Aspergillus nidulans, Aspergillus niger, Aspergillus aculeatus, Aspergillus uvarum, Aspergillus aculeatinus, Aspergillus carbonarius* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusafuim sporotrichiodes, Fusarium sulphureum, Fusarium torulosum, Fusarium trichothecioides*, or *Fusarium venentum* cell. In an even more preferred embodiment, the filamentous fungal host cell is a *Fusarium venentum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum. Trichoderma koningii, Trichoderma longibrachiatum, Trichoderma reesei, or Trichoderma viride* cell. In another even most preferred embodiment, the filamentous fungal host cell is *Trichoderma reesei* RutC3O.

It is understood that also the *Aspergillus saccharolyticus* of the present invention may serve as a host cell.

The fungal cell, into which the mixture of plasmid/fragment polynucleotide is to be introduced, may be any fungal cell useful in the present invention. A "recombination fungal cell" is defined herein as a cell capable of mediating shuffling of a number of homologous nucleotide sequences.

In a preferred embodiment, the fungal recombination cell is a yeast cell. In a more preferred embodiment, the yeast recombination cell is a *Candida, Hansenula, Kluyveromyces, Pichia, Saccharomyces, Schizosaccharomyces, or Yarrowia* cell.

In a most preferred embodiment, the yeast recombination cell is a *Kluyveromyces lactis, Saccharomyces carlsbergensis, Saccharomyces cerevisiae, Saccharomyces diastaticus, Saccharomyces douglasi, Saccharomyces kluyveri Saccharomyces norbensis, Saccharomyces oviformis*, or *Yarrowia lipolytica* cell.

In another preferred embodiment, the fungal recombination cell is a filamentous fungal cell. In a more preferred embodiment, the filamentous fungal recombination cell is an *Acremonium, Aspergillus, Fusarium, Humicola, Mucor, Mycellophthora, Neurospora, Penicillium, Thielavia, Tolypocladium*, or *Trichoderma* cell.

In a most preferred embodiment, the filamentous fungal recombination cell is an *Aspergillus awamori, Aspergillus foetidus, Aspergillus japonicus, Aspergillus nidulans, Aspergillus niger, Aspergillus aculeatus, Aspergillus uvarum, Aspergillus aculeatinus, Aspergillus carbonarius* or *Aspergillus oryzae* cell. In another most preferred embodiment, the filamentous fungal recombination cell is a *Fusarium bactridioides, Fusarium cerealis. Fusarium crookwellense. Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred embodiment, the filamentous fungal recombination cell is a *Humicola Insolens, Humicola lanuginosa, Mucor miehei, Mycellophthora thermophila, Neurospora crassa, Penicillum purpurogenum, Thielavia terrestris, Trichoderma harzianum, Trichoderma koningli, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known perse.

Suitable procedures for transformation of *Aspergillus* and *Trichoderma* host cells are described in EP 238 023.

Method for Producing Polypeptide

The present invention also relates to methods of producing a polypeptide of the present invention. In one aspect, the invention relates to a method of producing a polypeptide, said method comprising cultivating a host cell or a microorganism of the present invention. Thus, the invention relates to a method of producing a polypeptide, said method comprising cultivating a) a host cell of the present invention, such as a host cell comprising i) a polypeptide of the present invention, such as a polypeptide comprising an amino acid sequence selected from SEQ NO: 3, 4, 7, 10, and 13, a biologically active sequence variant of any of SEQ NO: 3, 4, 7, 10, and 13, wherein said variant has at least 92% sequence identity to said SEQ NO: 3, 4, 7, 10, and 13, or a biologically active fragment of at least 30 consecutive amino acids of any of the amino acid sequences of above;

ii) a polynucleotide of the present invention, such as a polynucleotide comprising a polynucleotide sequence encoding a polypeptide consisting of an amino acid sequence SEQ ID NO: 3, 4, 7, 10, and 13, or a polynucleotide sequence encoding a biologically active sequence variant of the amino acid sequence, wherein the variant has at least 92% sequence identity to said SEQ ID NO: 3, 4, 7, 10, and 13, or a polynucleotide sequence encoding a biologically active fragment of at least 30 consecutive amino acids of any of the amino acid sequences of above, or SEQ ID NO.: 1, 2, 5, 6, 8, 9, 11, 12, 14, 15, 16 or 17, 29, or a polynucleotide comprising a nucleic acid sequence having at least 70% identity to SEQ ID NO: 1, 2, 5, 6, 8, 9, 11, 12, 14, 15, 16 or 17, or a polynucleotide hybridising to SEQ ID NO.: 1, 2, 5, 6, 8, 9, 11, 12, 14, 15, 16 or 17, 29, or a polynucleotide complementary to any of the above; or iii) a nucleic acid vector comprising a polynucleotide sequence of the present invention, such as a polynucleotide mentioned under ii); or b) a microorganism of the present invention, such as a microorganism of the species *Aspergillus saccharolyticus*, such as the microorganism as deposited in the Centraalbereau voor Schimmelcultures (CBS) and having accession number CBS 127449, or a descendant or a functional mutant thereof The produced polypeptide is then preferably recovered from the microorganism and/or host cell, and/or recovered from the incubation broth of the host cell and/or microorganism.

The method of the invention is suitable both for producing a polypeptide of the present invention, such as a BGL polypeptide, for example BGL1, BGL2, BGL3, and/or BGL 4, identified as SEQ ID NO: 3, 7, 10, and 13, respectively, as well as functional variants thereof. However, the method may also be used for producing other polypeptides. The microorganism of the present invention, such as *Aspergillus saccharolyticus*, is suitable for the expression of transgenes, and thus, a gene encoding any gene of interest may be introduced into the genome of *Aspergillus saccharolyticus*, and expressed by that microorganism, and recovered from the incubation broth and/or from an extract of the microorganism cells.

In one embodiment, a bgl gene of the microorganism of the invention has been replaced with a heterologous polynucleotide sequence encoding polypeptide to be produced according to the present method, wherein said polypeptide may be recovered. In a preferred embodiment, the bgl1 gene of a microorganism of the invention has been replaced with a heterologous polynucleotide sequence encoding said polypeptide to be recovered.

For facilitating the production of polypeptides, the host cell and/or microorganism may be genetically modified, as explained elsewhere herein. Such modification includes selection markers, polyadenylation signals etc.

However, the polypeptides of the present invention (e.g. those identified by SEQ ID NO: 3, 4, 7, 10, and/or 13 or variant thereof) may also in one embodiment be produced chemically by liquid-phase or solid-phase synthesis. In a preferred embodiment, however, the polypeptides are produced by biosynthesis, wherein the polypeptide is produced in a host organism, such as a microorganism comprising a nucleic acid sequence or vector encoding a polypeptide of the present invention.

Similarly, the polypeptide of the present invention may be extracted from *Aspergillus saccharolyticus* for example as described herein in the examples.

Method for Degrading a Lignocellulosic Material

In one aspect, the present invention relates to methods for degradation, conversion or hydrolysis of a lignocellulosic material. Thus, one aspect of the present invention relates to a method for degrading or converting a lignocellulosic material, said method comprising incubating said lignocellulosic material with at least one polypeptide as described herein, at least one microorganism as defined herein, at least on recombinant host cell as described herein, at least one composition as defined herein and/or at least one kit-of parts as defined elsewhere herein. After incubation, the degraded lignocellolosic material may be recovered.

In one embodiment, the invention relates to a method for degrading or converting a lignocellulosic material, said method comprising i) incubating said lignocellulosic material with at least one polypeptide as described herein, ii) recovering the degraded lignocellulosic material. The polypeptide is for example BGL1 (SEQ ID NO: 3), BGL2 (SEQ ID NO: 7), BGL3 (SEQ ID NO: 10), or BGL4 (SEQ ID NO: 13), or functional variants thereof.

Another embodiment of the invention relates to a method for degrading or converting a lignocellulosic material, said method comprising i) incubating said lignocellulosic material with at least one microorganism as defined herein and ii) recovering the degraded lignocellulosic material.

Yet another embodiment of the present invention relates to a method for degrading or converting a lignocellulosic material, said method comprising i) incubating said lignocellulosic material with at least one recombinant host cell as described herein and ii) recovering the degraded lignocellulosic material.

A further embodiment of the present invention relates to a method for degrading or converting a lignocellulosic material, said method comprising i) incubating said lignocellulosic material with at least one composition as defined herein and ii) recovering the degraded lignocellulosic material.

Yet a further embodiment of the present invention relates to a method for degrading or converting a lignocellulosic material, said method comprising i) incubating said lignocellulosic material with at least one kit-of parts as defined elsewhere herein and ii) recovering the degraded lignocellulosic material.

In one embodiment the lignocellulosic material is as defined elsewhere herein and obtained from straw, maize stems, forestry waste, sawdust and/or wood-chips.

The lignocellulosic material and at least one polypeptide, at least one microorganism, at least one recombinant host cell, at least one composition and/or kit-of parts is incubated at a temperature in the range from 40 degrees C. to 70 degrees C., preferably in the range from 40 degrees C. to 60 degrees C., more preferably in the range from 40 degrees C. to 50 degrees C. In preferred embodiment the incubation temperature is 50 degrees C. which is the most applied temperature for incubation. However, in one preferred embodiment the lignocellulosic material is incubated at temperatures above 50 degrees C., where the polypeptide of the present invention is still active in contrast to a number of known beta-glucosidases.

In one embodiment the method comprises treating said lignocellulosic material with at least one additional component. The at least one additional component is for example selected from the group consisting of cellulase, endogluconase, cellobiohydrolase, beta-glucosidase, hemicellulase, esterase, laccase, protease and peroxidise. It is appreciated that the at least one component in separate embodiments is cellulase, endogluconase, cellobiohydrolase, beta-glucosidase, hemicellulase, esterase, laccase, protease or peroxidise.

In one embodiment of the method of the present invention, said lignocellulosic material is at least partly converted or degraded to monosaccharide glucose units. In one embodiment at least 50% of said lignocellulosic material is converted or degraded to monosaccharide glucose units, more preferably at least 60%, preferably at least 70%, more preferably at least 80%, preferably at least 90%, more preferably 95%. Preferably 97% said lignocellulosic material is converted or degraded to monosaccharide glucose units Moreover, the invention relates to a method of producing monosaccharides from a lignocellulosic material, said method comprising a) incubating the cellulosic material with at least one beta-glucosidase polypeptide of the invention, at least one recombinant host cell, at least one composition of the invention, at least one kit-of-parts, and/or at least one microorganism of the invention.

Given that the microorganism and/or host cell of the present invention are able to produce BGL polypeptide of high activity, the microorganism and/or hoist cell is suitable for on-site enzyme production, where the enzyme, such as BGL enzyme (e.g. BGL 1, BGL2, BGL3 and/or BGL4 or functional variants thereof) are produced on location as opposed to being delivered as a prepared enzyme solution. This is particularly useful because at least a part of the beta-glucosidase activity remains in the incubation broth of the microorganism. When the microorganism or host cell is used for on-site enzyme production, the degradation and/or conversion of a lignocellulosic material may be further facilitated by introducing an additional polynucleotide encoding a cellulase, an endogluconase, a cellobiohydrolase, a beta-glucosidase, a hemicellulase, an esterase, a laccase, a protease and/or a peroxidase.

Pretreatment of Solid Lignocellulosic Material

The first step in the process for converting solid lignocellulosic biomass material into lower saccharides, such as monosaccharides, involves preferably a pretreatment of the biomass, wherein the rigid structure of biomass are broken and the accessibility of the sugar polymers for the enzyme hydrolysis is increased. In one embodiment the pretreatment is subjecting the biomass to extreme temperatures, pressure and acid/base conditions or the milder biological approaches as described in Alvira et al 2010 *Bioresour Technol* 101, 4851-4861), Mosier el at 2005 *Bioresour Technol* 96, 673-686; Sun & Cheng 2002 *Bioresour Technol* 83, 1-11, hereby incorporated by reference.

Accordingly, the methods of the present invention for the degration and/or conversion of a lignocellulosic material preferably involve a step of pretreating the lignocellulosic material. The pretreatment include any treatment suitable for disrupting the rigid structure of the lignocellulosic raw material, and making sugar polymers accessible for enzymatic attack. For example, the pretreatment may include biological pretreatments physical pretreatments and chemical pretreatments, and combination thereof, including physico-chemical pretreatments.

In one embodiment, the method of the invention comprises pretreating the lignocellulosic material with an agent capable of converting said lignocellulosic material into cellobiose and/or cellodextrins. The agent is for example an acid, an endoglucanase and/or a cellobiohydrolase.

Biological pretreatments may involve fungal pretreatment, for example with lignin-degrading fungi, such as white-rot fungi such as *Phanerochaete chrysosporium, Ceriporia lacerata, Cyathus stercolerus, Ceriporiopsis subvermispora, Pycnoporus cinnarbarinus* and/or *Pleurotus ostreaus.*

Physical pretreatments may involve mechanical comminution, where the average particle size and cristallinity of the lignocellulosic material is reduced in order to increase the specific surface and reduce the degree of polymerization. This can be achieved by combination of chipping, grinding or milling depending on the final particle size of the material (e.g. 10-30 mm after chipping and 0.2-2 mm after milling or grinding). Another physical pretreatment form is extrusion, where the lignocellulosic material is subjected to heating, mixing and shearing, resulting in physical and chemical modifications during the passage through the extruder. Screw speed and barrel temperature disrupt the lignocellulose structure causing defibrillation, fibrillation and shortening of the fibers, which increases the accessibility of carbohydrates to enzymatic attack.

Chemical pretreatments may involve alkali pretreatments, where the lignocellulosic material is treated with for example sodium, potassium, calcium and ammonium hydroxides. Another alternative is acid pretreatment, which serves to solubilize the hemicellulosic fraction of the biomass and to make the cellulose more accessible to enzymes. Acid pretreatment can be performed with concentrated or diluted acid but utilization of concentrated acid is less attractive for ethanol production due to the formation of inhibiting compounds. Furthermore, equipment corrosion problems and acid recovery are important drawbacks when using concentrated acid pretreatments. Other examples of chemical pretreatments are Ozonolysis (lysis with ozone), Organosolvation (treatment with organic or aqueous solvent mixtures), and Ionic liquids (ILs) (i.e. salts) pretreatment.

Various combinations of biological, physical and chemical pretreatments are also within the scope of the present invention. In one example the lignocellulosic material is subject to physico-chemical pretreatments, such as SO2-steam explosion, in which the biomass is subjected to pressurised steam for a period of time ranging from seconds to several minutes, and then suddenly depressurised. This pretreatment combines mechanical forces and chemical effects due to the hydrolysis (autohydrolysis) of acetyl groups present in hemicellulose.

In one embodiment, the pretreatment involves alkali treatment, in another preferred embodiment the pretreatment involves acid treatment. In yet another embodiment the pretreatment comprises a step of organosolv treatment. In a further embodiment the pretreatment involves steam-, ammonia fiber- or $CO_2$ explosion, and/or wetoxidation. It is appreciated that any of the listed pretreatments can be used in separate embodiments or using one or more types of pretreatment in combination. A person skilled in the art knows how to pretreat biomass material prior to hydrolysis of cellulose, hemicelluse, cellobiose, cuclodextrin and/or pectin.

Further Processing of Degraded and/or Converted Lignocellulosic Material

By the method of the present invention, a lignocellulosic material is at least partly degraded to monosaccharide glucose units, and preferably, at least 50% of said lignocellulosic material is degraded to monosaccharide glucose units. Those monosaccharide glucose units may then be used for further chemical modification or processing, for chemical anabolism, and/or for generation of other chemical products.

So, in one embodiment, the monosaccharide glucose units are incubated with one or more fermenting microorganisms thereby producing a fermentation product. The fermenting microorganism is selected from any suitable microorganism, for example yeast, fungi or bacteria. The method may comprise obtaining at least one fermentation product from the fermentation. The at least one fermentation product is for example an alcohol, inorganic acid, organic acid, hydrocarbon, ketone, amino acid, and/or gas. The fermentation product is preferably recovered from the fermentation.

The monosaccharide glucose units may however, also be used for production of any chemical product, which normally requires glucose. In this way, the method of the present invention may be used for processes, which involved glucose, which is normally obtained from sources other than lignocellulosic material.

In one embodiment, the monosaccharide glucose units are used for the production of a chemical product selected from the group consisting of Formic Acid, Methanol, Carbon Monoxide (+H2 gives syngas), Carbon dioxide, Acetaldehyde, Acetic acid & anhydride, Ethanol, Glycine, Oxalic acid, Ethylene glycol, Ethylene oxide, Alanine, Glycerol, 3-Hydroxypropionic acid, Lactic acid, Malonic acid, Serine, Propionic acid, Acetone, Acetoin, Aspartic acid, Butanol, Fumaric acid, 3-Hydroxybutryolactone, Malic acid, Succinic acid, Threonine, Arabinitol, Furfural, Glutamic acid, Glutaric acid, Itaconic acid, Levulinic acid, Proline, Xylitol, Xylonic acid, Aconitic acid, Adipic acid, Citric acid, Fructose, 2,5 Furan dicarboxylic acid, Glucaric acid, Gluconic acid, Kojic & Comeric acid, Lysine, and/or Sorbitol. However, it is understood that the monosaccharide glucose units obtained from degradation/conversion of lignocellulosic material by a method of the present invention, may be used for any chemical process, and for the generation of any chemical product, wherein glucose is normally employed. In a preferred embodiment, the chemical product is isolated from the reaction.

Composition

The present invention also relates to compositions comprising one or more of the components of the present invention.

In one aspect, the present invention relates to a composition comprising a) a polypeptide of the present invention, such as a polypeptide comprising
- an amino acid sequence selected from SEQ NO: 3, 4, 7, 10, and 13,
- a biologically active sequence variant of any of SEQ NO: 3, 4, 7, 10, and 13, wherein said variant has at least 92% sequence identity to said SEQ NO: 3, 4, 7, 10, and 13, or
- a biologically active fragment of at least 30 consecutive amino acids of any of the amino acid sequences of a) through b);

b) a polynucleotide of the present invention, such as a polynucleotide comprising
- a polynucleotide sequence encoding a polypeptide consisting of an amino acid sequence SEQ ID NO: 3, 4, 7, 10, and 13,
- a polynucleotide sequence encoding a biologically active sequence variant of the amino acid sequence, wherein the variant has at least 92% sequence identity to said SEQ ID NO: 3, 4, 7, 10, and 13, and
- a polynucleotide sequence encoding a biologically active fragment of at least 30 consecutive amino acids of any of the amino acid sequences of a) through b), or
- SEQ ID NO.: 1, 2, 5, 6, 8, 9, 11, 12, 14, 15, 16, 17, or 29, or
- a polynucleotide comprising a nucleic acid sequence having at least 70% identity to SEQ ID NO: 1, 2, 5, 6, 8, 9, 11, 12, 14, 15, 16, 17, or 29, or
- a polynucleotide hybridising to SEQ ID NO.: 1, 2, 5, 6, 8, 9, 11, 12, 14, 15, 16, 17, or 29, and
- a polynucleotide complementary to any of the above;

c) a nucleic acid vector comprising a polynucleotide sequence of the present invention, such as a polynucleotide mentioned under b)

d) a host cell of the present invention, such as a host cell comprising a polypeptide mentioned under a), a polynucleotide of the present invention, such as mentioned under b) and/or a recombinant nucleic acid vector of the present invention, such as mentioned under c), e) a microorganism of the species *Aspergillus saccharolyticus*, such as the microorganism as deposited in the Centraalbereau voor Schimmeicultures (CBS) and having accession number CBS 127449, or a descendant or a functional mutant thereof In another aspect, the invention relates to a composition comprising a beta-glucosidase polypeptide of the present invention, or a biologically active variant or fragment thereof.

Thus, one aspect of the present invention, relates to a composition comprising a beta-glucosidase polypeptide of the present invention as defined previously herein. The composition preferably comprises a carrier/buffer. A non-limiting example of a suitable buffer is a citrate-phosphate buffer with pH in the range of 4 to 5.

Kit of Parts

The present invention in one aspect relates to a kit-of parts comprising at least one polypeptide of the present invention, at least one recombinant nucleic acid vector of the present invention, at least one recombinant host cell of the present invention, at least one isolated microorganism of the present invention, and/or at least one composition of the present invention, and at least one additional component.

In one embodiment the additional component is selected from the group consisting of cellulase, endogluconase, cellobiohydrolase, beta-glucosidase, hemicellulase, esterase, laccase, protease and peroxidise.

In one embodiment the kit-of-parts comprises at least one additional component. Such additional component is for example selected from enzymes degrading cellulose, such as endoglucanase, endo 1-4 β-glucanase, cellobiohydrolase, exo-1-4 β-glucanase, β-glucosidase, enzymes degrading hemicellulose of both the O-acetyl-4-O-methylglucoronoxylan-type e.g endoxylanase, acetylxylane-esterase, α-glucuronidase, β-xylosidase, α-arabinosidase or the O-acetylgalactoglucomannan-type such as endomannan, α-galactosidase, acetylglucomannan-esterase, β-mannosidase, β-glucosidase, enzymes degrading lignin e.g. lignin peroxidase, manganese peroxidase, laccase), enzymes degrading pectin e.g. endo-polygalacturonidases, exo-polygalacturonidase, rhamno-galacuronidase, pectinlyase, rhamnogalacturonan-lyase, pectin-methylesterase, rhamnogalacturonanacetylesterase, oligo-galacturonan-lyase, enzymes degrading starch such as α-amylase, β-amylase, isoamylase, pullulanase, α-1-6-glucanhydrolase) or any other reserve hydrocarbon such as, for example but not exclusively, fructans, inulin, chitin, chitosan, planteose, legumin, xyloglucan, mannan or laminaran.

In a preferred embodiment, the additional component is endoglucanase (EC 3.2.1.4). Another preferred embodiment, the additional component is cellobiohydrolase (EC 3.2.1.91).

It is appreciated that at least one, such as at least two, for example at least 3, such as at least 4, for example at least 5, such as at least 6, for example at least 7, such as at least 8, for example at least 9 additional components and that different groups of additional components may be used in combination such as at least one endoglucanase and at least one cellobiohydrolase.

In one embodiment, the at least one additional component is selected from cellulases, such as Accellerase®, Celluclast®, Cellic CTec2®, and/or AcelleraseDUET®.

The components of the kit-of parts of the present invention are packaged or marked for use together.

In one embodiment, the kit-of-parts can contains two components in one container, and a third component and any additional components in one or more separate containers. Optionally, a kit-of-parts further contains instructions for combining the components so as to formulate composition suitable for degradation or conversion of a cellulosic material, for hydrolyzing a polysaccharide and/or for fermenting a cellulosic material.

The components of the kit-of-parts are preferably comprised in individual compositions, it is however within the scope of the present invention that the components of the kit-of-parts all are comprised within the same composition.

In one embodiment, the kit-of-parts preferably comprises an adjuvant and/or a carrier. The choice of carrier depends on the specific use of the kit-of parts and will be obvious for those of skill in the art.

A carrier may be present independently of an adjuvant. The function of a carrier can for example be to increase the molecular weight of in particular peptide fragments in order to confer stability, to increase the biological activity, or to increase half-life.

The compositions provided by the kits-of-parts of the present invention may be used simultaneously or sequentially.

Additional Component

In the methods of the present invention for degrading a lignocellulosic material, the lignocellulosic material may also be treated with at least one additional component, Such additional component is for example selected from enzymes degrading cellulose, such as (endoglucanase, endo 1-4 β-glucanase, cellobiohydrolase, exo-1-4 β-glucanase, β-glucosidase), hemicellulose of both the O-acetyl-4-O-methylglucoronoxylan-type (endoxylanase, acetylxylane-esterase, α-glucuronidase, β-xylosidase, α-arabinosidase) or the O-acetylgalactoglucomannan-type (endomannan, α-galactosidase, acetylglucomannan-esterase, β-mannosidase, β-glucosidase), lignin (lignin peroxidase, manganese peroxidase, laccase), pectin (endo-polygalacturonidases, exo-polygalacturonidase, rhamno-galacuronidase, pectinlyase, rhamnogalacturonan-lyase, pectin-methylesterase, rhamnogalacturonanacetylesterase, oligo-galacturonan-lyase), starch (α-amylase, β-amylase, isoamylase, pullulanase, α-1-6-glucanhydrolase) or any other reserve hydrocarbon such as, for example but not exclusively, fructans, inulin, chitin, chitosan, planteose, legumin, xyloglucan, mannan or laminaran.

In a preferred embodiment, the additional component is endoglucanase (EC 3.2.1.4). Another preferred embodiment, the additional component is cellobiohydrolase (EC 3.2.1.91). It is appreciated that at least one, such as at least two, for example at least 3, such as at least 4, for example at least 5, such as at least 6, for example at least 7, such as at least 8, for example at least 9 additional components and that different groups of additional components may be used in combination such as at least one endoglucanase and at least one cellobiohydrolase.

The products of the cellulosic material degradation or conversion methods of the present invention may be used for a number of subsequent purposes.

In one aspect of the invention, the glucose monosaccharide products are used in a method for fermenting a cellulosic material, said method comprising a. treating the cellulosic material with at least one polypeptide of the present invention, at least one recombinant host cell of the present invention, at least one microorganism of the present invention, at least one composition of the present invention, at least one kit-of parts of the present invention, and
b. incubating the treated cellulosic material with one or more fermenting microorganisms.
c. obtaining at least one fermentation product In one embodiment the fermentation product is at least one alcohol, inorganic acid, ketone, amino acid, organic acids, hydrocarbons and/or gas.

EXAMPLES

The following examples are provided by way of illustration only and not by way of limitation. Those of skill in the art will readily recognize a variety of noncritical parameters that could be changed or modified to yield essentially similar results. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

Example 1

Discovery of a New Prominent Beta-Glucosidase Producing *Aspergillus* sp

Fungal Samples

This example comprises fungal samples from many different sources, including new isolations and "previously isolated fungi. Table 1 specifies strain numbers, identity, identification method, origin, and reference of each sample. New fungal isolates were from soil and decaying wood samples, isolated by multiple transfers on potato broth agar (PDA) plates supplemented with 50 ppm chloramphenicol and 50 ppm kanamycin, incubated at room temperature. Samples isolated in this work were all identified by ITS sequencing, using the method described below. All fungi were grown on potato dextrose agar (PDA, Sigma) at room temperature and maintained in 10% glycerol at −80° C.

The following Aspergilli reference strains were kindly donated by Professor Jens C. Frisvad, Technical University of Denmark: *A. niger* CBS 554.65$^T$, *A. homomorphus* CBS 101889$^T$. *A. aculeatinus* CBS 121060$^T$, *A. aculeatus* CBS 172.66$^T$, *A. uvarum* CBS 121591$^T$, and *A. japonuicus* CBS 114.51$^T$.

TABLE 1

Fungi included in the beta-glucosidase screening

| Identity (strain number) | ID method[1] | Origin | Reference[2] |
|---|---|---|---|
| *Alternaria radicina* (R27) | M | Poland | K. Tylkowska |
| *A. radicina* (R28) | M | Poland | K. Tylkowska |
| *Alternaria* sp. (AS1-2) | ITS | Jamaica | This work |
| *Amorphothea resinae* (Anja) | ITS | Denmark | This work |
| *Aspergillus* sp (AP) | ITS | Denmark | This work. (Sorensen et al.,) |
| *Aspergillus* sp. (1259) | M | Costa Rica | (Danielsen, 1997) |
| *A. fumigates* (AS3-1) | ITS | Jamaica | This work |
| *A. fumigatus* (AS11-2) | ITS | Jamaica | This work |
| *A. fumigatus* (AS11-3) | ITS | Jamaica | This work |
| *A. fumigatus* (AS12) | ITS | Jamaica | This work |
| *A. fumigatus* (AS2-3) | ITS | Jamaica | This work |
| *A. fumigatus* (AS2-3) | ITS | Jamaica | This work |
| *A. fumigatus* (AS9-7) | ITS | Jamaica | This work |
| *A. fumigatus* (AS11-4) | ITS | Jamaica | This work |
| *A. niger* (Hj1) | ITS | Denmark | This work. (Sorensen et al.,) |
| *A. niger* (IBT25747) | ITS | Not known | This work. (Sorensen et al.,) |
| *A. terreus* (AS4-1) | ITS | Jamaica | This work |
| *A. terreus* (AS9-2) | ITS | Jamaica | This work |
| *Chaetomium aureum* (1165) | M | Costa Rica | (Danielsen, 1997) |
| *C. globosum* (11.4 kont) | ITS | Denmark | This work. (Sorensen et al.,) |
| *Cladosporium* sp. (1160) | M | Costa Rica | (Danielsen, 1997) |
| *Cladosporium* sp. (1209) | M | Costa Rica | (Danielsen, 1997) |
| *Cladosporium* sp. (1195) | M | Costa Rica | (Danielsen, 1997) |
| *Cladosporium* sp. (1208) | M | Costa Rica | (Danielsen, 1997) |
| *C. cladosporiades* (2.1) | ITS | Denmark | This work. (Sorensen et al.,) |
| *Clanostachys rosea* (IBT9371) | M, UP-PCR | Denmark | (Bulat et al., 1998) |
| *C. rosea* (Gr3) | M, UP-PCR | Denmark | (Bulat et al., 1998) |
| *C. rosea* (Gr5) | M, UP-PCR | Denmark | (Bulat et al., 1998) |
| *Colletotrichum acutatum* (9955) | ITS | Denmark | T. Sundelin |
| *C. acutatum* (F5-3) | ITS | Costa Rica | (Schiller et al., 2006) |
| *C. acutatum* (F7-1) | ITS | Costa Rica | (Schiller et al., 2006) |
| *C. acutatum* (Lupin1A) | ITS | Not known | T. Sundelin |
| *C. acutatum* (SA2-2) | ITS | Denmark | (Sundelin et al., 2006) |
| *C. gloeosporioides* (2133A) | ITS | Denmark | T. Sundelin |
| *Coprinopsis cinerea* (AS2-2) | ITS | Jamaica | This work |
| *Drechslera* sp. (1178) | M | Costa Rica | (Danielsen, 1997) |
| *Fusarium* sp. (3.012) | M | Denmark | I. Weiergang |
| *Fusarium* sp. (3.015) | M | Denmark | I. Weiergang |
| *F. avenaceum/trincinctum* (1.8.1) | ITS | Denmark | This work. (Sorensen et al.,) |
| *F. culmorum* (IBT9615) | M | Norway | (Tobiasen at al., 2007) |
| *F. equiseti* (1236) | M | Costa Rica | (Danielsen, 1997) |
| *F. graminearum* (1237) | M | Costa Rica | (Danielsen, 1997) |
| *F. graminearum* (NRRL31084) | M | USA | (Tobiasen at al., 2007) |
| *F. graminearum* (IBT9203) | M | Costa Rica | (Tobiasen at al., 2007) |
| *F. moniliforme* (1247) | M | Costa Rica | (Danielsen, 1997) |
| *F. moniliforme* (1258) | M | Costa Rica | (Danielsen, 1997) |
| *F. oxysporum* (1244) | M | Costa Rica | (Danielsen, 1997) |
| *F. oxysporum* f.s.p. *pisi* (88.001) | M | Denmark | I. Weiergang |
| *F. semitectum* (1232) | M | Costa Rica | (Danielsen, 1997) |
| *F. semitectum* (1242) | M | Costa Rica | (Danielsen, 1997) |
| *Nigrospora* sp. (1168) | M | Costa Rica | (Danielsen, 1997) |
| *Penicillium* sp. (1219) | M | Costa Rica | (Danielsen, 1997) |
| *P. chrysogenum* or *P. commune* (11.5) | ITS | Denmark | This work, (Sorensen et al.,) |
| *P. chrysogenum* or *P. commune* (2.3A) | ITS | Denmark | This work, (Sorensen et al.,) |
| *P. paneum* (14) | ITS | Denmark | This work, (Sorensen et al.,) |
| *P. paneum* (2.8) | ITS | Denmark | This work, (Sorensen et al.,) |
| *P. spinolosum* (1.6) | itS | Denmark | This work, (Sorensen et al.,) |
| *P. spinolosum* (2.38) | ITS | Denmark | This work, (Sorensen et al.,) |

TABLE 1-continued

Fungi included in the beta-glucosidase screening

| Identity (strain number) | ID method[1] | Origin | Reference[2] |
|---|---|---|---|
| *P. spinolosum* (9.3.2) | ITS | Denmark | This work, (Sorensen et al.,) |
| *P. spinolosum* (9.4.2) | ITS | Denmark | This work, (Sorensen et al.,) |
| *P. swiecickii* or *P. raistrickii* (11.4) | ITS | Denmark | This work, (Sorensen et al.,) |
| *Pestalotiopsis* sp. (1220) | M | Costa Rica | (Danielsen, 1997) |
| *Pestalotiopsis* sp. (1226) | M | Costa Rica | (Danielsen, 1997) |
| *Rhizoctonia solani* (C596) | M, UP-PCR | Japan | (Lubeck & Poulsen, 2001) |
| *R. solani* (ST-11-6) | M, UP-PCR | Japan | (Lubeck & Poulsen, 2001) |
| *R. solani* (AH-1) | M, UP-PCR | Japan | (Lubeck & Poulsen, 2001) |
| *R. solani* (RH165) | M | Japan | (Lubeck & Poulsen, 2001) |
| *R. solani* (GM10) | M, UP-PCR | Japan | (Lubeck & Poulsen, 2001) |
| *Binuclear Rhizoctonia* (S21) | M | USA | (Lubeck & Poulsen, 2001) |
| *Binuclear Rhizoctonia* (SN-1-2) | M | Japan | (Lubeck & Poulsen, 2001) |
| *Rhizopus microsporum* (A51-1A) | ITS | Jamaica | This work |
| *R. microsporum* (A51-1B) | ITS | Jamaica | This work |
| *R. microsporum* (A52-4) | ITS | Jamaica | This work |
| *Spaeropsidales* (1190) | M | Costa Rica | (Danielsen, 1997) |
| *Stenocarpella* sp. (1198) | M | Costa Rica | (Danielsen, 1997) |
| *Stenocarpella* sp. (1214) | M | Costa Rica | (Danielsen, 1997) |
| *Stenocarpella* sp. (1239) | M | Costa Rica | (Danielsen, 1997) |
| *Thielavia* sp. (AS11-1) | ITS | Jamaica | This work |
| *Trichoderma harzianum* (5.1) | ITS | Denmark | This work, (Sorensen et al.,) |
| *T. harzianum* (O7) | M | Costa Rica | (Danielsen, 1997) |
| *T. harzianum* (IBT9385) | M, UP-PCR | Sweden | (Bulat et al., 1998) |
| *T. koningii* (1211) | M | Costa Rica | (Danielsen, 1997) |
| *T. koningii* (CB5850.68) | M, UP-PCR | Germany | (Bulat et al., 1998) |
| *T. virens* (I10) | ITS | Italy | (Sarrocco et al., 2006) |
| *T. viride* (IBT8186) | M, UP-PCR | Denmark | (Bulat et al., 1998) |
| *T. viridescens* (7.1) | ITS | Denmark | This work, (Sorensen et al.,) |

[1]Identification method: M = morphology, ITS = ITS and NCBI NCBI Blast of search, UP-PCR = PCR finger printing

[2]Where names are found instead of reference numbers, the fungal strains have not previously been published, but identified by the person specified. Prof. Krystyna Tylkowska, August Cheszkowski Agricultural University of Poznan, Poland, Thomas Sundelin, University of Copenhagen, DK, Inge Weiergang, Maribo Seed, Nordzucker AG.

Beta-Glucosidase Screening

For beta-glucosidase activity screening, three 0.5×0.5 cm squares were cut from PDA plates with 7 days old single fungal strains and incubated in liquid culture of 20 g/l wheat bran (Finax), 20 g/l corn steep liquor (Sigma), 3 g/l $NaNO_3$, 1 g/l $K_2HPO_4$, 0.5 g/l KCl, 0.5 g/l $MgSO_47H_2O$, 0.01 g/l $FeSO_47H_2O$ in a Falcon tube set-up with 10 ml of media shaking (180 rpm) at room temperature for another 7 days. The samples were centrifuged at 10,000 rpm for 10 min and the supernatants were subsequently assayed for beta-glucosidase activity and protein content.

Beta-glucosidase assay was carried out using 5 mM p-nitrophenyl-beta-D-glucopyranoside (pNPG) in 50 mM Na-Citrate buffer pH 4.8 as substrate for measuring beta-glucosidase activity. 15 μl sample and 150 μl substrate was incubated at 50° C. for 10 min in 200 μl PCR tubes in a thermocycler (Biorad); 30 μl of the reaction was transferred to a microtiter plate already containing 50 μl 1M $Na_2CO_3$ for termination of the reaction. Absorbance was read at 405 nm in a plate reader (Dynex Technologies Inc.). pNP was used to prepare a standard curve. One unit (U) of enzyme activity was defined as the amount of enzyme needed to hydrolyze 1 μmol pNPG in 1 minute. Protein quantification was done using the Pierce BCA protein assay kit microplate procedure according to manufacturer's instructions (Pierce Biotechnology).

Identification of Fungi Using Sequencing of ITS1 Region

DNA extraction was carried out by the method of Dellaporta et al. 1983, using bead beating (2×20 sec) of fungal biomass in extraction buffer (500 mM NaCl, 100 mM Tris pH8, 50 mM EDTA, 1 mM DTT) and 1×20 sec with SDS added to final concentration of 2%. Protein and cell debris was precipitated with potassium acetate at a final concentration of 1.4 M. DNA was precipitated with equal volumes of sample and 2-propanol, followed by washing with 70% ethanol, and finally resuspended in water. Two fungal primers ITS1 (5' TCCGTAGGTGAACCTGCGG 3') and ITS2 (5' GCTGCGTTCTTCATCGATGC 3') that match the conserved 18S and 5.8S rRNA genes, respectively, were used for the amplification of the non-coding IST1 region (White et al., 1990, Kumar et al., 2008). Approx 100 ng genomic DNA was used as template in a polymerase chain reaction with 1 U proof reading WALK polymerase (A&A Biotechnology), PCR buffer (50 mM Tris pH8, 0.23 mg/ml BSA, 0.5% Ficoll, 0.1 mM cresol red, 2.5 mM $MgCl_2$), 0.2 mM of dNTP, 0.4 μM of each primer ITS1 and ITS2. Using a thermocycler (BioRad), an initial denaturation step (94° C., 2 min) was followed by 35 cycles of denaturation (94° C., 30 sec), annealing (60° C., 30 sec), and elongation (72° C. 1 min), and a final elongation step (72° C., 2 min) following the last cycle. All products were checked by gel electrophoresis for a band size of approx. 600 bp. Depending on the purity of the sample, either GelOut or CleanUp was performed (EZNA kits from Promega) according to the manufacturer's instructions. DNA sequencing was performed by either MWG Eurofins, Germany or Starseq, Germany, directly sequencing the PCR products with the ITS1 or ITS4 primer. The sequence data was submitted to the GenBank NCBI nucleotide NCBI Blast of search database for fungal identification.

Molecular Phylogeny

Phylogenetic analysis of the ITS1 region of the fungus AP/*Aspergillus saccharolyticus* and different Aspergilli was carried out as described by Varga et al. (2007) and Samson et al. (2007). ClustalW multiple alignment was used for sequence alignment and manual improvement of the alignment was performed using BioEdit (http://www.mbio.ncsu.edu/BioEdit/bioedit.html). The PHYLIP program package version 3.69 was used for preparation of phylogenetic trees (Felsenstein, 2004). The distance matrix of the data set was calculated based on the Kimura method (Kimura, 1983) using the program "Dnadist". The phylogenetic tree was prepared by running the program "Neighbor" using the neighbor-joining method (Saitou & Nei, 1987) to obtain an unrooted trees. *A. flavus* was defined as the outgroup in the program "Retree", and finally the tree was visualized using the program TreeView (win32) (Page, 1996). Bootstrap values (Felsenstein, 1985) were calculated by running the program "Seqboot" to produce 1000 bootstrapped data sets from the original data set. Again, "dnadist" with the Kimura method was used to prepare distance matrices of the multiple data sets, and "neighbor" with the neighbor-joining method to obtain unrooted trees of the multiple data sets. Finally, the bootstrap values were obtained from the consensus tree which was identified by the majority-rule consensus method by running the program "Consense".

Strain AP/*Aspergillus saccharolyticus*, Culture Conditions and Enzyme Extract Preparation The fungal strain AP/*Aspergillus saccharolyticus* was grown on potato dextrose agar (Sigma) for sporulation. Spores were harvested after 7 days of growth by adding sterile water to the plate and scrape on the surface of the culture. The heavy spore suspension was filtered through Myra cloth. Two ml of the spore solution was inoculated into 200 ml seed medium (2.0 g/l wheat bran, 5 g/l corn steep powder, 0.25 g/l yeast extract, 0.75 g/l peptone, 1.4 g/l $(NH_4)_2SO_4$, 2.0 g/l $KH_2PO_4$, 0.4 g/l $CaCl_2$ $2H_2O$, 0.3 g/l $MgSO_4$ $H_2O$, 5.0 mg/l $FeSO_4$, 1.6 mg/l $MnSO_4$ $7H_2O$, 1.4 mg/l $ZnSO_4$ $7H_2O$, 2.0 $CoCl_2$ $6H_2O$) in an 500 ml Erlenmeyer flask, and incubated at 30° C. for 2 days, shaking at 160 rpm. Solid state fermentation at approximately 30% TS was carried out adding 100 ml of the cultivated seed medium to 1 l of a solid state fermentation medium comprising of 343 g wheat bran (TS of 87.4%), 9 g corn steep powder, 557 ml Czapek liquid (3 g/l $NaNO_a$, 1 g/l $K_2HPO_4$, 0.5 g/l KCl, 0.5 g/l $MgSO_4$ $7H_2O$, 0.01 g/l $FeSO_4$ $7H_2O$) (Samson et al., 2004a). Incubation was carried out in large flat boxes (20 cm×20 cm×5 cm) in order to allow a large surface area where the fermentation media had a height of approx. 2 cm. The samples were incubated at 30° C. without shaking. After 7 days incubation, liquid was extracted from the medium by pressing the medium by hand using gloves. The extract was centrifuged at 10000 g, and the supernatant filtered through Whatman filter paper.

Beta-Glucosidase Activity Assays

In this work specific activity (U/mg) is defined as units per amount of total protein. Specific beta-glucosidase activity was measured using two different substrates: pNPG and cellobiose. The assay using 5 mM pNPG in NaCitrate buffer pH 4.8 was performed as previously described; enzyme samples were assayed at different concentrations in triple determination to ensure substrate saturation in the assay. The assay using 6 mM cellobiose in 50 mM NaCitrate buffer pH 4.8 was performed as follows: 15 μl sample and 150 μl substrate was incubated at 50° C. for 10 min in PCR tubes in a thermocycler; 50 μl of the reaction was transferred to a HPLC vial already containing 1 ml 100 mM NaOH for termination of the reaction. The glucose concentration was measured at Dionex ICS3000 using gradient elution: 0-20% eluent B (0.5M NaAcetate in 100 mM NaOH) in 13 min followed by 2 min washing with 50% eluent B and 5 min re-equilibrating with 100% eluent A (100 mM NaOH). Samples were assayed at different concentrations in triple determination to ensure substrate saturation in the assay.

Kinetic Studies

For performing Michaelis-Menten kinetics beta-glucosidase activity was measured as described above, but using different substrate concentrations (pNPG 0.1-10 mM, cellobiose 0.2-18 mM), and with an enzyme dilution that ensured substrate saturation was reached within this range. Triple determinations were performed. A substrate saturation curve was prepared by plotting substrate concentration [S] vs reaction rate, v. The Michealis Menten constants Km and Vmax were determined from Hanes-Wolf plots where substrate concentration [S] is plotted against substrate concentration over reaction rate [S]/v, and the linear relationship of the data gives a slope of 1/Vmax, a y-intercept of Km/Vmax, and an x-intercept of −Km.

Glucose Tolerance

For testing glucose tolerance, 5 mM pNPG in NaCitrate buffer pH 4.8 was used as substrate with different glucose amounts added, ranging final glucose concentrations of 0-280 mM. The remaining activity (glucose tolerance) was measured spectrophotometrically by release of pNP at 50° C. reaction conditions, as described earlier. Triple determinations were performed. Using 20 mM cellobiose in NaCitrate buffer pH 4.8 as substrate and glucose concentrations ranging from 0-120 mM, 15 μl sample and 150 μl substrate with the different glucose concentrations was incubated at 50° C. for 10 min in PCR tubes in a thermocycler; 100 μl of the reaction was transferred to a tube already containing 100 μl 200 mM NaOH for termination of the reaction. The reactions were further diluted 512 times and final cellobiose concentration was measured at Dionex ICS3000 using gradient elution: 0-20% eluent B in 13 min followed by 2 min washing with 50% eluent 8 (0.5 M NaAcetate in 100 mM NaOH) and 5 min re-equilibrating with 100% eluent A (100 mM NaOH). The activity was calculated by the amount of cellobiose being hydrolyzed. Triple determinations were performed.

pH and Temperature Profile

For testing the thermostability of the enzyme extract, aliquots of the extracts were incubated in PCR tubes in a thermocycler with temperature gradient option at 12 different temperatures from 48.5 to 67.0° C. for different time periods (0-4 hours) followed by assaying the activity at 50° C. with 5 mM pNPG in NaCitrate buffer pH 4.8 as substrate. The rate of denaturation, $k_D$, was calculated as the slope of a semi-logarithmic plot of remaining activity vs incubation time. The half life was calculated as: $T_{1/2}=\ln(2)/k_D$.

For testing the pH optimum of the enzyme extracts, they were assayed at 50° C. with 5 mM pNPG in Citrate Phosphate buffer at different pH ranging from 2.65 to 7.25. Endoglucanase activity of Celluclast 1.5 L was assayed with AZO-CMC as described by the manufacturer (Megazyme), but testing the same pH range 2.65-7.25 as for the pNPG assay.

Hydrolysis of Cellodextrins

Hydrolysis of cellohexaose was carried out by mixing, in the ratio 1:1, 0.2 mM cellohexaose in 50 mM NaCitrate buffer pH 4.8 and enzyme diluted in 50 mM NaCitrate buffer pH 4.8 to a concentration of 3.7 μg/ml. The reaction was incubated at 50° C. and for a period of 30 min, 100 μl sample was placed on ice every 5 min. 100 μl 200 mM NaOH was added to terminate the reaction, and after another 1 fold dilution with 100 mM NaOH, the samples were analyzed at Dionex ICS3000 using gradient elution: 0-30% eluent B in 26 min followed by 2 min washing with 50% eluent B (0.5 M NaAcetate in 100 mM NaOH) and 5 min re-equilibrating with 100% eluent A (100 mM NaOH).

Hydrolysis of Pretreated Bagasse

Pretreated bagasse was kindly provided by BioGasol, Denmark. The bagasse had been pretreated using wet explosion (personal communication with BioGasol). Bagasse hydrolysis was carried out in 2 ml Eppendorf tubes in thermoshaker heating blocks. The pretreated bagasse was hydrolyzed at 5% dry matter (DM) with a total enzyme load of 10 mg protein per g DM. The ratio amount of Celluclast 1.5 L vs extract from strain AP/*Aspergillus saccharolyticus* or Novozym 188 was varied, ranging 0-100% of one compared to the other. The hydrolysis was carried out at 50° C. for 24 hours, using triple determinations. The samples were centrifuged and supernatants filtered through 0.45 μm filters before sugar analysis using the Ultimate 3000 HPLC (see below).

Analytical Equipment

DionexICS-3000 equipped with an amperometric detector using a gold working electrode and an Ag/AgCl pH reference electrode was used for measuring glucose, cellobiose, and cellooligomers by ionexchange chromatography, acquiring and interpreting data with the Chromeleon software (Dionex). 10 μl samples were run on a CarboPac PA1 column with 100 mM NaOH as eluent A and 0.5 M NaAcetate in 100 mM NaOH as eluent B. Gradient runs were performed as described in the different assays, all at a flow rate of 1 ml/min. Standards of glucose, cellobiose, -triose, -tetraose, -pentaose, and -hexaose were run at concentrations 3.125 μM-0.1 mM. Ultimate 3000 HPLC equipped with RI-101 detector (shodex) was used for measuring glucose and cellobiose by high pressure liquid chromatography, acquiring and interpreting data with the Chromeleon software (Dionex). 10 μl samples were run on a BIORAD aminex HPX-87H ion exclusion column, heated to 60° C., run with 4 mM $H_2SO_4$ as eluent at flow rate 0.6 ml/min. Standards of glucose and cellobiose were run at concentration 0.5-20 g/l.

Results

Beta-Glucosidase Activities in Broad Screening

Eighty six filamentous fungal strains, spanning 19 different fungal genera, were screened for extracellular beta-glucosidase activity using pNPG as substrate; most of the screened fungi belonging to the ascomycota phylum (Table 1). The screening showed a great variety in activity levels, with a few strains being remarkably better than the others (FIG. 1). All produced extracellular beta-glucosidase, though for about 35% of the assayed fungi the activity was negligible (<0.1 U/ml). Some genus tendencies are seen, with *Aspergillus*, a few *Fusarium, Penicillium*, and *Trichoderma viridescens* showing greatest beta-glucosidase activity at the assayed conditions. Where several strains belonging to same species were assayed, the variation at species level was in most cases insignificant, except for *A. niger* where a great variation was observed within the two strains, the stain Hj1 showing approximately two times the activity of strain F1.

Strain number AP (identified as an *Aspergillus* sp or *Aspergillus saccharolyticus*) and strain number Hj1 (identified as an *Aspergillus niger*) showed significantly greater activity than all other strains assayed at these conditions, with strain AP/*Aspergillus saccharolyticus* reaching more than ten times greater activity than the average of all the stains assayed.

Identity of the Prominent Beta-Glucosidase Producing *Aspergillus* sp.

Primers matching the conserved 18S and 5.8S rRNA genes were used for the amplification of the non-coding ITS1 region. A GenBank NCBI NCBI Blast of of the ITS1 sequence of strain AP/*Aspergillus saccharolyticus* resulted in the closest hit being the black aspergilli, *A. kanagawaensis, A. pervulus, A. cervinus, A. eculeatus, A. violaceofucus, A. japonicus*, and *A. bahamensis*, but only with an identity of 81-79%.

Strain AP/*Aspergillus saccharolyticus* was phylogenetically studied by preparing a phylogenetic tree of the ITS1 region of strain AP/*Aspergillus saccharolyticus*, some of the aspergilli mentioned above as well as other selected aspergilli in the section *Nigri* based on the work by Samson et al (2007) (FIG. 2). This placed AP/*Aspergillus saccharolyticus* on its own branch far from the other aspergilli. This low percentage identity of the strain AP/*Aspergillus saccharolyticus* compared to the data in the NCBI database and its location on a separate branch in the phylogenetic tree, clearly indicates that the strain AP/*Aspergillus saccharolyticus* is an unknown species.

*Aspergillus* Screening

The beta-glucosidase activity of the prominent *Aspergillus* sp (strain AP/*Aspergillus saccharolyticus*) was compared to neighbor Aspergilli in the submerged fermentation set up using wheat bran as growth medium as described in the screening. *A. niger* was specifically included as this fungus is a known and industrially used beta-glucosidase producer (Dekker, 1986). Based on the phylogenetic tree, the data is arranged so the column furthest from strain AP/*Aspergillus saccharolyticus* is the most distantly related strain in this *Aspergillus* screening. At the conditions tested, AP/*Aspergillus saccharolyticus* produces significantly greater amount of beta-glucosidase activity (FIG. 3). The protein levels (data not shown) in the assayed extracts did not vary much compared to the difference seen in enzyme activity. Relative to the other Aspergilli tested, strain AP/*Aspergillus saccharolyticus* is therefore more specialized towards beta-glucosidase productions at the tested conditions.

Potential of Strain AP/*Aspergillus saccharolyticus* Enzyme Extract Compared with Commercial Enzymes A solid state fermentation extract of the strain AP/*Aspergillus saccharolyticus* was compared to the commercially available Novozym 188, Celluclast 1.5 L, and Cellic CTec (Novozymes AS, Denmark). Solid state fermentation was chosen to obtain as concentrated an extract as possible. In the previous screening, pNPG activity of 6.6 U/ml (FIG. 3) and specific activity or 3.1 U/mg total protein (data not shown) were obtained for the submerged fermentation of strain AP/*Aspergillus saccharolyticus*. With the solid state fermentation, a pNPG activity of 105 U/ml and a specific activity of 5.7 U/mg total protein were obtained. The volume based activity is naturally increased as the water content of solid state is severely reduced compared to submerged fermentation. However, there is no definite conclusion whether the difference in specific activity (U/mg protein) is due to the solid state fermentation favoring the expression of specifically beta-glucosidase proteins or whether the wheat bran proteins in the extracts originating from the medium make up a larger percentage of the total proteins measured in one case compared to the other and thereby cause the difference observed in specific activity.

As the enzyme extract of strain AP/*Aspergillus saccharolyticus* is intended for use in combination with Celluclast 1.5 L for complete hydrolysis of cellulosic biomasses, the working pH must match the pH profile of Celluclast 1.5 L cellulose activity. Within pH 4.5-6 Celluclast activity stays above 90% of maximum activity measured (FIG. 4). The pH span of strain AP/*Aspergillus saccharolyticus* beta-glucosidase was examined using pNPG as substrate. Its profile is very similar to Novozym 188, with an optimum around pH 4.2 (FIG. 4). Within the pH range 3.8-4.8 the activity stays above 85% of maximum. pH 4.8 generally used in hydrolysis experiments with Celluclast 1.5 L and Novozym 188 is therefore also valid for the AP/*Aspergillus saccharolyticus* extract with beta-glucosidases.

Enzyme kinetics are preferably carried out on pure enzyme preparations, but are in this study used for the comparison of the beta-glucosidases of the crude enzyme extract of strain AP/*Aspergillus saccharolyticus* and the commercial enzyme preparation Novozym 188 and Cellic CTec. Any parameter expressed per amount of protein is always total protein content in the extract or commercial enzyme preparation, with no specific knowledge of how large a fraction that is beta-glucosidase proteins. Kinetic analysis was performed on both pNPG and cellobiose, measuring the specific activity at different substrate concentrations. By plotting reaction rate vs. substrate concentration, it was found that for all three samples, strain AP/*Aspergillus saccharolyticus*, Novozym 188 and Cellic CTec, the hydrolysis of pNPG only follows MM kinetics at low substrate concentrations, while evidence of substrate inhibition or transglycosylation is found at higher concentrations, seen by a decrease in reaction rate with increased substrate concentration (data no shown). With regards to cellobiose, no substrate inhibition was observed within the substrate concentrations tested. The MM kinetics parameters, Vmax and Km, were therefore only determined for cellobiose. The enzyme extract from strain AP/*Aspergillus saccharolyticus* and the commercial preparation Novozym 188 have similar affinity for cellobiose; and values being slightly better than Cellic CTec (Table 2), the lower the Km values the better the affinity. The maximum activity is, however, highest for Cellic CTec, but with strain AP/*Aspergillus saccharolyticus* being better than Novozym 188.

TABLE 2

Kinetic properties of strain AP/*Aspergillus saccharolyticus*, Novozym 188, and Cellic CTec with cellobiose as substrate for MM kinetics study

| | Vmax U/mg | Km mM |
|---|---|---|
| Strain AP | 11.3 | 1.09 |
| Novozym 188 | 7.5 | 1.06 |
| Cellic CTec | 22.9 | 1.69 |

Product inhibition was found to be substrate dependent, especially for strain AP/*Aspergillus saccharolyticus* beta-glucosidases (FIG. 5). Using pNPG as substrate, strain AP/*Aspergillus saccharolyticus* beta-glucosidases remain an activity of >80% at product concentrations 12 times higher than the substrate concentration. Cellic CTec is slightly lower (approx 75%), while the activity of Novozym 188 at this product-substrate ratio has dropped to just below 40%. The activities of strainAP, Cellic CTec, and Novozym 188 is calculated to reach half the maximum activity at concentrations 180, 115, and 60 mM glucose (equal to 36×, 23×, and 12× the substrate concentration), respectively. With regards to cellobiose, an activity drop to around 80% is found for both Strain AP/*Aspergillus saccharolyticus* and Novozym 188 when the product and substrate occur in equal concentrations. Over all, the profile of substrate inhibition is identical for strain AP/*Aspergillus saccharolyticus* and Novozym 188 when using cellobiose as substrate, while with pNPG, strain AP/*Aspergillus saccharolyticus* beta-glucosidases perform much better at high inhibitor concentrations than Novozym 188. This glucose inhibition study demonstrates the importance of testing the true substrate, cellobiose, and not just rely on pNPG data.

The thermostability of the enzymes was examined at temperatures ranging from 48.5 to 67.0° C. using pNPG as substrate. At temperatures up to 58° C. there was no significant difference between strain AP/*Aspergillus saccharolyticus* and Novozym 188 in terms of stability; both were fairly stable throughout the four hours of Incubation (data not shown). Meanwhile, the beta-glucosidases of Cellic CTec were much more sensitive to temperature increases. At temperatures ≥60° C., strain AP/*Aspergillus saccharolyticus* beta-glucosidases are dearly more stable than Novozym 188, and Cellic CTec is uncompetitive with any of them as it is severely inactivated even within the first half hour (FIG. 6). At 60.7° C., 65% of the activity remains for strain AP/*Aspergillus saccharolyticus* beta-glucosidases after 4 hours of incubation, while only 33% activity remains for Novozym 188. The inactivation roughly followed first order kinetics, with the rate constants of denaturation, $k_D$, defined by the slopes of the lines in a semi-logarithmic plot of the remaining activity vs. time for the different temperatures, and the half-life calculated as $T_{1/2}=\ln(2)/k_D$. The calculated half-life of strain AP/*Aspergillus saccharolyticus* at 60.7° C. was 440 min vs 180 min for Novozym 188. To reach a half-life of 180 min for Cellic CTec, the temperature should be lowered to around the tested 55.8° C., while for strain AP/*Aspergillus saccharolyticus* the temperature could be raised to around the tested 62.9° C.

Cellooligomers were used to make a hydrolytic time course study of strain AP/*Aspergillus saccharolyticus* extract, Novozym 188, Celluclast 1.5 L, and Cellic CTec (FIG. 7). Strain AP/*Aspergillus saccharolyticus* enzyme extract show clear exo-activity, with a cellopentaose and glucose concentration increase as the cellohexaose concentration decreased. Less rapidly, the cellotetraose and cellotriose concentrations increase too. Evidence of endo-activity or cellobiohydrolase activity is found, as the cellobiose concentration goes up relatively fast compared to the cellotetraose and cellotriose. On the contrary, Novozym 188 only shows beta-glucosidase exo-activity, with the only significant change over time being glucose and cellopentaose increase as cellohexaose decrease. The results suggest that the beta-glucosidases act by capturing the substrate, cleave the glycosidic bond, and release the products. They do not continuously cleave one bond after another upon capturing the substrate. Celluclast 1.5 L mainly possess cellobiohydrolase and endoglucanase activity, seen by the immediate increase in cellobiose and cellotriose, and lacking sufficient beta-glucosidase activity as the glucose concentration does not increase but the cellobiose concentration increases continually. As the only sample, Cellic CTec showed continuously increase in both cellobiose and glucose, indicating a combination of cellobiohydrolase and beta-glucosidase activity. Endoglucanase activity is most likely present too, identified by the formation of cellotriose.

Pretreated bagasse was hydrolyzed by strain AP/*Aspergillus saccharolyticus* beta-glucosidases combined with Celluclast 1.5 L to investigate its capabilities on a lignocellulosic substrate. This is compared with hydrolysis data of Novozym 188 and Celluclast 1.5 L. Strain AP/*Aspergillus saccharolyticus* beta-glucosidases and Novozym 188 beta-glucosidases are compared on total protein amount basis. A dosage-response plot of hydrolysis of 5% DM pretreated bagasse showed a leveling off in glucose yields at total enzyme dosages greater than 10 mg/gDM (data not shown). This total enzyme dosage was used for optimal enzyme ratio determination; the ratio of Celluclast 1.5 L and Strain AP/*Aspergillus saccharolyticus* extract or Novozym 188. The greatest yields were found with approximately 20% Novozym 188 (80% Celluclast 1.5 L) and 15% strain AP/*Aspergillus saccharolyticus* extract (85% Celluclast 1.5 L) (FIG. 8). Generally, the glucose yields were higher when using strain AP/*Aspergillus saccharolyticus* extract compared with Novozym 188, illustrating the possibility of substituting the commercial enzyme preparation with an extract from our newly isolated *Aspergillus* strain AP/*Aspergillus saccharolyticus*. These results for bagasse hydrolysis correlate well with the fact that the beta-glucosidases of strain AP/*Aspergillus saccharolyticus* extract has a higher reaction rate on cellobiose (Vmax, Table 2) compared to Novozym 188.

Discussion

Traditionally, two commonly used enzyme preparations that supplement each other in the hydrolysis of cellulosic biomasses are Novozym 188 and Celluclast 1.5 L (Novozymes AS, Denmark), contributing with beta-glucosidase activity, and endoglucanase and cellobiohydrolase activity, respectively (Berlin et al., 2005). Recently, an enzyme preparation containing all three components has been released into the market, Cellic CTec (Novozymes AS, Denmark). Costs related to enzymatic hydrolysis make this step a bottle neck in the process of creating a sugar plat form for biofuels, chemicals, and pharmaceuticals; therefore there is a need for more efficient enzymes, both in terms of reaction rates and stability (Berlin et al., 2005). Beta-glucosidases are widely distributed in nature, with especially fungi known to be industrial producers of these enzymes for cellulose hydrolysis. In this study, we present a prominent fungal beta-glucosidase producer naturally producing an enzyme cocktail with better beta-glucosidases compared to the commercial preparation Novozym 188 and markedly better thermostabily than both Novozym 188 and Cellic CTec. The work builds on a broad screening of 86 fungal strains collected by the authors as well as an in house collection of fungi kindly donated by various scientists. To our knowledge, broad screenings of fungal extracts for beta-glucosidase activity are not frequently published. In publication by Sternberg et al. (1977), 200 fungal strains were searched amongst for a strain producing large quantities of beta-glucosidases that could supplement the *Trichoderma viride* cellulases for cellulose saccharification. Generally, black Aspergilli were found to be superior in terms of beta-glucosidase production (Sternberg et al., 1977). Later, a study focusing on identification of acid- and thermotolerant extracellular beta-glucosidase activities in zygomycetes fungi was published were *Rhizomucor miehei* performed best (Tako et al., 2010). Screening for general cellulase activities in few cases include beta-glucosidase activities (Djarwanto & Tachibana, 2009, Jahangeer et al., 2005, Krogh et al., 2004, Pedersen et al., 2009), and other strategies for obtaining beta-glucosidases have been employed such as screening environmental DNA for beta-glucosidase activity rather than collecting microbial samples (Kim et al., 2007b), and a proteomics strategy to discover beta-glucosidases from *Aspergillus fumigatus* has been reported (Kim et al., 2007a). In this work, wheat bran was used as substrate in a submerged fermentation, as it is generally known as a good substrate for cellulases and beta-glucosidase production (Jager et al., 2001, Leite et al., 2008), being rich in carbohydrates and protein (Kent & Evers, 1994), and submerged fermentation allows for easy assaying of the extracellular enzymes of the fungi. The supernatants were tested for beta-glucosidase activity using pNPG at 50° C. pH4.8; which are optimal conditions for Celluclast 1.5 L, thus aiming at finding enzyme activities supplementing this enzyme preparation.

It was found that especially strains from the genera *Aspergillus, Fusarium, Penicillium*, and *Trichoderma* had the highest beta-glucosidase activity, with strains of *Aspergillus* being the best. These fungal genera have also been found in other screening programs for discovery of cellulolytic enzymes (Jahangeer et al., 2005, Sohail et al., 2009). Aspergilli in general have a high capacity for producing and secreting extracellular enzymes (Ward et al., 2006, de Vries & Visser, 2001), especially *A. niger*, with all classes of enzymes essential for cellulose degradation having been found amongst Aspergilli (de Vries & Visser, 2001). Within the *A. fumigati* strains, the expression level of beta-glucosidases at the tested conditions were very consistent, while great strain variation was found in *A. niger* (FIG. 1). This variation was not surprising as it correlates well with publications on citric acid, antioxidant, and urease production in *A. niger*, which is also very strain dependent (Ali, 2004, Kawai et al., 1994, Ghasemi et al., 2004).

Several studies have been published on the kinetics of Novozym 188 and *A. niger* beta-glucosidases, and it is apparent that substrate affinity, Km, does vary amongst strains within this species (Jager et al., 2001, Eyzaguirre et al., 2005, Krogh et al., 2010, Seidle of al., 2004). However, most common amongst the *A. niger* beta-glucosidases is that they have greater affinity for pNPG than for cellobiose; Jäger et al. (2001) report similar findings for other *Aspergillus* strain beta-glucosidases (Jager et al., 2001). We have, however, chosen to only calculate MM kinetics parameters related to hydrolysis of cellobiose as hydrolysis data of pNPG did not fit the MM equation. It is speculated that pNPG actually is a poor substitute in terms of assaying for beta-glucosidase activity, which was also concluded by e.g. Khan et al. 1985, and especially in this study it was additionally evident in relation to product inhibition. To compare activities, it is always desired to perform measurements at substrate saturation; however, with pNPG the saturation point could not be determined as substrate inhibition was the dominating factor at high substrate concentrations which correlates with studies carried out by Dekker (1986) and Eyzaguirre et al. (2005). As transglycosylation activity has been reported in several cases for different beta-glucosidases (Bhatia et al., 2002) it was speculated if the proposed substrate inhibition was rather a transglycosylation reaction at high product concentrations. However, the option of the enzyme carrying out transglycosylation by coupling the glucose product to a new pNPG at high pNPG concentrations was not investigated which could potentially mimic substrate inhibition in data evaluation. The effect of pNPG substrate inhibition or transglycosylation reaction on the measured reaction rates in the beta-glucosidase screening strategy was a factor that was not taken into account. However, the significance of the elevated activity of stain AP/*Aspergillus saccharolyticus* beta-glucosidase compared to all other assayed fungi would most likely be evident even had this been taken into account.

Product inhibition is a common phenomenon with beta-glucosidases; glucose being the main inhibitor, which can have a significant influence for process reaction in industrial applications (Berlin et al., 2005). The importance of testing such inhibitory effects on the true substrate, cellobiose, rather than the substitute, pNPG, was demonstrated in this study, as the beta-glucosidases of strain AP/*Aspergillus saccharolyticus* compared to Novozym 188 only showed low inhibition by glucose using pNPG as substrate, but when using cellobiose, the inhibition patterns of the two enzyme preparations were similar, with the activities only reaching 50% when twice the concentration of glucose is present compared to cellobiose concentration (FIG. 5). pNPG is an easy-to-use substrate, but can be misguiding in terms of beta-glucosidase performance in true "real life" hydrolysis conditions.

The extract of strain AP/*Aspergillus saccharolyticus* showed greater specific beta-glucosidase activity than Novozym 188, while that of Cellic CTec was found to be even greater (Table 2). The enzyme preparations were evaluated on basis of total extracellular proteins, which, however, also comprise proteins originating from the growth medium. It is therefore unknown how much of the measured protein is actually fungal proteins. Furthermore Aspergilli strains are known to possess several beta-glucosidases that can have different relative activities and specificities. e.g. three beta-glucosidases from *A. aculeatus* have been assayed with the findings that one has very weak and the two other very high activities towards cellobiose relative to pNPG (Sakamoto et al., 1985). The beta-glucosidase activity of the screened extract is therefore very likely the combined activity of several beta-glucosidases of the strain AP/*Aspergillus saccharolyticus*. Without further optimization, the specific activity of the solid state fermentation extract of strain AP/*Aspergillus saccharolyticus* was able to compete with Novozym 188 in hydrolysis of cellobiose, and in the case of cellohexaose the rate by which the cellohexaose concentration decreased and the glucose and cellopentaose increase was greatest for strain AP/*Aspergillus saccharolyticus* than Novozym 188. Increasing the degree of complexity and potential amount of inhibitors, etc, bagasse is one of many cellulose containing biomasses of interest for bioethanol purposes. Bagasse is a lignocellulosic waste product from the sugar cane industry produced in great quantities in countries such as Brazil and other tropical places (Soccol et al., 2010). Its utilization for fuel production is value contributing to the current processes (Leite et al., 2009). Hydrolysis of bagasse was here used to show that our stain AP/*Aspergillus saccharolyticus* enzyme extract supplemented with Celluclast (FIG. 8), did work on actual lignocellulosic material and was competitive with Novozym 188.

Thermostability and temperature optima presented in different publications are difficult to compare as the incubation time, reaction time, and temperatures tested vary. Generally, the dependence of temperature resembles a bell-shaped curve, with a maximum where the enzyme is actually not at its optimum as the maximum indicates the beginning of the irreversible denaturation process (Bisswanger, 2008). This method of directly assaying at different temperatures to determine the temperature profile is of no real use in terms of industrial hydrolysis as hydrolysis reactions are usually run for several hours and time dependent enzyme degradation will play a role. By pre-incubating the enzymes at distinct temperatures and assaying after different time intervals at normal assay temperatures, the beta-glucosidases of strain AP/*Aspergillus saccharolyticus* were found to have excellent temperature stability compared to Novozym 188 (FIG. 6). Novozym 188 has previously been reported to only maintain stability at temperatures at or below 50° C. (Krogh et al., 2010). Cellic CTec was found to be very unstable at elevated temperatures observed by the poor performance when assaying for activity after incubation above 50° C., which relates to the manufactures instructions of best performance at temperatures 40-50° C. (Novozymes A/S, 2010). The time course of the inactivation of all enzymes approximately followed a first order reaction from which the denaturation rates and half-lives at the different temperatures could be calculated, confirming the dominating status of strain AP/*Aspergillus saccharolyticus* beta-glucosidases in terms of thermostability.

In this work, a potential yet unidentified species has been identified: strain AP/*Aspergillus saccharolyticus*, belonging to the *Aspergillus nigri* group. This stain had significantly greater beta-glucosidase potential than all other fungi screened and was shown to be a valid substitute for Novozym 188, even performed better than Novozym 188 in some aspects, and definitely out-competed Cellic CTec in terms of thermostability.

Example 2

*Aspergillus saccharolyticus* sp. nov., a New Black *Aspergillus* Species Isolated on Treated Oak Wood in Denmark During a broad screening of different fungal strains collected in Denmark for prominent beta-glucosidase producing fungi (EXAMPLE 1), we discovered a uniseriate *Aspergillus*, morphologically similar to *A. japonicus*. However, both molecular data and an extrolite profile showed that this fungus differed significantly from known aspergilli from section *Nigri*. In this example we describe the relationship of this strain to other black aspergilli using the polyphasic approach with studies of ITS, calmodulin, and beta-tubulin sequence phylogeny, UP-PCR finger printing, macro- and micro-morphology, temperature tolerance, and extrolite production.

Materials and Methods

A strain of a novel species, *Aspergillus saccharolyticus*, was isolated in door from treated oak wood in Denmark. The isolate was maintained on potato dextrose agar at room temperature. All reference strains and accession numbers used for comparison are listed in Table 3.

TABLE 3

GenBank accession numbers of sequence data used to prepare the phylogenetic trees

| | ITS | Beta-tubulin | Calmodulin |
|---|---|---|---|
| *A. niger* CBS 554.65$^T$ | AJ223852 | AY585536 | AJ964872 |
| *A. tubingensis* CBS 134.48$^T$ | AJ223853 | AY820007 | AJ964876 |
| *A. japonicus* CBS 114.51$^T$ | AJ279985 | AY585542 | AJ964875 |
| *A. aculeatus* CBS 172.66$^T$ | AJ279988 | AY585540 | AJ964877 |
| *A. foetidus* CBS 565.65 | AJ280999 | AY585533 | FN594547 |
| *A. brasiliensis* CBS 101740$^T$ | AJ280010 | AY820006 | AM295175 |
| *A. heteromorphous* CBS 117.55$^T$ | AJ280013 | AY585529 | AM421461 |
| *A. ellipticus* CBS 707.79$^T$ | AJ280014 | AY585530 | AM117809 |
| *A. vadensis* CBS 113363$^T$ | AY585549 | AY588531 | EU163269 |
| *A. ibericus* CBS 121593$^T$ | AY656625 | AM419748 | AJ971805 |
| *A. castaricaensis* CBS 115574$^T$ | DQ900602 | AY820014 | EU163268 |
| *A. piperis* CBS 112811$^T$ | DQ900603 | AY820013 | EU163267 |
| *A. lacticoffeatus* CBS 101883$^T$ | DQ900604 | AY819998 | EU163270 |
| *A. carbonarius* CBS 111.26$^T$ | DQ900605 | AY585532 | AJ964873 |
| *A. sclerotioniger* CBS 115572$^T$ | DQ900606 | AY819996 | EU163271 |
| *A. homomorphus* CBS 101889$^T$ | EF166063 | AY820O15 | AM887865 |
| *A. aculeatinus* CBS 121060$^T$ | EU159211 | EU159220 | EU159241 |
| *A. sclerotiicarbonarius* CBS 121057$^T$ | EU159216 | EU159229 | EU159235 |
| *A. uvarum* CBS 121591$^T$ | AM745757 | AM745751 | AM745755 |
| *A. aculeatus* CBS 114.80 | AJ280005 | AY585539 | AM419750 |

TABLE 3-continued

GenBank accession numbers of sequence data used to prepare the phylogenetic trees

| | ITS | Beta-tubulin | Calmodulin |
|---|---|---|---|
| *A. saccharolyticus* CBS 127449[T] | HM853552 | HM853553 | HM853554 |
| *A. flavus* CBS 100927[T] | AF027863 | AY819992 | AY974341 |

Molecular Analysis

Fungal biomass for DNA extraction was obtained by scraping the surface of a PDA plate with a seven day old colony. DNA extraction was carried out as described by (Yu & Mohn, 1999), using bead beating for cell disruption. The two fungal primers Bt2a (5' GGTAACCAAATCGGTGCTGCTTTC) and Bt2b (5' ACCCTCAGTGTAGTGACCCTTGGC) were used to amplify a fragment of the beta-tubulin gene (Glass & Donaldson, 1995), while the primers Cmd5 (5' CCGAGTACAAGGAGGCCTTC) and Cmd6 (5' CCGATAGAGGTCATAACGTGG) were used to amplify a segment of the calmodulin gene (Hong et al., 2006), and the primers ITS1 (5' TCCGTAGGTGAACCTGCGG) and ITS4 (5' TCCTCCGCTTATTGATATG) were used to amplify the ribosomal rDNA spacers, ITS1 and ITS2 (White et al., 1990). Phylogenetic analysis of the beta-tubulin, calmodulin, and internal transcribed spacer region of rRNA (ITS1 and ITS2) sequences of the novel isolate was carried out as described by Varga et al. (2007), using the beta-tubulin, calmodulin, and ITS region sequences of the aspergilli presented in the article by Samson et al (Samson et al., 2007). ClustalW multiple alignment was used for sequence alignment and manual improvement of the alignment was performed using BioEdit (http://www.mbio.ncsu.edu/BioEdit/bioedit.html). The PHYLIP program package version 3.69 was used for preparation of phylogenetic trees (Felsenstein, 2004). The distance matrix of the data set was calculated based on the Kimura method (Kimura, 1983) using the program “Dnadist”. The phylogenetic tree was prepared by running the program “Neighbor” using the neighbor-joining method (Saitou & Nei, 1987) to obtain unrooted trees. *A. flavus* was defined as the outgroup in the program “Retree”, and finally the tree was visualized using the program TreeView (win32) (Page, 1996). Bootstrap values (Felsenstein, 1985) were calculated by running the program “Seqboot” to produce 1000 bootstrapped data sets from the original data set. Again, “dnadist” with the Kimura method was used to prepare distance matrices of the multiple data sets, and “neighbor” with the neighbor-joining method to obtain unrooted trees of the multiple data sets. Finally, the bootstrap values were obtained from the consensus tree which was identified by the majority-rule consensus method by running the program “Consense”.

UP-PCR fingerprinting was carried out using two different UP primers, L45 (5' GTAAAACGACGGCCAGT) and L15/AS19 (5' GAGGGTGGCGGCTAG) (Lubeck et al., 1999) for DNA amplification in separate reactions. The amplification was performed as described in Lübeck et al. (1999) except that the reactions were carried out in a 25 μl volume containing 50 mM Tris pH8, 0.23 mg/ml BSA, 0.5% Ficoll, 2.5 mM $MgCl_2$, 0.2 mM of dNTP, 0.4 μM of primer and 1 U RUN polymerase (A&A Biotechnology, Poland).

Morphological Analysis

For microscopic analysis, microscopic mounts were made in lactophenol from colonies grown on MEA (malt extract autolysate) and OA (oat meal agar).

For investigation of morphological characteristics, a dense spore suspension of *A. saccharolyticus* was three-point inoculated on the following media: CREA (creatine sucrose), CYA (Czapek yeast autolysate), CY20S (CYA with 20% sucrose), CY40S (CYA with 40% sucrose), CYAS (CYA with 50 g/l NaCl), MEA (malt extract autolysate), OA (oat meal agar) and YES (yeast extract sucrose) agar (Samson et al., 2004a), and incubated 7 days in the dark at 25° C. For temperature tolerance analysis, three-point inoculating was performed on CYA and incubated 7 days in the dark at different temperatures: room temp, 30° C., 33° C., 36° C., and 40° C.

Extrolite Analysis

Three 6 mm diameter plugs were taken from each strain grown as three-point inoculations in the dark at 25° C. for 7 and 14 days on YES, CYA20, CYA40, PDA, CYA media (Samson et al., 2004a, Nielsen et al., 2009). The plugs were transferred to a 2-mL vial and 1.4 mL of ethyl acetate containing 1% formic acid was added. The plugs were placed in an ultra sonication bath for 60 min. The ethyl acetate was transferred to a new vial in which the organic phase was evaporated to dryness by applying nitrogen airflow at 30° C. The residues were re-dissolved by ultrasonication for 10 min in 150 μL $ACN/H_2O$ (1:1, v/v) mixture.

HPLC-UV/VIS-high resolution mass spectrometry (LC-HRMS) analysis was performed with an Agilent 1100 system (Waldbronn, Germany) equipped with a diode array detector and coupled to a Micromass LCT (Micromass, Manchester, U.K.) equipped with an electrospray (ESI) (Nielsen et al, 2009, Nielsen & Smedsgaard, 2003). Separations of 2 μL samples was performed on a 50×2 mm inner diameter, 3 μm Luna $C_{18}$ II column (Phenomenex. Torrance, Calif.) using a linear water-ACN gradient at a flow of 0.300 ml/min with 15-100% ACN in 20 min followed by a plateau at 100% ACN for 3 min (Nielsen et al., 2009). Both solvents contained 20 mM formic acid. Samples were analyzed both in $ESI^-$ and $ESI^+$ mode.

For compound identification, each peak was matched against an internal reference standard database (~800 compounds) (Nielsen et al., 2009, Nielsen & Smedsgaard, 2003). Other peaks were tentatively identified by matching data from previous studies in our lab and searching the accurate mass in the ~13 500 fungal metabolites reported in Antibase 2010 (Laatsch, 2010).

Results and Discussion

In a screening program, fungal strains were obtained from different environmental habitats, Danish as well as international, and tested for beta-glucosidase activity (EXAMPLE 1). Some of the strains were found in door in Denmark on treated oak wood, and one of these strains showed an extraordinary good beta-glucosidase activity. In this example, a thorough characterization was carried out in order to identify the strain.

Morphological data showed that the strain was related to *A. japonicus* or *A. aculeatus*, but extrolite profiles and DNA sequencing data showed that the strain clearly was different from all known species. The genetic relatedness of this novel species, *A. saccharolyticus*, to other black aspergilli was investigated by comparing sequence data of parts of the beta-tubulin and calmodulin genes as well as the ITS region, using *A. flavus* as the out group. The black aspergilli chosen for comparison are the same as the ones presented by Samson et al. (2007). Phylogetic trees were prepared for *A. saccharolyticus* based on these sequence data and data obtained in this work, with especially the ITS and calmodulin sequence trees showing similar topology (FIGS. 9, 10, and 11). Based on the phylogenetic analysis of the ITS and calmodulin gene sequence data, *A. saccharolyticus* was with high bootstrap values found to belong to the clade with *A. homomorphus, A. aculeatinus, A. uvarum, A. japonicus*, and both *A. aculeatus* strains, while for the beta-tubulin gene sequence data *A. saccharolyticus* clustered with *A. homomorphus. A. aculeatinus, A. uvarum*, and *A. aculeatus* CBS 114.80. The separate grouping in the beta-tubulin tree of *A. japonicus* and *A. aculeatus* CBS 172.66$^T$ has consistently been shown in other publications (Varga et al., 2007, Samson et al., 2007. Noonim et al., 2008, de Vries et al., 2005, Samson et al., 2004b). For all three loci, *A. saccharolyticus* is placed on its own branch far from the other species in the clade supported by the majority-rule consensus analysis for all three loci and high bootstrap values for the beta-tubulin and calmodulin loci, but low bootstrap value (51%) for the ITS locus. Sequence alignment revealed that amongst the species from section Aculeati that are in clade with *A. saccharolyticus*, interspecific sequence divergences are ≤0.7%, 7.1%, and 5.7% for the ITS, calmodulin, and beta-tubulin regions, respectively. Meanwhile, the interspecific sequence divergences in the ITS, calmodulin, and beta-tubulin region between *A. saccharolyticus* and the other species in the clade are on average 12.9±0.6%, 20±0.5%, and 15.4±1.2%, respectively. The variation in sequence data observed between *A. saccharolyticus* and *A. homomorphus* is the same as the variation between *A. homomorphus* and the smaller clade(s) of *A. aculeatinus, A. uvarum, A. japonicus*, and both *A. aculeatus* strains. Searching the NCBI database does not give any closer genetic match. Based on this, there is a clear genetic foundation for proposing the new species, *A. saccharolyticus.*

Furthermore, this strain could readily be distinguished from other black aspergilli by Universally Primed-PCR analysis using each of the two UP primers, L45 and L15/AS19 (Supplementary Figure S3). UP-PCR is a PCR fingerprinting method that has demonstrated its applicability in different aspects of mycology. These applications constitute analysis of genome structures, identification of species, analysis of population and species diversity, revealing of genetic relatedness at infra- and inter-species level, and identification of UP-PCR markers at different taxonomic levels (strain, group and/or species) (Lübeck & Lübeck, 2005). Each of the analyzed aspergilli, *A. saccharolyticus, A. aculeatinus, A. ellipticus, A. homomorphus, A. niger, A. uvarum, A. aculeatus* and *A. japonicus*, produced a unique banding profile, and did not share any bands (FIG. 12). This is an illustration of clearly separated species, as strains within a species should at least have some similarities in their banding profiles (Lübeck & Lübeck, 2005).

The extrolite profiles further showed that *A. saccharolyticus* produced the largest chemical diversity on YES agar (25° C.), whereas CYA (25 and 30° C.), and CYAS, CY20S, CY20, CY40S, and PDA (all at 25° C.) yielded fewer peaks. The results further showed that it is a new species since it does not share any metabolites with other species in the *Nigri* section where e.g. the naphto-γ-pyrones are consistently produced (Nielsen et al., 2009) and only two compounds, ACU-1 and ACU-2, with series Aculeati (Table 4 and FIG. 13) whereas the well known compounds from the series: neooxaline, secalonic acids, cycloclavine and aculeasins were not detected (Parenicova et al., 2001). In addition, none of the 12 detected peaks matched with the approx. 13500 fungal extrolites in Antibase 2010 (Laatsch, 2010) thus providing that the species had not been investigated by natural products chemists.

TABLE 4

Physiological features and extrolite production by the strains of uniseriate species in *Aspergillus* section *Nigri*

| Species | Growth on CYAS (diam, mm) | Growth at 37° C. on CYA (diam, mm) | Extrolites |
|---|---|---|---|
| *A saccharalyticus* sp. nov (CBS127449*) | 11-44 | 7-14 | 12 compounds not described in the literature* including ACU-1* and ACU-2** |
| *A aculeatinus* (CBS121060CD5 121875, IBT 29275) | 37-54 | 18-52 | Aculeasins, neoxaline, secalonic acid D & P |
| *A aculeatus* (CBS 172.66*) | 0-4 | 15-26 | Secalonic acid D & P, ACU-1* and ACU-2** |
| *A japonicus* (CBS 114510, IBT 29220 IBT 26338, ITEM 4497) | 0 | 8-25 | Cycloclavine, festuclavine |
| *A uvarum* (CBS 121591T, ITEM 4634; ITEM 4856; ITEM 5024 | 54-73 | 11-14 | Asterric acid, dihydrogeodin, erdin, geodin secalonic acid D & P |

*No matches found among the 13 500 fungal metabolites listed in Antibase2010.

**ACU-1 and ACU-2 unidentified compounds with UV max 242 nm (100%) and 346 (88%) with mono isotopic messes of 315.1799 and 218.1268 Da respectively.

Morphologically, *A. saccharolyticus* is most closely related to *A. japonicus* (FIG. 14), but with larger conidia of 5-6 μm and vesicle size in the high margin of *A. japonicus*. Based on physiological features, differences between *A. saccharolyticus* and other uniseriate species in the *Nigri* section were found. Growth on CREA resembled that of *A. aculeatinus*, as moderate growth and medium acid production was observed, while growth on CYA mostly resembled that of *A. aculeatus*, however, the reverse side of *A. saccharolyticus* is olive-green/brownish with sulcate structure, while that os *A. aculeatus* is curry-yellowish/brown (FIG. 14 compared with (Samson et al., 2007)). MEA was a medium where colony size was clearly different, with *A. saccharolyticus* being smaller than the other uniseriate aspergilli. *A. saccharolyticus* grew better on CYA than *A. aculeatus* and *A. japonicus*, but groth was limited compared to *A. aculeatinus* and *A. uvarum*. Growth diameter of *A. saccharolyticus* on CYA at 37° C. was approximately the same as for *A. uvarum*, while *A. aculeatus* and *A. japonicus* were less inhibited, and *A. aculeatinus* even less inhibited measuring the larger diameter of all uniseriate at this elevated temperature (Table 4).

With regards to temperature tolerance, growth was examined on CYA at 30° C., 33° C., 36° C., and 40° C. The maximum temperature *A. saccharolyticus* was able to grow at was 36° C., but growth at this temperature was restricted compared to the lower temperatures, which is generally the case for the other uniseriate aspergilli as well (Samson et al., 2007). *A. saccharolyticus* showed a distinct change in morphology on CYA from 30° C. to 33° C., but maintaining good growth at both temperatures (FIG. 15). The same tendency has been observed for *A. aculeatinus* grown on MEA, while *A. japonicus*, and *A. aculeatus* showed no change in morphology at these temperatures, while growth of *A. uvarum* was inhibited at 33° C. (Samson et al., 2007).

The conclusion that *Aspergillus saccharolyticus* is a novel species is based on a polyphasic approach combining phylogenetic analysis of three genes and UP-PCR data for characterizing the genotype, and morphological, physiological, and chemotaxonomical characteristics for phenotype analysis. Because the strain was unique in its genetic phylogeny, UP-PCR profile, extrolite profile, morphological, and physiological characteristics, *Aspergillus saccharolyticus* is a novel species. *Aspergillus saccharolyticus* is an efficient producer of beta-glucosidases (EXAMPLE 1) and the name refers to its great ability to hydrolyze cellobiose and cellodextrins.

Latin Diagnosis of *Aspergillus Saccharolyticus* Sørensen, Lübeck et Frisvad sp. nov.

Coloniae post 7 dies 58-62 mm diam in agaro CYA, in CYA, 37° C.: 7-14 mm; in MEA 35-37, in YES 75-80 mm, in agaro farina avenacea confecto 39-42 mm, in CREA 30-34 mm. Coloniae primum albae, deinde obscure brunneae vel atrae, reversum cremeum vel dilute *brunneum. Condiorum capitula* primum *globosa*, stipes 200-850×5-7 μm, crassitunicatus, *levis*, vesiculae 25-40 μm diam, fere globosae; capitula uniseriata; phialides lageniformes, collulis *brevis,* 5.5-7 μm; conidia *globosa* vel subglobosa, 5-6.2 μm, echinulata. Sclerotia haud visa.

Typus CBS 127449$^T$ (=IBT 28509$^T$), isolatus e lignore Quercetorum in Gentofte, Dania.

Description of *Aspergillus saccharolyticus* Sørensen, Lübeck et Frisvad sp. nov.

*Aspergillus saccharolyticus* (sac.ca'ro.ly'ti.cus. N.L. masc. adj. *saccharolyticus*, being able to degrade cellobiose and cellodextrins).

Colony diameter at 7 days: CYA at 25° C.: 58-62 mm, at 37° C.: 7-14 mm; CYAS: 11-14 mm; YES: 75-80 mm; OA: 39-42 mm; CY20S: 42-54 mm; CY40S: 43-54 mm; MEA: 35-37 mm; CREA 30-34 mm, poor growth, good acid production, colony first white then dark brown to black (FIG. 14). Exudates absent, reverse cream-coloured to light greyish olive brown on CYA and light brown on YES. Conidial heads globose; stipes 200-850×5-7 μm, walls thick, smooth; vesicles 25-40 μm diam, globose; uniseriate, phialides flask shaped with a short broad collulum, 5.5-7 μm; conidia mostly globose, but some are subglobose, 5-6.2 μm, distinctly echinulate, with long sharp discrete spines, the spines being 0.6-0.8 μm long. Sclerotia have not been observed. The type strain CBS 127449$^T$ (=IBT 28509$^T$) was isolated from under a toilet seat made of treated oak wood, Gentofte, Denmark

Example 3

Cloning, Expression, and Characterization of a Novel Highly Efficient Beta-Glucosidase from *Aspergillus saccharolyticus*

As shown in the previous example 1, *Aspergillus saccharolyticus* produce beta-glucosidases with more efficient hydrolytic activity compared to commercial beta-glucosidase containing preparations, especially with regard to thermostability (EXAMPLE 1). In the present example, the most prominent beta-glucosidase from *A. saccharolyticus* are identified, isolated and characterized. The molecular cloning of the novel beta-glucosidase gene, bgl1 is reported, and a model prediction of its structure is presented. The novel beta-glucosidase was expressed in *T. reesei* for purification and the enzyme was then characterized by Michaelis-Menten kinetic studies, thermostability, pH optimum, glucose tolerance, and ability to hydrolyze cellodextrins.

Fungal Strain and Enzyme Extract Preparation

*A. saccharolyticus* CBS 127449$^T$ was initially isolated from treated hard wood (EXAMPLE 2) and routinely maintained on potato dextrose agar. A solid state fermentation enzyme extract of *A. saccharolyticus* was prepared as described in EXAMPLE 1.

Fractionation by Ion Exchange Chromatography

The enzyme extract of *A. saccharolyticus* was fractionated by ion exchange chromatography using an ÄKTA-purfier system with UNICORN software. HiTrap Q XL 1 ml anion column (GE Healthcare) was run at a flow rate of 1 ml/min, 5 CV of buffer A (Tris buffer pH 8) was used to equilibrate the column, 5 CV sample (approx 0.5 mg protein/ml) was loaded onto the column, followed by a 2 CV wash with buffer A. Gradient elution was carried out over 30 CV with buffer B (Tris buffer pH 8+1M NaCl) reaching 70% of the total volume. The column was finally washed with 5 CV buffer B and reequilibrated for the next run with buffer A. Aliquots of 1 ml were collected and assayed for beta-glucosidase activity as well as quantified in terms of protein content, as described below.

Assays for Beta-Glucosidase Activity and Protein Quantification

Beta-glucosidase activity was assayed using using 5 mM p-nitrophenyl-beta-D-glucopyranoside (pNPG) (Sigma) in 50 mM Na-Citrate buffer pH 4.8 as described in EXAMPLE 1.

Protein quantification was done using the Pierce BCA protein assay kit microplate procedure according to manufacturer's instructions (Pierce Biotechnology), using bovine serum albumin as standard.

Electrophoresis

Sample preparation and electrophoresis was performed using ClearPAGE precast gels and accessories (C.B.S. Scientific Company, Inc). Samples were prepared by mixing 65 vol % protein, 25% 4×LDS sample buffer (40% glycerol, 4% Ficoll-400, 0.8M Triethano amine pH 7.6, 6N HCl, 4% Lithium dodecyl sulphate, 2 mM EDTA di-sodium, 0.025% Brilliant blue G250, 0.025% Phenol red), and 10% 10× reducing agent (20 mM DTT) and heating for 10 min at 70° C. 25 μl of each sample were loaded on a ClearPAGE 4-12% SDS-gel, using ClearPAGE two-color SDS marker for band size approximation. The gel was stained with ClearPAGE Instant Blue stain by placing the gel in a small container, adding the Instant Blue stain till the gel was covered, followed by shaking the gel gently for 10-30 minutes till desired band intensity was achieved. No destaining was performed, but the gels were washed a few times in ultrapure water, with gently shaking.

Mass Spectrometry and Protein Identification

Bands of interest were excised from the gel, and in-gel digestion was performed as described by Kinter and Sherman (2000) (Kinter & Sherman, 2000). The trypsin digestion, and sample analysis was carried out by The Laboratory for Biotechnology and Bioanalysis 2 (LBB2). Washington State University, Pullman. Wash., USA, where analysis was performed by LC-MS/MS using LC Packings Ultimate Nano high-performance liquid chromatography system (with LC Packings monolithic column PS-DVB) and Esquire HCT electrospray ion trap (Bruker Daltonics, Billerica, Mass.) as described in their former publication (Noh et al., 2008). The Mascot search engine (www.matrix-science.com) was used to search the peptide finger prints against predicted peptides in the NCBI database with the significance threshold $p<0.05$.

Isolation and Cloning of Beta-Glucosidase Gene

Based on the *Aspergillus aculeatus* peptide match found in the LC-MS/MS analysis, the corresponding full length beta-glucosidase protein (GenBank: BAA10968) was submitted to a NCBI NCBI Blast of search in the protein entries of GenBank (http://NCBI Blast of .ncbi.nlm.nih.gov/NCBI Blast of .cgi) to identify similar beta-glucosidases. An alignment of these sequences was made with BioEdit (http://www.mbio.ncsu.edu/BioEdit/bioedit.html) to identify conserved regions. Degenerate primers were designed using the CODEHOP strategy (Rose et al., 2003): forward primer: 5'CACGAAATGTACCTCtggcccttygc and reverse primer 5'CCTTGATCACGTTGTCGccrttcykcca. Genomic DNA of *A. saccharolyticus* was isolated as described in EXAMPLE 1. The primers were used in polymerase chain reaction (PCR) with genomic DNA and RUN polymerase (A&A Biotechnology), obtaining a fragment of approximately 950 bp. The band was excised from the gel and sequenced using the sequencing service at MWG (MWG, Germany), and was by NCBI NCBI Blast of found to be related to other aspergilli beta-glucosidase fragments. From several rounds of genome walking (Guo & Xiong, 2006), the flanking regions were characterized, thereby obtaining the full genomic sequence of the gene. The start and stop codon was predicted by NCBI NCBI Blast of comparison and the GenScan Web server (http://genes.mit.edu/GENSCAN.html).

RNA was prepared from 4 day old fungal spores and mycelium grown on plates containing 20 g/l wheat bran, 20 g/l corn steep liquor, 3 g/l $NaNO_3$, 1 g/l $K_2HPO_4$, 0.5 g/l KCl, 0.5 g/l $MgSO_47H_2O$, 0.01 g/l $FeSO_47H_2O$, 15 g/l agar. The cells were disrupted by bead beating (2×20 sec) in Fenozol supplied with the Total RNA kit (A&A Biotechnology) and RNA purified following the kit protocol, cDNA was prepared from total RNA using First strand cDNA synthesis kit and random hexamer primers (Fermentas).

A cassette comprising *Magnaporthe grisea* Ribosomal promoter RP27, the beta-glucosidase genomic DNA gene, six histidine residues, and *Neurospora crassa* beta-tubulin terminator was constructed using PCR cloning techniques and cloned into the PciI site of pAN7-1. The plasmid pAN7-1 containing the *E. coli* hygB resistance gene was donated by Peter Punt (University of Leiden, The Netherlands) (Punt eof al., 1987). The promoter and terminator were from plasmid pSM565 (Bourett et al., 2002) and the beta-glucosidase gene was from *A. saccharolyticus* genomic DNA. PCR was performed using proofreading WALK polymerase (A&A Biotechnology), while restriction enzymes (fast digest PciI), alkaline phosphatase (fastAP), and ligase (T4 DNA ligase) were from Fermentas. The construct pAS3-gBGL was transformed into *E. coli* Top 10 competent cells (prepared using $CaCl_2$ (Sambrook & Russel, 2001)) and plated on LB plates (10 g/l bacto tryptone, 5 g/l yeast extract, 10 g/l NaCl, 15 g/l agar, pH 7.5) with ampicillin selection (100 ppm). Correct transformants were checked for by colony PCR using several different promoter, beta-glucosidase, and terminator specific primers. An overnight culture with a correct transformant was prepared and the constructed cloning vector purified the following day (E.Z.N.A. Plasmid Midi Kit, Omega Biotech). The final cloning vector, pAS3-gBGL, is sketched in FIG. 16.

Transformation and identification of active recombinant beta-glucosidase in *T. reesei* Protoplast preparation of *T. reesei* QM6a was carried out similarly to the procedure described by Pentillä et al. (1987) (Pentilla et al., 1987) 100 ml complete medium (10 g/l glucose, 2 g/l peptone, 1 g/l yeast extract, 1 g/l casamino acids, 6 g/l $NaNO_3$, 0.52 g/l KCl, 0.52 g/l $MgSO_4.7H_2O$, 1.52 g/l $KH_2PO_4$, 22 mg/l $ZnSO_4.7H_2O$, 11 mg/l $H_3BO_3$, 5 mg/l $MnCl_2.4H_2O$, 5 mg/l $FeSO_4.7H_2O$, 1.7 mg/l $CoCl_2.6H_2O$, 1.6 mg/l $CuSO_4.5H_2O$, 1.5 mg/l $Na_2MoO_4.2H_2O$, and 50 mg/l $Na_2EDTA$) in a 500 ml baffled flask was inoculated with fresh *T. reesei* conidia reaching a concentration of $10^6$ spores per ml and incubated for 16-22 hours at 30° C., 120 rpm. The mycelium was collected on double folded Miracloth (Andwin scientific) and washed with sterile water. The mycelium was suspended in 20 ml protoplasting solution (1.2 M $MgSO_4$, 50 mM $NaPO_4$ pH 5.8) with 60 mg VinoTaste Pro (Novozymes A/S) enzyme per ml, incubated for 2-4 hours at 30° C., 65 rpm, then filtered through double folded Miracloth, and washed with a few ml protoplasting solution. The protoplasts were overlaid with ST buffer (0.6 M sorbitol, 0.1M Tris-HCL pH 7.0) (approx. 20% the volume of protoplasting solution) and centrifuged at 1000 g for 10 min. Protoplasts were collected from the interphase and washed twice with STC buffer (1.0 M sorbitol, 10 mM $CaCl_2$ $2H_2O$, 10 mM Tris-HCl pH 7.5), finally resuspending in STC buffer at a concentration of approximately $5\times10^2$ for immediate use in transformation.

For transformation, 200 μl protoplasts, 10 μl plasmid DNA (>1 μg), and 50 μl PEG1 (25% PEG 6000 in STC buffer) were mixed gently and incubated on ice for 20 min. 2 ml PEG2 (25% PEG 6000, 50 mM CaCl2, 10 mM Tris-HCl pH7.5) was added and incubated 5 min at room temperature, followed by addition of 4 ml STC buffer. Aliquots of 1 ml were plates in recovery agar (1 g/l $MgSO_47H_2O$, 10 g/l $KH_2PO_4$, 6 g/l $(NH_4)_2SO_4$, 3 g/l NaCitrate $2H_2O$, 10 g/l Glucose, 182 g/l sorbitol (final 1M), 5 mg/l $FeSO_47H_2O$, 1.6 mg/l $MnSO_4H_2O$, 1.4 mg/l $ZnSO_4H_2O$, 2 mg/l $CaCl_22H_2O$, 15 g/l agar) with 100 ppm hygromycin as selection, and incubated at 28° C. over night. The following day, a top layer of the above described agar, again with 100 ppm hygromycin, but without sorbitol, was added, and the plates were incubated for another 2-4 days before colonies that had surfaced were picked and carried through multiple retransfers and streaking on selective medium to obtain pure colonies.

Identification of positive transformants was done by a simple pNPG activity screen, where three 0.5×0.5 cm agar plugs of the transformants were added to 10 ml growth medium (20 g/l wheat bran, 20 g/l corn steep liquor, 3 g/l $NaNO_3$, 1 g/l $K_2HPO_4$, 0.5 g/l KCl, 0.5 g/l $MgSO_47H_2O$, 0.01 g/l $FeSO_47H_2O$) in 50 ml Falcon tubes and incubated at 30° C., 180 rpm for five days. The supernatant was collected, centrifuged at 10,000 rpm for 10 min and assayed for beta-glucosidase activity using the pNPG assay described earlier. At these conditions, the wild type QM6a showed no significant activity, so positive transformants were identified by the presence of beta-glucosidase activity.

Purification of Expressed Beta-Glucosidases

Using the HisSpin Trap kit (GE Healthcare), following the protocol supplied with the kit, the optimal imidazole concentration for purification of the histidine tagged beta-glucosidases was found to be 0 mM imidazole.

The transformant having shown the greatest beta-glucosidase activity was cultured in 150 ml growth medium (specified above) in a 500 ml baffled flask, incubated at 30° C., 160 rpm for 6 days. The supernatant was centrifuged at 10,000 rpm for 10 min, filtered through a 0.22 μm filter (Millipore) and pH adjusted to 7.4.

The his-tagged beta-glucosidases were purified on the ÄKTApurifier system with UNICORN software, using a HisTrap HP 5 ml anion column (GE Healthcare), run at a flow rate of 5 ml/min. The column was equilibrated with 5 CV of binding buffer (20 mM sodium phosphate, 0.5M NaCl, pH 7.4), 100 ml sample was loaded onto the column, followed by washing with binding buffer till the absorbance reached the baseline. The his-tagged beta-glucosidases were eluted with 3 CV elution buffer (20 mM sodium phosphate, 0.5M NaCl, 500 mM imidazole, pH 7.4) and the peak (1 CV) collected by monitoring the absorbance.

Assays for Characterization of Purified Beta-Glucosidases

Michaelis Menten kinetics, glucose tolerance, thermostability, pH optimum, and cellodextrin hydrolysis were carried out as described in EXAMPLE 1.

Sequence Comparisons and Homology Modeling

Similar sequences were located by NCBI BLAST OF (Altschul et al., 1997) in the protein entries of GenBank (Benson et al., 2004) and aligned using hidden Markov models (Karplus et al., 2005) and CLUSTAL W (Thompson et al., 1994). Similar beta-glucosidase catalytic domain structures were obtained from the Protein Data Bank (PDB; (Berman et al., 2000)), then superimposed and compared with the program O (Jones et al., 1991). Multiple sequence alignments were used to generate the best pair-wise alignment of the *A. saccharolyticus* beta-glucosidase with that of the *T. neapolitana* beta-glucosidase 3B. This pair-wise alignment was the basis of creating a homology model, with PDB entry 2X40 (Pozzo et al., 2010) as the template in the program SOD (Kleywegt et al., 2001). The model was adjusted in O, using rotamers that would improve packing in the interior of the protein. The model is available upon request from the authors. The figure was prepared using O, MOLSCRIPT (Kraulis, 1991) and Molray (Harris & Jones, 2001).

Results

Identification of Beta-Glucosidase in *A. saccharolyticus* Extract

The enzyme extract of *A. saccharolyticus* produced by solid state fermentation on wheat bran, was fractionated by ion exchange chromatography, investigating the beta-glucosidase activity and protein content of each fraction (FIG. 17). Protein content could be measured in all fractions. Approximately 25% of the proteins did not bind to the column, but passed through prior to the start of the gradient elution, No beta-glucosidase activity was found in this initial flow-through. The fractions displaying the greatest beta-glucosidase activity were the fractions #15-17. These fractions with eluted beta-glucosidase were calculated to have a NaCl concentration of approximately 0.14-0.23M. From SDS-page, one dominating band of approximately 130 kDa was discovered in these fractions (FIG. 17). The intensity of this band in the different fractions followed the measured beta-glucosidase activity. The proteins in this band were found to be highly expressed relative to other proteins in the raw *A. saccharolyticus* extract (FIG. 18). The band of fraction 16 was excised from the gel, trypsin digested, analyzed by LC-MS/MS, and searched against the NCBI database for peptide matches using the Mascot program. The sample was identified as a beta-glucosidase, having peptides identical to several Aspergilli species, including *A. aculeatus* (Swiss-Prot: P48825), *A. terreus* (NCBI ref seq XP_001212225), *A. niger* (GenBank CAB75696), and *A. fumigatus* (NCBI ref seq XP_750327). The best match was the beta-glucosidase of *A. aculeatus*, with five peptide matches. Besides of beta-glucosidase peptides, also peptide matches of beta-galactosidase from different *Aspergillus* species were found suggesting that the analyzed band contained more than one protein. Only the results for the beta-glucosidase peptides were used for degenerate primer design to obtain the homologous beta-glucosidase of *A. saccharolyticus.*

Characterization of Beta-Glucosidase Gene, Bgl1, and Predicted Protein, BGL1

By the use of degenerate primers and genome walking, the genomic coding sequence of bgl1 of 2919 base pairs (incl stop coden) was obtained (GenBank HM853555). The sequence comprised seven exons, intercepted by six introns located at 58-119, 263-313, 359-414, 468-523, 1716-1776, 2636-2685 bp, which all followed the GT-AG rule at the intronlexon junctions. The gene encodes a 680 amino acid polypeptide, BGL1, predicted by NetAspGene 1.0 (Wang et al., 2009) and confirmed by mRNA isolation and sequencing of the derived cDNA. A signal peptide with a cleavage site between amino acid 19 and 20 was predicted by SignalP server (Bendtsen et al., 2004. Nielsen et al., 1997). A TATA-like sequence at position −138 bp, a CCAAT box at position −695 bp, and several CreI sites at positions −145, −619, −1186, −1294, and −1313 were identified upstream of the start codon. Analysis of the predicted cDNA gene sequence revealed 85% identity with bgl1 from *A. aculeatus* (GenBank 064088.1) (Kawaguchi et al., 1996) and 75% identity with bgl1 A. (NCBI ref seq XM_001398779) (Pel et al., 2007).

The pI of BGL was calculated to 4.96 and the molecular mass was calculated to 91 kDa using the ExPASy Proteomics server (Gasteiger et al., 2005). This prediction does not relate to the size of the band in fraction 16 (FIG. 18), but from the NetNGlyc 1.0 server (Blom et al., 2004) BGL has 12 asparagines that are potential N-linked glycosylation sites. The molecular weight of 130 kDa observed by SDSpage therefore probably reflects extensive glycosylation.

The previous MS/MS data of the band in faction 16 was by use of Mascot searched against possible trypsin fragments and expected MS/MS patterns of the BGL sequence. The observed MS/MS data matched the expected data, thus confirming that the cloned bgl gene codes for the protein present in fraction 16.

Analysis of the amino acid sequence of BGL resulted in 91% identity with beta-glucosidase BGL1 from *A. aculeatus* (GenBank BAA10968) (Kawaguchi et al., 1996) and 82% identity with beta-glucosidase GBL1 from *A. niger* (NCBI ref seq XP_001398816) (Pel et al., 2007). Alignment of the amino acid sequence of BGL from *A. saccharolyticus* with several aspergilli glycosyl hydrolase (GH) family 3 beta-glucosidases revealed a high degree of homology in highly conserved regions including the catalytic sites (FIG. 19), and PROSITE scan (Sigrist of al., 2010) confirmed the presence of a GH family 3 active site in BGL1, predicting the signature sequence to be between amino acids 248-264 (LLKSELGFQGFVMSDWGA) in the mature protein. The putative nucleophile, Asp261, of the mature BGL1 of *A. saccharolyticus* is located in this region (Henrissat, 1991).

Homology modeling studies show that *A. saccharolyticus* beta-glucosidase 1 catalytic module possesses a fold similar to that of beta-glucosidase 3B from *T. neapolitana* with 5 deletions and 8 insertions compared to it (FIG. 20). Although the sequence identity is relatively low (35%) it is obvious that the residues important for substrate binding and catalysis are conserved (FIG. 20A).

These results imply that BGL1 is a novel beta-glucosidase belonging to GH family 3.

Heterologous Expression of Bgl by *T. reesei*

The bgl gene was heterologously expressed in *T. reesei* from the constitutive RP27 ribosomal promoter. Positive transformants were selected by simple pNPG assay, where the negative control, wild type QM6a, showed no beta-glucosidase activity at the culture and assay conditions used. The transformant identified from the screening to have the highest beta-glucosidase activity was confirmed by PCR to have the expression cassette incorporated into its genomic DNA. Using a Ni sepharose column, the his-tagged proteins were purified from an extract of the transformant. An SDS-page gel of the eluent showed two bands (FIG. 18), one correlating in size with the band found in fractions 15-17 in the initial fractionation of the *A. saccharolyticus* extract (approximately 130 kDa) and another that was smaller (approximately 90 kDa) correlating with the predicted size of the protein. 3.8 mg purified protein was obtained from 100 ml filtered culture extract, which corresponded to about 2.7% of the total amount of protein in the culture extract.

Characterization of the Purified BGL1

The purified BGL1 was characterized by its activity on pNPG and cellobiose.

A substrate saturation plot of BGL1 revealed inhibition of the enzyme reaction, when pNPG in high concentrations was used as substrate. This was observed by a decrease in reaction rate with increasing substrate concentration rather than a leveling off toward a maximum velocity (FIG. 21A). Meanwhile, a MM kinetics relationship was found for cellobiose, where the reaction rate tends towards the maximum velocity (FIG. 21A). A Hanes plot of the cellobiose data gave a good distribution of the data points for preparation of a straight trendline from which $V_{max}$ and $K_M$ were determined to be 45 U/mg and 1.9 mM, respectively. Glucose inhibition was investigated with pNPG as substrate, showing a reduction in activity to 50% at a product concentration 30 times greater than the substrate concentration (FIG. 21B).

BGL1 was incubated at different temperatures for different time periods to investigate the thermostability and half-life of the enzyme. At regularly used hydrolysis temperature of 50° C., the enzyme was stable throughout the incubation period (data not shown). The enzyme is fairly stable at temperatures up to 58° C. at 4 hour incubation (FIG. 22A), but with temperatures above 60° C. the calculated half-life is approximately 6 hours (FIG. 22A). From 62° C. and up to 65° C. there is a gradually decrease in the half-life to less than 2.5 hours. The pH span of BGL was examined at 50° C. using pNPG as substrate. Its profile gives the typical bell-shape curve with an optimum around pH 4.2, and within the pH range 3.8-4.8 the activity stayed above 90% of maximum. At basic conditions, activity was below 10%, showing that acidic pH values are better suited for enzyme activity (FIG. 22B).

The ability of BGL1 to hydrolyze short chains of glucose units was studied with cellohexaose, -pentaose, -tetraose, and -triose, where only data for cellohexaose hydrolysis is shown here (FIG. 23). Initially, as the level of cellohexaose decreases, the concentration of primarily cellopentaose and glucose increase. Later, as the concentration of cellopentaose has increased, an increase in cellotetraose is observed, indicating that the enzyme hydrolyzes the different cellodextrins depending on the concentration in which they occur. Similar results were obtained using cellopentaose, -tetraose and -triose as initial substrates. These observations of the different cellodextrins increasing in concentration over time related to their length suggests that the enzyme hydrolyzes the different cellodextrins through exohydrolase action, removing one glucose unit at the time releasing glucose and the one unit shorter product before it associates with another substrate, rather than processively cleaving off glucose units.

Discussion

We have cloned a beta-glucosidase, BGL, from the novel species *A. saccharolyticus* (EXAMPLE 2) and expressed it in *T. reesei* in order to purify the enzyme for a specific characterization.

Initially, we used ionexchange fractionation of the raw enzyme extract of *A. saccharolyticus* followed by LC-MS/MS analysis of the dominating protein band in the fractions with high beta-glucosidase activity. This was applied for the identification of active beta-glucosidases from *A. saccharolyticus*. Aspergilli are known to possess several beta-glucosidases in their genomes, e.g. *A. niger* has 11 GH3 beta-glucosidases predicted (Pel et al., 2007) of which 6 were identified as extracellular proteins by the SignalP 1.0 server (Bendtsen et al., 2004, Nielsen et al., 1997). With this approach we intended to identify the key beta-glucosidase player amongst the potential several expressed beta-glucosidases of *A. saccharolyticus.*

Ion exchange separates molecules on the basis of differences in their net surface charge. The net surface charge of proteins will change gradually as pH of the environment changes (Amersham Biosciences, 2004). The isoelectric point (pI) of the 6 predicted *A. niger* secreted beta-glucosidases (Pel et al., 2007) were, using ExPASY proteomics server (Gasteiger et al., 2005), calculated to around pH 5. Assuming the pI of the secreted *A. saccharolyticus* beta-glucosidases are in the same range, an anion column was chosen for ion exchange using Tris buffer pH 8, as proteins will bind to an anion exchanger at pH above its isoelectric point (Amersham Biosciences, 2004). The beta-glucosidases of *A. saccharolyticus* did bind to the column at these conditions, with no activity found in the initial flow through fractions, and analysis of the later deducted amino acid sequence of BGL was calculated to have a pI of 4.96, correlating well with the above.

Proteomics is useful for the identification of secreted proteins and have been used for the identification of beta-glucosidases of *A. fumigatus* (Kim et al., 2007a). MS/MS peptide analysis followed by molecular techniques were here employed for the identification and cloning of beta-glucosidases from *A. saccharolyticus*. From LC-MS/MS analysis, peptides of a beta-glucosidase and a beta-galactosidase were identified in the protein band that was dominating in the protein fractions with high beta-glucosidase activity, Indicating that it had not been a pure band, but rather had it contained both a beta-glucosidase and a beta-galactosidase of *A. saccharolyticus*. Only the identification of the beta-glucosidase was further pursued.

By genome walking, the beta-glucosidase was successfully cloned, and the size of its cDNA corresponded well with the beta-glucosidases of *A. aculeatus* (GenBank: BAA10968) and *A. niger* (GenBank: XP_001398816) to which it is most closely related. However, the predicted polypeptide size of the cloned beta-glucosidase was only 91 kDa compared to the approximately 130 kDa band seen in the SDS page gel. Glycosylation of beta-glucosidases is common (Krogh et al., 2010, Murray et al., 2004, Dan et al., 2000, Jeya et al., 2010. Decker et al., 2000) and it was therefore assumed that the SDS page gel size estimation of the protein was mislead by glycosylation that makes the protein run slower in the gel, which has also been seen with beta-glucosidases from *Talaromyces emersonii* expressed in *T. reesei* (Murray et al., 2004). Several potential N-glycosylation sites were identified for BGL, supporting this assumption. Based on interest in obtaining knowledge of regulation of bgl expression in *A. saccharolyticus*, putative binding sites for the cellulose regulatory protein, CREI, were searched for upstream of the bgl gene. Five putative CreI sites were found within the 1350 pb sequence from genome walking have obtained upstream of the gene. CREI is known to be involved in carbon catabolite repression of many fungal cellulase genes.

BGL1 was based on its amino acid sequence characterized as belonging to the GH family 3, matching the active site signature (Henrissat, 1991, Cantarel et al., 2009). Several GH3 beta-glucosidases have been cloned and characterized, but few studies have been published on heterologous expression by *T. reesei*, while several have been expressed by *E. coli*, and some by Yeast (Bhatia et al., 2002). One example of expression by *T. reesei* is the beta-glucosidase, cel3a cDNA, of *T. emersonli* where the chb1 promoter and terminator of *T. reesei* were used (Murray et al., 2004). Another example is the *T. reesei* production strain by Novozymes A/S expressing *A. oryzae* beta-glucosidase for improved cellulose conversion (Merino & Cherry, 2007). We here present heterologous expression of bgl from A, *saccharolyticus* by *T. reesei* QM6a using the constitutive *M. grisea* ribosomal promoter RP27 and the *N. crassa* beta-tubulin terminator to control expression of the gDNA clone of bgl1, thereby successfully combining host, promoter, gene, and terminator from different eukaryotes. The host strain was transformed with the non-linearized plasmid for random insertion, giving recombinant protein yields of 3.8 mg/100 ml from 6 days cultivation of the best transformant. This is significantly greater than the expression levels reached with *T. emersonii* (Murray et al., 2004), but still low compared to the secretion capacity of *T. reesei* (Merino & Cherry, 2007).

Interestingly, it appeared that *T. reesei* secreted the heterologously expressed BGL1 in two different forms represented by the two bands on the SDSpage gel of the histidine-tag purified proteins. It is speculated that these two different bands represent different degrees of glycolysation, the large one being glycosylated to the same extent as found in the *A. saccharolyticus* secreted BGL, and the smaller one correlating with the predicted molecular mass thus not being glycosylated. Postsecretional modification of glycosylated proteins expressed by *T. reesei* is medium dependent, with the effect on extracellular hydrolases being most dominating in enriched medium (Stals et al., 2004), possibly explaining the different forms of the recombinant BGL beta-glucosidases. BGL1 is classified as a broad specificity beta-glucosidase as it can hydrolyze both aryl-beta-glycosides, cellobiose, and cellooligo-saccharides (Bhatia et al., 2002). Comparing the properties of *A. saccharolyticus* BGL to other *Aspergillus* beta-glucosidases, the observed inhibition at high pNPG substrate concentrations has also been reported for *A. niger* (Krogh et al., 2010, Seidle et al., 2004, Yan et al., 1998), *A. aculeatus* and *A. japonicus* (Decker et al., 2000). Whether the inhibition of *A. saccharolyticus* BGL is due to regular substrate inhibition kinetics with an additional pNPG binding to the substrate-enzyme complex hindering release of product, or if transglycosylation occurs with pNPG playing the role of the nucleophile competing with a water molecule in breaking the enzyme-product complex, is not known. BGL1 has $K_M$ value of cellobiose comparable with other reported values for *Aspergillus* beta-glucosidases, with $K_M$ values of 2-3 mM for *A. phoenicis, A. niger*, and *A. carbonarius* beta-glucosidases (Jager et al., 2001), 1 mM for *A. japonicus* (Korotkova et al., 2009), and a general literature search by Jäger et al. (2001) showing $K_M$ varying from 1.5-5.6 mM for *A. niger* (Jager et al., 2001). Meanwhile, the specific activity, $V_{max}$, of *A. saccharolyticus* BGL1 was significantly higher than values reported for other purified *Aspergillus* beta-glucosidases, with cellobiose as substrate in hydrolysis (Table 5) (Jager et al., 2001, Rajoka et al., 2006, Yan & Lin, 1997).

TABLE 5

Comparison of $V_{max}$ values reported in the literature for hydrolysis of cellobiose by purified beta-glucosidases, either heterologously expressed or directly purified from extract of origin

| Organism ID, enzyme ID | $V_{max}$ (U/mg) | Assay conditions (° C., pH) | Reference |
|---|---|---|---|
| *A. cellulolyticus* CBS 127449 | 49 | 50, 4.8 | This work |
| *A. niger* NIAB280 | 36.5 | 50, 5.0 | Rajoka et al. (2006) |
| *A. niger* CCRC31494 | 5.27 | 40, 4.0 | Yan and Lin (1997) |
| *A. niger* BKMF-1305 | 38.8 | 50, 4.0 | Jager et al. (2001) |
| *A. carbonarius* KLU-93 | 15.4 | 50, 4.0 | Jager et al. (2001) |
| *A. phoenicis* QM329 | 27.3 | 50, 4.0 | Jager et al. (2001) |

Hydrolysis of cellodextrins was facilitated by BGL1, as has also been found with *A. niger* beta-glucosidase, that similarly in exo-fashion removes one glucose unit at the time from the end of the cellodextrins, so that products released are subsequently used as substrates to be shortened by another glucose (Seidle et al., 2004).

Acidic pH being best suited for beta-glucosidase activity was also found for beta-glucosidases from *A. oryzae, A. phoenicis, A. carbonarius, A. aculeatus, A. foetidus. A. japonicus, A. niger*, and *A. tubingensis* with optima ranging pH 4-5, and close to no activity at alkaline conditions (Jager et al., 2001, Decker et al., 2000, Korotkova et al., 2009, Riou et al., 1998). Thermal stability, however, is more difficult to compare as different researches use different incubation conditions, times and temperatures. We found *A. saccharolyticus* BGL to be more thermostable compared with Novozym 188 from *A. niger*, as it retained more than 90% activity at 60° C. and still had approx. 10% activity at 67° C. after 2 hours of incubation, while Novozym 188 had 75% activity at 60° C. but no activity at 67° C. after 2 hours of incubation (EXAMPLE 1). After 4 hours of incubation these differences is much more pronounced as our BGL still had more than 70% activity while Novozym 188 drop to 40% activity at 60° C. Jäger et at (2001) studied beta-glucosidases from *A. phoenicis, A. niger, A. carbonarius*, finding them all to be stable at 2 hours incubation at 50° C. while activities of 87%, 64%, and 53%, respectively, remained after 2 hours incubation at 60° C. and total inactivation was observed after 2 hours at 70° C. (Jager et al., 2001). Compared to this, *A. saccharolyticus* BGL showed approximately the same stability as *A. phoenicis*. Rojaka et al. (2006) similarly find half-life of *A. niger* beta-glucosidase to be 8 hours at 50° C. and 4 hours at 60° C. (Rajoka et al., 2006), which is similar to our results (EXAMPLE 1), whereas Krogh et al. indicate a half-life for *A. niger* BG of 24 hours at 60° C. This is six times longer than measured by us and Rojaka et al. (2006). Decker et al. (2000) demonstrates that an *A. japonicus* and *A. tubingensis* beta-glucosidase were remarkably stable, maintaining 85% and 90% activity, respectively, after 20 hours incubation at 60° C. (Decker et al., 2000). However, Korotkova et al. (2009) found *A. japonicus* beta-glucosidase to only retain 57% of its activity after incubation for 1 hour at 50° C. (Korotkova et al., 2009), contradicting the findings of Dekker et al. (2000). The crude extract of *A. saccharolyticus*, from which BGL was identified, has previously been characterized by its beta-glucosidase activity and evaluated against two commercial enzyme preparations (EXAMPLE 1). Comparing the enzyme kinetics, temperature and pH profiles, glucose tolerance, and cellodextrin hydrolysis, a striking similarity was found for the crude extract and the purified BGL. Substrate inhibition (or transglycosylation activity) with pNPG was found in both cases, while none was observed for cellobiose within the tested concentrations. There was therefore no foundation for the calculation of $V_{max}$ for pNPG as no tendency of the activity approaching a maximum was seen rather the activity decreased with higher substrate concentrations. Therefore $V_{max}$ and $K_M$ were only calculated for cellobiose where the data correlated well with MM kinetics and a straight Hanes plot could be obtained for determination of the kinetic parameters. Calculated $K_M$ values for cellobiose were similar, 1.9 mM for the purified BGL vs. 1.09 mM for the crude extract, while the $V_{max}$ value expectedly increased for the purified BGL compared to the crude extract. The pure enzyme was inhibited by glucose to the same extent as the crude extract, the pH and temperature profiles were very similar, and the mode of hydrolysis of cellodextrins was consistent. This all together indicate that BGL is the main contributor to the beta-glucosidase activity observed in the crude extract of *A. saccharolyticus.*

The crystal structure of a beta-glucosidase from barley has recently been used as template to construct a homology model of a beta-glucosidase from *Penicillium purpurogenum* where superimposition of the modeled structure on the true structure from barley showed similar orientation and location of the conserved catalytic residues (Jeya et al., 2010). We chose to use the recently resolved crystal structure of a *T. neopolitana* beta-glucosidase to construct a homology model of the *A. saccharolyticus* BGL and found that the conserved catalytically important residues show that the enzyme possesses beta-glucosidase activity (FIG. 20A).

The deletion of loop X (FIG. 20B), having Ser370 described to have weak H-bonds with glucose in −1 subsite in *T. neapolitana* structure, makes the catalytic pocket wider where this may be important for substrate accessibility as well as to remove the product fast from the enzyme. The insertions and deletions lining the catalytic pocket (FIG. 20B) may play a major role in the dynamics of the enzyme. The motif KHFV, Lys163, His164, Phe165, Val166, in the *T. neapolitana* structure is considered to be important for substrate recognition (Pozzo et al., 2010). However, this motif in the *A. saccharolyticus* enzyme is slightly different, KHYI, Lys170, His171. Tyr172 and Ile173. The homology modeling revealed that the catalytic pocket of *A. saccharolyticus* beta-glucosidase is open compared to those of barley (PDB entry 1 LQ2) (Hrmova et al., 2004). *Pseudoalteromonas* sp. BB1 (PDB entry 3F94) and *T. neapolitana* (Pozzo et al., 2010) indicating possible high activity. The distance between the putative nucleophile (D261) and the acid/base (E490) is approximately 5.8 Å displaying the general characteristic of a retaining enzyme.

In conclusion, a novel highly efficient beta-glucosidase from the newly discovered species *A. saccharolyticus* has been identified and expressed. The enzyme has a great potential for use in industrial bioconversion processes due to its high degree of thermostability compared to the commercial beta-glucosidase from *A. niger* (Novozym 188) as well as a high specific activity.

Sequences

SEQ ID NO: 1: BGL1 gDNA

*Aspergillus saccharolyticus* BGL1 gDNA sequence

>Gene#BGL gDNA 2919 bp

SEQ ID NO: 2: BGL1 actual cDNA

*Aspergillus saccharolyticus* BGL1 cDNA sequence

>Gene#BGL actual cDNA 2582 bp

SEQ ID NO: 3: BGL1 protein

*Aspergillus saccharolyticus* BGL1 protein sequence

>Gene#BGL1 protein 861aa signal peptide is underlined amino acid residues shown in bold are involved in substrate binding Residues shown in italics are D (catalytic nucleophil) and E catalytic acid residue

MRLSWLEAAALTAASVVSADELAFASPFYPSPWANGQGEWADAYKRAVDIVSQMTL

DEKVNLTTGTGWELEKCVGQTGGVPRLDIGGMCLQDSPLGVRDSDYNSGFPAGVNV

AATWDRKLAYLRGQAMGQEFSDKGVDQLGPAAGPLGRSPDGGRNWEGFSPDPAL

TGVLFAETIKGIQDAGVIATAKHYILNEQEHFRQVSEAAGYGFNISDTISSNIDDKTIHEM

YLWPFADAVRAGVGAMCSYNQINNSYACQNSYTLNKLLKSELGFQGFVMS*D*WGAH

HSGVGSALAGLDMSMPGDVSFDSATSFWGTNLTVAVLNGTVPQWRVDDMAVRIMA

AYYKVGRDRLYQPPNFSSWTRDEYGFKYYYSQEGPYEKVNQYVNVQRNHSEVIRKV

GADSTVLLKNNNALPLTGKERKVALIGEDAGSNAYGANGCSDRGCDNGTLAMAWGS

GTAEFPYLVTPEQAIQAEVLKNKGSTYTITDNWALSQVEALAKTASVSLVFVNADSG*E*

GYISVDGNEGDRNNLTLWKNGDNLIKATASNCNNTIVVIHSVGAVLVDEWYDHPNVTA

ILWAAGLPGQESGNSLADVLYGRVNPGGKTPFTWGKTRASYGDYLVREPNNGHGAPQ

DNFSEGVFIDYRGFDKRNETPIYEFGHGLSYTTFNYSGLQVEVLNTSSSTPVATQTKP

APTFGEIGNASDYLYPEGLDRITAFIYPWLNSTDLKESSGDPDYGVDTAKYIPAGATNS

-continued

SAQPVLPAGGGFGGNPRLYDELIRVSVTVKNTGRVTGDAVPQLYVSLGGPNEPKVVL

RQFDRITLRPSEETVWTTTLTRRDLSNWDVAAQDWVITSYPKKVHVGSSSRQLPLHA

ALPKVQ

SEQ ID NO: 4: BGL1 protein without signal peptide
*Aspergillus saccharolyticus* BGL1 protein sequence without signal peptide
BGL1 protein without signal peptide

DELAFASPFYPSPWANGQGEWADAYKRAVDIVSQMTLDEKVNLTTGTG

WELEGCVGQTGGVPRLDIGGMCLQDSPLGVRDSDYNSGFPAGVNVAAT

WDRKLAYLRGQAMGQEFSDKGVDVQLGPAAGPLGRSPDGGRNWEGFSP

DPALTGVLFAETIKGIQDAGVIATAKHYILNEQEHFRQVSEAAGYGFN

ISDTISSNIDDKTIHEMYLWPFADAVRAGVGAVMCSYNQINNSYACQN

SYTLNKLLKSELGFQGFVMS_D_WGAHHSGVGSALAGLDMSMPGDVSFDS

ATSFWGTNLTVAVLNGTVPQWRVDDMAVRIMAAYYKVGRDRLYQPPNFSS

WTRDEYGFKYYYSQEGPYEKVNQYVNVQRNHSEVIRKVGADSTVLLK

NNNALPLTGKERKVALIGEDAGSNAYGANGCSDRGCDNGTLAMAWGSG

TAEFPYLVTPEQAIQAEVLKNKGSTYTITDNWALSQVEALAKTASVSL

VFVNADSG_E_GYISVDGNEGDRNNLTLWKNGDNLIKATASNCNNTIVVI

HSVGAVLVDEWYDHPNVTAILWAGLPGQESGNSLADVLYGRVNPGGKTP

FTWGKTRASYGDYLVREPNNGHGAPQDNFSEGVFIDYRGFDKRNE

TPIYEFGHGLSYTTFNYSGLQVEVLNTSSSTPVATQTKPAP

TFGEIGNASDYLYPEGLDRITAFIYPWLNSTDLKESSGDPDYGVDTAKY

IPAGATNSSAQPVLPAGGGFGGNPRLYDELIRVSVTVKNTGRVTGDAVP

QLYVSLGGPNEPKVVLRQFDRITLRPSEETVWTTTLTRRDLSNWDVAAQ

DWVITSYPKKVHVGSSSRQLPLHAALPKVQ

SEQ ID NO: 5; BGL2 gDNA
*Aspergillus saccharolyticus* BGL2 gDNA sequence
ATG start site and signal sequence as well as stop codon are highlighted bold
Introns are underlined gccttaaggccnaagagccgcccagatcgttattcatccaacaatgattg actgcctcgttgacattgactgtggtgctctggacactgattggttttct tctatcatatgtcatggtgtgtgcagactgcatatgtgattcgaggccgc gtgatccaagatccctgtttggactggggtaggaagacaggtagctatat cttcagcagcctgtcgggtcataaacggtgatggtaaggttttcctgagt ctgaccgtgtcctttcttccgttcaggggcattgacaatgactcctgtct ggcattatctcatttatctgaccctgcttcttccaggataccttgcagcc gatcaccgccgccgcgacgatgacgctgaagccttctcgcctccctacta tccggcccctccgggaggttggatatccgattggagtgctgcatacgcca -continued aagctcaggctgtggtgagcaatatgaccctagctgagaaagtcaacctc actaccggtaccggaatgttcatgggcccttgcgtcggtcaaacaggtag cgcacttcgattcgggataccaaacctctgtatgcaggactcccctctgg gaatccgcaactcggaccataataccgcgttccctcctggggtaactgtt ggagctacctgggacaaggatctgatgtaccagcgtggtgtcgaacttgg ggaagaagctcgcgggaaaggtgtgaacgttctgcttggtccagtggtcg gacccatgttcaggaagccactcggcggacgcgggtgggaaggcttcggc gccgatccgaccctgcaggcagttggaggcgcattgacgatccagggcat gcaaagcactggtgcgatagcttgtttgaaacatttcattgggaatgagc aagagatgtatcgcgagacctcggttctaactcaaggttattcatcgaac atcgatgaccgtaccctgcatgaactgtacttgtggccatttgcggaggg agtccgggctggcgtgggctctgtgatgatggcgtacaacgatgtgagtt cctcagacagtaggccagacggatttactgatcaggataggtgaatcgct cggcctgtagccagaatagcatgctcatcagcggcatccttaaggacgag ttaggcttccaggggtttgtcatgaccgactggctggctcagcagggcgg cgtctcgtctgccctcgccggacttgacatggctatgcctggcgatgggg ccatccctttgctcggggatgcttactggggatccgagctatcaaccgcc atcctcaacggaacagtgccgctggatcgactcaatgacatggtatgaga tcgtcaacctcctgctcctttcatactaagttttcaaggtcactcggatc gttgcgacttggtatcaaatgggtcaggatgaggattatcctctgcccaa cttttcgagcaacacgctcgacaaaacaggccctctctatcccggtgccc tgttctccccgacgggcgttgtcaaccaatatgtcgacgtgcaaggcaac cataacatcactgcgcacgctgttgcccgagatgcgatcactctcctcaa gaacgagaataacacattgcccctcaagcgcagtgccgctctcaaggtgt ttggtaccgatgctgggcccaacacttccggcctcaactcctgtagtgac atgggctgcgaccagggcgtccttacgatgggctggggaagtggtacctc gcacctcccttcactcgtcacgccgcaagaagccattgccaatcttacta cgtcgaattcgactaccttttacttgtcggatacgttccctgccaatctc gccaccccatccacttccgacatcgctgtggtcttcatcaacgctgactc tggcgagaactacatcactgtcgagtccaatccaggagaccgcaccagcg caggcttcgatgcgtggcacaacggcaacgcgctcgttcaagctgctgcg gccgagttctcgactgtggttgtagtgatccatactgttggccctatact gcttgaatcgtttattgacctccctagcgtcaaggctgtgcttattgctc acctccccggccagactgccggctattcgctcacggatgtcctgtatggc gaggtcagccctagcggccatctgccctacactatccctacatcggcgtc -continued aaactacccatcctccatggacatcatcacctcacagccacttttgtccc
agatccaggactggtttgatgaggggatttacatcgactatcgttacttt
ctacaagccaacatcaccccccgctaccctttcggctacggattgtcgta
cacgacgttccagtactcggcaccagttctgaccactgtgaccgaactga
gcaccgaatatcccgctgcgagagcaagcaaggcttcggtcccaacttat
cccacagatattcccgatcctcaagaagtcgcatggccgagcacgcttga
tcggatctggcgctacctgtacccgtatctggatgatcccgagagcgtta
ccaacacaagcacctactcgtacccggccggctactccaccacggcgcat
gcggccccgcgtgccgggggaggacagggtggcaaccctgcccttttcga
aaccgcttttgaggtagcggtgaccatcaccaacaccggcacacgaagtg
gacgagccgtggcacaactgtatgtgcaaatgccggatgaggcagttctt
ggagtagacaccccgaagagacagttgcgggcgtttgcgaagaccgggac
cctggcgtccggggagagcgaagtcgtgactatgaatgtgaccaggaaag
atttgagtgtgtgggatgtcacggtgcaggattggcgagcgccagttggt
ggagcgggtgtgactttctgggtaggggacagtgttgcagaagaggacct
gacggtgaaatgtgctgttgggagtgactaggggctcataggccttaag
gc SEQ ID NO: 6: BGL2 cDNA

*Aspergillus saccharolyticus* BGL2 cDNA sequence

SEQ ID NO: 7: BGL2 protein

*Aspergillus saccharolyticus* BGL2 protein sequence

Signal sequence is highlighted bold mtpvwhyliyltlllpgylaadhrrrdddaeafsppyypappggwisdws
aayakaqavvsnmtlaekvnlttgtgmfmgpcvgqtgsalrfgipnlcmq
dsplgirnsdhntafppgvtvgatwdkdlmyqrgvelgeeargkgvnvll
gpvvgpmfrkplggrgwegfgadptlqavggaltiqgmqstgalaclkhf
igneqemyretsvltqgyssniddrtlhelylwpfaegvragvgsvmmay
ndvnrsacsqnsmlisgilkdelgfqgfvmtdwlaqqggvssalagldma
mpgdgaipllgdaywgselstailngtvpldrlndmvtrivatwyqmgqd
edyplpnfssntldktgplypgalfsptgvvnqyvdvqgnhnitahavar
daitllknenntlplkrsaalkvfgtdagpntsglnscsdmgcdqgvltm
gwgsgtshlpslvtpqeaianlttsnsttfylsdtfpanlatpstsdiav
vfinadsgenyitvesnpgdrtsagfdawhngnalvqaaaaefstvvvvi
htvgpillesfidlpsvkavliahlpgqtagysltdvlygevspsghlpy
tiptsasnypssmdiitsqpllsqiqdwfdegiyidyryflqanitpryp
fgyglsyttfqysapvlttvtelsteypaaraskasvptyptdipdpqev
awpstldriwrylypylddpesvtntstysypagysttahaapragggqg
gnpalfetafevavtltntgtrsgravaqlyvqmpdeavlgvdtpkrqlr
afaktgtlasgesevvtmnvtrkdlsvwdvtvqdwrapvggagvtfwvgd
svaeedltvkcavgsd*

SEQ ID NO: 8: BGL3 gDNA

*Aspergillus saccharolyticus* BGL3 genomic DNA sequence

ATG start site and signal sequence as well as stop codon are highlighted bold

Introns are underlined gccttaaggcctaggaacgtcccagaacgttgatcccaggactggccaat
ttttccctttttcttttgtctgcagcgtgagaatagattgagcgtcggctt
gtcaagtcagccagctcctctttccctcaccttttcacaatgggtgtcag
tctgctagccaaggggcttgcgcttcttcacctctgcgccggtgtcactg
ccagtagcaatgactcaacaccgctgtacaagaaccccaatgcgccggtg
gaggatcgtgtcagtgaccttctgggccgcatgaccatccacgacaagac
gggacaactgatgcaaggtatgagtcttcctcgcgggtgatccgttaaat
gtcttggataatctgtgctgactgctactgcaggggatctcgcgaactgg
atgaacaccacaactggagcgttcaactacacgggtctggtcgcgaacat
ggaaatgaaggcgggaggattctacggtacgagtccttgatcatgctgat
tatcgcgatgggaaagctgactagcgggcagttggatatgcggtcccgtg
ggactggatggtgaccaacatcaagcatgcgcaggactacctgatccata
acaccacgcttggtattcctgcacttgttcagtcagaaggtaggcttgat
gcaaaagttttggggaggatgttgctcacggctgcaggtattcatgggtt
cctggttcagaacgccactattttcaattcccctattgcatatggttgct
ccttcaaccgtgaggtgagtggtggacaccaactccagtgagccctgcag
gctaatgatcgataacagctggtctccaaaatggccaaaatcatcagtca
agaatctctcactctgggcgtcaaccagctatttgcccctgtggttgacc
tggcccgtgagctgcggtatgggcgggtaagctcatgacttggacatagg
ctaggctaggctttttagctaattgattaacaggccgaagagacgttctc
ggaggacccataccttgctggcgagattggctacaactatgtgcaaggcc
tgcagagtctcaacgtttcggccactgtcaagcattttgcgggcttcagt
gcccctgaacaggggttgaacactgcgccagttcagggaggagagcgata
tcttcgtactacgtaagtacagctaacaatcttaagatttatgctgacat
gatgcagctggctgcactcattcaagcgtgcgatcatcgatgcaggtgca
tggagtgtcatgagcgcataccactcgtgagtttgatgcttttgggaaca
agattccttgcttacatgcatctagctacgatggcattcccgctgttgcc
gactggtttaccctgacaaaggttctgcgagaagagtggggtttcaagca
ctgggttttcagcgattcgggcgctactgatcgactgtgcaccgctttca
agctctgtcaagcctctccaatcgacatggaagcagtcaccctgcaggca
ctccctgctggtaacgacgttgagatgggtggtggctccttgtaagtatc
ctaggttggtaacctgcgagagactaaccctgtctagcaacttccagaag
atcccggagcttgtagagtccggaaggctggacatcgagactgttgacac
tgctgtctcgcgcattctgagggccaagttcgaaatgggtctctttgaga
acccccttccctgctgctcctgagtcggagtggcacaagttgatccacagc
tcagaggcggtcgagctcgctagaaccttggacaaggagtctatcgtctt
gctggagaaccacaacaagacccttcctttggacaagagcggcagcatcg -continued ccgttattgggcccatggcccatggcttcatgaacgtgagtgattggcct
atctcggcccagagcatctactaacttatatacagtatggagactacgtc
gtttacaagagccagtaccgcggtgtaacccctctggacggcatcaaagc
tgctgttggcgacaacgccacgatcaactacgcccagggctgcgagcggt
ggagcaacgaccagtccggcttcgatgaagccattgcagcggccaagaag
tcggacgtggctgttgtcgtcgtaggcacctggtctcgcgaccagaccga
gctgtggtccggttacaacgcgacgtgagttgcctattgcttgcatgtaa
tcccgagacgtcgccgctaaccaccaacagaaccggcgagcacattgatc
tggataacctcgccctcgtcggtgcccaaggcccgctcgtcaaggctatt
atcgacaccggcgtccccaccatcgtggtcctctccagcggcaagcccat
cacggacgtgacctggctcgcgaactcgaccgcggcgctcgtccagcaat
tctatccgtcggagcaaggcggcaatgcgctggccgacgtgctgttcggc
gactacaacccctctggcaagctgtccgtcagcttcccgcgcttcgtcgg
cgacctcccgatctactacgacttcctcaattcggcgcgcaacatcggcc
cggccggccacgccttccccaacggcaccctggaattcgagagccagtac
gtcctgggcgaccccaccgcgatctacgagttcgggtacggcaagagcta
cgtcgactttgactacggcgccgtcacgctgagccagaccaacgtgaccg
cctcggacacggtgacggtccgcgtggacgtgaccaacactgacgccacc
cgcgacggcaccgaggtcgtgcaggtgtatgtgtcggatgtgatcgcgct
ggtggtggtgccgaaccgggcgctcaagggcttcgagaaagtggtcatcc
cggctggcacgaccaagacggtggagattgatttgcaggtggaggacctg
gggctctggaaccgctcgatgcagtatgtcgttgagccgggagcgtttgc
ggtgttggtgggcagcagttcggcggatatccggggggaatgcgacgtttt
atgttgagtaggtctgatgcggatgggtgagtggtacagtgggtggcggc
aatcaccgggtcaattgcttcgatacctaccctgcttattgattgttcgc
tcaatcactttctttgaatacttctattaaagctcttgtgatgagtggct
ctagttggttgggatggtggttagttgaaggtagaagtgtagtctactgt
ctgtcatcaataaatagcgcgaaacagatgttattttgcagtcggggtga
caggtttttaaaactttatttgacgaaacgagaaaatatcagagagtaaa
tgattcgaaccgggatgactttgatctgagatctagacagtggtagcccc
ggcataagtgaagataaagagagatgcaacgggtgctgttcgatcgatcc
gattgcccattacgtggacctggaaagaaaccctaaatgctcgtctagcc
gtcctgcagccattctcccctggtttaacgagctctccaccctccgctcg
ccgttggtttgaccccataccgcggggtcatagctcaaagacacagccaa
taagaacatatccgcatccccgaagtaggcctaaccg SEQ ID NO: 9: BGL3 cDNA
*Aspergillus saccharolyticus* BGL3 cDNA sequence
ATG start site and signal sequence as well as stop codon are highlighted bold atgggtgtcagtctgctagccaaggggcttgcgcttcttcacctctgcgc
cggtgtcactgccagtagcaatgactcaacaccgctgtacaagaacccca
atgcgccggtggaggatcgtgtcagtgaccttctgggccgcatgaccatc
cacgacaagacgggacaactgatgcaaggggatctcgcgaactggatgaa
caccacaactggagcgttcaactacacgggtctggtcgcgaacatggaaa
tgaaggcgggaggattctacgttggatatgcggtcccgtgggactggatg
gtgaccaacatcaagcatgcgcaggactacctgatccataacaccacgct
tggtattcctgcacttgttcagtcagaaggtattcatgggttcctggttc
agaacgccactattttcaattcccctattgcatatggttgctccttcaac
cgtgaggccgaagagacgttctcggaggacccataccttgctggcgagat
tggctacaactatgtgcaaggcctgcagagtctcaacgtttcggccactg
tcaagcattttgcgggcttcagtgcccctgaacaggggttgaacactgcg
ccagttcagggaggagagcgatatcttcgtactacctacgatggcattcc
cgctgttgccgactggtttaccctgacaaaggttctgcgagaagagtggg
gtttcaagcactgggttttcagcgattcgggcgctactgatcgactgtgc
accgctttcaagctctgtcaagcctctccaatcgacatggaagcagtcac
cctgcaggcactccctgctggtaacgacgttgagatgggtggtggctcct
tcaacttccagaagatcccggagcttgtagagtccggaaggctggacatc
gagactgttgacactgctgtctcgcgcattctgagggccaagttcgaaat
gggtctctttgagaaccccttccctgctgctcctgagtcggagtggcaca
agttgatccacagctcagaggcggtcgagctcgctagaaccttggacaag
gagtctatcgtcttgctggagaaccacaacaagacccttcctttggacaa
gagcggcagcatcgccgttattgggcccatggcccatggcttcatgaact
atggagactacgtcgtttacaagagccagtaccgcggtgtaacccctctg
gacggcatcaaagctgctgttggcgacaacgccacgatcaactacgccca
gggctgcgagcggtggagcaacgaccagtccggcttcgatgaagccattg
cagcggccaagaagtcggacgtggctgttgtcgtcgtaggcacctggtct
cgcgaccagaccgagctgtggtccggttacaacgcgacaaccggcgagca
cattgatctggataacctcgccctcgtcggtgcccaaggcccgctcgtca
aggctattatcgacaccggcgtccccaccatcgtggtcctctccagcggc
aagcccatcacggacgtgacctggctcgcgaactcgaccgcggcgctcgt
ccagcaattctatccgtcggagcaaggcggcaatgcgctggccgacgtgc
tgttcggcgactacaacccctctggcaagctgtccgtcagcttcccgcgc
ttcgtcggcgacctcccgatctactacgacttcctcaattcggcgcgcaa
catcggcccggccggccacgccttccccaacggcaccctggaattcgaga
gccagtacgtcctgggcgaccccaccgcgatctacgagttcgggtacggc
aagagctacgtcgactttgactacggcgccgtcacgctgagccagaccaa
cgtgaccgcctcggacacggtgacggtccgcgtggacgtgaccaacactg
acgccacccgcgacggcaccgaggtcgtgcaggtgtatgtgtcggatgtg
atcgcgctggtggtggtgccgaaccgggcgctcaagggcttcgagaaagt
ggtcatcccggctggcacgaccaagacggtggagattgatttgcaggtgg
aggacctggggctctggaaccgctcgatgcagtatgtcgttgagccggga -continued gcgtttgcggtgttggtgggcagcagttcggcggatatccgggggaatgc gacgttttatgttgagtag

SEQ ID NO: 10: BGL3 protein
*Aspergillus saccharolyticus* BGL3 protein sequence
Signal sequence is highlighted bold mgvsllakglallhlcagvtassndstplyknpnapvedrvsdllgrmti hdktgqlmqgdlanwmntttgafnytglvanmemkaggfyvgyavpwdwm vtnikhaqdylihnttlgipalvqsegihgfivqnatifnspiaygcsfn reaeetfsedpylageigynyvqglqslnvsatvkhfagfsapeqglnla pvqggerylrttydgipavadwttltkvlreewgfkhwvfsdsgatdric tafklcqaspidmeavtlqalpagndvemgggsfnfqkipelvesgrldi etvdtavsrilrakfemgifenpfpaapesewhklihsseavelartldk esivllenhnktlpldksgsiavigpmahgfmnygdyvvyksqyrgvtpi dgikaavgdnatinyaqgcerwsndqsgfdeaiaaakksdvavvvvgtws rdqtelwsgynattgehididnlalvgaqgplvkaiidtgvptivvlssg kpitdvtwlanstaalvqqfypseqggnaladvlfgdynpsgklsvsfpr fvgdlpiyydflnsarnigpaghafpngtlefesqyvigdptaiyefgyg ksyvdfdygavtlsqtnvtasdtvtvrvdvtntdatrdgtevvqvyvsdv ialvvvpnralkgfekvvipagttktveidlqvedlglwnrsmqyvvepg afavlvgsssadirgnatfyve*

SEQ ID NO: 11: BGL4 gDNA
*Aspergillus saccharolyticus* BGL4 gDNA sequence
ATG start site and signal sequence as well as stop codon are highlighted bold
Introns are underlined gccttaaggcctacgaaactcccagccacctacctaaccctcattcttgc cctggatattccactgctgaaacctgcagatggccgtcttagagcctttc agttcttgtttttctgccgatatttacccgggagtcaggcaattctgcgg agtattcggagcattaggtgggattgaccaactcggtcttcttgtacagt ccactcgatgcattggactaaaggtataaatacgtcaggcagtcgcggag gcaaaatatcgagacaggcaagcgagtccagcagaatgtacggtctagca tcttttgcggccttgttgggcggtctttcactttgctccgcggccccgac tgagcaaaatattacaagcgatacttacttttatggcgattctccgcccg tctacccctcccgtacgtgcaacactgtgcttttctaccatgtcctcaat actggcccaaccatctagcggacggtgccggaaccgggtcctgggccgca gcctacgtaaaggcaaagagttttgtcgctcaactcacagacgaggagaa gatcaacttcacagccgggtatactgccagtaatggctgctcaggcaaca ttccagcagtctctcgtctcggcttccccgggctttgtgtttctgatgca ggaaatgggctggtaagtgcacaaggtcgcgctggattgaccatgaccgc taacatttacgcagcgtggaaccgattttgtgaatggctggccaagtggc attcacgtgggagcaaggtaagagatgtcacagccactgcatccgtggca -continued aacgagtaatgattccattctatctagctggaataaaactcttgcacacc aacgcgccctatacatgggacaggagttccatcgaaagggggtaaatctc ctactgggcccagttgttggcccacttggtcgtgtcgtggaaggtggtcg taactgggaaggctttgccaacgatccttacctcagcggtgcgctggtgt atgagactgtgcagggtgtgcaggaagccggtgtcggcgtttcggtcaag gtatgtgcataccatcttactggaaagtcatctgagtcatggctaagggt tgaatcaaagcactacatcggaaacgagcaagagaccaacagaaaccccg agactgagaacggcgtcactgttgcctcagtttcctctaacatcgacgac aaaactatccatgaactgtatctttggccatttcaagacgccgttctggc gggaagtgtctccgtgatgtgctcgtacaaccgagtcaataattcctaca gctgccagaacagtaagacgctgaatggtcttctgaagaccgaactgggc ttccaaggtaagacggcctaatcaatcctccgcatcattgctgatatttg caaggctacgttgtcactgattgggatgcccaacacgccgggatcgctgg tgctaatgccggcctggacatggtcatgccaagtaccaccacatgggggt ccaatctcacgacggccattgccaacggcagcatggaagcatcgagactg gacgatatggtcactaggtaggttagatcaccttccacctttgatactca ttcttactcaatcaggatcgttgcctcctggtaccaattaaaccaagaca ccgactttccctcaccaggcattgggatgcccgtcgacgtctactccgag catgagatcgtcattggaacttctgccgatgagaaggacgctttgctgca aagcgcaatcgagggacacgtcctcgttaaaaaccaaggctccgtcctcc ctctccagtcgccacgcctagtctccgtgttcggctacgacgccaaagcc ccggagtccctggacctagccccccgtctctctaagtgtcgctccgcccac gcaaaacaacacactctgggtgggcggaggttccggtgccaacaatcccg catacgttatcgccccccttggacgccatccagcaacaagcctatgaagac aacaccgccgtcctctgggacgtgacatcgttcgacccagacgtcgaccc cgcctcccacgcctgcctagttttcatcaacagctacgcctccgaaggca gtgaccggacaggtctggtggactccgacagcgacacgctggtaaccaac gtcgccagcaaatgcaacaacacgatcgtcgtgatccacaacgcgggcat ccgtctcgtgtataactggatcgaccacgagaacgttaccgctgtgatct tcgcccatcttccaggccaagacacaggcaaagctctcgtggatttactg tacggccgcgccaacccctcgggccgcctcccctacaccgtcgccaagca ggcctccgactacggcgcagtcttacaccccgtgcagcccgtcgcgcctt acggcctgttcccgcaggacaacttcaccgagggagtatacatcgactac cgcgccttcgacaaggaggacatcactccgcagttcgagttcggcttcgg tctctcgtacaccaccttcgattattccagcctgaacatccaacgcacct cggtcgaggccacacagtaccctcctgcggcggttatccaggaaggaggc aacccgcggctgtgggatgttttggtcaacgtcacggcgcaggtggagaa cgccggctcggtcgacggcgcggaggtcgcacagctgtacgtgggcatcc ccaatggaccgatccgtcagctgcgcgggttcgataaggtgaatatcctg gctggggagacggtgacggtcacgttcgccttgacgagacgtgatttgag tacgtggagtgtggaggcgcaggagtgggagctgcagcagggagaatata -continued aggtgtatgtgggacgatcgagtcgggatctgcctctgacggggagtttg accttgtgaagtgtagtattgccaggagatgacacttggatgataattga aaatcttccactccattctaatgcaatttagtctgcatctattcaactgc tgtaaaacccgtcccaagtgcaaatcaaaccacaaaccacaaaagttaac ataaccgtccatcgcagaccggtctcagaatcctacaacaatcaatataa tcaccacgccccaccgatgcctcatctccaatacccgcgcccacccgccc ccaacatcccagacttaaccgtccccaactcttcaccatcaacatcctcc tccaccaagcctacatcccagacataatattcctcaactcctccgcatcc ccgaactaggccttaaccg SEQ ID NO: 12: BGL4 cDNA
*Aspergillus saccharolyticus* BGL4 cDNA sequence
ATG start site and signal sequence as welt as stop codon are highlighted bold atgtacggtctagcatcttttgcggccttgttgggcggtctttcactttg ctccgcggccccgactgagcaaaatattacaagcgatacttacttttatg gcgattctccgcccgtctacccctccccggacggtgccggaaccgggtcc tgggccgcagcctacgtaaaggcaaagagttttgtcgctcaactcacaga cgaggagaagatcaacttcacagccgggtatactgccagtaatggctgct caggcaacattccagcagtctctcgtctcggcttccccgggctttgtgtt tctgatgcaggaaatgggctgcgtggaaccgattttgtgaatggctggcc aagtggcattcacgtgggagcaagctggaataaaactcttgcacaccaac gcgccctatacatgggacaggagttccatcgaaaggggtaaatctccta ctgggcccagttgttggcccacttggtcgtgtcgtggaaggtggtcgtaa ctgggaaggctttgccaacgatccttacctcagcggtgcgctggtgtatg agactgtgcagggtgtgcaggaagccggtgtcggcgtttcggtcaagcac tacatcggaaacgagcaagagaccaacagaaaccccgagactgagaacgg cgtcactgttgcctcagtttcctctaacatcgacgacaaaactatccatg aactgtatctttggccatttcaagacgccgttctggcgggaagtgtctcc gtgatgtgctcgtacaaccgagtcaataattcctacagctgccagaacag taagacgctgaatggtcttctgaagaccgaactgggcttccaaggctacg ttgtcactgattgggatgcccaacacgccgggatcgctggtgctaatgcc ggcctggacatggtcatgccaagtaccaccacatgggggtccaatctcac gacggccattgccaacggcagcatggaagcatcgagactggacgatatgg tcactaggatcgttgcctcctggtaccaattaaaccaagacaccgacttt ccctcaccaggcattgggatgcccgtcgacgtctactccgagcatgagat cgtcattggaacttctgccgatgagaaggacgctttgctgcaaagcgcaa tcgagggacacgtcctcgttaaaaaccaaggctccgtcctccctctccag tcgccacgcctagtctccgtgttcggctacgacgccaaagccccggagtc cctggacctagcccccgtctctctaagtgtcgctccgcccacgcaaaaca acacactctgggtgggcggaggttccggtgccaacaatcccgcatacgtt atcgccccccttggacgccatccagcaacaagcctatgaagacaacaccgc -continued cgtcctctgggacgtgacatcgttcgacccagacgtcgaccccgcctccc acgcctgcctagttttcatcaacagctacgcctccgaaggcagtgaccgg acaggtctggtggactccgacagcgacacgctggtaaccaacgtcgccag caaatgcaacaacacgatcgtcgtgatccacaacgcgggcatccgtctcg tgtataactggatcgaccacgagaacgttaccgctgtgatcttcgcccat cttccaggccaagacacaggcaaagctctcgtggatttactgtacggccg cgccaacccctcgggccgcctcccctacaccgtcgccaagcaggcctccg actacggcgcagtcttacaccccgtgcagcccgtcgcgccttacggcctg ttcccgcaggacaacttcaccgagggagtatacatcgactaccgcgcctt cgacaaggaggacatcactccgcagttcgagttcggcttcggtctctcgt acaccaccttcgattattccagcctgaacatccaacgcacctcggtcgag gccacacagtaccctcctgcggcggttatccaggaaggaggcaacccgcg gctgtgggatgttttggtcaacgtcacggcgcaggtggagaacgccggct cggtcgacggcgcggaggtcgcacagctgtacgtgggcatccccaatgga ccgatccgtcagctgcgcgggttcgataaggtgaatatcctggctgggga gacggtgacggtcacgttcgccttgacgagacgtgatttgagtacgtgga gtgtggaggcgcaggagtgggagctgcagcagggagaatataaggtgtat gtgggacgatcgagtcgggatctgcctctgacggggagtttgaccttgtg a

SEQ ID NO: 13: BGL4 protein
*Aspergillus saccharolyticus* bgl4 protein sequence
Signal sequence is highlighted bold myglasfaallgglslcsaapteqnitsdtyfygdsppvypspdgagtgs waaayvkaksfvaqltdeekinftagytasngcsgnipavsrlgfpglcv sdagnglrgtdfvngwpsgihvgaswnktlahqralymgqefhrkgvnll lgpvvgplgrvveggrnwegfandpylsgalvyetvqgvqeagvgvsvkh yigneqetnrnpetengvtvasvssniddktihelylwpfqdavlagsvs vmcsynrvnnsyscqnsktlngllktelgfqgyvvtdwdaqhagiagana gldmvmpstttwgsnlttaiangsmeasriddmvtrivaswyqlnqdtdf pspgigmpvdvyseheivigtsadekdallqsaieghvlvknqgsvlplq sprlvsvfgydakapesldlapvslsvapptqnntlwvgggsgannpayv iapldaiqqqayedntavlwdvtsfdpdvdpashaclvfinsyasegsdr tglvdsdsdtlvtnvaskcnntivvihnagirlvynwidhenvtavifah lpgqdtgkalvdllygranpsgrlpytvakqasdygavlhpvqpvapygl fpqdnftegvyidyrafdkeditpqfefgfglsyttfdysslniqrtsve atqyppaaviqeggnprfwdvlvnvtaqvenagsvdgaevaqlyvgipng pirqlrgfdkvnilagetvtvtfaltrrdlstwsveaqewelqqgeykvy vgrssrdlpltgsltl*

SEQ ID NO: 14: beta-tubulin gene

>*Aspergillus* AP, *Aspergillus saccharolyticus* beta-tubulin, partial coding sequence SEQ ID NO: 15: calmodulin gene >*Aspergillus* AP, *Aspergillus saccharolyticus* calmodulin, partial coding sequence SEQ ID NO: 16: ITS gene >*Aspergillus* AP, *Aspergillus saccharolyticus* ITS, partial coding sequence SEQ ID NO: 17: BGL1 protein signature sequence BGL1, predicting the signature sequence to be between amino acids 248-264 (LLKSELGFQGFVMSDWGA)

SEQ ID NO: 18-28: gene primers

ITS gene primers

```
ITS1        (5' TCCGTAGGTGAACCTGCGG 3')
ITS2        (5' GCTGCGTTCTTCATCGATGC 3')
ITS4        (5' TCCTCCGCTTATTGATATG)
```

beta-tubulin gene primers

```
Bt2a        (5' GGTAACCAAATCGGTGCTGCTTTC)
Bt2b        (5' ACCCTCAGTGTAGTGACCCTTGGC)
```

calmodulin gene primers

```
Cmd5        (5' CCGAGTACAAGGAGGCCTTC)
Cmd6        (5' CCGATAGAGGTCATAACGTGG)
```

Primers for UP-PCR fingerprinting

```
L45         (5' GTAAAACGACGGCCAGT)
L15/AS19    (5' GAGGGTGGCGGCTAG)
```

Degenerate primers

```
5' CACGAAATGTACCTCtggcccttygc
5' CCTTGATCACGTTGTCGccrttcykcca,
```

Where y is A or T.

SEQ ID NO: 29: BGL1 gDNA

*Aspergillus saccharolyticus* BGL1 gDNA sequence including upstream sequence

ATG start site and signal sequence as well as stop codon are highlighted bold

Introns are underlined cggttaaggcctaactcggagagggaccaacgggatgcagaggtggagat gcggggaatggctggggaggataataccgtatgtatccgcgtgtcatgac accaggtataccttattctcgtctgccaactatcaccactgcagtgagtg cttgctcgctggcagacctgcggggaacaacacagactggactgatacaa tggataccaccttccatcttcatcttcttgtcagcttctcgggtgtcatt caagtccgatatttgtccgattagcctgtatccgaagcggatcggaatgt aaacgaggaacgggataacttaagtttacggagtattctggttccagtcg agaatgctgggcagctcccggccgatcgtatgctgcttgctgcctgaatg -continued ataataattatctattttattctgagagaaaattcttggattattttctt gtattccttaaatctttataaaacagagtgcagttggagattcatgtccg agagagatgctgagtgttaagactgtaagtaagtagaggaagtggtaagt tgtttggattgaactggaaagcgtcacaggattacatacaggcacctccc ggccccactgcggtcggggaacttcttccagtccacagggcagcagtact caatatccatccaatatccatccttccactacatccaccatcatcattgt ttcccggatggcaggatactggcaccacgctctgacgtggggctcggcca ttccagttatcccagctcaattccctgcaggtctgctgcgaactattgac cgcgaaaatgaaagtttttttgggagttgatgttccacggtgccgtgcgc aggtgaatgcaagcaagagcagcgatccagagatggagagtgaatgaatc acggtaagtagcatcgcttgacttgcctgcgttccggtcgttccatgctt tttctcgactctccctcgctgtctgtctctctctcgatctggattcctcc ctgtcgatccatccccatgcttagagccaaaacaactaagccgatggggc tggctggccttcgactgctggcgggcgagacagcattcaaagagtggact acttgtggtagctccgcagcatcagccaagaaagtctaggttgatgttag ttattcactcgtctgctggtctctgagtctcatagctgtggcgcccccct cctgccgttgctggggttatttatatcccctcccttcccccccccctgatc ggatatgtttgtcttcccacaataagttgtgttacctcgccatcttcctc aattgctcgagactagctcgtcccttccgcttccttcagctacctcgacg ccatcatgaggctcagttggctcgaggctgccgccttgacggctgcatcc gtcgtcagcgctgtatgttttgccgcttgtttggatggatgactgggtgt gaaactgacatttgtgctcgctaggatgaacttgccttcgcttcccccctt ctatccttccccttgggccaatggccagggcgagtgggcggatgcctaca agcgcgcagtggacattgtttcccagatgactctggacgagaaggtcaat ctgaccaccggaactgggtatgggagcgtaattcatgcggtccgcatcgc ctgctaacatattccaagctgggagctggagaagtgcgtcggtcaaactg gtggtgttccaaggtatgcactgattgaatgggtttctactagaacggtt aattgacaattgtgcctagactcgacatcggtggaatgtgtcttcaggac agtccgctcggagtccgtgattgtaagtctcgttaggagccgacatcaaa cgtgtcttattaacaatgtgtcttccagcggactacaattcgggattccc cgctggcgtcaacgttgctgcgacttgggacaggaagctcgcctatctcc gtgggcaggccatgggtcaagaatttagtgacaagggagttgatgtccag ctggggccggccgccgggcccctgggcagaagtcccgatggaggtcggaa ctgggaagggttttcgcccgacccagcactcactggtgtgctctttgccg agacgatcaagggtatccaagatgccggggtcatcgccacagctaagcac tacattctcaatgagcaggaacatttccgccaagtctcggaggctgcggg ctacggtttcaacatctctgataccatcagctccaacatcgacgacaaaa ccattcatgagatgtacctctggcccttcgcggatgccgtgcgtgccggt gtgggcgccgtcatgtgctcctacaaccagattaacaacagttacgcctg ccagaacagctacacactgaacaagcttctgaagtcggagctcggctttc -continued aaggatttgttatgtcggactggggtgctcaccacagtggtgtcggctct gctttggccgggttggatatgtctatgcccggtgacgtttcttttgattc tgccaccagtttctggggtaccaacctgactgttgccgttctcaatggaa ccgtcccgcagtggcgtgttgacgacatggccgttcgtatcatggctgcc tactacaaggttggccgtgatcgcttgtaccagccgcccaacttcagctc ctggactcgggacgagtacggcttcaagtactactactcccaggaaggcc cctacgagaaggtcaatcaatatgtcaatgtgcagcgcaaccacagcgaa gtcattcgcaaggtgggagccgacagcactgtcctgttgaagaacaacaa tgctcttcctctgactggaaaggagcgcaaggttgctctcatcggcgagg atgctggatctaacgcctacggtgccaacggctgcagtgaccgcggatgc gacaacgggacgctcgccatggcctggggcagtggcaccgcagagttccc atacctggtcactcccgagcaggccattcaagccgaggtgctcaagaaca agggcagcacttacactatcaccgacaactgggcattgagccaggtggag gccctcgctaagacggctaggtgagcccttccattcatgatactggtctg ccgtgacaatccactgacaagtcgctcgcagtgtctccctggtctttgtg aatgccgactcgggcgaaggctacatctcggttgatggcaacgagggtga ccgcaacaacctcaccctgtggaagaacggggacaatctcatcaaggcta ctgccagcaactgcaacaacaccattgttgtcatccactccgttggggct gttctggtggacgaatggtatgaccacccgaacgtcactgcgattctctg ggctggcttgcctggccaggagtctggcaattctcttgccgatgtcctct acggccgcgtcaaccctggcggtaagacgcccttcacctggggcaagacg agagcgtcttacggggactacctggttcgggagcccaacaacggccacgg agccccgcaggataacttctcggagggtgttttcatcgactaccgcggct ttgacaagcgcaatgagaccccgatctacgagttcggacacggtctgagc tacaccaccttcaactattcgggcctgcaggtggaggttctcaacacgtc ttccagcactccggtcgctacccagaccaagcccgcacccactttcggcg agattggcaacgcgtcggactacttgtaccctgagggattggaccgaatt accgcgttcatctaccccctggctcaactccacggacctcaaggagtcatc tggtgacccggactatggggtggacaccgccaagtatattcccgccggcg ccaccaacagctcggcccagcctgttctgccggctggcggtggcttcggt ggtaacccgcgtctctacgatgagctgatccgtgtttcggttaccgtcaa -continued gaacactggtcgtgtcactggggacgccgtgcctcaattggtaagttgct cgtccggggagttggtagatcgcgtactaacatgagacagtatgtatcgc ttggcggacctaatgagcccaaggtggtgctgcgccagttcgaccgcatc acgctccggccttcggaggagacggtgtggacgactactctgacccgtcg cgatctgtccaactgggatgttgcggctcaggactgggttattacttcct acccgaagaaggttcacgtgggtagctcttcgcgtcagctgccgcttcat gcggcgctgcctaaggtgcaatgagcggatggggattgggtgcgatgggg atgatgctgtatacttctttccagtcgggagactacgaattgatgactat gttattgtaaagacgagcgatccagggatccaggtacaggaggggtgtag tgtaatgtaagcgtaatgatctggggtcgggtggctgtggcggtggaggt gaagcggcgggcgggcggaagacagcgacgtcatccgacttccaccggca cttcgtctccctttggtaacttccatcatttctccgacctctgcctggtt ttcgtctatccatcctgacgcctcaattcccatcatctttctttgaattt tgctccacgcttgactttgaattgattgcctccaaaacaagccaccacaa gacagcgcagccactcaaaccatcgaagggactctatccggaattggc Deposit of Microorganisms Under the Budapest Treaty The following biological material has been deposited under the terms of the Budapest Treaty with the Centraalbereau voor Schimmelcultures (CBS), Uppsalaan 8, 3584 CT Utrecht, The Netherlands; P.O. Box 85167, 3508 AD Utrecht, The Netherlands and given the following accession number

| Deposit | Accession Number | |
|---|---|---|
| CBS | 127449 | *Aspergillus saccharolyticus* |

*Aspergillus* AP/*Aspergillus saccharolyticus* (=IBT 28509)
Date of Deposit: Jun. 30, 2010

The strain has been deposited under conditions that assure that access to the cultures will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However it should be understood that the availability of a deposit does not constitute a license to practice the subject invention in derogation of patent rights granted by governmental action NCBI Blast of NCBI Blast of

The invention claimed is:

1. A recombinant host cell of a microorganism, the host cell comprising a recombinant nucleic acid sequence or its complementary sequence, the expression product thereof being capable of hydrolyzing a β1-4 glucose-glucose linkage, the recombinant nucleic acid sequence being selected from the group consisting of:

a. a polynucleotide sequence encoding a polypeptide consisting of an amino acid sequence SEQ ID NO: 4, b. a polynucleotide sequence encoding a biologically active sequence variant of said amino acid sequence, wherein the variant has at least 96% sequence identity to said SEQ ID NO: 4, c. SEQ ID NO: 1, SEQ ID NO: 2, or SEQ ID NO: 29, d. a polynucleotide comprising a nucleic acid sequence having at least 85% identity to SEQ ID NO: 1, SEQ ID NO: 2, or SEQ ID NO: 29, and e. a polynucleotide complementary to any of a) to d).

2. The host cell according to claim 1, wherein said microorganism or descendant thereof, comprises a beta-glucosidase (BGL) polypeptide and/or a gene encoding said polypeptide.

3. The host cell according to claim 2, wherein said beta-glucosidase (BGL) polypeptide is BGL1 (SEQ ID NO: 4).

4. The host cell according to claim 1, wherein said microorganism or descendant thereof, comprise a nucleic acid sequence, which is at least 90% identical to SEQ ID NO: 16.

5. The host cell according to claim 1, wherein said microorganism or descendant thereof, comprise a nucleic acid sequence, which is at least 90% identical to SEQ ID NO: 15.

6. The host cell according to claim 1, wherein said microorganism or descendant thereof, comprise a nucleic acid sequence, which is at least 88% identical to SEQ ID NO: 14.

7. An isolated polynucleotide comprising a recombinant nucleic acid sequence or its complementary sequence, the expression product thereof being capable of hydrolyzing a β1-4 glucose-glucose linkage, the recombinant nucleic acid sequence being selected from the group consisting of:

a. a polynucleotide sequence encoding a polypeptide consisting of an amino acid sequence SEQ ID NO: 4, b. a polynucleotide sequence encoding a biologically active sequence variant of said amino acid sequence, wherein the variant has at least 96% sequence identity to said SEQ ID NO: 4, c. SEQ ID NO: 1, SEQ ID NO: 2, or SEQ ID NO: 29, d. a polynucleotide comprising a nucleic acid sequence having at least 85% identity to SEQ ID NO: 1, SEQ ID NO: 2, or SEQ ID NO: 29, and e. a polynucleotide complementary to any of a) to d).

8. The host cell according to claim 1, wherein said microorganism comprises a fungus.

9. The host cell according to claim 8, wherein the fungus comprises a filamentous fungus.

10. The host cell according to claim 8, wherein the fungus is selected from the group consisting of: *Trichoderma* and *Aspergillus*.

11. The host cell according to claim 8, wherein the fungus comprises a white rot fungus.

12. The host cell according to claim 1, wherein said microorganism comprises a yeast.

13. The host cell according to claim 1, wherein said microorganism comprises bacteria.

* * * * *

SEQUENCE LISTING

```
<160> NUMBER OF SEQ ID NOS: 29

<210> SEQ ID NO 1
<211> LENGTH: 2919
<212> TYPE: DNA
<213> ORGANISM: Aspergillus saccharolyticus

<400> SEQUENCE: 1

atgaggctca gttggctcga ggctgccgcc ttgacggctg catccgtcgt cagcgctgta      60

tgttttgccg cttgtttgga tggatgactg ggtgtgaaac tgacatttgt gctcgctagg     120
```

-continued

```
atgaacttgc cttcgcttcc cccttctatc cttccccttg ggccaatggc cagggcgagt    180
gggcggatgc ctacaagcgc gcagtggaca ttgtttccca gatgactctg gacgagaagg    240
tcaatctgac caccggaact gggtatggga gcgtaattca tgcggtccgc atcgcctgct    300
aacatattcc aagctgggag ctggagaagt gcgtcggtca aactggtggt gttccaaggt    360
atgcactgat tgaatgggtt tctactagaa cggttaattg acaattgtgc ctagactcga    420
catcggtgga atgtgtcttc aggacagtcc gctcggagtc cgtgattgta agtctcgtta    480
ggagccgaca tcaaacgtgt cttattaaca atgtgtcttc cagcggacta caattcggga    540
ttccccgctg gcgtcaacgt tgctgcgact tgggacagga agctcgccta tctccgtggg    600
caggccatgg gtcaagaatt tagtgacaag ggagttgatg tccagctggg gccggccgcc    660
gggcccctgg gcagaagtcc cgatggaggt cggaactggg aagggttttc gcccgaccca    720
gcactcactg gtgtgctctt tgccgagacg atcaagggta tccaagatgc cggggtcatc    780
gccacagcta agcactacat tctcaatgag caggaacatt tccgccaagt ctcggaggct    840
gcgggctacg gtttcaacat ctctgatacc atcagctcca acatcgacga caaaaccatt    900
catgagatgt acctctggcc cttcgcggat gccgtgcgtg ccggtgtggg cgccgtcatg    960
tgctcctaca accagattaa caacagttac gcctgccaga acagctacac actgaacaag   1020
cttctgaagt cggagctcgg ctttcaagga tttgttatgt cggactgggg tgctcaccac   1080
agtggtgtcg gctctgcttt ggccgggttg gatatgtcta tgcccggtga cgtttctttt   1140
gattctgcca ccagtttctg ggtaccaac ctgactgttg ccgttctcaa tggaaccgtc   1200
ccgcagtggc gtgttgacga catggccgtt cgtatcatgg ctgcctacta caaggttggc   1260
cgtgatcgct tgtaccagcc gcccaacttc agctcctgga ctcgggacga gtacggcttc   1320
aagtactact actcccagga aggcccctac gagaaggtca atcaatatgt caatgtgcag   1380
cgcaaccaca gcgaagtcat tcgcaaggtg ggagccgaca gcactgtcct gttgaagaac   1440
aacaatgctc ttcctctgac tggaaaggag cgcaaggttg ctctcatcgg cgaggatgct   1500
ggatctaacg cctacggtgc caacggctgc agtgaccgcg gatgcgacaa cgggacgctc   1560
gccatggcct ggggcagtgg caccgcagag ttcccatacc tggtcactcc cgagcaggcc   1620
attcaagccg aggtgctcaa gaacaagggc agcacttaca ctatcaccga caactgggca   1680
ttgagccagg tggaggccct cgctaagacg gctaggtgag cccttccatt catgatactg   1740
gtctgccgtg acaatccact gacaagtcgc tcgcagtgtc tccctggtct ttgtgaatgc   1800
cgactcgggc gaaggctaca tctcggttga tggcaacgag ggtgaccgca acaacctcac   1860
cctgtggaag aacggggaca atctcatcaa ggctactgcc agcaactgca acaacaccat   1920
tgttgtcatc cactccgttg ggctgttct ggtggacgaa tggtatgacc acccgaacgt   1980
cactgcgatt ctctgggctg gcttgcctgg ccaggagtct ggcaattctc ttgccgatgt   2040
cctctacggc cgcgtcaacc ctggcggtaa gacgcccttc acctggggca agacgagagc   2100
gtcttacggg gactacctgg ttcgggagcc caacaacggc cacggagccc cgcaggataa   2160
cttctcggag ggtgttttca tcgactaccg cggctttgac aagcgcaatg agaccccgat   2220
ctacgagttc ggacacggtc tgagctacac caccttcaac tattcgggcc tgcaggtgga   2280
ggttctcaac acgtcttcca gcactccggt cgctacccag accaagcccg cacccacttt   2340
cggcgagatt ggcaacgcgt cggactactt gtaccctgag ggattggacc gaattaccgc   2400
gttcatctac ccctggctca actccacgga cctcaaggag tcatctggtg acccggacta   2460
```

```
tggggtggac accgccaagt atattcccgc cggcgccacc aacagctcgg cccagcctgt   2520

tctgccggct ggcggtggct tcggtggtaa cccgcgtctc tacgatgagc tgatccgtgt   2580

ttcggttacc gtcaagaaca ctggtcgtgt cactggggac gccgtgcctc aattggtaag   2640

ttgctcgtcc ggggagttgg tagatcgcgt actaacatga gacagtatgt atcgcttggc   2700

ggacctaatg agcccaaggt ggtgctgcgc cagttcgacc gcatcacgct ccggccttcg   2760

gaggagacgg tgtggacgac tactctgacc cgtcgcgatc tgtccaactg ggatgttgcg   2820

gctcaggact gggttattac ttcctacccg aagaaggttc acgtgggtag ctcttcgcgt   2880

cagctgccgc ttcatgcggc gctgcctaag gtgcaatga                         2919
```

<210> SEQ ID NO 2
<211> LENGTH: 2583
<212> TYPE: DNA
<213> ORGANISM: Aspergillus saccharolyticus

<400> SEQUENCE: 2

```
atgaggctca gttggctcga ggctgccgcc ttgacggctg catccgtcgt cagcgctgat     60

gaacttgcct tcgcttcccc cttctatcct tccccttggg ccaatggcca gggcgagtgg    120

gcggatgcct acaagcgcgc agtggacatt gtttcccaga tgactctgga cgagaaggtc    180

aatctgacca ccggaactgg ctgggagctg gagaagtgcg tcggtcaaac tggtggtgtt    240

ccaagactcg acatcggtgg aatgtgtctt caggacagtc cgctcggagt ccgtgattcg    300

gactacaatt cgggattccc cgctggcgtc aacgttgctg cgacttggga caggaagctc    360

gcctatctcc gtgggcaggc catgggtcaa gaatttagtg acaagggagt tgatgtccag    420

ctggggccgg ccgccgggcc cctgggcaga agtcccgatg gaggtcggaa ctgggaaggg    480

ttttcgcccg acccagcact cactggtgtg ctctttgccg agacgatcaa gggtatccaa    540

gatgccgggg tcatcgccac agctaagcac tacattctca atgagcagga acatttccgc    600

caagtctcgg aggctgcggg ctacggtttc aacatctctg ataccatcag ctccaacatc    660

gacgacaaaa ccattcatga gatgtacctc tggcccttcg cggatgccgt gcgtgccggt    720

gtgggcgccg tcatgtgctc ctacaaccag attaacaaca gttacgcctg ccagaacagc    780

tacacactga acaagcttct gaagtcggag ctcggctttc aaggatttgt tatgtcggac    840

tggggtgctc accacagtgg tgtcggctct gctttggccg ggttggatat gtctatgccc    900

ggtgacgttt cttttgattc tgccaccagt ttctggggta ccaacctgac tgttgccgtt    960

ctcaatggaa ccgtcccgca gtggcgtgtt gacgacatgg ccgttcgtat catggctgcc   1020

tactacaagg ttggccgtga tcgcttgtac cagccgccca acttcagctc ctggactcgg   1080

gacgagtacg gcttcaagta ctactactcc caggaaggcc cctacgagaa ggtcaatcaa   1140

tatgtcaatg tgcagcgcaa ccacagcgaa gtcattcgca aggtgggagc cgacagcact   1200

gtcctgttga agaacaacaa tgctcttcct ctgactggaa aggagcgcaa ggttgctctc   1260

atcggcgagg atgctggatc taacgcctac ggtgccaacg gctgcagtga ccgcggatgc   1320

gacaacggga cgctcgccat ggcctggggc agtggcaccg cagagttccc atacctggtc   1380

actcccgagc aggccattca agccgaggtg ctcaagaaca agggcagcac ttacactatc   1440

accgacaact gggcattgag ccaggtggag gccctcgcta agacggctag tgtctccctg   1500

gtctttgtga atgccgactc gggcgaaggc tacatctcgg ttgatggcaa cgagggtgac   1560

cgcaacaacc tcaccctgtg gaagaacggg gacaatctca tcaaggctac tgccagcaac   1620

tgcaacaaca ccattgttgt catccactcc gttggggctg ttctggtgga cgaatggtat   1680
```

-continued

```
gaccacccga acgtcactgc gattctctgg gctggcttgc ctggccagga gtctggcaat   1740

tctcttgccg atgtcctcta cggccgcgtc aaccctggcg gtaagacgcc cttcacctgg   1800

ggcaagacga gagcgtctta cggggactac ctggttcggg agcccaacaa cggccacgga   1860

gccccgcagg ataacttctc ggagggtgtt ttcatcgact accgcggctt tgacaagcgc   1920

aatgagaccc cgatctacga gttcggacac ggtctgagct acaccacctt caactattcg   1980

ggcctgcagg tggaggttct caacacgtct tccagcactc cggtcgctac ccagaccaag   2040

cccgcaccca ctttcggcga gattggcaac gcgtcggact acttgtaccc tgagggattg   2100

gaccgaatta ccgcgttcat ctacccctgg ctcaactcca cggacctcaa ggagtcatct   2160

ggtgacccgg actatggggt ggacaccgcc aagtatattc ccgccggcgc caccaacagc   2220

tcggcccagc ctgttctgcc ggctggcggt ggcttcggtg gtaacccgcg tctctacgat   2280

gagctgatcc gtgtttcggt taccgtcaag aacactggtc gtgtcactgg ggacgccgtg   2340

cctcaattgt atgtatcgct tggcggacct aatgagccca aggtggtgct gcgccagttc   2400

gaccgcatca cgctccggcc ttcggaggag acggtgtgga cgactactct gacccgtcgc   2460

gatctgtcca actgggatgt tgcggctcag gactgggtta ttacttccta cccgaagaag   2520

gttcacgtgg gtagctcttc gcgtcagctg ccgcttcatg cggcgctgcc taaggtgcaa   2580

tga                                                                  2583
```

<210> SEQ ID NO 3
<211> LENGTH: 860
<212> TYPE: PRT
<213> ORGANISM: Aspergillus saccharolyticus

<400> SEQUENCE: 3

```
Met Arg Leu Ser Trp Leu Glu Ala Ala Ala Leu Thr Ala Ala Ser Val
1               5                   10                  15

Val Ser Ala Asp Glu Leu Ala Phe Ala Ser Pro Phe Tyr Pro Ser Pro
            20                  25                  30

Trp Ala Asn Gly Gln Gly Glu Trp Ala Asp Ala Tyr Lys Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asp Ile Gly Gly Met Cys Leu Gln Asp Ser Pro Leu Gly
                85                  90                  95

Val Arg Asp Ser Asp Tyr Asn Ser Gly Phe Pro Ala Gly Val Asn Val
            100                 105                 110

Ala Ala Thr Trp Asp Arg Lys Leu Ala Tyr Leu Arg Gly Gln Ala Met
        115                 120                 125

Gly Gln Glu Phe Ser Asp Lys Gly Val Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Ile Ala Thr Ala Lys His Tyr Ile
            180                 185                 190

Leu Asn Glu Gln Glu His Phe Arg Gln Val Ser Glu Ala Ala Gly Tyr
        195                 200                 205
```

-continued

```
Gly Phe Asn Ile Ser Asp Thr Ile Ser Ser Asn Ile Asp Asp Lys Thr
    210                 215                 220

Ile His Glu Met Tyr Leu Trp Pro Phe Ala Asp Ala Val Arg Ala Gly
225                 230                 235                 240

Val Gly Ala Val Met Cys Ser Tyr Asn Gln Ile Asn Asn Ser Tyr Ala
                245                 250                 255

Cys Gln Asn Ser Tyr Thr Leu Asn Lys Leu Leu Lys Ser Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Val Ser
    290                 295                 300

Phe Asp Ser Ala Thr Ser Phe Trp Gly Thr Asn Leu Thr Val Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Tyr
        355                 360                 365

Tyr Ser Gln Glu Gly Pro Tyr Glu Lys Val Asn Gln Tyr Val Asn Val
    370                 375                 380

Gln Arg Asn His Ser Glu Val Ile Arg Lys Val Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Leu Ile Gly Glu Asp Ala Gly Ser Asn Ala Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys Asn Lys Gly Ser Thr Tyr Thr Ile
465                 470                 475                 480

Thr Asp Asn Trp Ala Leu Ser Gln Val Glu Ala Leu Ala Lys Thr Ala
                485                 490                 495

Ser Val Ser Leu Val Phe Val Asn Ala Asp Ser Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Thr Ala Ser Asn Cys Asn Asn Thr
    530                 535                 540

Ile Val Val Ile His Ser Val Gly Ala Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Gly Lys Thr Pro Phe Thr Trp Gly Lys Thr Arg Ala Ser Tyr Gly
        595                 600                 605

Asp Tyr Leu Val Arg Glu Pro Asn Asn Gly His Gly Ala Pro Gln Asp
    610                 615                 620
```

Asn Phe Ser Glu Gly Val Phe Ile Asp Tyr Arg Gly Phe Asp Lys Arg
625 630 635 640

Asn Glu Thr Pro Ile Tyr Glu Phe Gly His Gly Leu Ser Tyr Thr Thr
645 650 655

Phe Asn Tyr Ser Gly Leu Gln Val Glu Val Leu Asn Thr Ser Ser Ser
660 665 670

Thr Pro Val Ala Thr Gln Thr Lys Pro Ala Pro Thr Phe Gly Glu Ile
675 680 685

Gly Asn Ala Ser Asp Tyr Leu Tyr Pro Glu Gly Leu Asp Arg Ile Thr
690 695 700

Ala Phe Ile Tyr Pro Trp Leu Asn Ser Thr Asp Leu Lys Glu Ser Ser
705 710 715 720

Gly Asp Pro Asp Tyr Gly Val Asp Thr Ala Lys Tyr Ile Pro Ala Gly
725 730 735

Ala Thr Asn Ser Ser Ala Gln Pro Val Leu Pro Ala Gly Gly Gly Phe
740 745 750

Gly Gly Asn Pro Arg Leu Tyr Asp Glu Leu Ile Arg Val Ser Val Thr
755 760 765

Val Lys Asn Thr Gly Arg Val Thr Gly Asp Ala Val Pro Gln Leu Tyr
770 775 780

Val Ser Leu Gly Gly Pro Asn Glu Pro Lys Val Val Leu Arg Gln Phe
785 790 795 800

Asp Arg Ile Thr Leu Arg Pro Ser Glu Glu Thr Val Trp Thr Thr Thr
805 810 815

Leu Thr Arg Arg Asp Leu Ser Asn Trp Asp Val Ala Ala Gln Asp Trp
820 825 830

Val Ile Thr Ser Tyr Pro Lys Lys Val His Val Gly Ser Ser Ser Arg
835 840 845

Gln Leu Pro Leu His Ala Ala Leu Pro Lys Val Gln
850 855 860

<210> SEQ ID NO 4
<211> LENGTH: 841
<212> TYPE: PRT
<213> ORGANISM: Aspergillus saccharolyticus

<400> SEQUENCE: 4

Asp Glu Leu Ala Phe Ala Ser Pro Phe Tyr Pro Ser Pro Trp Ala Asn
1 5 10 15

Gly Gln Gly Glu Trp Ala Asp Ala Tyr Lys Arg Ala Val Asp Ile Val
20 25 30

Ser Gln Met Thr Leu Asp Glu Lys Val Asn Leu Thr Thr Gly Thr Gly
35 40 45

Trp Glu Leu Glu Lys Cys Val Gly Gln Thr Gly Gly Val Pro Arg Leu
50 55 60

Asp Ile Gly Gly Met Cys Leu Gln Asp Ser Pro Leu Gly Val Arg Asp
65 70 75 80

Ser Asp Tyr Asn Ser Gly Phe Pro Ala Gly Val Asn Val Ala Ala Thr
85 90 95

Trp Asp Arg Lys Leu Ala Tyr Leu Arg Gly Gln Ala Met Gly Gln Glu
100 105 110

Phe Ser Asp Lys Gly Val Asp Val Gln Leu Gly Pro Ala Ala Gly Pro
115 120 125

Leu Gly Arg Ser Pro Asp Gly Gly Arg Asn Trp Glu Gly Phe Ser Pro
130 135 140

```
Asp Pro Ala Leu Thr Gly Val Leu Phe Ala Glu Thr Ile Lys Gly Ile
145                 150                 155                 160

Gln Asp Ala Gly Val Ile Ala Thr Ala Lys His Tyr Ile Leu Asn Glu
                165                 170                 175

Gln Glu His Phe Arg Gln Val Ser Glu Ala Ala Gly Tyr Gly Phe Asn
            180                 185                 190

Ile Ser Asp Thr Ile Ser Ser Asn Ile Asp Asp Lys Thr Ile His Glu
        195                 200                 205

Met Tyr Leu Trp Pro Phe Ala Asp Ala Val Arg Ala Gly Val Gly Ala
    210                 215                 220

Val Met Cys Ser Tyr Asn Gln Ile Asn Asn Ser Tyr Ala Cys Gln Asn
225                 230                 235                 240

Ser Tyr Thr Leu Asn Lys Leu Leu Lys Ser Glu Leu Gly Phe Gln Gly
                245                 250                 255

Phe Val Met Ser Asp Trp Gly Ala His His Ser Gly Val Gly Ser Ala
            260                 265                 270

Leu Ala Gly Leu Asp Met Ser Met Pro Gly Asp Val Ser Phe Asp Ser
        275                 280                 285

Ala Thr Ser Phe Trp Gly Thr Asn Leu Thr Val Ala Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Tyr Gln Pro Pro Asn Phe
                325                 330                 335

Ser Ser Trp Thr Arg Asp Glu Tyr Gly Phe Lys Tyr Tyr Tyr Ser Gln
            340                 345                 350

Glu Gly Pro Tyr Glu Lys Val Asn Gln Tyr Val Asn Val Gln Arg Asn
        355                 360                 365

His Ser Glu Val Ile Arg Lys Val Gly Ala Asp Ser Thr Val Leu Leu
    370                 375                 380

Lys Asn Asn Asn Ala Leu Pro Leu Thr Gly Lys Glu Arg Lys Val Ala
385                 390                 395                 400

Leu Ile Gly Glu Asp Ala Gly Ser Asn Ala Tyr Gly Ala Asn Gly Cys
                405                 410                 415

Ser Asp Arg Gly Cys Asp Asn Gly Thr Leu Ala Met Ala Trp Gly Ser
            420                 425                 430

Gly Thr Ala Glu Phe Pro Tyr Leu Val Thr Pro Glu Gln Ala Ile Gln
        435                 440                 445

Ala Glu Val Leu Lys Asn Lys Gly Ser Thr Tyr Thr Ile Thr Asp Asn
    450                 455                 460

Trp Ala Leu Ser Gln Val Glu Ala Leu Ala Lys Thr Ala Ser Val Ser
465                 470                 475                 480

Leu Val Phe Val Asn Ala Asp Ser Gly Glu Gly Tyr Ile Ser Val Asp
                485                 490                 495

Gly Asn Glu Gly Asp Arg Asn Asn Leu Thr Leu Trp Lys Asn Gly Asp
            500                 505                 510

Asn Leu Ile Lys Ala Thr Ala Ser Asn Cys Asn Asn Thr Ile Val Val
        515                 520                 525

Ile His Ser Val Gly Ala Val Leu Val Asp Glu Trp Tyr Asp His Pro
    530                 535                 540

Asn Val Thr Ala Ile Leu Trp Ala Gly Leu Pro Gly Gln Glu Ser Gly
545                 550                 555                 560
```

Asn Ser Leu Ala Asp Val Leu Tyr Gly Arg Val Asn Pro Gly Gly Lys
565 570 575

Thr Pro Phe Thr Trp Gly Lys Thr Arg Ala Ser Tyr Gly Asp Tyr Leu
580 585 590

Val Arg Glu Pro Asn Asn Gly His Gly Ala Pro Gln Asp Asn Phe Ser
595 600 605

Glu Gly Val Phe Ile Asp Tyr Arg Gly Phe Asp Lys Arg Asn Glu Thr
610 615 620

Pro Ile Tyr Glu Phe Gly His Gly Leu Ser Tyr Thr Thr Phe Asn Tyr
625 630 635 640

Ser Gly Leu Gln Val Glu Val Leu Asn Thr Ser Ser Ser Thr Pro Val
645 650 655

Ala Thr Gln Thr Lys Pro Ala Pro Thr Phe Gly Glu Ile Gly Asn Ala
660 665 670

Ser Asp Tyr Leu Tyr Pro Glu Gly Leu Asp Arg Ile Thr Ala Phe Ile
675 680 685

Tyr Pro Trp Leu Asn Ser Thr Asp Leu Lys Glu Ser Ser Gly Asp Pro
690 695 700

Asp Tyr Gly Val Asp Thr Ala Lys Tyr Ile Pro Ala Gly Ala Thr Asn
705 710 715 720

Ser Ser Ala Gln Pro Val Leu Pro Ala Gly Gly Gly Phe Gly Gly Asn
725 730 735

Pro Arg Leu Tyr Asp Glu Leu Ile Arg Val Ser Val Thr Val Lys Asn
740 745 750

Thr Gly Arg Val Thr Gly Asp Ala Val Pro Gln Leu Tyr Val Ser Leu
755 760 765

Gly Gly Pro Asn Glu Pro Lys Val Val Leu Arg Gln Phe Asp Arg Ile
770 775 780

Thr Leu Arg Pro Ser Glu Glu Thr Val Trp Thr Thr Thr Leu Thr Arg
785 790 795 800

Arg Asp Leu Ser Asn Trp Asp Val Ala Ala Gln Asp Trp Val Ile Thr
805 810 815

Ser Tyr Pro Lys Lys Val His Val Gly Ser Ser Ser Arg Gln Leu Pro
820 825 830

Leu His Ala Ala Leu Pro Lys Val Gln
835 840

<210> SEQ ID NO 5
<211> LENGTH: 3002
<212> TYPE: DNA
<213> ORGANISM: Aspergillus saccharolyticus
<220> FEATURE:
<221> NAME/KEY: misc_feature
<222> LOCATION: (12)..(12)
<223> OTHER INFORMATION: n is a, c, g, or t

<400> SEQUENCE: 5
gccttaaggc cnaagagccg cccagatcgt tattcatcca acaatgattg actgcctcgt 60
tgacattgac tgtggtgctc tggacactga ttggttttct tctatcatat gtcatggtgt 120
gtgcagactg catatgtgat tcgaggccgc gtgatccaag atccctgttt ggactggggt 180
aggaagacag gtagctatat cttcagcagc ctgtcgggtc ataaacggtg atggtaaggt 240
tttcctgagt ctgaccgtgt cctttcttcc gttcaggggc attgacaatg actcctgtct 300
ggcattatct catttatctg accctgcttc ttccaggata ccttgcagcc gatcaccgcc 360
gccgcgacga tgacgctgaa gccttctcgc ctccctacta tccggcccct ccgggaggtt 420

```
ggatatccga ttggagtgct gcatacgcca aagctcaggc tgtggtgagc aatatgaccc    480
tagctgagaa agtcaacctc actaccggta ccggaatgtt catgggccct tgcgtcggtc    540
aaacaggtag cgcacttcga ttcgggatac caaacctctg tatgcaggac tcccctctgg    600
gaatccgcaa ctcggaccat aataccgcgt tccctcctgg ggtaactgtt ggagctacct    660
gggacaagga tctgatgtac cagcgtggtg tcgaacttgg ggaagaagct cgcgggaaag    720
gtgtgaacgt tctgcttggt ccagtggtcg gacccatgtt caggaagcca ctcggcggac    780
gcgggtggga aggcttcggc gccgatccga ccctgcaggc agttggaggc gcattgacga    840
tccagggcat gcaaagcact ggtgcgatag cttgtttgaa acatttcatt gggaatgagc    900
aagagatgta tcgcgagacc tcggttctaa ctcaaggtta ttcatcgaac atcgatgacc    960
gtaccctgca tgaactgtac ttgtggccat ttgcggaggg agtccgggct ggcgtgggct   1020
ctgtgatgat ggcgtacaac gatgtgagtt cctcagacag taggccagac ggatttactg   1080
atcaggatag gtgaatcgct cggcctgtag ccagaatagc atgctcatca gcggcatcct   1140
taaggacgag ttaggcttcc aggggtttgt catgaccgac tggctggctc agcagggcgg   1200
cgtctcgtct gccctcgccg gacttgacat ggctatgcct ggcgatgggg ccatcccttt   1260
gctcggggat gcttactggg gatccgagct atcaaccgcc atcctcaacg gaacagtgcc   1320
gctggatcga ctcaatgaca tggtatgaga tcgtcaacct cctgctcctt tcatactaag   1380
ttttcaaggt cactcggatc gttgcgactt ggtatcaaat gggtcaggat gaggattatc   1440
ctctgcccaa cttttcgagc aacacgctcg acaaaacagg ccctctctat cccggtgccc   1500
tgttctcccc gacgggcgtt gtcaaccaat atgtcgacgt gcaaggcaac cataacatca   1560
ctgcgcacgc tgttgcccga gatgcgatca ctctcctcaa gaacgagaat aacacattgc   1620
ccctcaagcg cagtgccgct ctcaaggtgt ttggtaccga tgctgggccc aacacttccg   1680
gcctcaactc ctgtagtgac atgggctgcg accagggcgt ccttacgatg ggctggggaa   1740
gtggtacctc gcacctccct tcactcgtca cgccgcaaga agccattgcc aatcttacta   1800
cgtcgaattc gactaccttt tacttgtcgg atacgttccc tgccaatctc gccaccccat   1860
ccacttccga catcgctgtg gtcttcatca acgctgactc tggcgagaac tacatcactg   1920
tcgagtccaa tccaggagac cgcaccagcg caggcttcga tgcgtggcac aacggcaacg   1980
cgctcgttca agctgctgcg gccgagttct cgactgtggt tgtagtgatc catactgttg   2040
gccctatact gcttgaatcg tttattgacc tccctagcgt caaggctgtg cttattgctc   2100
acctccccgg ccagactgcc ggctattcgc tcacggatgt cctgtatggc gaggtcagcc   2160
ctagcggcca tctgccctac actatcccta catcggcgtc aaactaccca tcctccatgg   2220
acatcatcac ctcacagcca cttttgtccc agatccagga ctggtttgat gaggggattt   2280
acatcgacta tcgttacttt ctacaagcca acatcacccc ccgctaccct ttcggctacg   2340
gattgtcgta cacgacgttc cagtactcgg caccagttct gaccactgtg accgaactga   2400
gcaccgaata tcccgctgcg agagcaagca aggcttcggt cccaacttat cccacagata   2460
ttcccgatcc tcaagaagtc gcatggccga gcacgcttga tcggatctgg cgctacctgt   2520
acccgtatct ggatgatccc gagagcgtta ccaacacaag cacctactcg tacccggccg   2580
gctactccac cacggcgcat gcggccccgc gtgccggggg aggacagggt ggcaaccctg   2640
cccttttcga aaccgctttt gaggtagcgg tgaccatcac caacaccggc acacgaagtg   2700
gacgagccgt ggcacaactg tatgtgcaaa tgccggatga ggcagttctt ggagtagaca   2760
```

-continued

```
ccccgaagag acagttgcgg gcgtttgcga agaccgggac cctggcgtcc ggggagagcg   2820

aagtcgtgac tatgaatgtg accaggaaag atttgagtgt gtgggatgtc acggtgcagg   2880

attggcgagc gccagttggt ggagcgggtg tgactttctg ggtaggggac agtgttgcag   2940

aagaggacct gacggtgaaa tgtgctgttg ggagtgacta gggggctcat aggccttaag   3000

gc                                                                  3002
```

<210> SEQ ID NO 6
<211> LENGTH: 2601
<212> TYPE: DNA
<213> ORGANISM: Aspergillus saccharolyticus

<400> SEQUENCE: 6

```
atgactcctg tctggcatta tctcatttat ctgaccctgc ttcttccagg ataccttgca     60

gccgatcacc gccgccgcga cgatgacgct gaagccttct cgcctcccta ctatccggcc    120

cctccgggag gttggatatc cgattggagt gctgcatacg ccaaagctca ggctgtggtg    180

agcaatatga ccctagctga gaaagtcaac ctcactaccg gtaccggaat gttcatgggc    240

ccttgcgtcg gtcaaacagg tagcgcactt cgattcggga taccaaacct ctgtatgcag    300

gactcccctc tgggaatccg caactcggac cataataccg cgttccctcc tggggtaact    360

gttggagcta cctgggacaa ggatctgatg taccagcgtg gtgtcgaact tggggaagaa    420

gctcgcggga aaggtgtgaa cgttctgctt ggtccagtgg tcggacccat gttcaggaag    480

ccactcggcg gacgcgggtg ggaaggcttc ggcgccgatc cgaccctgca ggcagttgga    540

ggcgcattga cgatccaggg catgcaaagc actggtgcga tagcttgttt gaaacatttc    600

attgggaatg agcaagagat gtatcgcgag acctcggttc taactcaagg ttattcatcg    660

aacatcgatg accgtaccct gcatgaactg tacttgtggc catttgcgga gggagtccgg    720

gctggcgtgg gctctgtgat gatggcgtac aacgatgtga atcgctcggc ctgtagccag    780

aatagcatgc tcatcagcgg catccttaag gacgagttag gcttccaggg gtttgtcatg    840

accgactggc tggctcagca gggcggcgtc tcgtctgccc tcgccggact tgacatggct    900

atgcctggcg atggggccat ccctttgctc ggggatgctt actggggatc cgagctatca    960

accgccatcc tcaacggaac agtgccgctg gatcgactca atgacatggt cactcggatc   1020

gttgcgactt ggtatcaaat gggtcaggat gaggattatc ctctgcccaa cttttcgagc   1080

aacacgctcg acaaaacagg ccctctctat cccggtgccc tgttctcccc gacgggcgtt   1140

gtcaaccaat atgtcgacgt gcaaggcaac cataacatca ctgcgcacgc tgttgcccga   1200

gatgcgatca ctctcctcaa gaacgagaat aacacattgc ccctcaagcg cagtgccgct   1260

ctcaaggtgt ttggtaccga tgctgggccc aacacttccg gcctcaactc ctgtagtgac   1320

atgggctgcg accagggcgt ccttacgatg ggctggggaa gtggtacctc gcacctccct   1380

tcactcgtca cgccgcaaga agccattgcc aatcttacta cgtcgaattc gactaccttt   1440

tacttgtcgg atacgttccc tgccaatctc gccaccccat ccacttccga catcgctgtg   1500

gtcttcatca acgctgactc tggcgagaac tacatcactg tcgagtccaa tccaggagac   1560

cgcaccagcg caggcttcga tgcgtggcac aacggcaacg cgctcgttca agctgctgcg   1620

gccgagttct cgactgtggt tgtagtgatc catactgttg gccctatact gcttgaatcg   1680

tttattgacc tccctagcgt caaggctgtg cttattgctc acctccccgg ccagactgcc   1740

ggctattcgc tcacggatgt cctgtatggc gaggtcagcc ctagcggcca tctgccctac   1800

actatcccta catcggcgtc aaactaccca tcctccatgg acatcatcac ctcacagcca   1860
```

```
cttttgtccc agatccagga ctggtttgat gaggggattt acatcgacta tcgttacttt   1920

ctacaagcca acatcacccc ccgctaccct ttcggctacg gattgtcgta cacgacgttc   1980

cagtactcgg caccagttct gaccactgtg accgaactga gcaccgaata tcccgctgcg   2040

agagcaagca aggcttcggt cccaacttat cccacagata ttcccgatcc tcaagaagtc   2100

gcatggccga gcacgcttga tcggatctgg cgctacctgt acccgtatct ggatgatccc   2160

gagagcgtta ccaacacaag cacctactcg tacccggccg gctactccac cacggcgcat   2220

gcggccccgc gtgccggggg aggacagggt ggcaaccctg cccttttcga aaccgctttt   2280

gaggtagcgg tgaccatcac caacaccggc acacgaagtg gacgagccgt ggcacaactg   2340

tatgtgcaaa tgccggatga ggcagttctt ggagtagaca ccccgaagag acagttgcgg   2400

gcgtttgcga agaccgggac cctggcgtcc ggggagagcg aagtcgtgac tatgaatgtg   2460

accaggaaag atttgagtgt gtgggatgtc acggtgcagg attggcgagc gccagttggt   2520

ggagcgggtg tgactttctg ggtaggggac agtgttgcag aagaggacct gacggtgaaa   2580

tgtgctgttg ggagtgacta g                                             2601
```

<210> SEQ ID NO 7
<211> LENGTH: 866
<212> TYPE: PRT
<213> ORGANISM: Aspergillus saccharolyticus

<400> SEQUENCE: 7

```
Met Thr Pro Val Trp His Tyr Leu Ile Tyr Leu Thr Leu Leu Leu Pro
1               5                   10                  15

Gly Tyr Leu Ala Ala Asp His Arg Arg Arg Asp Asp Asp Ala Glu Ala
            20                  25                  30

Phe Ser Pro Pro Tyr Tyr Pro Ala Pro Pro Gly Gly Trp Ile Ser Asp
        35                  40                  45

Trp Ser Ala Ala Tyr Ala Lys Ala Gln Ala Val Val Ser Asn Met Thr
    50                  55                  60

Leu Ala Glu Lys Val Asn Leu Thr Thr Gly Thr Gly Met Phe Met Gly
65                  70                  75                  80

Pro Cys Val Gly Gln Thr Gly Ser Ala Leu Arg Phe Gly Ile Pro Asn
                85                  90                  95

Leu Cys Met Gln Asp Ser Pro Leu Gly Ile Arg Asn Ser Asp His Asn
            100                 105                 110

Thr Ala Phe Pro Pro Gly Val Thr Val Gly Ala Thr Trp Asp Lys Asp
        115                 120                 125

Leu Met Tyr Gln Arg Gly Val Glu Leu Gly Glu Glu Ala Arg Gly Lys
    130                 135                 140

Gly Val Asn Val Leu Leu Gly Pro Val Val Gly Pro Met Phe Arg Lys
145                 150                 155                 160

Pro Leu Gly Gly Arg Gly Trp Glu Gly Phe Gly Ala Asp Pro Thr Leu
                165                 170                 175

Gln Ala Val Gly Gly Ala Leu Thr Ile Gln Gly Met Gln Ser Thr Gly
            180                 185                 190

Ala Ile Ala Cys Leu Lys His Phe Ile Gly Asn Glu Gln Glu Met Tyr
        195                 200                 205

Arg Glu Thr Ser Val Leu Thr Gln Gly Tyr Ser Ser Asn Ile Asp Asp
    210                 215                 220

Arg Thr Leu His Glu Leu Tyr Leu Trp Pro Phe Ala Glu Gly Val Arg
225                 230                 235                 240
```

```
Ala Gly Val Gly Ser Val Met Met Ala Tyr Asn Asp Val Asn Arg Ser
                245                 250                 255

Ala Cys Ser Gln Asn Ser Met Leu Ile Ser Gly Ile Leu Lys Asp Glu
            260                 265                 270

Leu Gly Phe Gln Gly Phe Val Met Thr Asp Trp Leu Ala Gln Gln Gly
        275                 280                 285

Gly Val Ser Ser Ala Leu Ala Gly Leu Asp Met Ala Met Pro Gly Asp
    290                 295                 300

Gly Ala Ile Pro Leu Leu Gly Asp Ala Tyr Trp Gly Ser Glu Leu Ser
305                 310                 315                 320

Thr Ala Ile Leu Asn Gly Thr Val Pro Leu Asp Arg Leu Asn Asp Met
                325                 330                 335

Val Thr Arg Ile Val Ala Thr Trp Tyr Gln Met Gly Gln Asp Glu Asp
            340                 345                 350

Tyr Pro Leu Pro Asn Phe Ser Ser Asn Thr Leu Asp Lys Thr Gly Pro
        355                 360                 365

Leu Tyr Pro Gly Ala Leu Phe Ser Pro Thr Gly Val Val Asn Gln Tyr
    370                 375                 380

Val Asp Val Gln Gly Asn His Asn Ile Thr Ala His Ala Val Ala Arg
385                 390                 395                 400

Asp Ala Ile Thr Leu Leu Lys Asn Glu Asn Asn Thr Leu Pro Leu Lys
                405                 410                 415

Arg Ser Ala Ala Leu Lys Val Phe Gly Thr Asp Ala Gly Pro Asn Thr
            420                 425                 430

Ser Gly Leu Asn Ser Cys Ser Asp Met Gly Cys Asp Gln Gly Val Leu
        435                 440                 445

Thr Met Gly Trp Gly Ser Gly Thr Ser His Leu Pro Ser Leu Val Thr
    450                 455                 460

Pro Gln Glu Ala Ile Ala Asn Leu Thr Thr Ser Asn Ser Thr Thr Phe
465                 470                 475                 480

Tyr Leu Ser Asp Thr Phe Pro Ala Asn Leu Ala Thr Pro Ser Thr Ser
                485                 490                 495

Asp Ile Ala Val Val Phe Ile Asn Ala Asp Ser Gly Glu Asn Tyr Ile
            500                 505                 510

Thr Val Glu Ser Asn Pro Gly Asp Arg Thr Ser Ala Gly Phe Asp Ala
        515                 520                 525

Trp His Asn Gly Asn Ala Leu Val Gln Ala Ala Ala Ala Glu Phe Ser
    530                 535                 540

Thr Val Val Val Val Ile His Thr Val Gly Pro Ile Leu Leu Glu Ser
545                 550                 555                 560

Phe Ile Asp Leu Pro Ser Val Lys Ala Val Leu Ile Ala His Leu Pro
                565                 570                 575

Gly Gln Thr Ala Gly Tyr Ser Leu Thr Asp Val Leu Tyr Gly Glu Val
            580                 585                 590

Ser Pro Ser Gly His Leu Pro Tyr Thr Ile Pro Thr Ser Ala Ser Asn
        595                 600                 605

Tyr Pro Ser Ser Met Asp Ile Ile Thr Ser Gln Pro Leu Leu Ser Gln
    610                 615                 620

Ile Gln Asp Trp Phe Asp Glu Gly Ile Tyr Ile Asp Tyr Arg Tyr Phe
625                 630                 635                 640

Leu Gln Ala Asn Ile Thr Pro Arg Tyr Pro Phe Gly Tyr Gly Leu Ser
                645                 650                 655
```

```
Tyr Thr Thr Phe Gln Tyr Ser Ala Pro Val Leu Thr Thr Val Thr Glu
            660                 665                 670

Leu Ser Thr Glu Tyr Pro Ala Ala Arg Ala Ser Lys Ala Ser Val Pro
        675                 680                 685

Thr Tyr Pro Thr Asp Ile Pro Asp Pro Gln Glu Val Ala Trp Pro Ser
    690                 695                 700

Thr Leu Asp Arg Ile Trp Arg Tyr Leu Tyr Pro Tyr Leu Asp Asp Pro
705                 710                 715                 720

Glu Ser Val Thr Asn Thr Ser Thr Tyr Ser Tyr Pro Ala Gly Tyr Ser
                725                 730                 735

Thr Thr Ala His Ala Ala Pro Arg Ala Gly Gly Gly Gln Gly Gly Asn
            740                 745                 750

Pro Ala Leu Phe Glu Thr Ala Phe Glu Val Ala Val Thr Ile Thr Asn
        755                 760                 765

Thr Gly Thr Arg Ser Gly Arg Ala Val Ala Gln Leu Tyr Val Gln Met
    770                 775                 780

Pro Asp Glu Ala Val Leu Gly Val Asp Thr Pro Lys Arg Gln Leu Arg
785                 790                 795                 800

Ala Phe Ala Lys Thr Gly Thr Leu Ala Ser Gly Glu Ser Glu Val Val
                805                 810                 815

Thr Met Asn Val Thr Arg Lys Asp Leu Ser Val Trp Asp Val Thr Val
            820                 825                 830

Gln Asp Trp Arg Ala Pro Val Gly Gly Ala Gly Val Thr Phe Trp Val
        835                 840                 845

Gly Asp Ser Val Ala Glu Glu Asp Leu Thr Val Lys Cys Ala Val Gly
    850                 855                 860

Ser Asp
865
```

<210> SEQ ID NO 8
<211> LENGTH: 3587
<212> TYPE: DNA
<213> ORGANISM: Aspergillus saccharolyticus

<400> SEQUENCE: 8

```
gccttaaggc ctaggaacgt cccagaacgt tgatcccagg actggccaat ttttcccttt      60

tcttttgtct gcagcgtgag aatagattga gcgtcggctt gtcaagtcag ccagctcctc     120

tttccctcac cttttcacaa tgggtgtcag tctgctagcc aaggggcttg cgcttcttca     180

cctctgcgcc ggtgtcactg ccagtagcaa tgactcaaca ccgctgtaca agaaccccaa     240

tgcgccggtg gaggatcgtg tcagtgacct tctgggccgc atgaccatcc acgacaagac     300

gggacaactg atgcaaggta tgagtcttcc tcgcgggtga tccgttaaat gtcttggata     360

atctgtgctg actgctactg caggggatct cgcgaactgg atgaacacca caactggagc     420

gttcaactac acgggtctgg tcgcgaacat ggaaatgaag gcgggaggat tctacggtac     480

gagtccttga tcatgctgat tatcgcgatg ggaaagctga ctagcgggca gttggatatg     540

cggtcccgtg ggactggatg gtgaccaaca tcaagcatgc gcaggactac ctgatccata     600

acaccacgct tggtattcct gcacttgttc agtcagaagg taggcttgat gcaaaagttt     660

tggggaggat gttgctcacg gctgcaggta ttcatgggtt cctggttcag aacgccacta     720

ttttcaattc ccctattgca tatggttgct ccttcaaccg tgaggtgagt ggtggacacc     780

aactccagtg agccctgcag gctaatgatc gataacagct ggtctccaaa atggccaaaa     840

tcatcagtca agaatctctc actctgggcg tcaaccagct atttgcccct gtggttgacc     900
```

-continued

```
tggcccgtga gctgcggtat gggcgggtaa gctcatgact tggacatagg ctaggctagg    960
ctttttagct aattgattaa caggccgaag agacgttctc ggaggaccca taccttgctg   1020
gcgagattgg ctacaactat gtgcaaggcc tgcagagtct caacgtttcg gccactgtca   1080
agcattttgc gggcttcagt gcccctgaac aggggttgaa cactgcgcca gttcagggag   1140
gagagcgata tcttcgtact acgtaagtac agctaacaat cttaagattt atgctgacat   1200
gatgcagctg gctgcactca ttcaagcgtg cgatcatcga tgcaggtgca tggagtgtca   1260
tgagcgcata ccactcgtga gtttgatgct tttgggaaca agattccttg cttacatgca   1320
tctagctacg atggcattcc cgctgttgcc gactggttta ccctgacaaa ggttctgcga   1380
gaagagtggg gtttcaagca ctgggttttc agcgattcgg gcgctactga tcgactgtgc   1440
accgctttca agctctgtca agcctctcca atcgacatgg aagcagtcac cctgcaggca   1500
ctccctgctg gtaacgacgt tgagatgggt ggtggctcct tgtaagtatc ctaggttggt   1560
aacctgcgag agactaaccc tgtctagcaa cttccagaag atcccggagc ttgtagagtc   1620
cggaaggctg gacatcgaga ctgttgacac tgctgtctcg cgcattctga gggccaagtt   1680
cgaaatgggt ctctttgaga acccccttccc tgctgctcct gagtcggagt ggcacaagtt   1740
gatccacagc tcagaggcgg tcgagctcgc tagaaccttg gacaaggagt ctatcgtctt   1800
gctggagaac cacaacaaga cccttccttt ggacaagagc ggcagcatcg ccgttattgg   1860
gcccatggcc catggcttca tgaacgtgag tgattggcct atctcggccc agagcatcta   1920
ctaacttata tacagtatgg agactacgtc gtttacaaga gccagtaccg cggtgtaacc   1980
cctctggacg gcatcaaagc tgctgttggc gacaacgcca cgatcaacta cgcccagggc   2040
tgcgagcggt ggagcaacga ccagtccggc ttcgatgaag ccattgcagc ggccaagaag   2100
tcggacgtgg ctgttgtcgt cgtaggcacc tggtctcgcg accagaccga gctgtggtcc   2160
ggttacaacg cgacgtgagt tgcctattgc ttgcatgtaa tcccgagacg tcgccgctaa   2220
ccaccaacag aaccggcgag cacattgatc tggataacct cgccctcgtc ggtgcccaag   2280
gcccgctcgt caaggctatt atcgacaccg gcgtccccac catcgtggtc ctctccagcg   2340
gcaagcccat cacggacgtg acctggctcg cgaactcgac cgcggcgctc gtccagcaat   2400
tctatccgtc ggagcaaggc ggcaatgcgc tggccgacgt gctgttcggc gactacaacc   2460
cctctggcaa gctgtccgtc agcttcccgc gcttcgtcgg cgacctcccg atctactacg   2520
acttcctcaa ttcggcgcgc aacatcggcc cggccggcca cgccttcccc aacggcaccc   2580
tggaattcga gagccagtac gtcctgggcg accccaccgc gatctacgag ttcgggtacg   2640
gcaagagcta cgtcgacttt gactacggcg ccgtcacgct gagccagacc aacgtgaccg   2700
cctcggacac ggtgacggtc cgcgtggacg tgaccaacac tgacgccacc cgcgacggca   2760
ccgaggtcgt gcaggtgtat gtgtcggatg tgatcgcgct ggtggtggtg ccgaaccggg   2820
cgctcaaggg cttcgagaaa gtggtcatcc cggctggcac gaccaagacg gtggagattg   2880
atttgcaggt ggaggacctg gggctctgga accgctcgat gcagtatgtc gttgagccgg   2940
gagcgtttgc ggtgttggtg ggcagcagtt cggcggatat ccgggggaat gcgacgtttt   3000
atgttgagta ggtctgatgc ggatgggtga gtggtacagt gggtggcggc aatcaccggg   3060
tcaattgctt cgatacctac cctgcttatt gattgttcgc tcaatcactt tctttgaata   3120
cttctattaa agctcttgtg atgagtggct ctagttggtt gggatggtgg ttagttgaag   3180
gtagaagtgt agtctactgt ctgtcatcaa taaatagcgc gaaacagatg ttattttgca   3240
```

-continued

```
gtcggggtga caggttttta aaactttatt tgacgaaacg agaaaatatc agagagtaaa   3300

tgattcgaac cgggatgact ttgatctgag atctagacag tggtagcccc ggcataagtg   3360

aagataaaga gagatgcaac gggtgctgtt cgatcgatcc gattgcccat tacgtggacc   3420

tggaaagaaa ccctaaatgc tcgtctagcc gtcctgcagc cattctcccc tggtttaacg   3480

agctctccac cctccgctcg ccgttggttt gaccccatac cgcggggtca tagctcaaag   3540

acacagccaa taagaacata tccgcatccc cgaagtaggc ctaaccg                 3587
```

<210> SEQ ID NO 9
<211> LENGTH: 2169
<212> TYPE: DNA
<213> ORGANISM: Aspergillus saccharolyticus

<400> SEQUENCE: 9

```
atgggtgtca gtctgctagc caaggggctt gcgcttcttc acctctgcgc cggtgtcact     60

gccagtagca atgactcaac accgctgtac aagaacccca atgcgccggt ggaggatcgt    120

gtcagtgacc ttctgggccg catgaccatc cacgacaaga cgggacaact gatgcaaggg    180

gatctcgcga actggatgaa caccacaact ggagcgttca actacacggg tctggtcgcg    240

aacatggaaa tgaaggcggg aggattctac gttggatatg cggtcccgtg ggactggatg    300

gtgaccaaca tcaagcatgc gcaggactac ctgatccata acaccacgct tggtattcct    360

gcacttgttc agtcagaagg tattcatggg ttcctggttc agaacgccac tattttcaat    420

tcccctattg catatggttg ctccttcaac cgtgaggccg aagagacgtt ctcggaggac    480

ccataccttg ctggcgagat tggctacaac tatgtgcaag gcctgcagag tctcaacgtt    540

tcggccactg tcaagcattt tgcgggcttc agtgcccctg aacaggggtt gaacactgcg    600

ccagttcagg gaggagagcg atatcttcgt actacctacg atggcattcc cgctgttgcc    660

gactggttta ccctgacaaa ggttctgcga gaagagtggg gtttcaagca ctgggttttc    720

agcgattcgg gcgctactga tcgactgtgc accgctttca agctctgtca agcctctcca    780

atcgacatgg aagcagtcac cctgcaggca ctccctgctg gtaacgacgt tgagatgggt    840

ggtggctcct tcaacttcca gaagatcccg gagcttgtag agtccggaag gctggacatc    900

gagactgttg acactgctgt ctcgcgcatt ctgagggcca agttcgaaat gggtctcttt    960

gagaacccct tccctgctgc tcctgagtcg gagtggcaca agttgatcca cagctcagag   1020

gcggtcgagc tcgctagaac cttggacaag gagtctatcg tcttgctgga gaaccacaac   1080

aagacccttc ctttggacaa gagcggcagc atcgccgtta ttgggcccat ggcccatggc   1140

ttcatgaact atggagacta cgtcgtttac aagagccagt accgcggtgt aacccctctg   1200

gacggcatca aagctgctgt tggcgacaac gccacgatca actacgccca gggctgcgag   1260

cggtggagca acgaccagtc cggcttcgat gaagccattg cagcggccaa gaagtcggac   1320

gtggctgttg tcgtcgtagg cacctggtct cgcgaccaga ccgagctgtg gtccggttac   1380

aacgcgacaa ccggcgagca cattgatctg gataacctcg ccctcgtcgg tgcccaaggc   1440

ccgctcgtca aggctattat cgacaccggc gtccccacca tcgtggtcct ctccagcggc   1500

aagcccatca cggacgtgac ctggctcgcg aactcgaccg cggcgctcgt ccagcaattc   1560

tatccgtcgg agcaaggcgg caatgcgctg gccgacgtgc tgttcggcga ctacaacccc   1620

tctggcaagc tgtccgtcag cttcccgcgc ttcgtcggcg acctcccgat ctactacgac   1680

ttcctcaatt cggcgcgcaa catcggcccg gccggccacg ccttccccaa cggcaccctg   1740

gaattcgaga gccagtacgt cctgggcgac cccaccgcga tctacgagtt cgggtacggc   1800
```

-continued aagagctacg tcgactttga ctacggcgcc gtcacgctga gccagaccaa cgtgaccgcc 1860
tcggacacgg tgacggtccg cgtggacgtg accaacactg acgccacccg cgacggcacc 1920
gaggtcgtgc aggtgtatgt gtcggatgtg atcgcgctgg tggtggtgcc gaaccgggcg 1980
ctcaagggct tcgagaaagt ggtcatcccg gctggcacga ccaagacggt ggagattgat 2040
ttgcaggtgg aggacctggg gctctggaac cgctcgatgc agtatgtcgt tgagccggga 2100
gcgtttgcgg tgttggtggg cagcagttcg gcggatatcc gggggaatgc gacgttttat 2160
gttgagtag 2169

<210> SEQ ID NO 10
<211> LENGTH: 722
<212> TYPE: PRT
<213> ORGANISM: Aspergillus saccharolyticus

<400> SEQUENCE: 10

Met Gly Val Ser Leu Leu Ala Lys Gly Leu Ala Leu Leu His Leu Cys
1 5 10 15

Ala Gly Val Thr Ala Ser Ser Asn Asp Ser Thr Pro Leu Tyr Lys Asn
20 25 30

Pro Asn Ala Pro Val Glu Asp Arg Val Ser Asp Leu Leu Gly Arg Met
35 40 45

Thr Ile His Asp Lys Thr Gly Gln Leu Met Gln Gly Asp Leu Ala Asn
50 55 60

Trp Met Asn Thr Thr Thr Gly Ala Phe Asn Tyr Thr Gly Leu Val Ala
65 70 75 80

Asn Met Glu Met Lys Ala Gly Gly Phe Tyr Val Gly Tyr Ala Val Pro
85 90 95

Trp Asp Trp Met Val Thr Asn Ile Lys His Ala Gln Asp Tyr Leu Ile
100 105 110

His Asn Thr Thr Leu Gly Ile Pro Ala Leu Val Gln Ser Glu Gly Ile
115 120 125

His Gly Phe Leu Val Gln Asn Ala Thr Ile Phe Asn Ser Pro Ile Ala
130 135 140

Tyr Gly Cys Ser Phe Asn Arg Glu Ala Glu Glu Thr Phe Ser Glu Asp
145 150 155 160

Pro Tyr Leu Ala Gly Glu Ile Gly Tyr Asn Tyr Val Gln Gly Leu Gln
165 170 175

Ser Leu Asn Val Ser Ala Thr Val Lys His Phe Ala Gly Phe Ser Ala
180 185 190

Pro Glu Gln Gly Leu Asn Thr Ala Pro Val Gln Gly Gly Glu Arg Tyr
195 200 205

Leu Arg Thr Thr Tyr Asp Gly Ile Pro Ala Val Ala Asp Trp Phe Thr
210 215 220

Leu Thr Lys Val Leu Arg Glu Glu Trp Gly Phe Lys His Trp Val Phe
225 230 235 240

Ser Asp Ser Gly Ala Thr Asp Arg Leu Cys Thr Ala Phe Lys Leu Cys
245 250 255

Gln Ala Ser Pro Ile Asp Met Glu Ala Val Thr Leu Gln Ala Leu Pro
260 265 270

Ala Gly Asn Asp Val Glu Met Gly Gly Gly Ser Phe Asn Phe Gln Lys
275 280 285

Ile Pro Glu Leu Val Glu Ser Gly Arg Leu Asp Ile Glu Thr Val Asp
290 295 300

-continued

Thr Ala Val Ser Arg Ile Leu Arg Ala Lys Phe Glu Met Gly Leu Phe
305 310 315 320

Glu Asn Pro Phe Pro Ala Ala Pro Glu Ser Glu Trp His Lys Leu Ile
325 330 335

His Ser Ser Glu Ala Val Glu Leu Ala Arg Thr Leu Asp Lys Glu Ser
340 345 350

Ile Val Leu Leu Glu Asn His Asn Lys Thr Leu Pro Leu Asp Lys Ser
355 360 365

Gly Ser Ile Ala Val Ile Gly Pro Met Ala His Gly Phe Met Asn Tyr
370 375 380

Gly Asp Tyr Val Val Tyr Lys Ser Gln Tyr Arg Gly Val Thr Pro Leu
385 390 395 400

Asp Gly Ile Lys Ala Ala Val Gly Asp Asn Ala Thr Ile Asn Tyr Ala
405 410 415

Gln Gly Cys Glu Arg Trp Ser Asn Asp Gln Ser Gly Phe Asp Glu Ala
420 425 430

Ile Ala Ala Ala Lys Lys Ser Asp Val Ala Val Val Val Val Gly Thr
435 440 445

Trp Ser Arg Asp Gln Thr Glu Leu Trp Ser Gly Tyr Asn Ala Thr Thr
450 455 460

Gly Glu His Ile Asp Leu Asp Asn Leu Ala Leu Val Gly Ala Gln Gly
465 470 475 480

Pro Leu Val Lys Ala Ile Ile Asp Thr Gly Val Pro Thr Ile Val Val
485 490 495

Leu Ser Ser Gly Lys Pro Ile Thr Asp Val Thr Trp Leu Ala Asn Ser
500 505 510

Thr Ala Ala Leu Val Gln Gln Phe Tyr Pro Ser Glu Gln Gly Gly Asn
515 520 525

Ala Leu Ala Asp Val Leu Phe Gly Asp Tyr Asn Pro Ser Gly Lys Leu
530 535 540

Ser Val Ser Phe Pro Arg Phe Val Gly Asp Leu Pro Ile Tyr Tyr Asp
545 550 555 560

Phe Leu Asn Ser Ala Arg Asn Ile Gly Pro Ala Gly His Ala Phe Pro
565 570 575

Asn Gly Thr Leu Glu Phe Glu Ser Gln Tyr Val Leu Gly Asp Pro Thr
580 585 590

Ala Ile Tyr Glu Phe Gly Tyr Gly Lys Ser Tyr Val Asp Phe Asp Tyr
595 600 605

Gly Ala Val Thr Leu Ser Gln Thr Asn Val Thr Ala Ser Asp Thr Val
610 615 620

Thr Val Arg Val Asp Val Thr Asn Thr Asp Ala Thr Arg Asp Gly Thr
625 630 635 640

Glu Val Val Gln Val Tyr Val Ser Asp Val Ile Ala Leu Val Val Val
645 650 655

Pro Asn Arg Ala Leu Lys Gly Phe Glu Lys Val Val Ile Pro Ala Gly
660 665 670

Thr Thr Lys Thr Val Glu Ile Asp Leu Gln Val Glu Asp Leu Gly Leu
675 680 685

Trp Asn Arg Ser Met Gln Tyr Val Val Glu Pro Gly Ala Phe Ala Val
690 695 700

Leu Val Gly Ser Ser Ser Ala Asp Ile Arg Gly Asn Ala Thr Phe Tyr
705 710 715 720

Val Glu

<210> SEQ ID NO 11
<211> LENGTH: 3269
<212> TYPE: DNA
<213> ORGANISM: Aspergillus saccharolyticus

<400> SEQUENCE: 11
gccttaaggc ctacgaaact cccagccacc tacctaaccc tcattcttgc cctggatatt 60
ccactgctga aacctgcaga tggccgtctt agagcctttc agttcttgtt tttctgccga 120
tatttacccg ggagtcaggc aattctgcgg agtattcgga gcattaggtg ggattgacca 180
actcggtctt cttgtacagt ccactcgatg cattggacta aaggtataaa tacgtcaggc 240
agtcgcggag gcaaaatatc gagacaggca agcgagtcca gcagaatgta cggtctagca 300
tcttttgcgg ccttgttggg cggtctttca ctttgctccg cggccccgac tgagcaaaat 360
attacaagcg atacttactt ttatggcgat tctccgcccg tctacccctc ccgtacgtgc 420
aacactgtgc ttttctacca tgtcctcaat actggcccaa ccatctagcg gacggtgccg 480
gaaccgggtc ctgggccgca gcctacgtaa aggcaaagag ttttgtcgct caactcacag 540
acgaggagaa gatcaacttc acagccgggt atactgccag taatggctgc tcaggcaaca 600
ttccagcagt ctctcgtctc ggcttccccg ggctttgtgt ttctgatgca ggaaatgggc 660
tggtaagtgc acaaggtcgc gctggattga ccatgaccgc taacatttac gcagcgtgga 720
accgattttg tgaatggctg gccaagtggc attcacgtgg gagcaaggta agagatgtca 780
cagccactgc atccgtggca aacgagtaat gattccattc tatctagctg gaataaaact 840
cttgcacacc aacgcgccct atacatggga caggagttcc atcgaaaggg ggtaaatctc 900
ctactgggcc cagttgttgg cccacttggt cgtgtcgtgg aaggtggtcg taactgggaa 960
ggctttgcca acgatcctta cctcagcggt gcgctggtgt atgagactgt gcagggtgtg 1020
caggaagccg gtgtcggcgt ttcggtcaag gtatgtgcat accatcttac tggaaagtca 1080
tctgagtcat ggctaagggt tgaatcaaag cactacatcg gaaacgagca agagaccaac 1140
agaaaccccg agactgagaa cggcgtcact gttgcctcag tttcctctaa catcgacgac 1200
aaaactatcc atgaactgta tctttggcca tttcaagacg ccgttctggc gggaagtgtc 1260
tccgtgatgt gctcgtacaa ccgagtcaat aattcctaca gctgccagaa cagtaagacg 1320
ctgaatggtc ttctgaagac cgaactgggc ttccaaggta agacggccta atcaatcctc 1380
cgcatcattg ctgatatttg caaggctacg ttgtcactga ttgggatgcc caacacgccg 1440
ggatcgctgg tgctaatgcc ggcctggaca tggtcatgcc aagtaccacc acatgggggt 1500
ccaatctcac gacggccatt gccaacggca gcatggaagc atcgagactg gacgatatgg 1560
tcactaggta ggttagatca ccttccacct ttgatactca ttcttactca atcaggatcg 1620
ttgcctcctg gtaccaatta aaccaagaca ccgactttcc ctcaccaggc attgggatgc 1680
ccgtcgacgt ctactccgag catgagatcg tcattggaac ttctgccgat gagaaggacg 1740
ctttgctgca aagcgcaatc gagggacacg tcctcgttaa aaaccaaggc tccgtcctcc 1800
ctctccagtc gccacgccta gtctccgtgt tcggctacga cgccaaagcc ccggagtccc 1860
tggacctagc cccgtctct ctaagtgtcg ctccgcccac gcaaaacaac acactctggg 1920
tgggcggagg ttccggtgcc aacaatcccg catacgttat cgccccccttg gacgccatcc 1980 agcaacaagc ctatgaagac aacaccgccg tcctctggga cgtgacatcg ttcgacccag 2040
acgtcgaccc cgcctcccac gcctgcctag ttttcatcaa cagctacgcc tccgaaggca 2100

```
gtgaccggac aggtctggtg gactccgaca gcgacacgct ggtaaccaac gtcgccagca   2160

aatgcaacaa cacgatcgtc gtgatccaca acgcgggcat ccgtctcgtg tataactgga   2220

tcgaccacga gaacgttacc gctgtgatct tcgcccatct tccaggccaa gacacaggca   2280

aagctctcgt ggatttactg tacggccgcg ccaacccctc gggccgcctc ccctacaccg   2340

tcgccaagca ggcctccgac tacggcgcag tcttacaccc cgtgcagccc gtcgcgcctt   2400

acggcctgtt cccgcaggac aacttcaccg agggagtata catcgactac cgcgccttcg   2460

acaaggagga catcactccg cagttcgagt tcggcttcgg tctctcgtac accaccttcg   2520

attattccag cctgaacatc caacgcacct cggtcgaggc cacacagtac cctcctgcgg   2580

cggttatcca ggaaggaggc aacccgcggc tgtgggatgt tttggtcaac gtcacggcgc   2640

aggtggagaa cgccggctcg gtcgacggcg cggaggtcgc acagctgtac gtgggcatcc   2700

ccaatggacc gatccgtcag ctgcgcgggt tcgataaggt gaatatcctg gctggggaga   2760

cggtgacggt cacgttcgcc ttgacgagac gtgatttgag tacgtggagt gtggaggcgc   2820

aggagtggga gctgcagcag ggagaatata aggtgtatgt gggacgatcg agtcgggatc   2880

tgcctctgac ggggagtttg accttgtgaa gtgtagtatt gccaggagat gacacttgga   2940

tgataattga aaatcttcca ctccattcta atgcaattta gtctgcatct attcaactgc   3000

tgtaaaaccc gtcccaagtg caaatcaaac cacaaaccac aaaagttaac ataaccgtcc   3060

atcgcagacc ggtctcagaa tcctacaaca atcaatataa tcaccacgcc ccaccgatgc   3120

ctcatctcca atacccgcgc ccacccgccc ccaacatccc agacttaacc gtccccaact   3180

cttcaccatc aacatcctcc tccaccaagc ctacatccca gacataatat tcctcaactc   3240

ctccgcatcc ccgaactagg ccttaaccg                                     3269
```

<210> SEQ ID NO 12
<211> LENGTH: 2301
<212> TYPE: DNA
<213> ORGANISM: Aspergillus saccharolyticus

<400> SEQUENCE: 12

```
atgtacggtc tagcatcttt tgcggccttg ttgggcggtc tttcactttg ctccgcggcc     60

ccgactgagc aaaatattac aagcgatact tacttttatg gcgattctcc gcccgtctac    120

ccctccccgg acggtgccgg aaccgggtcc tgggccgcag cctacgtaaa ggcaaagagt    180

tttgtcgctc aactcacaga cgaggagaag atcaacttca cagccgggta tactgccagt    240

aatggctgct caggcaacat tccagcagtc tctcgtctcg gcttccccgg gctttgtgtt    300

tctgatgcag gaaatgggct gcgtggaacc gattttgtga atggctggcc aagtggcatt    360

cacgtgggag caagctggaa taaaactctt gcacaccaac gcgccctata catgggacag    420

gagttccatc gaaagggggt aaatctccta ctgggcccag ttgttggccc acttggtcgt    480

gtcgtggaag gtggtcgtaa ctgggaaggc tttgccaacg atccttacct cagcggtgcg    540

ctggtgtatg agactgtgca gggtgtgcag gaagccggtg tcggcgtttc ggtcaagcac    600

tacatcggaa acgagcaaga gaccaacaga aaccccgaga ctgagaacgg cgtcactgtt    660

gcctcagttt cctctaacat cgacgacaaa actatccatg aactgtatct ttggccattt    720

caagacgccg ttctggcggg aagtgtctcc gtgatgtgct cgtacaaccg agtcaataat    780

tcctacagct gccagaacag taagacgctg aatggtcttc tgaagaccga actgggcttc    840

caaggctacg ttgtcactga ttgggatgcc caacacgccg ggatcgctgg tgctaatgcc    900
```

-continued

```
ggcctggaca tggtcatgcc aagtaccacc acatgggggt ccaatctcac gacggccatt    960

gccaacggca gcatggaagc atcgagactg gacgatatgg tcactaggat cgttgcctcc   1020

tggtaccaat taaaccaaga caccgacttt ccctcaccag gcattgggat gcccgtcgac   1080

gtctactccg agcatgagat cgtcattgga acttctgccg atgagaagga cgctttgctg   1140

caaagcgcaa tcgagggaca cgtcctcgtt aaaaaccaag gctccgtcct ccctctccag   1200

tcgccacgcc tagtctccgt gttcggctac gacgccaaag ccccggagtc cctggaccta   1260

gcccccgtct ctctaagtgt cgctccgccc acgcaaaaca acacactctg ggtgggcgga   1320

ggttccggtg ccaacaatcc cgcatacgtt atcgcccccct tggacgccat ccagcaacaa   1380

gcctatgaag acaacaccgc cgtcctctgg gacgtgacat cgttcgaccc agacgtcgac   1440

cccgcctccc acgcctgcct agttttcatc aacagctacg cctccgaagg cagtgaccgg   1500

acaggtctgg tggactccga cagcgacacg ctggtaacca acgtcgccag caaatgcaac   1560

aacacgatcg tcgtgatcca caacgcgggc atccgtctcg tgtataactg gatcgaccac   1620

gagaacgtta ccgctgtgat cttcgcccat cttccaggcc aagacacagg caaagctctc   1680

gtggatttac tgtacggccg cgccaacccc tcgggccgcc tcccctacac cgtcgccaag   1740

caggcctccg actacggcgc agtcttacac cccgtgcagc ccgtcgcgcc ttacggcctg   1800

ttcccgcagg acaacttcac cgagggagta tacatcgact accgcgcctt cgacaaggag   1860

gacatcactc cgcagttcga gttcggcttc ggtctctcgt acaccacctt cgattattcc   1920

agcctgaaca tccaacgcac ctcggtcgag gccacacagt accctcctgc ggcggttatc   1980

caggaaggag gcaacccgcg gctgtgggat gttttggtca acgtcacggc gcaggtggag   2040

aacgccggct cggtcgacgg cgcggaggtc gcacagctgt acgtgggcat ccccaatgga   2100

ccgatccgtc agctgcgcgg gttcgataag gtgaatatcc tggctgggga gacggtgacg   2160

gtcacgttcg ccttgacgag acgtgatttg agtacgtgga gtgtggaggc gcaggagtgg   2220

gagctgcagc agggagaata taaggtgtat gtgggacgat cgagtcggga tctgcctctg   2280

acggggagtt tgaccttgtg a                                             2301
```

<210> SEQ ID NO 13
<211> LENGTH: 766
<212> TYPE: PRT
<213> ORGANISM: Aspergillus saccharolyticus

<400> SEQUENCE: 13

```
Met Tyr Gly Leu Ala Ser Phe Ala Ala Leu Leu Gly Gly Leu Ser Leu
1               5                   10                  15

Cys Ser Ala Ala Pro Thr Glu Gln Asn Ile Thr Ser Asp Thr Tyr Phe
            20                  25                  30

Tyr Gly Asp Ser Pro Pro Val Tyr Pro Ser Pro Asp Gly Ala Gly Thr
        35                  40                  45

Gly Ser Trp Ala Ala Ala Tyr Val Lys Ala Lys Ser Phe Val Ala Gln
    50                  55                  60

Leu Thr Asp Glu Glu Lys Ile Asn Phe Thr Ala Gly Tyr Thr Ala Ser
65                  70                  75                  80

Asn Gly Cys Ser Gly Asn Ile Pro Ala Val Ser Arg Leu Gly Phe Pro
                85                  90                  95

Gly Leu Cys Val Ser Asp Ala Gly Asn Gly Leu Arg Gly Thr Asp Phe
            100                 105                 110

Val Asn Gly Trp Pro Ser Gly Ile His Val Gly Ala Ser Trp Asn Lys
        115                 120                 125
```

```
Thr Leu Ala His Gln Arg Ala Leu Tyr Met Gly Gln Glu Phe His Arg
    130                 135                 140

Lys Gly Val Asn Leu Leu Leu Gly Pro Val Val Gly Pro Leu Gly Arg
145                 150                 155                 160

Val Val Glu Gly Gly Arg Asn Trp Glu Gly Phe Ala Asn Asp Pro Tyr
                165                 170                 175

Leu Ser Gly Ala Leu Val Tyr Glu Thr Val Gln Gly Val Gln Glu Ala
            180                 185                 190

Gly Val Gly Val Ser Val Lys His Tyr Ile Gly Asn Glu Gln Glu Thr
        195                 200                 205

Asn Arg Asn Pro Glu Thr Glu Asn Gly Val Thr Val Ala Ser Val Ser
    210                 215                 220

Ser Asn Ile Asp Asp Lys Thr Ile His Glu Leu Tyr Leu Trp Pro Phe
225                 230                 235                 240

Gln Asp Ala Val Leu Ala Gly Ser Val Ser Val Met Cys Ser Tyr Asn
                245                 250                 255

Arg Val Asn Asn Ser Tyr Ser Cys Gln Asn Ser Lys Thr Leu Asn Gly
            260                 265                 270

Leu Leu Lys Thr Glu Leu Gly Phe Gln Gly Tyr Val Val Thr Asp Trp
        275                 280                 285

Asp Ala Gln His Ala Gly Ile Ala Gly Ala Asn Ala Gly Leu Asp Met
    290                 295                 300

Val Met Pro Ser Thr Thr Thr Trp Gly Ser Asn Leu Thr Thr Ala Ile
305                 310                 315                 320

Ala Asn Gly Ser Met Glu Ala Ser Arg Leu Asp Asp Met Val Thr Arg
                325                 330                 335

Ile Val Ala Ser Trp Tyr Gln Leu Asn Gln Asp Thr Asp Phe Pro Ser
            340                 345                 350

Pro Gly Ile Gly Met Pro Val Asp Val Tyr Ser Glu His Glu Ile Val
        355                 360                 365

Ile Gly Thr Ser Ala Asp Glu Lys Asp Ala Leu Leu Gln Ser Ala Ile
    370                 375                 380

Glu Gly His Val Leu Val Lys Asn Gln Gly Ser Val Leu Pro Leu Gln
385                 390                 395                 400

Ser Pro Arg Leu Val Ser Val Phe Gly Tyr Asp Ala Lys Ala Pro Glu
                405                 410                 415

Ser Leu Asp Leu Ala Pro Val Ser Leu Ser Val Ala Pro Pro Thr Gln
            420                 425                 430

Asn Asn Thr Leu Trp Val Gly Gly Gly Ser Gly Ala Asn Asn Pro Ala
        435                 440                 445

Tyr Val Ile Ala Pro Leu Asp Ala Ile Gln Gln Gln Ala Tyr Glu Asp
    450                 455                 460

Asn Thr Ala Val Leu Trp Asp Val Thr Ser Phe Asp Pro Asp Val Asp
465                 470                 475                 480

Pro Ala Ser His Ala Cys Leu Val Phe Ile Asn Ser Tyr Ala Ser Glu
                485                 490                 495

Gly Ser Asp Arg Thr Gly Leu Val Asp Ser Asp Ser Asp Thr Leu Val
            500                 505                 510

Thr Asn Val Ala Ser Lys Cys Asn Asn Thr Ile Val Val Ile His Asn
        515                 520                 525

Ala Gly Ile Arg Leu Val Tyr Asn Trp Ile Asp His Glu Asn Val Thr
    530                 535                 540
```

-continued

```
Ala Val Ile Phe Ala His Leu Pro Gly Gln Asp Thr Gly Lys Ala Leu
545                 550                 555                 560

Val Asp Leu Leu Tyr Gly Arg Ala Asn Pro Ser Gly Arg Leu Pro Tyr
                565                 570                 575

Thr Val Ala Lys Gln Ala Ser Asp Tyr Gly Ala Val Leu His Pro Val
            580                 585                 590

Gln Pro Val Ala Pro Tyr Gly Leu Phe Pro Gln Asp Asn Phe Thr Glu
        595                 600                 605

Gly Val Tyr Ile Asp Tyr Arg Ala Phe Asp Lys Glu Asp Ile Thr Pro
    610                 615                 620

Gln Phe Glu Phe Gly Phe Gly Leu Ser Tyr Thr Thr Phe Asp Tyr Ser
625                 630                 635                 640

Ser Leu Asn Ile Gln Arg Thr Ser Val Glu Ala Thr Gln Tyr Pro Pro
                645                 650                 655

Ala Ala Val Ile Gln Glu Gly Gly Asn Pro Arg Leu Trp Asp Val Leu
            660                 665                 670

Val Asn Val Thr Ala Gln Val Glu Asn Ala Gly Ser Val Asp Gly Ala
        675                 680                 685

Glu Val Ala Gln Leu Tyr Val Gly Ile Pro Asn Gly Pro Ile Arg Gln
    690                 695                 700

Leu Arg Gly Phe Asp Lys Val Asn Ile Leu Ala Gly Glu Thr Val Thr
705                 710                 715                 720

Val Thr Phe Ala Leu Thr Arg Arg Asp Leu Ser Thr Trp Ser Val Glu
                725                 730                 735

Ala Gln Glu Trp Glu Leu Gln Gln Gly Glu Tyr Lys Val Tyr Val Gly
            740                 745                 750

Arg Ser Ser Arg Asp Leu Pro Leu Thr Gly Ser Leu Thr Leu
        755                 760                 765
```

<210> SEQ ID NO 14
<211> LENGTH: 370
<212> TYPE: DNA
<213> ORGANISM: Aspergillus saccharolyticus

<400> SEQUENCE: 14

```
ccatctctgg tgagcacggc cttgatggcg ctggtgtgta agtgcagaca acccccagat      60

tgcgggccaa gcgggtgcgc ggcaaagcgt gcaagtgatt aataaaaagc ccagttacaa     120

tggctcctcc gaccttcagc tggagcgcat gaacgtctac ttcaacgagg ttcgtccttc     180

cccgagtctt ccccgccagt tttcccgcca gctcctcatc ccttcaccag gccagcggta     240

acaagtatgt tcctcgtgcc gtcctcgtcg atctcgagcc cggtaccatg gacgcggtcc     300

gtgccggtcc cttcggccag cttttccgcc ccgacaactt cgttttcggt cagtccggtg     360

ctggtaacaa                                                            370
```

<210> SEQ ID NO 15
<211> LENGTH: 427
<212> TYPE: DNA
<213> ORGANISM: Aspergillus saccharolyticus

<400> SEQUENCE: 15

```
taacaggaca aggatggcga tggttagtgc agtccttacc cctcaatcaa tccacccggt      60

accatgatta tcacgacgct acaaccatga caccctcccg aatagtgaac aagatttgat     120

tgattttaca tgacaggaca aatcaccacc aaggagttgg gtactgttat gcgttccctg     180

ggccagaacc cttccgagtc tgagctccag gacatgatta atgaggtcga tgctgacaac     240
```

aacggcacta tcgactttcc cggtatgtga tggtgatgag tggagctcga gcataagatt 300
gacaggtacc agaattcctt acaatgatgg cccgtaagat gaaagacacc gattctgagg 360
aggaaatccg ggaggctttc aaagtcttcg atcgcgacaa caacggcttc atttccgccg 420
cggagct 427

<210> SEQ ID NO 16
<211> LENGTH: 448
<212> TYPE: DNA
<213> ORGANISM: Aspergillus saccharolyticus

<400> SEQUENCE: 16
cctcccaccc gtgtctaccg tacctcagtt gcttcggcgg gcccgcctta acggtggccc 60
gggggcttgc ccccgggaca gcgcccgccg gagacccttt aaacaagaac ccttgccatg 120
aatgccttgt agtctgagtt gatgattaaa ttcattaaaa ctttcaacaa tggatctctt 180
ggttccggca tcgatgaaga acgcagcgaa atgcgataac taatgtgaat tgcagaattc 240
agtgaatcat cgagtctttg aacgcacatt gcgcccccctg gcattccggg gggcatgcct 300
gtccgagcgt catttcgccc ctccagcccg gctggttgtt gggcctcgcc ccccccgggg 360
ggcgggcccc gagagaaatg gcggcaccgt ccggtccccg agcgtatggg tttacccgct 420
cttagggccc ggtcggggct ttagcctc 448

<210> SEQ ID NO 17
<211> LENGTH: 18
<212> TYPE: PRT
<213> ORGANISM: Aspergillus saccharolyticus

<400> SEQUENCE: 17

Leu Leu Lys Ser Glu Leu Gly Phe Gln Gly Phe Val Met Ser Asp Trp
1               5                   10                  15

Gly Ala

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 18
tccgtaggtg aacctgcgg 19

<210> SEQ ID NO 19
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 19
gctgcgttct tcatcgatgc 20

<210> SEQ ID NO 20
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 20
tcctccgctt attgatatg 19

<210> SEQ ID NO 21
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 21
ggtaaccaaa tcggtgctgc tttc 24

<210> SEQ ID NO 22
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 22
accctcagtg tagtgaccct tggc 24

<210> SEQ ID NO 23
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 23
ccgagtacaa ggaggccttc 20

<210> SEQ ID NO 24
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 24
ccgatagagg tcataacgtg g 21

<210> SEQ ID NO 25
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 25
gtaaaacgac ggccagt 17

<210> SEQ ID NO 26
<211> LENGTH: 15
<212> TYPE: DNA
<213> ORGANISM: Artificial sequence
<220> FEATURE:
<223> OTHER INFORMATION: Oligonucleotide primer

<400> SEQUENCE: 26
gagggtggcg gctag 15

<210> SEQ ID NO 27
<211> LENGTH: 26
<212> TYPE: DNA

```
<213> ORGANISM: Artificial sequence
<220> FEATURE:
<223> OTHER INFORMATION: Oligonucleotide primer

<400> SEQUENCE: 27

cacgaaatgt acctctggcc cttwgc                                          26


<210> SEQ ID NO 28
<211> LENGTH: 28
<212> TYPE: DNA
<213> ORGANISM: Artificial sequence
<220> FEATURE:
<223> OTHER INFORMATION: Oligonucleotide primer
<220> FEATURE:
<221> NAME/KEY: W is A or T
<222> LOCATION: (23)..(24)

<400> SEQUENCE: 28

ccttgatcac gttgtcgccr ttcwkcca                                        28


<210> SEQ ID NO 29
<211> LENGTH: 4698
<212> TYPE: DNA
<213> ORGANISM: Aspergillus saccharolyticus

<400> SEQUENCE: 29

cggttaaggc ctaactcgga gagggaccaa cgggatgcag aggtggagat gcggggaatg     60

gctggggagg ataataccgt atgtatccgc gtgtcatgac accaggtata ccttattctc    120

gtctgccaac tatcaccact gcagtgagtg cttgctcgct ggcagacctg cggggaacaa    180

cacagactgg actgatacaa tggataccac cttccatctt catcttcttg tcagcttctc    240

gggtgtcatt caagtccgat atttgtccga ttagcctgta tccgaagcgg atcggaatgt    300

aaacgaggaa cgggataact taagtttacg gagtattctg gttccagtcg agaatgctgg    360

gcagctcccg gccgatcgta tgctgcttgc tgcctgaatg ataataatta tctattttat    420

tctgagagaa aattcttgga ttattttctt gtattcctta aatctttata aaacagagtg    480

cagttggaga ttcatgtccg agagagatgc tgagtgttaa gactgtaagt aagtagagga    540

agtggtaagt tgtttggatt gaactggaaa gcgtcacagg attacataca ggcacctccc    600

ggccccactg cggtcgggga acttcttcca gtccacaggg cagcagtact caatatccat    660

ccaatatcca tccttccact acatccacca tcatcattgt ttcccggatg gcaggatact    720

ggcaccacgc tctgacgtgg ggctcggcca ttccagttat cccagctcaa ttccctgcag    780

gtctgctgcg aactattgac cgcgaaaatg aaagtttttt tgggagttga tgttccacgg    840

tgccgtgcgc aggtgaatgc aagcaagagc agcgatccag agatggagag tgaatgaatc    900

acggtaagta gcatcgcttg acttgcctgc gttccggtcg ttccatgctt tttctcgact    960

ctccctcgct gtctgtctct ctctcgatct ggattcctcc ctgtcgatcc atccccatgc   1020

ttagagccaa aacaactaag ccgatggggc tggctggcct tcgactgctg gcgggcgaga   1080

cagcattcaa agagtggact acttgtggta gctccgcagc atcagccaag aaagtctagg   1140

ttgatgttag ttattcactc gtctgctggt ctctgagtct catagctgtg gcgcccccct   1200

cctgccgttg ctggggttat ttatatcccc tcccttcccc ccccctgatc ggatatgttt   1260

gtcttcccac aataagttgt gttacctcgc catcttcctc aattgctcga gactagctcg   1320

tcccttccgc ttccttcagc tacctcgacg ccatcatgag gctcagttgg ctcgaggctg   1380

ccgccttgac ggctgcatcc gtcgtcagcg ctgtatgttt tgccgcttgt ttggatggat   1440
```

-continued

```
gactgggtgt gaaactgaca tttgtgctcg ctaggatgaa cttgccttcg cttcccctt   1500
ctatccttcc ccttgggcca atggccaggg cgagtgggcg gatgcctaca agcgcgcagt   1560
ggacattgtt tcccagatga ctctggacga gaaggtcaat ctgaccaccg gaactgggta   1620
tgggagcgta attcatgcgg tccgcatcgc ctgctaacat attccaagct gggagctgga   1680
gaagtgcgtc ggtcaaactg gtggtgttcc aaggtatgca ctgattgaat gggtttctac   1740
tagaacggtt aattgacaat tgtgcctaga ctcgacatcg gtggaatgtg tcttcaggac   1800
agtccgctcg gagtccgtga ttgtaagtct cgttaggagc cgacatcaaa cgtgtcttat   1860
taacaatgtg tcttccagcg gactacaatt cgggattccc cgctggcgtc aacgttgctg   1920
cgacttggga caggaagctc gcctatctcc gtgggcaggc catgggtcaa gaatttagtg   1980
acaagggagt tgatgtccag ctggggccgg ccgccgggcc cctgggcaga agtcccgatg   2040
gaggtcggaa ctgggaaggg ttttcgcccg acccagcact cactggtgtg ctctttgccg   2100
agacgatcaa gggtatccaa gatgccgggg tcatcgccac agctaagcac tacattctca   2160
atgagcagga acatttccgc caagtctcgg aggctgcggg ctacggtttc aacatctctg   2220
ataccatcag ctccaacatc gacgacaaaa ccattcatga gatgtacctc tggcccttcg   2280
cggatgccgt gcgtgccggt gtgggcgccg tcatgtgctc ctacaaccag attaacaaca   2340
gttacgcctg ccagaacagc tacacactga acaagcttct gaagtcggag ctcggctttc   2400
aaggatttgt tatgtcggac tggggtgctc accacagtgg tgtcggctct gctttggccg   2460
ggttggatat gtctatgccc ggtgacgttt cttttgattc tgccaccagt ttctggggta   2520
ccaacctgac tgttgccgtt ctcaatggaa ccgtcccgca gtggcgtgtt gacgacatgg   2580
ccgttcgtat catggctgcc tactacaagg ttggccgtga tcgcttgtac cagccgccca   2640
acttcagctc ctggactcgg gacgagtacg gcttcaagta ctactactcc caggaaggcc   2700
cctacgagaa ggtcaatcaa tatgtcaatg tgcagcgcaa ccacagcgaa gtcattcgca   2760
aggtgggagc cgacagcact gtcctgttga agaacaacaa tgctcttcct ctgactggaa   2820
aggagcgcaa ggttgctctc atcggcgagg atgctggatc taacgcctac ggtgccaacg   2880
gctgcagtga ccgcggatgc gacaacggga cgctcgccat ggcctggggc agtggcaccg   2940
cagagttccc atacctggtc actcccgagc aggccattca agccgaggtg ctcaagaaca   3000
agggcagcac ttacactatc accgacaact gggcattgag ccaggtggag gccctcgcta   3060
agacggctag gtgagccctt ccattcatga tactggtctg ccgtgacaat ccactgacaa   3120
gtcgctcgca gtgtctccct ggtctttgtg aatgccgact cgggcgaagg ctacatctcg   3180
gttgatggca acgagggtga ccgcaacaac ctcaccctgt ggaagaacgg ggacaatctc   3240
atcaaggcta ctgccagcaa ctgcaacaac accattgttg tcatccactc cgttggggct   3300
gttctggtgg acgaatggta tgaccacccg aacgtcactg cgattctctg ggctggcttg   3360
cctggccagg agtctggcaa ttctcttgcc gatgtcctct acggccgcgt caaccctggc   3420
ggtaagacgc ccttcacctg ggcaagacg agagcgtctt acggggacta cctggttcgg   3480
gagcccaaca acggccacgg agccccgcag gataacttct cggagggtgt tttcatcgac   3540
taccgcggct ttgacaagcg caatgagacc ccgatctacg agttcggaca cggtctgagc   3600
tacaccacct tcaactattc gggcctgcag gtggaggttc tcaacacgtc ttccagcact   3660
ccggtcgcta cccagaccaa gcccgcaccc actttcggcg agattggcaa cgcgtcggac   3720
tacttgtacc ctgagggatt ggaccgaatt accgcgttca tctacccctg gctcaactcc   3780
acggacctca aggagtcatc tggtgacccg gactatgggg tggacaccgc caagtatatt   3840
```

-continued

| | |
|---|---|
| cccgccggcg ccaccaacag ctcggcccag cctgttctgc cggctggcgg tggcttcggt | 3900 |
| ggtaacccgc gtctctacga tgagctgatc cgtgtttcgg ttaccgtcaa gaacactggt | 3960 |
| cgtgtcactg gggacgccgt gcctcaattg gtaagttgct cgtccgggga gttggtagat | 4020 |
| cgcgtactaa catgagacag tatgtatcgc ttggcggacc taatgagccc aaggtggtgc | 4080 |
| tgcgccagtt cgaccgcatc acgctccggc cttcggagga gacggtgtgg acgactactc | 4140 |
| tgacccgtcg cgatctgtcc aactgggatg ttgcggctca ggactgggtt attacttcct | 4200 |
| acccgaagaa ggttcacgtg ggtagctctt cgcgtcagct gccgcttcat gcggcgctgc | 4260 |
| ctaaggtgca atgagcggat ggggattggg tgcgatgggg atgatgctgt atacttcttt | 4320 |
| ccagtcggga gactacgaat tgatgactat gttattgtaa agacgagcga tccagggatc | 4380 |
| caggtacagg aggggtgtag tgtaatgtaa gcgtaatgat ctggggtcgg gtggctgtgg | 4440 |
| cggtggaggt gaagcggcgg gcgggcggaa gacagcgacg tcatccgact tccaccggca | 4500 |
| cttcgtctcc ctttggtaac ttccatcatt tctccgacct ctgcctggtt ttcgtctatc | 4560 |
| catcctgacg cctcaattcc catcatcttt ctttgaattt tgctccacgc ttgactttga | 4620 |
| attgattgcc tccaaaacaa gccaccacaa gacagcgcag ccactcaaac catcgaaggg | 4680 |
| actctatccg gaattggc | 4698 |